United States Patent
Li et al.

(10) Patent No.: US 11,214,801 B2
(45) Date of Patent: *Jan. 4, 2022

(54) RNAI AGENTS AND COMPOSITIONS FOR INHIBITING EXPRESSION OF APOLIPOPROTEIN C-III (APOC3)

(71) Applicant: Arrowhead Pharmaceuticals, Inc., Pasadena, CA (US)

(72) Inventors: Zhen Li, Westfield, NJ (US); Rui Zhu, Middleton, WI (US); Tao Pei, Middleton, WI (US); Steven Kanner, Berkeley, CA (US); So Wong, Oregon, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,188

(22) Filed: Jan. 31, 2020

(65) Prior Publication Data

US 2020/0299690 A1 Sep. 24, 2020

Related U.S. Application Data

(62) Division of application No. 16/126,740, filed on Sep. 10, 2018, now Pat. No. 10,597,657.

(60) Provisional application No. 62/720,434, filed on Aug. 21, 2018, provisional application No. 62/643,927, filed on Mar. 16, 2018, provisional application No. 62/556,818, filed on Sep. 11, 2017.

(51) Int. Cl.
| | | |
|---|---|---|
| C12N 15/113 | (2010.01) | |
| C07H 3/02 | (2006.01) | |
| A61P 3/04 | (2006.01) | |
| A61P 1/18 | (2006.01) | |
| A61P 9/10 | (2006.01) | |
| A61K 9/00 | (2006.01) | |

(52) U.S. Cl.
CPC .............. *C12N 15/113* (2013.01); *A61P 1/18* (2018.01); *A61P 3/04* (2018.01); *A61P 9/10* (2018.01); *C07H 3/02* (2013.01); *A61K 9/0019* (2013.01); *C12N 2310/11* (2013.01); *C12N 2310/14* (2013.01); *C12N 2310/315* (2013.01); *C12N 2310/317* (2013.01); *C12N 2310/321* (2013.01); *C12N 2310/322* (2013.01); *C12N 2310/3233* (2013.01); *C12N 2310/332* (2013.01); *C12N 2310/343* (2013.01); *C12N 2310/346* (2013.01); *C12N 2310/351* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,030,453 A | 7/1991 | Lenk et al. |
| 5,885,968 A | 3/1999 | Biessen et al. |
| 5,962,016 A | 10/1999 | Willis |
| 5,998,203 A | 12/1999 | Matulic-Adamic et al. |
| 6,680,068 B2 | 1/2004 | Campbell et al. |
| 8,084,600 B2 | 12/2011 | Natt et al. |
| 8,097,716 B2 | 1/2012 | Weiler et al. |
| 8,344,128 B2 | 1/2013 | Natt et al. |
| 8,404,831 B2 | 3/2013 | Natt et al. |
| 10,597,657 B2 * | 3/2020 | Li .............................. A61P 3/04 |
| 2002/0162126 A1 | 10/2002 | Beach et al. |
| 2003/0012812 A1 | 1/2003 | Tormo et al. |
| 2004/0072779 A1 | 4/2004 | Kreutzer et al. |
| 2004/0142025 A1 | 7/2004 | Maclachlan et al. |
| 2004/0147475 A1 | 7/2004 | Li et al. |
| 2004/0204377 A1 | 10/2004 | Rana |
| 2004/0208921 A1 | 10/2004 | Ho et al. |
| 2004/0234586 A1 | 11/2004 | Meloche et al. |
| 2004/0259247 A1 | 12/2004 | Tuschl et al. |
| 2005/0008617 A1 | 1/2005 | Chen et al. |
| 2005/0069577 A1 | 3/2005 | Diamond et al. |
| 2005/0255487 A1 | 11/2005 | Khvorova et al. |
| 2006/0240093 A1 | 10/2006 | Maclachlan et al. |
| 2007/0135372 A1 | 6/2007 | Maclachlan et al. |
| 2007/0203084 A1 | 8/2007 | Weiler et al. |

(Continued)

FOREIGN PATENT DOCUMENTS

| | | |
|---|---|---|
| WO | 2000044914 A1 | 8/2000 |
| WO | 2000053722 A2 | 9/2000 |

(Continued)

OTHER PUBLICATIONS

Sharp et al.; "RNA interference-2001"; Genes & Development; 15:485-490; 2001.

(Continued)

*Primary Examiner* — Brian Whiteman
(74) *Attorney, Agent, or Firm* — Robert M. Teigen; Paul Vandervelde; Meibo Chen

(57) ABSTRACT

The present disclosure relates to RNAi agents, e.g., double stranded RNAi agents, capable of inhibiting Apolipoprotein C-III (also called APOC3, apoC-III, APOC-III, and APO C-III) gene expression, and compositions that include APOC3 RNAi agents. The APOC3 RNAi agents disclosed herein may be conjugated to targeting ligands, including ligands that include N-acetyl-galactosamine, to facilitate the delivery to cells, including to hepatocytes. Pharmaceutical compositions that include one or more APOC3 RNAi agents, optionally with one or more additional therapeutics, are also described. Delivery of the APOC3 RNAi agents in vivo provides for inhibition of APOC3 gene expression, and can result in lower triglycerides and/or cholesterol levels in the subject. The APOC3 RNAi agents can be used in methods of treatment of APOC3-related diseases and disorders, including hypertriglyceridemia, cardiovascular disease, and other metabolic-related disorders and diseases.

30 Claims, 27 Drawing Sheets

Specification includes a Sequence Listing.

(56) References Cited

U.S. PATENT DOCUMENTS

| | | | |
|---|---|---|---|
| 2008/0113351 | A1 | 5/2008 | Naito et al. |
| 2009/0182136 | A1 | 7/2009 | Wengel et al. |
| 2009/0209626 | A1 | 8/2009 | Khvorova et al. |
| 2009/0291131 | A1 | 11/2009 | Maclachlan et al. |
| 2010/0015705 | A1 | 1/2010 | Vodyanyk et al. |
| 2010/0056768 | A1 | 3/2010 | Wengel |
| 2011/0200582 | A1 | 8/2011 | Baryza et al. |
| 2012/0184595 | A1 | 7/2012 | MacDonald et al. |
| 2016/0122761 | A1 | 5/2016 | Prakash et al. |
| 2016/0272970 | A1* | 9/2016 | Rozema ................ C12N 15/111 |
| 2018/0064819 | A1* | 3/2018 | Li .......................... C07H 21/04 |
| 2020/0157545 | A1* | 5/2020 | Vargeese ............. C12N 15/1137 |

FOREIGN PATENT DOCUMENTS

| | | |
|---|---|---|
| WO | 2007128477 A2 | 11/2007 |
| WO | 2008022309 A2 | 2/2008 |
| WO | 2010083615 A1 | 7/2010 |
| WO | 2011104169 A1 | 9/2011 |
| WO | 2012083185 A2 | 6/2012 |
| WO | 2012177947 A2 | 12/2012 |
| WO | 2013032829 A1 | 3/2013 |
| WO | 2013158141 A1 | 10/2013 |
| WO | 2013165816 A2 | 11/2013 |
| WO | 2015051366 A2 | 4/2015 |
| WO | 2016011123 A1 | 1/2016 |
| WO | 2016081444 A1 | 5/2016 |
| WO | 2017156012 A1 | 9/2017 |
| WO | 2018044350 A1 | 3/2018 |

OTHER PUBLICATIONS

Sharpe et al.; "Human apolipoproteins AI, AII, CII and CIII. cDNA sequences and mRNA abundance" Nucleic Acids Res.; 1984; 12(9): 3917-3932.

Sioud and Sorensen, Biochem Biophys Res Commun. 2003, 312(4): 1220-1225.

Sioud 2005 J. Mol. Biol. 348:1079-1090.

Song et al.,2003 Nature Medicine, vol. 9, No. 3, 347-351.

Song et al. 2005 Nat Biotech. 23: 709-717.

Soutschek et al. 2004 Nature 432:173-178.

Sun et al.; "Asymmetric RNA duplexes mediate RNA interference in mammalian cells"; Nature Biotechnology; vol. 26; No. 12; 2008; 1379-1382.

Usman et al.; TIBS; 1992; 17:334-339.

Usman et al. 1994 Nucleic Acids Symp. Ser. 31:163-164.

Vickers et al., Journal of Biological Chemistry, 278(9):7108-7118 (2003).

Vu-Dac et al.; "Retinoids Increase Human Apo C-III Expression at the Transcriptional Level ia the Retinoid X Receptor"; J. Clin. Invest.; 1998; vol. 102; No. 3; pp. 625-632.

Wang et al.; "Association of Apolipoprotein C3 Genetic Polymorphisms with the Risk of Ischemic Stroke in the Northern Chinese Han Population"; PloS One; e0163910; 2016.

Yamato et al.; "Enhanced specificity of HPV16 E6E/ siRNA by RNA-DNA chimera modification"; Cancer Gene Therapy; 2011; 18; 587-597.

Zhang G et al., "High Levels of Foreign Gene Expression in Hepatocytes after Tail Vein Injections of Naked Plasmid DNA"; Human Gene Therapy; vol. 10; 1735-1737; 1999.

Levy-Wilson et al.; "Isolation and DNA Sequence of Full-Length cDNA for Human Preapolipoprotein CIII"; DNA; vol. 3; No. 5; 1984; pp. 359-364.

Baenziger et al.; "Galactose and N-Acetylgalactosamine-Specific Endocytosis of Glycopeptides by Isolated Rat Hepatocytes"; Cell; vol. 22; 611-620; 1980.

Bernstein, et al.; "Role for a bidentate ribonuclease in the initiation step of RNA interference"; 2001; Nature 409:363-366.

Biessen et al.; "Synthesis of Cluster Galactosides with High Affinity for the Hepatic Asialoglycoprotein Receptor"; J. Med. Chem.; 38; 1538-1546; 1995.

BURGIN et al. 1996 Biochemistry 35: 14090-14097.

Caplen et al. 2001 Proc. Natl. Acad. Sci. (USA), 98: 9742-9747.

CHU and RANA; "Potent RNAi by short RNA triggers"; RNA; 2008; 14: 1714-1719.

Connolly et al.; "Binding and Endocytosis of Cluster Blycosides by Rabbit Hepatocytes"; The Journal of Biological Chemistry; vol. 257, No. 2; 939-945; 1982.

Czauderna et al.; "Structural variations and stabilizing modifications of synthetic siRNAs in mammalian cells" Nucleic Acids Research; vol. 31, No. 11; 2705-2716; 2003.

Dammerman, M et al.; "An apolipoprotein CIII haplotype protective against hypertriglyceridemia is specified by promoter and 3' untranslated region polymorphisms"; Proc. Natl. Acad. Sci. U.S.A.; vol. 90; pp. 4562-4566; 1993.

De Silva et al.; "Overexpression of Human Apolipoprotein C-III in Transgenic Mice Results in an Accumulation of Apolipoprotein B48 Remnants That Is Corrected by Excess Apolipoprotein E"; J. Biol. Chem.; 1994; vol. 269; pp. 2324-2335.

Donze and Picard, 2002, 30(10): e46.

Dowler et al.; Nucleic Acids Research; 2006; vol. 34; No. 6; 1669-1675.

Duxbury et al., J. Surgical Research, 2004, 117: 339-344.

Elbashir et al. 2001 Genes Dev. 15: 188-200.

Elbashir et al., Nature, 411:494-498 (2001).

Elbashir et al., EMBO J., 20(23):6877-6888 (2001).

Farhood, et al., Biochimica et Biophysica Acta, 1235, (1995), 289-295.

Gambling et al.; Kidney International, vol. 65; 2004; pp. 1774-1781.

Gautier et al. 1987 Nucleic Acids. Res. 15: 6625-6641.

Henschel et al.; "DEQOR: a web-based tool for the design and quality control of siRNAs"; Nucleic Acids Research vol. 32; Web Server Issue: W113-W120; 2004.

Hertz et al.; "Mode of Action of Peroxisome Proliferators as Hypolipidemic Drugs"; J. Biol. Chem.; vol. 270; No. 22; Issue of Jun. 2, 1995; pp. 13470-13475.

Hutvagner et al. 2001 Science 293: 834-838.

Inoue et al. 1987 Nucleic Acids Res. 15: 6131-6148.

Inoue et al. 1987 FEBS Lett. 215: 327-330.

Iobst et al.; "Selective Sugar Binding to the Carbohydrate Recognition Domains of the Rat Hepatic and Macrophage Asialoglycoprotein Receptors"; The Journal of Biological Chemistry; vol. 271, No. 12; 6686-6693; 1996.

Ito et al.; "Hypertriglyceridemia as a Result of Human Apo CIII Gene Expression in Transgenic Mice"; Science; 1990; 249; pp. 790-793.

Karathanasis; "Apolipoprotein multigene family: Tandem organization of human apolipoprotein AI, CIII, and AIV genes"; Proc. Natl. Acad. Sci. U.S.A.; vol. 82; pp. 6374-6378; Oct. 1985.

Kardassis et al.; "SMAD Proteins Transactivate the Human ApoCIII Promoter by Interacting Physically and Functionally with Hepatocyte Nuclear Factor 4"; J. Biol. Chem.; vol. 275; No. 52; Issue of Dec. 29, 2000; pp. 41405-41414.

Kardassis et al.; "Direct Physical Interactions between HNF-4 and Sp1 Mediate Synergistic Transactivation of the Apolipoprotein CIII Promoter"; Biochemistry; 2002; 41; 1217-1228.

Kraynack et al., RNA, 12:163-176 (2006).

Li et al.; "Common Genetic Variation in the Promoter of the Human apo CIII Gene Abolishes Regulation by Insulin and May Contribute to Hypertriglyceridemia"; J. Clin. Invest.; vol. 96; 1995; pp. 2601-2605.

Li, Y. et al.; "Apolipoprotein C3 gene variants and the risk of coronary heart disease: A meta-analysis"; Meta Gene 9; 104-109; 2016.

Liu et al.; "RNA duplexes with abasic substitutions are potent and allele-selective inhibitors of huntingtin and ataxin-3 expression"; Nucleic Acids Research; vol. 41, No. 18; pp. 8788-8801; 2013.

Maeda et al.; "Molecular cloning of a human apoC-III variant: Thr 74-Ala 74 mutation prevents O-glycosylation"; J. Lipid Res.; vol. 28; 1987; 1405-1409.

Maeda et al.; "Targeted Disruption of the Apolipoprotein C-III Gene in Mice Results in Hypotriglyceridemia and Protection from Postprandial Hypertriglyceridemia"; J. Biol. Chem.; vol. 269; No. 38; Issue of Sep. 23, 1994; pp. 23610-23616.

(56) References Cited

OTHER PUBLICATIONS

McCaffrey et al.; RNA interference in adult mice; Nature; vol. 418; Jul. 4, 2002; pp. 38-39.
Miller, et al., Biochemistry, 1998, 37(37): 12875-83.
Moens et al.; "Inhibition of ApoCIII: the next PCSK9?"; Current Opinion in Lipidology; vol. 25, Issue 6; p. 418-422; 2014.
Nyakanen et al. 2001 Cell 107:309-321.
Ogami et al.; "Purification and Characterization of a Heat Stable Nuclear Factor CIIIb1 Involved in the Regulation of the Human ApoC-III Gene"; J. Biol. Chem.; vol. 266; No. 15; Issue of May 25, 1991; pp. 9640-9646.
Olivieri et al.; "ApoC-III gene polymorphisms and risk of coronary artery disease"; J. Lipid Res.; 2002; vol. 43; 1450-1457.
GenBank NM_000040.1 (2017).
Parrish et al. 2000 Molecular Cell 6: 1077-1087.
Protter et al.; "Isoloation and Sequence Analysis of the Human Apolipoprotein CIII Gene and the Intergenic Region between the Apo AI and Apo CIII Genes"; DNA; vol. 3; No. 6; 1984; pp. 449-456.
Raspe et al.; "Identification of Rev-erbα as a physiological repressor of apoC-III gene transcription"; J. Lipid Res. vol. 43; pp. 2172-2179; 2002.
Saleheen, D. et al.; "Human knockouts and phenotypic analysis in a cohort with a high rate of consanguinity" Nature; 235-239; 2017.
Scherer, "Approaches for the sequence-specific knockdown of mRNA" Nature Biotechnology, 21(12): 1457-1465 (2003).
Schiffelers et al. 2004 Nucl. Acids Res. 32: el49, pp. 1-10.
Schoonjans et al.; "3-Hydroxy-3-methyglutaryl CoA reductase inhibitors reduce serum triglyceride levels through modulation of apolipoprotein C-III and lipoprotein lipase"; FEBS Letters; 452; 1999; 160-164.
Shachter, Neil S.; "Apolipoproteins C-I and C-III as important modulators of lipoprotein metabolism"; Current Opinion in Lipidology; 2001; 12:297-304.
Partial Supplementary European Search Report for corresponding European Application No. 18853495.2 dated May 20, 2021.

\* cited by examiner

SEQUENCE LISTING

<160> NUMBER OF SEQ ID NOS: 837

<210> SEQ ID NO 1
<211> LENGTH: 533
<212> TYPE: DNA
<213> ORGANISM: Homo sapiens
<220> FEATURE:
<223> OTHER INFORMATION: Homo Sapiens apolipoprotein C3 (APOC3)
      transcript, GenBank NM_000040.1

<400> SEQUENCE: 1
tgctcagttc atccctagag gcagctgctc caggaacaga ggtgccatgc agccccgggt      60
actccttgtt gttgccctcc tggcgctcct ggcctctgcc cgagcttcag aggccgagga    120
tgcctccctt ctcagcttca tgcagggtta catgaagcac gccaccaaga ccgccaagga    180

-continued

```
tgcactgagc agcgtgcagg agtcccaggt ggcccagcag gccaggggct gggtgaccga    240
tggcttcagt tccctgaaag actactggag caccgttaag gacaagttct ctgagttctg    300
ggatttggac cctgaggtca gaccaacttc agccgtggct gcctgagacc tcaataccccc   360 aagtccacct gcctatccat cctgcgagct ccttgggtcc tgcaatctcc agggctgccc    420
ctgtaggttg cttaaaaggg acagtattct cagtgctctc ctaccccacc tcatgcctgg    480 ccccccctcca ggcatgctgg cctcccaata aagctggaca agaagctgct atg          533
```

<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 2
ucacugagaa uacugcccu c                                                 21

<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 3
ucacugagaa uacugcccu c                                                 21

<210> SEQ ID NO 4
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 4
ucacugagaa uacugcccg u                                                 21

<210> SEQ ID NO 5
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 5
ucacugagaa uacugcccg u                                                 21

<210> SEQ ID NO 6
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 6
ucacugagaa uacugcccu c                                                 21

<210> SEQ ID NO 7
<211> LENGTH: 21

```
<212> TYPE: RNA
<213> ORGANISM: Artificial sequence
<220> FEATURE:
<223> OTHER INFORMATION: RNAi agent antisense strand modified sequence

<400> SEQUENCE: 7
uucuugucca gcuuuauugg c                                              21

<210> SEQ ID NO 8
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 8
uucuugucca gcuuuauugg c                                              21

<210> SEQ ID NO 9
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 9
agaauacugu cccuuuuagg g                                              21

<210> SEQ ID NO 10
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 10
agaauacugu cccuuuuagg g                                              21

<210> SEQ ID NO 11
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 11
agaauacugu cccuuuuaag c                                              21

<210> SEQ ID NO 12
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 12
agaauacugu cccuuuuaag c                                              21

<210> SEQ ID NO 13
<211> LENGTH: 21
<212> TYPE: RNA
<213> ORGANISM: Artificial sequence
<220> FEATURE:
<223> OTHER INFORMATION: RNAi agent antisense strand modified sequence
```

```
<400> SEQUENCE: 13
ugagaauacu gucccuuugc c                                              21

<210> SEQ ID NO 14
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 14
ugagaauacu gucccuuugc c                                              21

<210> SEQ ID NO 15
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 15
gagggacagu auucucagun a                                              21

<210> SEQ ID NO 16
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 16
gagggacagu auucucagun a                                              21

<210> SEQ ID NO 17
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 17
acgggacagu auucucagun a                                              21

<210> SEQ ID NO 18
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)
```

```
<400> SEQUENCE: 18
acgggacagu auucucagun a                                              21

<210> SEQ ID NO 19
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 19
gagggacagu auucucagun a                                              21

<210> SEQ ID NO 20
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 20
gagggacagu auucucagug a                                              21

<210> SEQ ID NO 21
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 21
gagggacagu auucucagug a                                              21

<210> SEQ ID NO 22
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 22
gccaauaaag cuggacaaga a                                              21

<210> SEQ ID NO 23
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 23
gccaauaaag cuggacaaga a                                              21

<210> SEQ ID NO 24
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
```

```
<221> NAME/KEY: modified_base
<222> LOCATION: 10
<223> OTHER INFORMATION: n = 2'-O-methylinosine-3'-phosphate

<400> SEQUENCE: 24
gccaauaaan cuggacaaga a                                              21

<210> SEQ ID NO 25
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = inosine (hypoxanthine)

<400> SEQUENCE: 25
gccaauaaan cuggacaaga a                                              21

<210> SEQ ID NO 26
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 26
cccuaaaagg gacaguauuc u                                              21

<210> SEQ ID NO 27
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 27
cccuaaaagg gacaguauuc u                                              21

<210> SEQ ID NO 28
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 28
gcuuaaaagg gacaguauuc u                                              21

<210> SEQ ID NO 29
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 29
gcuuaaaagg gacaguauuc u                                              21

<210> SEQ ID NO 30
<211> LENGTH: 21
<212> TYPE: RNA
```

```
<213> ORGANISM: Artificial sequence
<220> FEATURE:
<223> OTHER INFORMATION: RNAi agent sense strand modified sequence

<400> SEQUENCE: 30
ggcaaaggga caguauucuc a                                              21

<210> SEQ ID NO 31
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 31
ggcaaaggga caguauucuc a                                              21

<210> SEQ ID NO 32
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 32
gggacaguau ucucagugc                                                 19

<210> SEQ ID NO 33
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 33
caauaaagcu ggacaagaa                                                 19

<210> SEQ ID NO 34
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 34
uuaaaaggga caguauucu                                                 19

<210> SEQ ID NO 35
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 35
cggguacucc uuguuguug                                                 19

<210> SEQ ID NO 36
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 36
```

```
gguacuccuu guuguugcc                                                19

<210> SEQ ID NO 37
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 37
gcugggugac cgauggcuu                                                19

<210> SEQ ID NO 38
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 38
gaccgauggc uucaguucc                                                19

<210> SEQ ID NO 39
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 39
gcuucaguuc ccugaaaga                                                19

<210> SEQ ID NO 40
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 40
ucaguucccu gaaagacua                                                19

<210> SEQ ID NO 41
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 41
gacuacugga gcaccguua                                                19

<210> SEQ ID NO 42
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 42
acuacuggag caccguuaa                                                19

<210> SEQ ID NO 43
<211> LENGTH: 19
<212> TYPE: RNA
<213> ORGANISM: Artificial sequence
```

```
<220> FEATURE:
<223> OTHER INFORMATION: APOC3 gene transcript (mRNA) target sequence

<400> SEQUENCE: 43
gcaccguuaa ggacaaguu                                                19

<210> SEQ ID NO 44
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 44
accguuaagg acaaguucu                                                19

<210> SEQ ID NO 45
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 45
ccguuaagga caaguucuc                                                19

<210> SEQ ID NO 46
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 46
ccucaauacc ccaagucca                                                19

<210> SEQ ID NO 47
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 47
aaaagggaca guauucuca                                                19

<210> SEQ ID NO 48
<211> LENGTH: 19
<212> TYPE: RNA
<213> ORGANISM: Artificial sequence
<220> FEATURE:
<223> OTHER INFORMATION: APOC3 gene transcript (mRNA) target sequence

<400> SEQUENCE: 48
agggacagua uucucagug                                                19

<210> SEQ ID NO 49
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 49
ucacugagaa uacugnccc                                                19
```

```
<210> SEQ ID NO 50
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 50
gcacugagaa uacuguccc                                                    19

<210> SEQ ID NO 51
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n =

<400> SEQUENCE: 51
ncacugagaa uacuguccc                                                    19

<210> SEQ ID NO 52
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 52
ncacugagaa uacuguccn                                                    19

<210> SEQ ID NO 53
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 53
uucuugucca gcuuuauug                                                    19

<210> SEQ ID NO 54
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 54
nucuugucca gcuuuauug                                                    19
```

```
<210> SEQ ID NO 55
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 55
nucuugucca gcuuuauun                                                    19

<210> SEQ ID NO 56
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 56
ugaauacugu cccuuuuaa                                                    19

<210> SEQ ID NO 57
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 57
agaauacugu cccuuuuaa                                                    19

<210> SEQ ID NO 58
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 58
agaauacugu cccuuuuag                                                    19

<210> SEQ ID NO 59
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 59
ngaauacugu cccuuuuaa                                                    19

<210> SEQ ID NO 60
<211> LENGTH: 19
<212> TYPE: RNA
<213> ORGANISM: Artificial sequence
<220> FEATURE:
<223> OTHER INFORMATION: RNAi agent antisense strand core 19-mer base
```

```
        sequence
<220> FEATURE:
<221> NAME/KEY: modified_base
<222> LOCATION: 1
<223> OTHER INFORMATION: n = any nucleobase

<400> SEQUENCE: 60
ngaauacugu cccuuuuag                                              19

<210> SEQ ID NO 61
<211> LENGTH: 19
<212> TYPE: RNA
<213> ORGANISM: Artificial sequence
<220> FEATURE:
<223> OTHER INFORMATION: RNAi agent antisense strand core 19-mer base
        sequence
<220> FEATURE:
<221> NAME/KEY: modified_base
<222> LOCATION: 1, 19
<223> OTHER INFORMATION: n = any nucleobase

<400> SEQUENCE: 61
ngaauacugu cccuuuuan                                              19

<210> SEQ ID NO 62
<211> LENGTH: 19
<212> TYPE: RNA
<213> ORGANISM: Artificial sequence
<220> FEATURE:
<223> OTHER INFORMATION: RNAi agent antisense strand core 19-mer base
        sequence

<400> SEQUENCE: 62
uaacaacaag gaguacccg                                              19

<210> SEQ ID NO 63
<211> LENGTH: 19
<212> TYPE: RNA
<213> ORGANISM: Artificial sequence
<220> FEATURE:
<223> OTHER INFORMATION: RNAi agent antisense strand core 19-mer base
        sequence

<400> SEQUENCE: 63
caacaacaag gaguacccg                                              19

<210> SEQ ID NO 64
<211> LENGTH: 19
<212> TYPE: RNA
<213> ORGANISM: Artificial sequence
<220> FEATURE:
<223> OTHER INFORMATION: RNAi agent antisense strand core 19-mer base
        sequence
<220> FEATURE:
<221> NAME/KEY: modified_base
<222> LOCATION: 1
<223> OTHER INFORMATION: n = any nucleobase

<400> SEQUENCE: 64
naacaacaag gaguacccg                                              19

<210> SEQ ID NO 65
<211> LENGTH: 19
<212> TYPE: RNA
<213> ORGANISM: Artificial sequence
<220> FEATURE:
<223> OTHER INFORMATION: RNAi agent antisense strand core 19-mer base
        sequence
<220> FEATURE:
```

```
<221> NAME/KEY: modified_base
<222> LOCATION: 1, 19
<223> OTHER INFORMATION: n = any nucleobase

<400> SEQUENCE: 65
naacaacaag gaguacccn                                                  19

<210> SEQ ID NO 66
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 66
ugcaacaaca aggaguacc                                                  19

<210> SEQ ID NO 67
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 67
ggcaacaaca aggaguacc                                                  19

<210> SEQ ID NO 68
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 68
ngcaacaaca aggaguacc                                                  19

<210> SEQ ID NO 69
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 69
ngcaacaaca aggaguacn                                                  19

<210> SEQ ID NO 70
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 70
```
uagccaucgg ucacccagc                                           19

<210> SEQ ID NO 71
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 71
aagccaucgg ucacccagc                                           19

<210> SEQ ID NO 72
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 72
nagccaucgg ucacccagc                                           19

<210> SEQ ID NO 73
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 73
nagccaucgg ucacccagn                                           19

<210> SEQ ID NO 74
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 74
ugaacugaag ccaucgguc                                           19

<210> SEQ ID NO 75
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 75
ggaacugaag ccaucgguc                                           19

<210> SEQ ID NO 76
<211> LENGTH: 19
<212> TYPE: RNA

```
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 76
ngaacugaag ccaucgguc                                                    19

<210> SEQ ID NO 77
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 77
ngaacugaag ccaucggun                                                    19

<210> SEQ ID NO 78
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 78
ucuuucaggg aacugaagc                                                    19

<210> SEQ ID NO 79
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 79
ncuuucaggg aacugaagc                                                    19

<210> SEQ ID NO 80
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 80
ncuuucaggg aacugaagn                                                    19

<210> SEQ ID NO 81
```

```
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 81
uagucuuuca gggaacuga                                                 19

<210> SEQ ID NO 82
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 82
nagucuuuca gggaacuga                                                 19

<210> SEQ ID NO 83
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 83
nagucuuuca gggaacugn                                                 19

<210> SEQ ID NO 84
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 84
uaacggugcu ccaguaguc                                                 19

<210> SEQ ID NO 85
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 85
naacggugcu ccaguaguc                                                 19

<210> SEQ ID NO 86
<211> LENGTH: 19
<212> TYPE: RNA
```

```
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 86
naacggugcu ccaguagun                                                    19

<210> SEQ ID NO 87
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 87
uuaacggugc uccaguagu                                                    19

<210> SEQ ID NO 88
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 88
nuaacggugc uccaguagu                                                    19

<210> SEQ ID NO 89
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 89
nuaacggugc uccaguagn                                                    19

<210> SEQ ID NO 90
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 90
uacuuguccu uaacggugc                                                    19

<210> SEQ ID NO 91
<211> LENGTH: 19
<212> TYPE: RNA
<213> ORGANISM: Artificial sequence
<220> FEATURE:
```

```
<223> OTHER INFORMATION: RNAi agent antisense strand core 19-mer base
      sequence

<400> SEQUENCE: 91
aacuuguccu uaacggugc                                                  19

<210> SEQ ID NO 92
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 92
nacuuguccu uaacggugc                                                  19

<210> SEQ ID NO 93
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 93
nacuuguccu uaacggugn                                                  19

<210> SEQ ID NO 94
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 94
ugaacuuguc cuuaacggu                                                  19

<210> SEQ ID NO 95
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 95
agaacuuguc cuuaacggu                                                  19

<210> SEQ ID NO 96
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase
```

```
<400> SEQUENCE: 96
ngaacuuguc cuuaacggu                                                19

<210> SEQ ID NO 97
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 97
ngaacuuguc cuuaacggn                                                19

<210> SEQ ID NO 98
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 98
uagaacuugu ccuuaacgg                                                19

<210> SEQ ID NO 99
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 99
gagaacuugu ccuuaacgg                                                19

<210> SEQ ID NO 100
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 100
nagaacuugu ccuuaacgg                                                19

<210> SEQ ID NO 101
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 101
```

```
nagaacuugu ccuuaacgn                                              19

<210> SEQ ID NO 102
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 102
uggacuuggg guauugagg                                              19

<210> SEQ ID NO 103
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 103
nggacuuggg guauugagg                                              19

<210> SEQ ID NO 104
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 104
nggacuuggg guauugagn                                              19

<210> SEQ ID NO 105
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 105
ugagaauacu gucccuuuu                                              19

<210> SEQ ID NO 106
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 106
ugagaauacu gucccuuug                                              19

<210> SEQ ID NO 107
<211> LENGTH: 19
```

```
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 107
ngagaauacu gucccuuuu                                                    19

<210> SEQ ID NO 108
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 108
ngagaauacu gucccuuug                                                    19

<210> SEQ ID NO 109
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 109
ngagaauacu gucccuuun                                                    19

<210> SEQ ID NO 110
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 110
uacugagaau acugucccu                                                    19

<210> SEQ ID NO 111
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 111
cacugagaau acugucccu                                                    19

<210> SEQ ID NO 112
<211> LENGTH: 19
<212> TYPE: RNA
<213> ORGANISM: Artificial sequence
```

```
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 112
nacugagaau acugucccu                                                      19

<210> SEQ ID NO 113
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 113
nacugagaau acugucccn                                                      19

<210> SEQ ID NO 114
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 114
gggacaguau ucucaguga                                                      19

<210> SEQ ID NO 115
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 18
<223> OTHER INFORMATION: n = inosine (hypoxanthine)

<400> SEQUENCE: 115
gggacaguau ucucaguna                                                      19

<210> SEQ ID NO 116
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 116
gggacaguau ucucagugc                                                      19

<210> SEQ ID NO 117
<211> LENGTH: 19
<212> TYPE: RNA
<213> ORGANISM: Artificial sequence
<220> FEATURE:
<223> OTHER INFORMATION: RNAi agent sense strand core 19-mer base
```

```
                  sequence
<220> FEATURE:
<221> NAME/KEY: modified_base
<222> LOCATION: 19
<223> OTHER INFORMATION: n = any nucleobase

<400> SEQUENCE: 117
gggacaguau ucucagugn                                                 19

<210> SEQ ID NO 118
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 118
nggacaguau ucucagugn                                                 19

<210> SEQ ID NO 119
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 119
caauaaagcu ggacaagaa                                                 19

<210> SEQ ID NO 120
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 8
<223> OTHER INFORMATION: n = inosine (hypoxanthine)

<400> SEQUENCE: 120
caauaaancu ggacaagaa                                                 19

<210> SEQ ID NO 121
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 121
caauaaagcu ggacaagan                                                 19

<210> SEQ ID NO 122
<211> LENGTH: 19
<212> TYPE: RNA
<213> ORGANISM: Artificial sequence
```

```
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 122
naauaaagcu ggacaagan                                                     19

<210> SEQ ID NO 123
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 123
uuaaaaggga caguauuca                                                     19

<210> SEQ ID NO 124
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 124
uuaaaaggga caguauucu                                                     19

<210> SEQ ID NO 125
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 125
cuaaaaggga caguauucu                                                     19

<210> SEQ ID NO 126
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 126
uuaaaaggga caguauucn                                                     19

<210> SEQ ID NO 127
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
```

```
<223> OTHER INFORMATION: n = any nucleobase

<400> SEQUENCE: 127
cuaaaaggga caguauucn                                           19

<210> SEQ ID NO 128
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 128
nuaaaaggga caguauucn                                           19

<210> SEQ ID NO 129
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 129
cggguacucc uuguuguua                                           19

<210> SEQ ID NO 130
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 130
cggguacucc uuguuguug                                           19

<210> SEQ ID NO 131
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 131
cggguacucc uuguuguun                                           19

<210> SEQ ID NO 132
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
```

```
<400> SEQUENCE: 132
nggguacucc uuguuguun                                                19

<210> SEQ ID NO 133
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 133
gguacuccuu guuguugca                                                19

<210> SEQ ID NO 134
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 134
gguacuccuu guuguugcc                                                19

<210> SEQ ID NO 135
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 135
gguacuccuu guuguugcn                                                19

<210> SEQ ID NO 136
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 136
nguacuccuu guuguugcn                                                19

<210> SEQ ID NO 137
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 137
gcugggugac cgauggcua                                                19

<210> SEQ ID NO 138
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 138
gcugggugac cgauggcuu                                                     19

<210> SEQ ID NO 139
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 139
gcugggugac cgauggcun                                                     19

<210> SEQ ID NO 140
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 140
ncugggugac cgauggcun                                                     19

<210> SEQ ID NO 141
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 141
gaccgauggc uucaguuca                                                     19

<210> SEQ ID NO 142
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 142
gaccgauggc uucaguucc                                                     19

<210> SEQ ID NO 143
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<220> FEATURE:
<221> NAME/KEY: modified_base
<222> LOCATION: 19
<223> OTHER INFORMATION: n = any nucleobase

<400> SEQUENCE: 143
gaccgauggc uucaguucn                                                   19

<210> SEQ ID NO 144
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 144
naccgauggc uucaguucn                                                   19

<210> SEQ ID NO 145
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 145
gcuucaguuc ccugaaaga                                                   19

<210> SEQ ID NO 146
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 146
gcuucaguuc ccugaaagn                                                   19

<210> SEQ ID NO 147
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 147
ncuucaguuc ccugaaagn                                                   19

<210> SEQ ID NO 148
<211> LENGTH: 19
<212> TYPE: RNA
<213> ORGANISM: Artificial sequence
<220> FEATURE:
```

```
<223> OTHER INFORMATION: RNAi agent sense strand core 19-mer base
      sequence

<400> SEQUENCE: 148
ucaguucccu gaaagacua                                                       19

<210> SEQ ID NO 149
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 149
ucaguucccu gaaagacun                                                       19

<210> SEQ ID NO 150
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 150
ncaguucccu gaaagacun                                                       19

<210> SEQ ID NO 151
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 151
gacuacugga gcaccguua                                                       19

<210> SEQ ID NO 152
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 152
gacuacugga gcaccguun                                                       19

<210> SEQ ID NO 153
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<220> FEATURE:
<221> NAME/KEY: modified_base
<222> LOCATION: 1, 19
<223> OTHER INFORMATION: n = any nucleobase

<400> SEQUENCE: 153
nacuacugga gcaccguun                                                    19

<210> SEQ ID NO 154
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 154
acuacuggag caccguuaa                                                    19

<210> SEQ ID NO 155
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 155
acuacuggag caccguuan                                                    19

<210> SEQ ID NO 156
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 156
ncuacuggag caccguuan                                                    19

<210> SEQ ID NO 157
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 157
gcaccguuaa ggacaagua                                                    19

<210> SEQ ID NO 158
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 158
```

```
gcaccguuaa ggacaaguu                                                        19

<210> SEQ ID NO 159
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 159
gcaccguuaa ggacaagun                                                        19

<210> SEQ ID NO 160
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 160
ncaccguuaa ggacaagun                                                        19

<210> SEQ ID NO 161
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 161
accguuaagg acaaguuca                                                        19

<210> SEQ ID NO 162
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 162
accguuaagg acaaguucu                                                        19

<210> SEQ ID NO 163
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 163
accguuaagg acaaguucn                                                        19
```

<210> SEQ ID NO 164
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 164
nccguuaagg acaaguucn                                                19

<210> SEQ ID NO 165
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 165
ccguuaagga caaguucua                                                19

<210> SEQ ID NO 166
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 166
ccguuaagga caaguucuc                                                19

<210> SEQ ID NO 167
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 167
ccguuaagga caaguucun                                                19

<210> SEQ ID NO 168
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 168
ncguuaagga caaguucun                                                19

```
<210> SEQ ID NO 169
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 169
ccucaauacc ccaagucca                                               19

<210> SEQ ID NO 170
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 170
ccucaauacc ccaguccn                                                19

<210> SEQ ID NO 171
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 171
ncucaauacc ccaguccn                                                19

<210> SEQ ID NO 172
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 172
aaaagggaca guauucuca                                               19

<210> SEQ ID NO 173
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 173
caaagggaca guauucuca                                               19

<210> SEQ ID NO 174
<211> LENGTH: 19
<212> TYPE: RNA
<213> ORGANISM: Artificial sequence
<220> FEATURE:
<223> OTHER INFORMATION: RNAi agent sense strand core 19-mer base
```

```
                        sequence
<220> FEATURE:
<221> NAME/KEY: modified_base
<222> LOCATION: 19
<223> OTHER INFORMATION: n = any nucleobase

<400> SEQUENCE: 174
aaaagggaca guauucucn                                                      19

<210> SEQ ID NO 175
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 175
caaagggaca guauucucn                                                      19

<210> SEQ ID NO 176
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 176
naaagggaca guauucucn                                                      19

<210> SEQ ID NO 177
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 177
agggacagua uucucagua                                                      19

<210> SEQ ID NO 178
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 178
agggacagua uucucagug                                                      19

<210> SEQ ID NO 179
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
```

```
<221> NAME/KEY: modified_base
<222> LOCATION: 19
<223> OTHER INFORMATION: n = any nucleobase

<400> SEQUENCE: 179
agggacagua uucucagun                                                        19

<210> SEQ ID NO 180
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 180
ngggacagua uucucagun                                                        19

<210> SEQ ID NO 181
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 181
uaacaacaag gaguacccgu u                                                     21

<210> SEQ ID NO 182
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 182
uaacaacaag gaguacccgu u                                                     21

<210> SEQ ID NO 183
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 183
uaacaacaag gaguacccgg u                                                     21

<210> SEQ ID NO 184
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 184
uaacaacaag gaguacccgg g                                                     21

<210> SEQ ID NO 185
<211> LENGTH: 21
<212> TYPE: RNA
<213> ORGANISM: Artificial sequence
<220> FEATURE:
```

<223> OTHER INFORMATION: RNAi agent antisense strand modified sequence

<400> SEQUENCE: 185
uaacaacaag gaguacccgg g                                              21

<210> SEQ ID NO 186
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 186
ugcaacaaca aggaguaccu u                                              21

<210> SEQ ID NO 187
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 187
ugcaacaaca aggaguaccu u                                              21

<210> SEQ ID NO 188
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 188
ugcaacaaca aggaguaccc u                                              21

<210> SEQ ID NO 189
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 189
ugcaacaaca aggaguaccc g                                              21

<210> SEQ ID NO 190
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 190
ugcaacaaca aggaguaccc g                                              21

<210> SEQ ID NO 191
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 191
uagccaucgg ucacccagcu u                                              21

```
<210> SEQ ID NO 192
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 192
uagccaucgg ucacccagcu u                                              21

<210> SEQ ID NO 193
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 193
uagccaucgg ucacccagcc u                                              21

<210> SEQ ID NO 194
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 194
uagccaucgg ucacccagcc c                                              21

<210> SEQ ID NO 195
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 195
uagccaucgg ucacccagcc c                                              21

<210> SEQ ID NO 196
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 196
ugaacugaag ccaucggucu u                                              21

<210> SEQ ID NO 197
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 197
ugaacugaag ccaucggucu u                                              21

<210> SEQ ID NO 198
<211> LENGTH: 21
<212> TYPE: RNA
<213> ORGANISM: Artificial sequence
<220> FEATURE:
<223> OTHER INFORMATION: RNAi agent antisense strand modified sequence
```

```
<400> SEQUENCE: 198
ugaacugaag ccaucgguca u                                              21

<210> SEQ ID NO 199
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 199
ugaacugaag ccaucgguca c                                              21

<210> SEQ ID NO 200
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 200
ugaacugaag ccaucgguca c                                              21

<210> SEQ ID NO 201
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 201
ucuuucaggg aacugaagcu u                                              21

<210> SEQ ID NO 202
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 202
ucuuucaggg aacugaagcu u                                              21

<210> SEQ ID NO 203
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 203
ucuuucaggg aacugaagcc u                                              21

<210> SEQ ID NO 204
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 204
ucuuucaggg aacugaagcc a                                              21

<210> SEQ ID NO 205
<211> LENGTH: 21
```

```
<212> TYPE: RNA
<213> ORGANISM: Artificial sequence
<220> FEATURE:
<223> OTHER INFORMATION: RNAi agent antisense strand modified sequence

<400> SEQUENCE: 205
ucuuucaggg aacugaagcc a                                              21

<210> SEQ ID NO 206
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 206
uaacggugcu ccaguagucu u                                              21

<210> SEQ ID NO 207
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 207
uaacggugcu ccaguagucu u                                              21

<210> SEQ ID NO 208
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 208
uaacggugcu ccaguagucu u                                              21

<210> SEQ ID NO 209
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 209
uaacggugcu ccaguagucu u                                              21

<210> SEQ ID NO 210
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 210
uaacggugcu ccaguagucu u                                              21

<210> SEQ ID NO 211
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 211
```
uuaacggugc uccaguaguu u                                                   21

<210> SEQ ID NO 212
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 212
uuaacggugc uccaguaguu u                                                   21

<210> SEQ ID NO 213
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 213
uuaacggugc uccaguaguc u                                                   21

<210> SEQ ID NO 214
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 214
uuaacggugc uccaguaguc u                                                   21

<210> SEQ ID NO 215
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 215
uuaacggugc uccaguaguc u                                                   21

<210> SEQ ID NO 216
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 216
uacuuguccu uaacggugcu u                                                   21

<210> SEQ ID NO 217
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 217
uacuuguccu uaacggugcu u                                                   21

<210> SEQ ID NO 218
<211> LENGTH: 21
<212> TYPE: RNA
<213> ORGANISM: Artificial sequence

```
<220> FEATURE:
<223> OTHER INFORMATION: RNAi agent antisense strand modified sequence

<400> SEQUENCE: 218
uacuuguccu uaacggugcu u                                              21

<210> SEQ ID NO 219
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 219
uacuuguccu uaacggugcu c                                              21

<210> SEQ ID NO 220
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 220
uacuuguccu uaacggugcu c                                              21

<210> SEQ ID NO 221
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 221
ugaacuuguc cuuaacgguu u                                              21

<210> SEQ ID NO 222
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 222
ugaacuuguc cuuaacgguu u                                              21

<210> SEQ ID NO 223
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 223
ugaacuuguc cuuaacggug u                                              21

<210> SEQ ID NO 224
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 224
ugaacuuguc cuuaacggug c                                              21
```

```
<210> SEQ ID NO 225
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 225
ugaacuuguc cuuaacggug c                                              21

<210> SEQ ID NO 226
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 226
uagaacuugu ccuuaacggu u                                              21

<210> SEQ ID NO 227
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 227
uagaacuugu ccuuaacggu u                                              21

<210> SEQ ID NO 228
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 228
uagaacuugu ccuuaacggu u                                              21

<210> SEQ ID NO 229
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 229
uagaacuugu ccuuaacggu g                                              21

<210> SEQ ID NO 230
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 230
uagaacuugu ccuuaacggu g                                              21

<210> SEQ ID NO 231
<211> LENGTH: 21
<212> TYPE: RNA
<213> ORGANISM: Artificial sequence
<220> FEATURE:
<223> OTHER INFORMATION: RNAi agent antisense strand modified sequence
```

<400> SEQUENCE: 231
uggacuuggg guauugaggu u                                    21

<210> SEQ ID NO 232
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 232
uggacuuggg guauugaggu u                                    21

<210> SEQ ID NO 233
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 233
uggacuuggg guauugaggu u                                    21

<210> SEQ ID NO 234
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 234
uggacuuggg guauugaggu c                                    21

<210> SEQ ID NO 235
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 235
uggacuuggg guauugaggu c                                    21

<210> SEQ ID NO 236
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 236
ugagaauacu gucccuuuuu u                                    21

<210> SEQ ID NO 237
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 237
ugagaauacu gucccuuuuu u                                    21

<210> SEQ ID NO 238

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 238
ugagaauacu gucccuuuua u                                              21

<210> SEQ ID NO 239
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 239
ugagaauacu gucccuuuua a                                              21

<210> SEQ ID NO 240
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 240
ugagaauacu gucccuuuua a                                              21

<210> SEQ ID NO 241
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 241
uacugagaau acugucccuu u                                              21

<210> SEQ ID NO 242
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 242
uacugagaau acugucccuu u                                              21

<210> SEQ ID NO 243
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 243
uacugagaau acugucccuu u                                              21

<210> SEQ ID NO 244
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 244
```
uacugagaau acugucccuu u                                             21

<210> SEQ ID NO 245
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 245
uacugagaau acugucccuu u                                             21

<210> SEQ ID NO 246
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 246
cggguacucc uuguuguuau u                                             21

<210> SEQ ID NO 247
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 247
cggguacucc uuguuguuau u                                             21

<210> SEQ ID NO 248
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 248
ccggguacuc cuuguuguua                                               20

<210> SEQ ID NO 249
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 249
cccggguacu ccuuguuguu a                                             21

<210> SEQ ID NO 250
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 250
cccggguacu ccuuguuguu a                                             21

<210> SEQ ID NO 251
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 251
gguacuccuu guuguugcau u                                    21

<210> SEQ ID NO 252
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 252
gguacuccuu guuguugcau u                                    21

<210> SEQ ID NO 253
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 253
ggguacuccu uguuguugca                                      20

<210> SEQ ID NO 254
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 254
cggguacucc uuguuguugc a                                    21

<210> SEQ ID NO 255
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 255
cggguacucc uuguuguugc a                                    21

<210> SEQ ID NO 256
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 256
gcugggugac cgauggcuau u                                    21

<210> SEQ ID NO 257
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 257
gcugggugac cgauggcuau u                                    21

<210> SEQ ID NO 258
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 258
ggcuggguga ccgauggcua                                               20

<210> SEQ ID NO 259
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 259
gggcugggug accgauggcu a                                             21

<210> SEQ ID NO 260
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 260
gggcugggug accgauggcu a                                             21

<210> SEQ ID NO 261
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 261
gaccgauggc uucaguucau u                                             21

<210> SEQ ID NO 262
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 262
gaccgauggc uucaguucau u                                             21

<210> SEQ ID NO 263
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 263
ugaccgaugg cuucaguuca                                               20

<210> SEQ ID NO 264
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 264
gugaccgaug gcuucaguuc a                                         21

<210> SEQ ID NO 265
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 265
gugaccgaug gcuucaguuc a                                         21

<210> SEQ ID NO 266
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 266
gcuucaguuc ccugaaagau u                                         21

<210> SEQ ID NO 267
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 267
gcuucaguuc ccugaaagau u                                         21

<210> SEQ ID NO 268
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 268
ggcuucaguu cccugaaaga                                           20

<210> SEQ ID NO 269
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 269
uggcuucagu ucccugaaag a                                         21

<210> SEQ ID NO 270
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 270
uggcuucagu ucccugaaag a                                         21

```
<210> SEQ ID NO 271
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 271
gacuacugga gcaccguuau u                                              21

<210> SEQ ID NO 272
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 272
gacuacugga gcaccguuau u                                              21

<210> SEQ ID NO 273
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 273
agacuacugg agcaccguua                                                20

<210> SEQ ID NO 274
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 274
aagacuacug gagcaccguu a                                              21

<210> SEQ ID NO 275
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 275
aagacuacug gagcaccguu a                                              21

<210> SEQ ID NO 276
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 276
acuacuggag caccguuaau u                                              21

<210> SEQ ID NO 277
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 277
acuacuggag caccguuaau u                                              21

<210> SEQ ID NO 278
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 278
gacuacugga gcaccguuaa                                                20

<210> SEQ ID NO 279
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 279
agacuacugg agcaccguua a                                              21

<210> SEQ ID NO 280
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 280
agacuacugg agcaccguua a                                              21

<210> SEQ ID NO 281
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 281
gcaccguuaa ggacaaguau u                                              21

<210> SEQ ID NO 282
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 282
gcaccguuaa ggacaaguau u                                              21

<210> SEQ ID NO 283
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 283
agcaccguua aggacaagua                                                20

<210> SEQ ID NO 284
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 284
gagcaccguu aaggacaagu a                                              21

<210> SEQ ID NO 285
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 285
gagcaccguu aaggacaagu a                                              21

<210> SEQ ID NO 286
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 286
accguuaagg acaaguucau u                                              21

<210> SEQ ID NO 287
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 287
accguuaagg acaaguucau u                                              21

<210> SEQ ID NO 288
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 288
caccguuaag gacaaguuca                                                20

<210> SEQ ID NO 289
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 289
gcaccguuaa ggacaaguuc a                                              21

<210> SEQ ID NO 290
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 290
```

```
gcaccguuaa ggacaaguuc a                                             21
```

<210> SEQ ID NO 291
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 291

```
ccguuaagga caaguucuau u                                             21
```

<210> SEQ ID NO 292
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 292

```
ccguuaagga caaguucuau u                                             21
```

<210> SEQ ID NO 293
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 293

```
accguuaagg acaaguucua                                               20
```

<210> SEQ ID NO 294
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 294

```
caccguuaag gacaaguucu a                                             21
```

<210> SEQ ID NO 295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 295

```
caccguuaag gacaaguucu a                                             21
```

<210> SEQ ID NO 296
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 296

```
ccucaauacc ccaaguccau u                                             21
```

<210> SEQ ID NO 297
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 297
ccucaauacc ccaaguccau u                                              21

<210> SEQ ID NO 298
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 298
accucaauac cccaagucca                                                20

<210> SEQ ID NO 299
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 299
gaccucaaua ccccaagucc a                                              21

<210> SEQ ID NO 300
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 300
gaccucaaua ccccaagucc a                                              21

<210> SEQ ID NO 301
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 301
aaaagggaca guauucucau u                                              21

<210> SEQ ID NO 302
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 302
aaaagggaca guauucucau u                                              21

<210> SEQ ID NO 303
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 303
uaaaagggac aguauucuca                                                20
```

<210> SEQ ID NO 304
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 304
uuaaaaggga caguauucuc a                                              21

<210> SEQ ID NO 305
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 305
uuaaaaggga caguauucuc a                                              21

<210> SEQ ID NO 306
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 306
agggacagua uucucaguau u                                              21

<210> SEQ ID NO 307
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 307
agggacagua uucucaguau u                                              21

<210> SEQ ID NO 308
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 308
aagggacagu auucucagua                                                20

<210> SEQ ID NO 309
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 309
aaagggacag uauucucagu a                                              21

<210> SEQ ID NO 310
<211> LENGTH: 21
<212> TYPE: RNA
<213> ORGANISM: Artificial sequence
<220> FEATURE:
<223> OTHER INFORMATION: RNAi agent sense strand modified sequence

```
<400> SEQUENCE: 310
aaagggacag uauucucagu a                                              21

<210> SEQ ID NO 311
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 311
uacuuguccu uaacggugcu u                                              21

<210> SEQ ID NO 312
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 312
uacuuguccu uaacggugcu c                                              21

<210> SEQ ID NO 313
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 313
aacuuguccu uaacggugcu u                                              21

<210> SEQ ID NO 314
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 314
uggacuuggg guauugaggu u                                              21

<210> SEQ ID NO 315
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 315
uggacuuggg guauugaggu c                                              21

<210> SEQ ID NO 316
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 316
ucuuucaggg aacugaagcu u                                              21

<210> SEQ ID NO 317
```

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 317
ucuuucaggg aacugaagcc u                                              21

<210> SEQ ID NO 318
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 318
ugaacugaag ccaucggucu u                                              21

<210> SEQ ID NO 319
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 319
ugaacugaag ccaucgguca c                                              21

<210> SEQ ID NO 320
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 320
ugagaauacu gucccuuuug g                                              21

<210> SEQ ID NO 321
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 321
ugagaauacu gucccuuuug cg                                             22

<210> SEQ ID NO 322
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 322
uaacggugcu ccaguagucu u                                              21

<210> SEQ ID NO 323
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 323
```
uaacggugcu ccaguagucg u                                              21

<210> SEQ ID NO 324
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 324
uacugagaau acugucccuu u                                              21

<210> SEQ ID NO 325
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 325
uacugagaau acugucccug u                                              21

<210> SEQ ID NO 326
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 326
uuaacggugc uccaguaguc u 21

<210> SEQ ID NO 327
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 327
uuaacggugc uccaguaggc u 21

<210> SEQ ID NO 328
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 328
uagccaucgg ucacccagcu u 21

<210> SEQ ID NO 329
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 329
aagccaucgg ucacccagcu u 21

<210> SEQ ID NO 330
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 330
uagaacuugu ccuuaacggu u                                              21

<210> SEQ ID NO 331
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 331
uagaacuugu ccuuaacggu g                                              21

<210> SEQ ID NO 332
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 332
ugaacuuguc cuuaacgguu u                                              21

<210> SEQ ID NO 333
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 333
agaacuuguc cuuaacgguu u                                              21

<210> SEQ ID NO 334
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 334
ugaacuuguc cuuaacggug c                                              21

<210> SEQ ID NO 335
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 335
ugcaacaaca aggaguaccu u                                              21

<210> SEQ ID NO 336
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 336
ugcaacaaca aggaguaccc g                                              21
```

```
<210> SEQ ID NO 337
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 337
uaacaacaag gaguacccgu u                                              21

<210> SEQ ID NO 338
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 338
ugcacugaga auacuguccc uu                                             22

<210> SEQ ID NO 339
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 339
agcacugaga auacuguccc uu                                             22

<210> SEQ ID NO 340
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 340
cuacuugucc uuaacggugc uu                                             22

<210> SEQ ID NO 341
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 341
aacuuguccu uaacggugcu c                                              21

<210> SEQ ID NO 342
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 342
uacuuguccu uaacggugc                                                 19

<210> SEQ ID NO 343
<211> LENGTH: 22
<212> TYPE: RNA
<213> ORGANISM: Artificial sequence
<220> FEATURE:
```

```
<223> OTHER INFORMATION: RNAi agent antisense strand modified sequence

<400> SEQUENCE: 343
uacuuguccu u

```
<210> SEQ ID NO 350
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 350
ugagaauacu gucccuuuug g                                              21

<210> SEQ ID NO 351
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 351
agagaauacu gucccuuuug g                                              21

<210> SEQ ID NO 352
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 352
ugcaacaaca aggaguacc                                                 19

<210> SEQ ID NO 353
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 353
ugcaacaaca aggaguaccc u                                              21

<210> SEQ ID NO 354
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 354
ugcaacaaca aggaguaccu u                                              21

<210> SEQ ID NO 355
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 355
ugcaacaaca aggaguaccu u                                              21

<210> SEQ ID NO 356
<211> LENGTH: 21
<212> TYPE: RNA
<213> ORGANISM: Artificial sequence
<220> FEATURE:
<223> OTHER INFORMATION: RNAi agent antisense strand modified sequence
```

```
<400> SEQUENCE: 356
ugcaacaaca aggaguaccu u                                              21

<210> SEQ ID NO 357
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 357
agcaacaaca aggaguaccu u                                              21

<210> SEQ ID NO 358
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 358
ucugaagcca ucggucaccc a                                              21

<210> SEQ ID NO 359
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 359
acugaagcca ucggucaccc a                                              21

<210> SEQ ID NO 360
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 360
uggaacugaa gccaucgguc a                                              21

<210> SEQ ID NO 361
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 361
uggaacugaa gccaucgguc c                                              21

<210> SEQ ID NO 362
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 362
uucuuucagg gaacugaagc c                                              21

<210> SEQ ID NO 363
<211> LENGTH: 21
```

```
<212> TYPE: RNA
<213> ORGANISM: Artificial sequence
<220> FEATURE:
<223> OTHER INFORMATION: RNAi agent antisense strand modified sequence

<400> SEQUENCE: 363
uuuaacggug cuccaguagu c                                              21

<210> SEQ ID NO 364
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 364
uccuuaacgg ugcuccagua g                                              21

<210> SEQ ID NO 365
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 365
uuccuuaacg gugcuccagu a                                              21

<210> SEQ ID NO 366
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 366
uuccuuaacg gugcuccagu c                                              21

<210> SEQ ID NO 367
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 367
uacuuguccu uaacggugcu c                                              21

<210> SEQ ID NO 368
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 368
aacuuguccu uaacggugcu c                                              21

<210> SEQ ID NO 369
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 369
```
uugaggucuc aggcagccac u                                          21

<210> SEQ ID NO 370
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 370
uuauugaggu cucaggcagc c                                          21

<210> SEQ ID NO 371
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 371
uguauugagg ucucaggcag c                                          21

<210> SEQ ID NO 372
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 372
ucacugagaa uacugucccu u                                          21

<210> SEQ ID NO 373
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 373
ucacugagaa uacugucccu u                                          21

<210> SEQ ID NO 374
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 374
ucuuuuaagc aaccuacagg g                                          21

<210> SEQ ID NO 375
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 375
ugagaauacu gucccuuuuc c                                          21

<210> SEQ ID NO 376
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 376
uuauugaggu cucaggcagc c        21

<210> SEQ ID NO 377
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 377
ugagaauacu gucccuuuuc c        21

<210> SEQ ID NO 378
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 378
ugagaauacu gucccuuuuc u        21

<210> SEQ ID NO 379
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 379
uucuugucca gcuuuauugg g        21

<210> SEQ ID NO 380
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 380
uagucuuuca gggaacugaa g        21

<210> SEQ ID NO 381
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 381
uagucuuuca gggaacugaa c        21

<210> SEQ ID NO 382
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 382
ucacugagaa uacugucccu u        21

```
<210> SEQ ID NO 383
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 383
ucacugagaa uacuguccgu u                                                 21

<210> SEQ ID NO 384
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 384
uagucuuuca gggaacugac g                                                 21

<210> SEQ ID NO 385
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 385
uagucuuuca gggaacugag g                                                 21

<210> SEQ ID NO 386
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 386
uagucuuuca gggaacugac c                                                 21

<210> SEQ ID NO 387
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 387
uagucuuuca gggaacugag c                                                 21

<210> SEQ ID NO 388
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 388
agaauacugu cccuuuuagg c                                                 21

<210> SEQ ID NO 389
<211> LENGTH: 21
<212> TYPE: RNA
<213> ORGANISM: Artificial sequence
<220> FEATURE:
<223> OTHER INFORMATION: RNAi agent antisense strand modified sequence
```

-continued

<400> SEQUENCE: 389
agaauacugu cccuuuuaag g                                              21

<210> SEQ ID NO 390
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 390
ugcaacaaca aggaguaccc u                                              21

<210> SEQ ID NO 391
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 391
uagucuuuca gggaacugaa g                                              21

<210> SEQ ID NO 392
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 392
agaauacugu cccuuuuaag c                                              21

<210> SEQ ID NO 393
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 393
ugagaauacu gucccuuugc c                                              21

<210> SEQ ID NO 394
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 394
ucacugagaa uacugucccu c                                              21

<210> SEQ ID NO 395
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 395
uucuugucca gcuuuauugg c                                              21

<210> SEQ ID NO 396

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 396
agaauacugu cccuuuuagg u                                              21

<210> SEQ ID NO 397
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 397
agaauacugu cccuuuuacg c                                              21

<210> SEQ ID NO 398
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 398
agaauacugu cccuuuuaga c                                              21

<210> SEQ ID NO 399
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 399
agaauacugu cccuuuuagg c                                              21

<210> SEQ ID NO 400
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 400
uucuugucca gcuuuauugg c                                              21

<210> SEQ ID NO 401
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 401
ucacugagaa uacugucccu g                                              21

<210> SEQ ID NO 402
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 402
```
ucacugagaa uacugucccc u                                              21

<210> SEQ ID NO 403
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 403
ucacugagaa uacugucccu c                                              21

<210> SEQ ID NO 404
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 404
ucacugagaa uacugucccu c                                              21

<210> SEQ ID NO 405
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 405
ucacugagaa uacugucccu c                                              21

<210> SEQ ID NO 406
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 406
ucacugagaa uacugucccu c                                              21

<210> SEQ ID NO 407
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 407
agugcauccu uggcggucuu u                                              21

<210> SEQ ID NO 408
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 408
agugcauccu uggcggucuu u                                              21

<210> SEQ ID NO 409
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 409
aguagucuuu cagggaacug a                                              21

<210> SEQ ID NO 410
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 410
aguagucuuu cagggaacug a                                              21

<210> SEQ ID NO 411
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 411
uguagucuuu cagggaacug a                                              21

<210> SEQ ID NO 412
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 412
ucuuaacggu gcuccaguag u                                              21

<210> SEQ ID NO 413
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 413
uccuuuuaag caaccuacag g                                              21

<210> SEQ ID NO 414
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 414
uccuuuuaag caaccuacag c                                              21

<210> SEQ ID NO 415
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 415
uagucuuuca gggaacugac c                                              21
```

```
<210> SEQ ID NO 416
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 416
gcaccguuaa ggacaaguau u                                                   21

<210> SEQ ID NO 417
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 417
gagcaccguu aaggacaagu a                                                   21

<210> SEQ ID NO 418
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 418
gcaccguuaa ggacaagua                                                      19

<210> SEQ ID NO 419
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 419
gcaccguuaa ggacaaguu                                                      19

<210> SEQ ID NO 420
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 420
ccucaauacc ccaagucca                                                      19

<210> SEQ ID NO 421
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 421
gaccucaaua ccccaagucc a                                                   21

<210> SEQ ID NO 422
<211> LENGTH: 19
<212> TYPE: RNA
<213> ORGANISM: Artificial sequence
<220> FEATURE:
```

<223> OTHER INFORMATION: RNAi agent sense strand modified sequence

<400> SEQUENCE: 422
gcuucaguuc ccugaaaga                                                 19

<210> SEQ ID NO 423
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 423
ggcuucaguu cccugaaaga                                                20

<210> SEQ ID NO 424
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 424
gaccgauggc uucaguuca                                                 19

<210> SEQ ID NO 425
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 425
gugaccgaug gcuucaguuc a                                              21

<210> SEQ ID NO 426
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 426
ccaaaaggga caguauucuc a                                              21

<210> SEQ ID NO 427
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 427
cgcaaaaggg acaguauucu ca                                             22

<210> SEQ ID NO 428
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 428
gacuacugga gcaccguua                                                 19

```
<210> SEQ ID NO 429
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 429
gacuacugga gcacuguua                                                      19

<210> SEQ ID NO 430
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 430
cgacuacugg agcaccguua                                                     20

<210> SEQ ID NO 431
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 431
gacuacugga gcaucguua                                                      19

<210> SEQ ID NO 432
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 432
agggacagua uucucagua                                                      19

<210> SEQ ID NO 433
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 433
cagggacagu auucucagua                                                     20

<210> SEQ ID NO 434
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 434
gacuacugga gcaccguuaa                                                     20

<210> SEQ ID NO 435
<211> LENGTH: 20
<212> TYPE: RNA
<213> ORGANISM: Artificial sequence
<220> FEATURE:
<223> OTHER INFORMATION: RNAi agent sense strand modified sequence
```

```
<400> SEQUENCE: 435
gccuacugga gcaccguuaa                                               20

<210> SEQ ID NO 436
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 436
gccuacugga gcacuguuaa                                               20

<210> SEQ ID NO 437
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 437
gcugggugac cgauggcua                                                19

<210> SEQ ID NO 438
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 438
gcugggugac cgauggcuu                                                19

<210> SEQ ID NO 439
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 439
gcugggugac cgaugacua                                                19

<210> SEQ ID NO 440
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 440
ccguuaagga caaguucua                                                19

<210> SEQ ID NO 441
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 441
caccguuaag gacaaguucu a                                             21

<210> SEQ ID NO 442
<211> LENGTH: 19
```

```
<212> TYPE: RNA
<213> ORGANISM: Artificial sequence
<220> FEATURE:
<223> OTHER INFORMATION: RNAi agent sense strand modified sequence

<400> SEQUENCE: 442
accguuaagg acaaguuca                                                  19

<210> SEQ ID NO 443
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 443
accguuaagg acaaguucu                                                  19

<210> SEQ ID NO 444
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 444
gcaccguuaa ggacaaguuc a                                               21

<210> SEQ ID NO 445
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 445
gguacuccuu guuguugca                                                  19

<210> SEQ ID NO 446
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 446
cggguacucc uuguuguugc a                                               21

<210> SEQ ID NO 447
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 447
cggguacucc uuguuguua                                                  19

<210> SEQ ID NO 448
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 448
```

|  |  |
|---|---|
| gggacaguau ucucagugca | 20 |

<210> SEQ ID NO 449
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 449

|  |  |
|---|---|
| gggacaguau ucucagugcu | 20 |

<210> SEQ ID NO 450
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 450

|  |  |
|---|---|
| gcaccguuaa ggacaaguuu u | 21 |

<210> SEQ ID NO 451
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 451

|  |  |
|---|---|
| gagcaccguu aaggacaagu a | 21 |

<210> SEQ ID NO 452
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 452

|  |  |
|---|---|
| ggagcaccgu uaaggacaag ua | 22 |

<210> SEQ ID NO 453
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 453

|  |  |
|---|---|
| gagcaccguu aaggacaagu u | 21 |

<210> SEQ ID NO 454
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 454

|  |  |
|---|---|
| ggagcaccgu uaaggacaag uu | 22 |

<210> SEQ ID NO 455
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 455
aaaagggaca guauucucau u                                              21

<210> SEQ ID NO 456
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 456
caaaagggac aguauucuca                                                20

<210> SEQ ID NO 457
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 457
ccaaaaggga caguauucuc a                                              21

<210> SEQ ID NO 458
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 458
ccaaaaggga caguauucuc u                                              21

<210> SEQ ID NO 459
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 459
gguacuccuu guuguugcau u                                              21

<210> SEQ ID NO 460
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 460
ggguacuccu uguuguugca                                                20

<210> SEQ ID NO 461
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 461
gguacuccuu guuguugca                                                 19
```

```
<210> SEQ ID NO 462
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 462
gguacuccuu guuguugcu                                                   19

<210> SEQ ID NO 463
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 463
ugggugaccg auggcuucag a                                                21

<210> SEQ ID NO 464
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 464
ugggugaccg auggcuucag u                                                21

<210> SEQ ID NO 465
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 465
ugaccgaugg cuucaguucc a                                                21

<210> SEQ ID NO 466
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 466
ggaccgaugg cuucaguucc a                                                21

<210> SEQ ID NO 467
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 467
ggcuucaguu cccugaaaga a                                                21

<210> SEQ ID NO 468
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 468
gacuacugga gcaccguuaa a                                              21

<210> SEQ ID NO 469
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 469
cuacuggagc accguuaagg a                                              21

<210> SEQ ID NO 470
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 470
uacuggagca ccguuaagga a                                              21

<210> SEQ ID NO 471
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 471
gacuggagca ccguuaagga a                                              21

<210> SEQ ID NO 472
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 472
gagcaccguu aaggacaagu a                                              21

<210> SEQ ID NO 473
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 473
gagcaccguu aaggacaagu u                                              21

<210> SEQ ID NO 474
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 474
aguggcugcc ugagaccuca a                                              21

<210> SEQ ID NO 475
```

```
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 475
ggcugccuga gaccucaaua a                                              21

<210> SEQ ID NO 476
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 476
gcugccugag accucaauac a                                              21

<210> SEQ ID NO 477
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 477
aagggacagu auucucagug a                                              21

<210> SEQ ID NO 478
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 478
acgggacagu auucucagug a                                              21

<210> SEQ ID NO 479
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 479
cccuguaggu ugcuuaaaag a                                              21

<210> SEQ ID NO 480
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 480
ggaaaaggga caguauucuc a                                              21

<210> SEQ ID NO 481
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 481
```

```
ggaaaaggga caguauucuc a                                              21

<210> SEQ ID NO 482
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 482
gagggacagu auucucagug a                                              21

<210> SEQ ID NO 483
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 483
ggcaaaggga caguauucuc a                                              21

<210> SEQ ID NO 484
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 484
ggcaaaggga caguauucuc a                                              21

<210> SEQ ID NO 485
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 485
ugaccgaugg cuucanuucc a                                              21

<210> SEQ ID NO 486
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 486
ugaccgaugg cuucaguucc a                                              21

<210> SEQ ID NO 487
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate
```

```
<400> SEQUENCE: 487
ugaccgaugg cuucanuucc a                                              21

<210> SEQ ID NO 488
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 488
gagggacagu auucucagug a                                              21

<210> SEQ ID NO 489
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 489
ggcugccuga gaccucaaua a                                              21

<210> SEQ ID NO 490
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 490
ggnaaaggga caguauucuc a                                              21

<210> SEQ ID NO 491
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1
<223> OTHER INFORMATION: n = 2'-O-methyl-2-aminoadenosine-3'-phosphate

<400> SEQUENCE: 491
ngaaaaggga caguauucuc a                                              21

<210> SEQ ID NO 492
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1, 2
<223> OTHER INFORMATION: n = 2'-O-methyl-2-aminoadenosine-3'-phosphate

<400> SEQUENCE: 492
nnaaaaggga caguauucuc a                                              21

<210> SEQ ID NO 493
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 493 cccauaaag cuggacaaga a                                              21

<210> SEQ ID NO 494
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 494 gccauaaag cuggacaaga a                                              21

<210> SEQ ID NO 495
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 495
cuucaguucc cugaaagacu a                                             21

<210> SEQ ID NO 496
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 496
guucaguucc cugaaagacu a                                             21

<210> SEQ ID NO 497
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 497
gcuuaaaagg gacaguauuc u                                             21

<210> SEQ ID NO 498
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 498
gggacaguau ucucagugau u                                             21

<210> SEQ ID NO 499
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1
```

<223> OTHER INFORMATION: n = 2'-O-methyl-2-aminoadenosine-3'-phosphate

<400> SEQUENCE: 499 naggacagu auucucagug a                       21

<210> SEQ ID NO 500
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 500
gagggacagu auucucanug a                      21

<210> SEQ ID NO 501
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 501
gagggacagu auucucagun a                      21

<210> SEQ ID NO 502
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 502
acgggacagu auucucagug a                      21

<210> SEQ ID NO 503
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 503
gggacaguau ucucagugau u                      21

<210> SEQ ID NO 504
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 504
cggacaguau ucucagugau u                      21

<210> SEQ ID NO 505
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 505
ggcaaaggga caguauucuc a                                              21

<210> SEQ ID NO 506
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 8
<223> OTHER INFORMATION: n = 2'-O-methylinosine-3'-phosphate

<400> SEQUENCE: 506
ggcaaagnga caguauucuc a                                              21

<210> SEQ ID NO 507
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 7
<223> OTHER INFORMATION: n = 2'-O-methylinosine-3'-phosphate

<400> SEQUENCE: 507
ggcaaangga caguauucuc a                                              21

<210> SEQ ID NO 508
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 508
aggguacucc uuguuguugc a                                              21

<210> SEQ ID NO 509
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 509
cuucaguucu cugaaagacu a                                              21

<210> SEQ ID NO 510
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 510
cuucaguuuc cugaaagacu a                                              21

<210> SEQ ID NO 511
<211> LENGTH: 21
<212> TYPE: RNA
```

```
<213> ORGANISM: Artificial sequence
<220> FEATURE:
<223> OTHER INFORMATION: RNAi agent sense strand modified sequence

<400> SEQUENCE: 511
cgucaguucc cugaaagacu a                                              21

<210> SEQ ID NO 512
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 512
ccucaguucc cugaaagacu a                                              21

<210> SEQ ID NO 513
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 513
cgucaguucu cugaaagacu a                                              21

<210> SEQ ID NO 514
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 514
ggucaguucc cugaaagacu a                                              21

<210> SEQ ID NO 515
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 515
gcucaguucc cugaaagacu a                                              21

<210> SEQ ID NO 516
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 516
gccuaaaagg gacaguauuc u                                              21

<210> SEQ ID NO 517
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 517
ccuuaaaagg gacaguauuc u                                              21
```

<210> SEQ ID NO 518
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-O-methylinosine-3'-phosphate

<400> SEQUENCE: 518
gcuuaaaagg nacaguauuc u        21

<210> SEQ ID NO 519
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methylinosine-3'-phosphate

<400> SEQUENCE: 519
gcuuaaaagn gacaguauuc u        21

<210> SEQ ID NO 520
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-O-methylinosine-3'-phosphate

<400> SEQUENCE: 520
gcuuaaaang gacaguauuc u        21

<210> SEQ ID NO 521
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 521
cccuaaaagg gacaguauuc u        21

<210> SEQ ID NO 522
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 522
aggguacucc uuguuguunc a        21

<210> SEQ ID NO 523

```
<210> SEQ ID NO 523
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 523
aggguacucc uuguuguugc a                                              21

<210> SEQ ID NO 524
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 524
cuucaguucc cugaaaganu a                                              21

<210> SEQ ID NO 525
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 525
cuucaguucc cugaaagacu a                                              21

<210> SEQ ID NO 526
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 526
gcuuaaaagg gacaguauun u                                              21

<210> SEQ ID NO 527
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 527
gcuuaaaagg gacaguauuc u                                              21

<210> SEQ ID NO 528
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 528
```
ggcaaaggga caguauucun a						21

<210> SEQ ID NO 529
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 529
ggcaaaggga caguauucuc a						21

<210> SEQ ID NO 530
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 530
gagggacagu auucucagun a						21

<210> SEQ ID NO 531
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 531
gccaauaaag cuggacaana a						21

<210> SEQ ID NO 532
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 532
gccaauaaag cuggacaaga a						21

<210> SEQ ID NO 533
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 533
aggguacucu nuguuguugc a						21

<210> SEQ ID NO 534
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-fluoroinosine-3'-phosphate

<400> SEQUENCE: 534
aggguacunc uuguuguugc a                                             21

<210> SEQ ID NO 535
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 535
cuucaguucc nugaaagacu a                                             21

<210> SEQ ID NO 536
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-fluoroinosine-3'-phosphate

<400> SEQUENCE: 536
cuucaguucn cugaaagacu a                                             21

<210> SEQ ID NO 537
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-fluoroinosine-3'-phosphate

<400> SEQUENCE: 537
cuucaguunc cugaaagacu a                                             21

<210> SEQ ID NO 538
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 538
gcuuaaaagg nacaguauuc u                                             21

<210> SEQ ID NO 539
<211> LENGTH: 21

<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-fluoroinosine-3'-phosphate

<400> SEQUENCE: 539
gcuuaaaagn gacaguauuc u                                            21

<210> SEQ ID NO 540
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-fluoroinosine-3'-phosphate

<400> SEQUENCE: 540
gcuuaaaang gacaguauuc u                                            21

<210> SEQ ID NO 541
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 541
ggcaaaggga naguauucuc a                                            21

<210> SEQ ID NO 542
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-fluoroinosine-3'-phosphate

<400> SEQUENCE: 542
ggcaaaggna caguauucuc a                                            21

<210> SEQ ID NO 543
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-fluoroinosine-3'-phosphate
<220> FEATURE:
<221> NAME/KEY: modified_base
<222> LOCATION: 20
<223> OTHER INFORMATION: n = 2'-O-methylinosine-3'-phosphate

<400> SEQUENCE: 543
gagggacanu auucucagun a                                     21

<210> SEQ ID NO 544
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 544
gccaauaaag nuggacaaga a                                     21

<210> SEQ ID NO 545
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-fluoroinosine-3'-phosphate

<400> SEQUENCE: 545
gccaauaaan cuggacaaga a                                     21

<210> SEQ ID NO 546
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-O-methylinosine-3'-phosphate

<400> SEQUENCE: 546
gccuaaaagg nacaguauuc u                                     21

<210> SEQ ID NO 547
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 547
gccuaaaagg nacaguauuc u                                     21

<210> SEQ ID NO 548
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 548
accuaaaagg gacaguauuc u                                     21

```
<210> SEQ ID NO 549
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 549
gcguaaaagg gacaguauuc u                                              21

<210> SEQ ID NO 550
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 550
gucuaaaagg gacaguauuc u                                              21

<210> SEQ ID NO 551
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 551
gagggacagu auucucagug a                                              21

<210> SEQ ID NO 552
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 552
gggacaguau ucucagunau u                                              21

<210> SEQ ID NO 553
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 553
gccaauaaag cuggacaaga a                                              21

<210> SEQ ID NO 554
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 554
gccuaaaagg gacaguauuc u                                              21

<210> SEQ ID NO 555
<211> LENGTH: 21
<212> TYPE: RNA
```

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 555
gccuaaaagg nacaguauuc u                                              21

<210> SEQ ID NO 556
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 556
gagggacagu auuccagug a                                               21

<210> SEQ ID NO 557
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 557
gagggacagu auucucaguna                                               21

<210> SEQ ID NO 558
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 558
gccaauaaag cuggacaaga a                                              21

<210> SEQ ID NO 559
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 559
gccaauaaag cuggacaaga a                                              21

<210> SEQ ID NO 560
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 560
gccaauaaag cuggacaaga a                                              21

<210> SEQ ID NO 561
<211> LENGTH: 21

```
<212> TYPE: RNA
<213> ORGANISM: Artificial sequence
<220> FEATURE:
<223> OTHER INFORMATION: RNAi agent sense strand modified sequence

<400> SEQUENCE: 561
gccaauaaag cuggacaaga a                                              21

<210> SEQ ID NO 562
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 562
gccaauaaag cuggacaaga a                                              21

<210> SEQ ID NO 563
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-fluoroinosine-3'-phosphate

<400> SEQUENCE: 563
gccaauaaan cuggacaaga a                                              21

<210> SEQ ID NO 564
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-fluoroinosine-3'-phosphate

<400> SEQUENCE: 564
gccaauaaan cuggacaaga a                                              21

<210> SEQ ID NO 565
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methylinosine-3'-phosphate

<400> SEQUENCE: 565
gccaauaaan cuggacaaga a                                              21

<210> SEQ ID NO 566
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
```

<223> OTHER INFORMATION: n = 2'-O-methylinosine-3'-phosphate

<400> SEQUENCE: 566
gccaauaaag cungacaaga a                                              21

<210> SEQ ID NO 567
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 567
gccaauaaag cugnacaaga a                                              21

<210> SEQ ID NO 568
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 568
gccuaaaagg gacaguauuc u                                              21

<210> SEQ ID NO 569
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 569
gccuaaaagg gacaguauuc u                                              21

<210> SEQ ID NO 570
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 570
gccuaaaagg nacaguauuc u                                              21

<210> SEQ ID NO 571
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 11
<223> OTHER INFORMATION: n = 2'-fluoroinosine-3'-phosphate

<400> SEQUENCE: 571
gccuaaaagg nacaguauuc u                                              21

```
<210> SEQ ID NO 572
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 572
acgggacagu auucucagun a                                               21

<210> SEQ ID NO 573
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 573
cagggacagu auucucagug a                                               21

<210> SEQ ID NO 574
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 574
cagggacagu auucucagun a                                               21

<210> SEQ ID NO 575
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 575 agggacagu auucucagug a                                                21

<210> SEQ ID NO 576
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 576 agggacagu auucucagun a                                                21

<210> SEQ ID NO 577
<211> LENGTH: 21
<212> TYPE: RNA
<213> ORGANISM: Artificial sequence
<220> FEATURE:
<223> OTHER INFORMATION: RNAi agent sense strand modified sequence
```

<400> SEQUENCE: 577
agaccgccaa ggaugcacuu u                                              21

<210> SEQ ID NO 578
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 15
<223> OTHER INFORMATION: n = 2'-O-methylinosine-3'-phosphate

<400> SEQUENCE: 578
agaccgccaa ggauncacuu u                                              21

<210> SEQ ID NO 579
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 579 ucaguuccccu gaaagacuac u                                             21

<210> SEQ ID NO 580
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 580 ucaguuccccu gaaagacuac a                                             21

<210> SEQ ID NO 581
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 15
<223> OTHER INFORMATION: n = 2'-O-methylinosine-3'-phosphate

<400> SEQUENCE: 581
acuacuggag caccnuuaag a                                              21

<210> SEQ ID NO 582
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 582
ccuguagguu gcuuaaaagg a                                              21

<210> SEQ ID NO 583
<211> LENGTH: 21
<212> TYPE: RNA
<213> ORGANISM: Artificial sequence
<220> FEATURE:
<223> OTHER INFORMATION: RNAi agent sense strand modified sequence

```
<400> SEQUENCE: 583
gcuguagguu gcuuaaaagg a                                            21

<210> SEQ ID NO 584
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 584
ggucaguucu cugaaagacu a                                            21

<210> SEQ ID NO 585
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 585
uaacaacaag gaguacccgu u                                            21

<210> SEQ ID NO 586
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 586
uaacaacaag gaguacccgg u                                            21

<210> SEQ ID NO 587
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 587
uaacaacaag gaguacccgg g                                            21

<210> SEQ ID NO 588
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 588
ugcaacaaca aggaguaccu u                                            21

<210> SEQ ID NO 589
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 589
```

-continued ugcaacaaca aggaguaccc u                                              21

<210> SEQ ID NO 590
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 590
ugcaacaaca aggaguaccc g                                              21

<210> SEQ ID NO 591
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 591
uagccaucgg ucacccagcu u                                              21

<210> SEQ ID NO 592
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 592
uagccaucgg ucacccagcc u                                              21

<210> SEQ ID NO 593
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 593
uagccaucgg ucacccagcc c                                              21

<210> SEQ ID NO 594
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 594
ugaacugaag ccaucggucu u                                              21

<210> SEQ ID NO 595
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 595

-continued ugaacugaag ccaucgguca u                                       21

<210> SEQ ID NO 596
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 596
ugaacugaag ccaucgguca c                                       21

<210> SEQ ID NO 597
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 597
ucuuucaggg aacugaagcu u                                       21

<210> SEQ ID NO 598
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 598
ucuuucaggg aacugaagcc u                                       21

<210> SEQ ID NO 599
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 599
ucuuucaggg aacugaagcc a                                       21

<210> SEQ ID NO 600
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 600
uaacggugcu ccaguagucu u                                       21

<210> SEQ ID NO 601
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 601
uuaacggugc uccaguaguu u                                       21

<210> SEQ ID NO 602
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 602
uuaacggugc uccaguaguc u                                              21

<210> SEQ ID NO 603
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 603
uacuuguccu uaacggugcu u                                              21

<210> SEQ ID NO 604
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 604
uacuuguccu uaacggugcu c                                              21

<210> SEQ ID NO 605
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 605
ugaacuuguc cuuaacgguu u                                              21

<210> SEQ ID NO 606
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 606
ugaacuuguc cuuaacggug u                                              21

<210> SEQ ID NO 607
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 607
ugaacuuguc cuuaacggug c                                              21

<210> SEQ ID NO 608
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 608
uagaacuugu ccuuacggu u                                              21

<210> SEQ ID NO 609
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 609
uagaacuugu ccuuacggu g                                              21

<210> SEQ ID NO 610
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 610
uggacuuggg guauugaggu u                                             21

<210> SEQ ID NO 611
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 611
uggacuuggg guauugaggu c                                             21

<210> SEQ ID NO 612
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 612
ugagaauacu gucccuuuuu u                                             21

<210> SEQ ID NO 613
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 613
ugagaauacu gucccuuuua u                                             21

-continued

```
<210> SEQ ID NO 614
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 614
ugagaauacu gucccuuuua a                                              21

<210> SEQ ID NO 615
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 615
uacugagaau acugcccuu u                                               21

<210> SEQ ID NO 616
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 616
cggguacucc uuguuguuau u                                              21

<210> SEQ ID NO 617
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 617 ccgguacuc cuuguuguua                                                 20

<210> SEQ ID NO 618
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 618
cccggguacu ccuuguuguu a                                              21

<210> SEQ ID NO 619
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 619
gguacuccuu guuguugcau u                                              21

<210> SEQ ID NO 620
```

```
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 620
ggguacuccu uguuguugca                                                 20

<210> SEQ ID NO 621
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 621
cggguacucc uuguuguugc a                                               21

<210> SEQ ID NO 622
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 622
gcugggugac cgauggcuau u                                               21

<210> SEQ ID NO 623
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 623
ggcuggguga ccgauggcua                                                 20

<210> SEQ ID NO 624
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 624
gggcugggug accgauggcu a                                               21

<210> SEQ ID NO 625
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 625
gaccgauggc uucaguucau u                                               21

<210> SEQ ID NO 626
<211> LENGTH: 20
```

```
<212> TYPE: RNA
<213> ORGANISM: Artificial sequence
<220> FEATURE:
<223> OTHER INFORMATION: RNAi agent sense strand underlying base
      sequence

<400> SEQUENCE: 626
ugaccgaugg cuucaguuca                                                      20

<210> SEQ ID NO 627
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 627
gugaccgaug gcuucaguuc a                                                    21

<210> SEQ ID NO 628
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 628
gcuucaguuc ccugaaagau u                                                    21

<210> SEQ ID NO 629
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 629
ggcuucaguu cccugaaaga                                                      20

<210> SEQ ID NO 630
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 630
uggcuucagu ucccugaaag a                                                    21

<210> SEQ ID NO 631
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 631
gacuacugga gcaccguuau u                                                    21

<210> SEQ ID NO 632
<211> LENGTH: 20
<212> TYPE: RNA
```

```
<213> ORGANISM: Artificial sequence
<220> FEATURE:
<223> OTHER INFORMATION: RNAi agent sense strand underlying base
      sequence

<400> SEQUENCE: 632
agacuacugg agcaccguua                                                      20

<210> SEQ ID NO 633
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 633
aagacuacug gagcaccguu a                                                    21

<210> SEQ ID NO 634
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 634
acuacuggag caccguuaau u                                                    21

<210> SEQ ID NO 635
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 635
gacuacugga gcaccguuaa                                                      20

<210> SEQ ID NO 636
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 636
agacuacugg agcaccguua a                                                    21

<210> SEQ ID NO 637
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 637
gcaccguuaa ggacaaguau u                                                    21

<210> SEQ ID NO 638
<211> LENGTH: 20
<212> TYPE: RNA
<213> ORGANISM: Artificial sequence
```

```
<220> FEATURE:
<223> OTHER INFORMATION: RNAi agent sense strand underlying base
      sequence

<400> SEQUENCE: 638
agcaccguua aggacaagua                                              20

<210> SEQ ID NO 639
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 639
gagcaccguu aaggacaagu a                                            21

<210> SEQ ID NO 640
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 640
accguuaagg acaaguucau u                                            21

<210> SEQ ID NO 641
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 641
caccguuaag gacaaguuca                                              20

<210> SEQ ID NO 642
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 642
gcaccguuaa ggacaaguuc a                                            21

<210> SEQ ID NO 643
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 643
ccguuaagga caaguucuau u                                            21

<210> SEQ ID NO 644
<211> LENGTH: 20
<212> TYPE: RNA
<213> ORGANISM: Artificial sequence
<220> FEATURE:
```

```
<223> OTHER INFORMATION: RNAi agent sense strand underlying base
      sequence

<400> SEQUENCE: 644
accguuaagg acaaguucua                                                    20

<210> SEQ ID NO 645
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 645
caccguuaag gacaaguucu a                                                  21

<210> SEQ ID NO 646
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 646
ccucaauacc ccaaguccau u                                                  21

<210> SEQ ID NO 647
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 647
accucaauac cccaagucca                                                    20

<210> SEQ ID NO 648
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 648
gaccucaaua ccccaagucc a                                                  21

<210> SEQ ID NO 649
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 649
aaaagggaca guauucucau u                                                  21

<210> SEQ ID NO 650
<211> LENGTH: 20
<212> TYPE: RNA
<213> ORGANISM: Artificial sequence
<220> FEATURE:
<223> OTHER INFORMATION: RNAi agent sense strand underlying base
```

```
                                    sequence

<400> SEQUENCE: 650
uaaaagggac aguauucuca                                                   20

<210> SEQ ID NO 651
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 651
uuaaaaggga caguauucuc a                                                 21

<210> SEQ ID NO 652
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 652
agggacagua uucucaguau u                                                 21

<210> SEQ ID NO 653
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 653
aagggacagu auucucagua                                                   20

<210> SEQ ID NO 654
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 654
aaagggacag uauucucagu a                                                 21

<210> SEQ ID NO 655
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 655
aacuuguccu uaacggugcu u                                                 21

<210> SEQ ID NO 656
<211> LENGTH: 21
<212> TYPE: RNA
<213> ORGANISM: Artificial sequence
<220> FEATURE:
<223> OTHER INFORMATION: RNAi agent antisense strand underlying base
      sequence
```

```
<400> SEQUENCE: 656
ugagaauacu gucccuuuug g                                              21

<210> SEQ ID NO 657
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 657
ugagaauacu gucccuuuug cg                                             22

<210> SEQ ID NO 658
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 658
uaacggugcu ccaguagucg u                                              21

<210> SEQ ID NO 659
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 659
uacugagaau acugcccug u                                               21

<210> SEQ ID NO 660
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 660
uuaacggugc uccaguaggc u                                              21

<210> SEQ ID NO 661
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 661
aagccaucgg ucacccagcu u                                              21

<210> SEQ ID NO 662
<211> LENGTH: 21
<212> TYPE: RNA
<213> ORGANISM: Artificial sequence
<220> FEATURE:
<223> OTHER INFORMATION: RNAi agent antisense strand underlying base
      sequence
```

-continued

```
<400> SEQUENCE: 662
agaacuuguc cuuaacgguu u                                              21

<210> SEQ ID NO 663
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 663
ugcacugaga auacuguccc uu                                             22

<210> SEQ ID NO 664
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 664
agcacugaga auacuguccc uu                                             22

<210> SEQ ID NO 665
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 665
cuacuugucc uuaacggugc uu                                             22

<210> SEQ ID NO 666
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 666
aacuuguccu uaacggugcu c                                              21

<210> SEQ ID NO 667
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 667
uacuuguccu uaacggugc                                                 19

<210> SEQ ID NO 668
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 668
```
uacuuguccu uaacggugcu cc                                    22

<210> SEQ ID NO 669
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 669
uacuuguccu uaacggugcu cuu                                   23

<210> SEQ ID NO 670
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 670
uacuuguccu uaacggugcu cca                                   23

<210> SEQ ID NO 671
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 671
aacuuguccu uaacggugc                                        19

<210> SEQ ID NO 672
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 672
aacuuguccu uaacggugcu cc                                    22

<210> SEQ ID NO 673
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 673
ugagaauacu gucccuuuug u                                     21

<210> SEQ ID NO 674
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 674

```
agagaauacu gucccuuuug g                                              21

<210> SEQ ID NO 675
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 675
ugcaacaaca aggaguacc                                                 19

<210> SEQ ID NO 676
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 676
agcaacaaca aggaguaccu u                                              21

<210> SEQ ID NO 677
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 677
ucugaagcca ucggucaccc a                                              21

<210> SEQ ID NO 678
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 678
acugaagcca ucggucaccc a                                              21

<210> SEQ ID NO 679
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 679
uggaacugaa gccaucgguc a                                              21

<210> SEQ ID NO 680
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 680
uggaacugaa gccaucgguc c                                              21
```

<210> SEQ ID NO 681
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 681
uucuuucagg gaacugaagc c                                              21

<210> SEQ ID NO 682
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 682
uuuaacggug cuccaguagu c                                              21

<210> SEQ ID NO 683
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 683
uccuuaacgg ugcuccagua g                                              21

<210> SEQ ID NO 684
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 684
uuccuuaacg gugcuccagu a                                              21

<210> SEQ ID NO 685
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 685
uuccuuaacg gugcuccagu c                                              21

<210> SEQ ID NO 686
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 686
uugaggucuc aggcagccac u                                              21

```
<210> SEQ ID NO 687
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 687
uuauugaggu cucaggcagc c                                             21

<210> SEQ ID NO 688
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 688
uguauugagg ucucaggcag c                                             21

<210> SEQ ID NO 689
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 689
ucacugagaa uacugucccu u                                             21

<210> SEQ ID NO 690
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 690
ucuuuuaagc aaccuacagg g                                             21

<210> SEQ ID NO 691
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 691
ugagaauacu gucccuuuuc c                                             21

<210> SEQ ID NO 692
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 692
ugagaauacu gucccuuuuc u                                             21
```

```
<210> SEQ ID NO 693
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 693
uucuugucca gcuuuauugg g                                              21

<210> SEQ ID NO 694
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 694
uagucuuuca gggaacugaa g                                              21

<210> SEQ ID NO 695
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 695
uagucuuuca gggaacugaa c                                              21

<210> SEQ ID NO 696
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 696
ucacugagaa uacuguccgu u                                              21

<210> SEQ ID NO 697
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 697
uagucuuuca gggaacugac g                                              21

<210> SEQ ID NO 698
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 698
uagucuuuca gggaacugag g                                              21

<210> SEQ ID NO 699
```

```
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 699
uagucuuuca gggaacugac c                                              21

<210> SEQ ID NO 700
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 700
uagucuuuca gggaacugag c                                              21

<210> SEQ ID NO 701
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 701
agaauacugu cccuuuuagg c                                              21

<210> SEQ ID NO 702
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 702
agaauacugu cccuuuuaag g                                              21

<210> SEQ ID NO 703
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 703
agaauacugu cccuuuuaag c                                              21

<210> SEQ ID NO 704
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 704
ugagaauacu gucccuuugc c                                              21

<210> SEQ ID NO 705
<211> LENGTH: 21
```

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 705
ucacugagaa uacugucccu c                                                  21

<210> SEQ ID NO 706
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 706
uucuugucca gcuuuauugg c                                                  21

<210> SEQ ID NO 707
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 707
agaauacugu cccuuuuagg u                                                  21

<210> SEQ ID NO 708
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 708
agaauacugu cccuuuuacg c                                                  21

<210> SEQ ID NO 709
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 709
agaauacugu cccuuuuaga c                                                  21

<210> SEQ ID NO 710
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 710
ucacugagaa uacugucccu g                                                  21

<210> SEQ ID NO 711
<211> LENGTH: 21
<212> TYPE: RNA
```

-continued

```
<213> ORGANISM: Artificial sequence
<220> FEATURE:
<223> OTHER INFORMATION: RNAi agent antisense strand underlying base
      sequence

<400> SEQUENCE: 711
ucacugagaa uacugucccc u                                              21

<210> SEQ ID NO 712
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 712
agugcauccu uggcggucuu u                                              21

<210> SEQ ID NO 713
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 713
aguagucuuu cagggaacug a                                              21

<210> SEQ ID NO 714
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 714
uguagucuuu cagggaacug a                                              21

<210> SEQ ID NO 715
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 715
ucuuaacggu gcuccaguag u                                              21

<210> SEQ ID NO 716
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 716
uccuuuuaag caaccuacag g                                              21

<210> SEQ ID NO 717
<211> LENGTH: 21
<212> TYPE: RNA
<213> ORGANISM: Artificial sequence
```

```
<220> FEATURE:
<223> OTHER INFORMATION: RNAi agent antisense strand underlying base
      sequence

<400> SEQUENCE: 717
uccuuuuaag caaccuacag c                                                 21

<210> SEQ ID NO 718
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 718
gcaccguuaa ggacaaguau u                                                 21

<210> SEQ ID NO 719
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 719
gagcaccguu aaggacaagu a                                                 21

<210> SEQ ID NO 720
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 720
gcaccguuaa ggacaagua                                                    19

<210> SEQ ID NO 721
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 721
gcaccguuaa ggacaaguu                                                    19

<210> SEQ ID NO 722
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 722
ccucaauacc ccaagucca                                                    19

<210> SEQ ID NO 723
<211> LENGTH: 21
<212> TYPE: RNA
<213> ORGANISM: Artificial sequence
<220> FEATURE:
```

<223> OTHER INFORMATION: RNAi agent sense strand underlying base
      sequence

<400> SEQUENCE: 723
gaccucaaua ccccaagucc a                                          21

<210> SEQ ID NO 724
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 724
gcuucaguuc ccugaaaga                                             19

<210> SEQ ID NO 725
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 725
ggcuucaguu cccugaaaga                                            20

<210> SEQ ID NO 726
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 726
gaccgauggc uucaguuca                                             19

<210> SEQ ID NO 727
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 727
gugaccgaug gcuucaguuc a                                          21

<210> SEQ ID NO 728
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 728
ccaaagggga caguauucuc a                                          21

<210> SEQ ID NO 729
<211> LENGTH: 22
<212> TYPE: RNA
<213> ORGANISM: Artificial sequence
<220> FEATURE:
<223> OTHER INFORMATION: RNAi agent sense strand underlying base -continued

<400> SEQUENCE: 729
cgcaaaaggg acaguauucu ca                                          22

<210> SEQ ID NO 730
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 730
gacuacugga gcaccguua                                              19

<210> SEQ ID NO 731
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 731
gacuacugga gcacuguua                                              19

<210> SEQ ID NO 732
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 732
cgacuacugg agcaccguua                                             20

<210> SEQ ID NO 733
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 733
gacuacugga gcaucguua                                              19

<210> SEQ ID NO 734
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 734
agggacagua uucucagua                                              19

<210> SEQ ID NO 735
<211> LENGTH: 20
<212> TYPE: RNA
<213> ORGANISM: Artificial sequence
<220> FEATURE:
<223> OTHER INFORMATION: RNAi agent sense strand underlying base
      sequence

```
<400> SEQUENCE: 735
cagggacagu auucucagua                                              20

<210> SEQ ID NO 736
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 736
gacuacugga gcaccguuaa                                              20

<210> SEQ ID NO 737
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 737
gccuacugga gcaccguuaa                                              20

<210> SEQ ID NO 738
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 738
gccuacugga gcacuguuaa                                              20

<210> SEQ ID NO 739
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 739
gcugggugac cgauggcua                                               19

<210> SEQ ID NO 740
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 740
gcugggugac cgauggcuu                                               19

<210> SEQ ID NO 741
<211> LENGTH: 19
<212> TYPE: RNA
<213> ORGANISM: Artificial sequence
<220> FEATURE:
<223> OTHER INFORMATION: RNAi agent sense strand underlying base
      sequence
```

```
<400> SEQUENCE: 741
gcugggugac cgaugacua                                                    19

<210> SEQ ID NO 742
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 742
ccguuaagga caaguucua                                                    19

<210> SEQ ID NO 743
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 743
caccguuaag gacaaguucu a                                                 21

<210> SEQ ID NO 744
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 744
accguuaagg acaaguuca                                                    19

<210> SEQ ID NO 745
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 745
accguuaagg acaaguucu                                                    19

<210> SEQ ID NO 746
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 746
gcaccguuaa ggacaaguuc a                                                 21

<210> SEQ ID NO 747
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 747
```
gguacuccuu guuguugca                                    19

<210> SEQ ID NO 748
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 748
cgdguacucc uuguuguugc a                                 21

<210> SEQ ID NO 749
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 749
cggguacucc uuguuguua                                    19

<210> SEQ ID NO 750
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 750
gggacaguau ucucagugca                                   20

<210> SEQ ID NO 751
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 751
gggacaguau ucucagugcu                                   20

<210> SEQ ID NO 752
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 752
gcaccguuaa ggacaaguuu u                                 21

<210> SEQ ID NO 753
<211> LENGTH: 22
<212> TYPE: RNA
<213> ORGANISM: Artificial sequence
<220> FEATURE:
<223> OTHER INFORMATION: RNAi agent sense strand underlying base
      sequence

<400> SEQUENCE: 753

-continued

| | |
|---|---|
| ggagcaccgu uaaggacaag ua | 22 |

<210> SEQ ID NO 754
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 754

| | |
|---|---|
| gagcaccguu aaggacaagu u | 21 |

<210> SEQ ID NO 755
<211> LENGTH: 22
<212> TYPE: RNA
<213> ORGANISM: Artificial sequence
<220> FEATURE:
<223> OTHER INFORMATION: RNAi agent sense strand underlying base
      sequence

<400> SEQUENCE: 755

| | |
|---|---|
| ggagcaccgu uaaggacaag uu | 22 |

<210> SEQ ID NO 756
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 756

| | |
|---|---|
| aaaagggaca guauucucau u | 21 |

<210> SEQ ID NO 757
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 757

| | |
|---|---|
| caaaagggac aguauucuca | 20 |

<210> SEQ ID NO 758
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 758

| | |
|---|---|
| ccaaaaggga caguauucuc u | 21 |

<210> SEQ ID NO 759
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 759

| | |
|---|---|
| gguacuccuu guguugcau u | 21 |

<210> SEQ ID NO 760
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 760
ggguacuccu uguuguugca                                               20

<210> SEQ ID NO 761
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 761
gguacuccuu guuguugcu                                                19

<210> SEQ ID NO 762
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 762
ugggugaccg auggcuucag a                                             21

<210> SEQ ID NO 763
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 763
ugggugaccg auggcuucag u                                             21

<210> SEQ ID NO 764
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 764
ugaccgaugg cuucaguucc a                                             21

<210> SEQ ID NO 765
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 765
ggaccgaugg cuucaguucc a                                             21

<210> SEQ ID NO 766
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 766
ggcuucaguu cccugaaaga a                                                 21

<210> SEQ ID NO 767
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 767
gacuacugga gcaccguuaa a                                                 21

<210> SEQ ID NO 768
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 768
cuacuggagc accguuaagg a                                                 21

<210> SEQ ID NO 769
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 769
uacuggagca ccguuaagga a                                                 21

<210> SEQ ID NO 770
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 770
gacuggagca ccguuaagga a                                                 21

<210> SEQ ID NO 771
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 771
aguggcugcc ugagaccuca a                                                 21

```
<210> SEQ ID NO 772
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 772
ggcugccuga gaccucaaua a                                              21

<210> SEQ ID NO 773
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 773
gcugccugag accucaauac a                                              21

<210> SEQ ID NO 774
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 774
aagggacagu auucucagug a                                              21

<210> SEQ ID NO 775
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 775
acgggacagu auucucagug a                                              21

<210> SEQ ID NO 776
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 776
cccuguaggu ugcuuaaaag a                                              21

<210> SEQ ID NO 777
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 777
ggaaaaggga caguauucuc a                                              21

<210> SEQ ID NO 778
```

```
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 7
<223> OTHER INFORMATION: n = inosine (hypoxanthine)

<400> SEQUENCE: 778
ggcaaangga caguauucuc a                                              21

<210> SEQ ID NO 779
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = inosine (hypoxanthine)

<400> SEQUENCE: 779
gcuuaaaagn gacaguauuc u                                              21

<210> SEQ ID NO 780
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 780
ugaccgaugg cuucanuucc a                                              21

<210> SEQ ID NO 781
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 3
<223> OTHER INFORMATION: n = 2-aminoadenine

<400> SEQUENCE: 781
ggnaaaggga caguauucuc a                                              21

<210> SEQ ID NO 782
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 1
<223> OTHER INFORMATION: n = 2-aminoadenine
```

-continued

<400> SEQUENCE: 782
ngaaaaggga caguauucuc a                                              21

<210> SEQ ID NO 783
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 1, 2
<223> OTHER INFORMATION: n = 2-aminoadenine

<400> SEQUENCE: 783
nnaaaaggga caguauucuc a                                              21

<210> SEQ ID NO 784
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 784
cccaauaaag cuggacaaga a                                              21

<210> SEQ ID NO 785
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9
<223> OTHER INFORMATION: n = inosine (hypoxanthine)

<400> SEQUENCE: 785
gcuuaaaang gacaguauuc u                                              21

<210> SEQ ID NO 786
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 786
cuucaguucc cugaaagacu a                                              21

<210> SEQ ID NO 787
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 787
guucaguucc cugaaagacu a                                              21

<210> SEQ ID NO 788

```
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9
<223> OTHER INFORMATION: n = inosine (hypoxanthine)

<400> SEQUENCE: 788
aggguacunc uuguuguugc a                                              21

<210> SEQ ID NO 789
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 789
gggacaguau ucucagugau u                                              21

<210> SEQ ID NO 790
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 1
<223> OTHER INFORMATION: n = 2-aminoadenine

<400> SEQUENCE: 790
nagggacagu auucucagug a                                              21

<210> SEQ ID NO 791
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 791
gagggacagu auucucanug a                                              21

<210> SEQ ID NO 792
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = inosine (hypoxanthine)

<400> SEQUENCE: 792
cuucaguucn cugaaagacu a                                              21
```

<210> SEQ ID NO 793
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 793
cggacaguau ucucagugau u                                              21

<210> SEQ ID NO 794
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 8
<223> OTHER INFORMATION: n = inosine (hypoxanthine)

<400> SEQUENCE: 794
ggcaaagnga caguauucuc a                                              21

<210> SEQ ID NO 795
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 795
aggguacucc uuguuguugc a                                              21

<210> SEQ ID NO 796
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 796
cuucaguucu cugaaagacu a                                              21

<210> SEQ ID NO 797
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 797
cuucaguuuc cugaaagacu a                                              21

<210> SEQ ID NO 798
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 798
cgucaguucc cugaaagacu a                                              21

<210> SEQ ID NO 799
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 799
ccucaguucc cugaaagacu a                                              21

<210> SEQ ID NO 800
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 800
cgucaguucu cugaaagacu a                                              21

<210> SEQ ID NO 801
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 801
ggucaguucc cugaaagacu a                                              21

<210> SEQ ID NO 802
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 802
gcucaguucc cugaaagacu a                                              21

<210> SEQ ID NO 803
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 803
gccuaaaagg gacaguauuc u                                              21

<210> SEQ ID NO 804
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 804
ccuuaaaagg gacaguauuc u    21

<210> SEQ ID NO 805
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 805
gcuuaaaagg nacaguauuc u    21

<210> SEQ ID NO 806
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9
<223> OTHER INFORMATION: n = inosine (hypoxanthine)

<400> SEQUENCE: 806
cuucaguunc cugaaagacu a    21

<210> SEQ ID NO 807
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 807
aggguacucc uuguuguunc a    21

<210> SEQ ID NO 808
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 808
cuucaguucc cugaaaganu a    21

<210> SEQ ID NO 809
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:

<221> NAME/KEY: modified_base
<222> LOCATION: 20
<223> OTHER INFORMATION: n = inosine (hypoxanthine)

<400> SEQUENCE: 809
gcuuaaaagg gacaguauun u                                              21

<210> SEQ ID NO 810
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 810
ggcaaaggga caguauucun a                                              21

<210> SEQ ID NO 811
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 811
gccaauaaag cuggacaana a                                              21

<210> SEQ ID NO 812
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = inosine (hypoxanthine)

<400> SEQUENCE: 812
aggguacucn uuguuguugc a                                              21

<210> SEQ ID NO 813
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 813
cuucaguucc nugaaagacu a                                              21

<210> SEQ ID NO 814
<211> LENGTH: 21

-continued

```
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 814
ggcaaaggga naguauucuc a                                              21

<210> SEQ ID NO 815
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9, 20
<223> OTHER INFORMATION: n = inosine (hypoxanthine)

<400> SEQUENCE: 815
gagggacanu auucucagun a                                              21

<210> SEQ ID NO 816
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 816
gccaauaaag nuggacaaga a                                              21

<210> SEQ ID NO 817
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = inosine (hypoxanthine)

<400> SEQUENCE: 817
gcuuaaaagn gacaguauuc u                                              21

<210> SEQ ID NO 818
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 818
```

```
gccuaaaagg nacaguauuc u                                          21

<210> SEQ ID NO 819
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 819
accuaaaagg gacaguauuc u                                          21

<210> SEQ ID NO 820
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 820
gcguaaaagg gacaguauuc u                                          21

<210> SEQ ID NO 821
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 821
gucuaaaagg gacaguauuc u                                          21

<210> SEQ ID NO 822
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 822
gggacaguau ucucagunau u                                          21

<210> SEQ ID NO 823
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 13
<223> OTHER INFORMATION: n = inosine (hypoxanthine)

<400> SEQUENCE: 823
gccaauaaag cungacaaga a                                          21

<210> SEQ ID NO 824
<211> LENGTH: 21
```

```
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9
<223> OTHER INFORMATION: n = inosine (hypoxanthine)

<400> SEQUENCE: 824
gcuuaaaang gacaguauuc u                                              21

<210> SEQ ID NO 825
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 825
cagggacagu auucucagug a                                              21

<210> SEQ ID NO 826
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 826
aggggacagu auucucagug a                                              21

<210> SEQ ID NO 827
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 827
aggggacagu auucucagun a                                              21

<210> SEQ ID NO 828
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 828
agaccgccaa ggaugcacuu u                                              21

<210> SEQ ID NO 829
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
```

```
<221> NAME/KEY: modified_base
<222> LOCATION: 15
<223> OTHER INFORMATION: n = inosine (hypoxanthine)

<400> SEQUENCE: 829
agaccgccaa ggauncacuu u                                              21

<210> SEQ ID NO 830
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 830
ucaguucccu gaaagacuac u                                              21

<210> SEQ ID NO 831
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 831
ucaguucccu gaaagacuac a                                              21

<210> SEQ ID NO 832
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 15
<223> OTHER INFORMATION: n = inosine (hypoxanthine)

<400> SEQUENCE: 832
acuacuggag caccnuuaag a                                              21

<210> SEQ ID NO 833
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 833
ccuguagguu gcuuaaaagg a                                              21

<210> SEQ ID NO 834
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 834
gcuguagguu gcuuaaaagg a                                              21

<210> SEQ ID NO 835
```

```
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 835
ggucaguucu cugaaagacu a                                              21

<210> SEQ ID NO 836
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14
<223> OTHER INFORMATION: n = inosine (hypoxanthine)

<400> SEQUENCE: 836
gccaauaaag cugnacaaga a                                              21

<210> SEQ ID NO 837
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 837
cagggacagu auucucagun a                                              21
```

RNAI AGENTS AND COMPOSITIONS FOR INHIBITING EXPRESSION OF APOLIPOPROTEIN C-III (APOC3)

CROSS REFERENCE TO RELATED APPLICATIONS

This application is a divisional of U.S. patent application Ser. No. 16/126,740, filed Sep. 10, 2018, which claims priority from U.S. Provisional Patent Application Ser. No. 62/720,434, filed on Aug. 21, 2018, U.S. Provisional Patent Application Ser. No. 62/643,927, filed on Mar. 16, 2018, and U.S. Provisional Patent Application Ser. No. 62/556,818, filed on Sep. 11, 2017, the contents of each of which are incorporated herein by reference in their entirety.

SEQUENCE LISTING

This application contains a Sequence Listing which has been submitted in ASCII format and is hereby incorporated by reference in its entirety. The ASCII copy is named 30655-US2_SeqList and is 195 kb in size.

FIELD OF THE INVENTION

The present disclosure relates to RNA interference (RNAi) agents, e.g., double stranded RNAi agents, for inhibition of apolipoprotein C-Ill gene expression, compositions that include apolipoprotein C-III RNAi agents, and methods of use thereof.

BACKGROUND

Apolipoprotein C-III (also called APOC3, apoC-III, APOC-III, and APO C-III), encoded by the human Apolipoprotein C-III gene, has recently emerged as a promising target for the treatment of diseases associated with hypertriglyceridemia. Elevated serum triglyceride (TG) levels have been identified as an independent risk factor for cardiovascular disease, and as a contributing factor in the development of atherosclerosis. Individuals with severe hypertriglyceridemia (often >1000 mg/dL) are also at risk of recurrent pancreatitis. Triglycerides are primarily transported in the blood as a major component of very low density lipoprotein (VLDL) and chylomicron particles, which are known as TG-rich lipoproteins. Lipoproteins are composed of a hydrophobic triacylglycerol and cholesteryl ester core, and a hydrophilic outer layer of phospholipids, cholesterol, and apoproteins. APOC3 is one of these apoproteins.

APOC3 is primarily synthesized in the liver and plays an important role in the production, metabolism, and clearance of TG-rich lipoproteins from plasma. Several gain-of-function polymorphisms have been identified in the promoter region of the APOC3 gene, which are postulated to be contributing factors in development of hypertriglyceridemia (See, e.g., Wang, Y., et al., Association of Apolipoprotein C3 Genetic Polymorphisms with the Risk of Ischemic Stroke in the Northern Chinese Han Population, 11 *PLoS One* e0163910 (2016); Li, Y., et al., Apolipoprotein C3 gene variants and the risk of coronary heart disease: A meta-analysis 9 *Meta Gene* 104-109 (2016)). Increased APOC3 synthesis in the liver promotes secretion of TG-rich VLDL. In addition, over-abundance of APOC3 inhibits the activity of lipoprotein lipase and hepatic lipase, further increasing serum TG levels by delaying the catabolism of TG-rich lipoproteins. Furthermore, elevated APOC3 also delays the hepatic clearance of TG-rich lipoprotein and their remnant particles by interfering with their binding to hepatic receptors. Several large genetic analysis studies have reported that individuals with loss-of-function mutations of APOC3 exhibit low levels of triglyceride and reduced incidence of cardiovascular disease. (See, e.g., Bemelot Moens, S. J., et al., Inhibition of ApoCIII: the next PCSK9? 25 *Curr Opin Lipidol* 418-422 (2014); Saleheen, D., et al., Human knockouts and phenotypic analysis in a cohort with a high rate of consanguinity, 544 *Nature* 235-239 (2017)).

Currently, hypertriglyceridemia is often treated with fibrates or in combination with statins in moderate cases; however, in most cases, the reduction in serum TG is modest. Additionally, available therapeutics are often ineffective in patients with monogenic causes of very severe hypertriglyceridemia (such as patients with familial chylomicronemia syndrome) because the disease-causing mutations lead to dysfunctional lipoprotein lipase and functional lipoprotein lipase is required for optimal response to standard therapies. There is a need for an effective therapeutic that can provide a substantial TG lowering effect for the treatment of diseases where APOC3 may play a role, such as hypertriglyceridemia induced pancreatitis, metabolic syndrome, type II diabetes mellitus, familial chylomicronemia syndrome, familial partial lipodystrophy, obesity, hyperlipidenmia, hypertriglyceridemia, abnormal lipid and/or cholesterol metabolism, atherosclerosis, cardiovascular disease, coronary artery disease, and other metabolic-related disorders and diseases. Certain other APOC3-specific RNA interference (RNAi) agents have been shown to inhibit expression of APOC3 gene expression, for example, in International Patent Application Publication No. WO 2016/011123 A1, to Weiler et al., which is incorporated herein by reference in its entirety. The APOC3 RNAi agents disclosed herein, however, were not previously disclosed or known and provide for highly potent and efficient inhibition of the expression of an APOC3 gene.

SUMMARY

There exists a need for novel APOC3 RNA interference (RNAi) agents (also herein termed RNAi agent, RNAi trigger, or trigger) that are able to selectively and efficiently inhibit the expression of an APOC3 gene. Further, there exists a need for compositions that include novel APOC3-specific RNAi agents for the treatment of diseases associated with, among other things, elevated triglyceride (TG) levels.

In general, the present disclosure features APOC3 gene-specific RNAi agents, compositions that include APOC3 RNAi agents, and methods for inhibiting expression of an APOC3 gene in vitro and/or in vivo using the APOC3 RNAi agents and compositions that include APOC3 RNAi agents described herein. The APOC3 RNAi agents disclosed herein can selectively and efficiently decrease or inhibit expression of an APOC3 gene, and thereby reduce TG levels and/or cholesterol levels in a subject, e.g., a human or animal subject.

The described APOC3 RNAi agents can be used in methods for therapeutic treatment (including the prophylactic and preventative treatment) of symptoms and diseases associated with elevated TG levels and/or elevated cholesterol levels, including, but not limited to, obesity, hyperlipidemia, hypertriglyceridemia, abnormal lipid and/or cholesterol metabolism, atherosclerosis, cardiovascular disease, coronary artery disease, hypertriglyceridemia induced pancreatitis, metabolic syndrome, type II diabetes mellitus, familial chylomicronemia syndrome, familial partial lipodystrophy, and other metabolic-related disorders and diseases. The APOC3 RNAi agents disclosed herein can selectively reduce APOC3 gene expression, which can lead to a reduction in, among other things, TG levels and/or cholesterol levels, in a subject. The methods disclosed herein include the administration of one or more APOC3 RNAi agents to a subject, e.g., a human or animal subject, using any suitable methods known in the art, such as subcutaneous injection or intravenous administration.

In one aspect, the disclosure features RNAi agents for inhibiting expression of the human APOC3 gene, wherein the RNAi agent includes a sense strand and an antisense strand. Also described herein are compositions that include or consist of an RNAi agent capable of inhibiting the expression of an APOC3 gene, wherein the APOC3 RNAi agent includes or consists of a sense strand and an antisense strand, and the composition further includes at least one pharmaceutically acceptable excipient. The compositions described herein that include one or more of the disclosed APOC3 RNAi agents are able to selectively and efficiently decrease expression of an APOC3 gene. The compositions that include one or more APOC3 RNAi agents can be administered to a subject, such as a human or animal subject, for the treatment (including prophylactic treatment or inhibition) of symptoms and diseases associated with elevated TG levels, elevated cholesterol, and/or enhanced APOC3 expression.

An APOC3 RNAi agent described herein includes a sense strand (also referred to as a passenger strand), and an antisense strand (also referred to as a guide strand). The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the sense and/or antisense strands are independently 16, 17, 18, 19, 20, 21, 22, 23, 24, 25, 26, 27, 28, 29, or 30 nucleotides in length. The RNAi agents described herein, upon delivery to a cell expressing APOC3, inhibit the expression of one or more APOC3 genes in vivo or in vitro.

A sense strand of the APOC3 RNAi agents described herein includes at least 16 consecutive nucleotides that have at least 85% identity to a core stretch sequence (also referred to herein as a "core stretch" or "core sequence") of the same number of nucleotides in an APOC3 mRNA. In some embodiments, the sense strand core stretch having at least 85% identity to a sequence in an APOC3 mRNA is 16, 17, 18, 19, 20, 21, 22, or 23 nucleotides in length. In some embodiments, the sense strand core stretch having at least 85% identity to a sequence in an APOC3 mRNA is 19 nucleotides in length. In some embodiments, this sense strand core stretch is 17 nucleotides in length.

An antisense strand of an APOC3 RNAi agent includes at least 16 consecutive nucleotides that have at least 85% complementarity to a core stretch of the same number of nucleotides in an APOC3 mRNA and to a core stretch of the same number of nucleotides in the corresponding sense strand. In some embodiments, the antisense strand core stretch having at least 85% complementarity to a sequence in an APOC3 mRNA or the corresponding sense strand is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length.

In some embodiments, the APOC3 RNAi agents disclosed herein target the portion of an APOC3 gene having the sequence of any of the sequences disclosed in Table 1.

Examples of APOC3 RNAi agent sense strands and antisense strands that can be included in the APOC3 RNAi agents disclosed herein are provided in Tables 3, 4, and 5. Examples of APOC3 RNAi agent duplexes are provided in Tables 3 and 6. Examples of 19-nucleotide core stretch sequences that that consist of or are included in the sense strands and antisense strands of APOC3 RNAi agents disclosed herein, are provided in Table 2.

In another aspect, the disclosure features methods for delivering APOC3 RNAi agents to liver cells in a subject, such as a mammal, in vivo. Also described herein are compositions for use in such methods. The one or more APOC3 RNAi agents can be delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors, or Dynamic Polyconjugates™ (DPCs) (see, for example WO 2000/053722, WO 2008/0022309, WO 2011/104169, and WO 2012/083185, each of which is incorporated herein by reference).

In some embodiments, an APOC3 RNAi agent is delivered to target cells or tissues by covalently linking or conjugating the RNAi agent to a targeting group, such as an asialoglycoprotein receptor ligand. In some embodiments, an asialoglycoprotein receptor ligand includes, consists of, or consists essentially of, a galactose or galactose derivative cluster. In some embodiments, an APOC3 RNAi agent is linked to a targeting ligand comprising the galactose derivative N-acetyl-galactosamine. In some embodiments, a galactose derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer. In some embodiments, the APOC3 RNAi agents that are conjugated to targeting ligands that include N-acetyl-galactosamine are selectively internalized by liver cells, and hepatocytes in particular, either through receptor-mediated endocytosis or by other means. Example targeting groups useful for delivering RNAi agents are disclosed, for example, in International Patent Application Publication Nos. WO 2018/044350 and WO 2017/156012, which are incorporated herein by reference in their entirety.

A targeting group can be linked to the 3' or 5' end of a sense strand or an antisense strand of an APOC3 RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

A targeting group, with or without a linker, can be linked to the 5' or 3' end of any of the sense and/or antisense strands disclosed in Tables 2, 3, 4 and 5. A linker, with or without a targeting group, can be attached to the 5' or 3' end of any of the sense and/or antisense strands disclosed in Tables 2, 3, 4 and 5.

In some embodiments, described herein are compositions that include one or more APOC3 RNAi agents having the duplex sequences disclosed in Table 6.

In a further aspect, described herein are pharmaceutical compositions that include one or more described APOC3 RNAi agent(s), optionally combined with one or more additional (i.e., second, third, etc.) therapeutics. In some embodiments, the pharmaceutical compositions that include one or more described APOC3 RNAi agent(s), optionally combined with one or more additional (i.e., second, third, etc.) therapeutics, can be formulated in a pharmaceutically acceptable carrier or diluent. In some embodiments, these compositions can be administered to a subject, such as a mammal. In some embodiments, the mammal is a human.

In some embodiments, the compositions described herein include a combination or cocktail of at least two APOC3 RNAi agents having different nucleotide sequences. In some embodiments, the two or more different APOC3 RNAi agents are each separately and independently linked to targeting groups. In some embodiments, the two or more different APOC3 RNAi agents are each linked to targeting groups that include or consist of targeting ligands that include one or more moieties that target the asialoglycoprotein receptor. In some embodiments, the two or more different APOC3 RNAi agents are each linked to targeting groups that include or consist of targeting ligands that include one or more galactose derivatives. In some embodiments, the two or more different APOC3 RNAi agents are each linked to targeting groups that include or consist of targeting ligands that include one or more N-acetyl-galactosanmines.

In another aspect, the disclosure features methods for inhibiting APOC3 gene expression in a subject, wherein the methods include administering to a subject or to a cell of a subject an amount of an APOC3 RNAi agent capable of inhibiting the expression of an APOC3 gene, wherein the APOC3 RNAi agent comprises a sense strand and an antisense strand, and wherein the antisense strand includes the sequence of any one of the antisense strand nucleotide sequences in Table 2, Table 3, or Table 4. In some embodiments, compositions for delivering an APOC3 RNAi agent to a liver cell, particularly hepatocytes, in vivo are described, the compositions comprising: an APOC3 RNAi agent conjugated to a targeting group. In some embodiments, the targeting group is an asialoglycoprotein receptor ligand.

In some embodiments, disclosed herein are methods of inhibiting expression of an APOC3 gene, wherein the methods include administering to a subject or to a cell of a subject an amount of an APOC3 RNAi agent capable of inhibiting the expression of an APOC3 gene, wherein the APOC3 RNAi agent comprises a sense strand and an antisense strand, and wherein the sense strand includes the sequence of any one of the sense strand nucleotide sequences in Table 2, Table 3, or Table 5. Also described herein are compositions for use in such methods.

In a further aspect, the disclosure features methods of treatment (including preventative or prophylactic treatment) of diseases or symptoms caused by elevated TG levels and/or elevated cholesterol levels, wherein the methods include administering to a subject in need thereof an APOC3 RNAi agent having an antisense strand that includes the sequence of any of the sequences in Tables 2, 3, or 4. In some embodiments, described herein are methods of treatment (including preventative or prophylactic treatment) of diseases or symptoms caused by elevated TG levels and/or elevated cholesterol levels, wherein the methods include administering to a subject in need thereof an APOC3 RNAi agent having a sense strand comprising the sequence of any of the sequences in Tables 2, 3, or 5. Also described herein are compositions for use in such methods.

Also described are methods of treating a human subject having a pathological state (such as a condition or disease), or being at risk of developing a pathological state, that is mediated at least in part by APOC3 gene expression, the methods comprising the step of administering to the subject a therapeutically effective amount of an APOC3 RNAi agent and/or APOC3 RNAi agent-containing composition. The method of treating a subject with an APOC3 RNAi agent and/or APOC3 RNAi agent-containing composition can optionally be combined with one or more steps of administering one or more additional (i.e., second, third, etc.) therapeutics or treatments. The APOC3 RNAi agent and additional therapeutics can be administered in a single composition or they can be administered separately. An additional therapeutic can be another APOC3 RNAi agent (e.g., an APOC3 RNAi agent that targets a different sequence within the APOC3 gene). An additional therapeutic can also be a small molecule drug, antibody, antibody fragment, and/or aptamer. In some embodiments, the one or more additional therapeutics is a statin, such as atorvastatin, fluvastatin, pravastatin, pitavastatin, rosuvastatin, or simvastatin.

In some embodiments, the described APOC3 RNAi agent(s) are optionally combined with one or more additional therapeutics, wherein the one or more additional therapeutics is administered separately in separate dosage forms from the RNAi agent (e.g., the APOC3 RNAi agent is administered by subcutaneous injection, while the additional therapeutic involved in the method of treatment dosing regimen is administered orally). In some embodiments, the described APOC3 RNAi agent(s) are administered to a subject in need thereof via subcutaneous injection, and the one or more optional additional therapeutics are administered orally, which together provide for a treatment regimen for diseases and conditions associated with elevated TG and/or cholesterol levels. In some embodiments, the described APOC3 RNAi agent(s) are administered to a subject in need thereof via subcutaneous injection, and the one or more optional additional therapeutics are administered via a separate subcutaneous injection. In some embodiments, the APOC3 RNAi agent and one or more additional therapeutics are combined into a single dosage form (e.g., a "cocktail" formulated into a single composition for subcutaneous injection). The APOC3 RNAi agents, with or without the one or more additional therapeutics, can be combined with one or more excipients to form pharmaceutical compositions.

In some embodiments, disclosed herein are methods for inhibiting expression of an APOC3 gene, the methods include administering to the cell or subject an APOC3 RNAi agent that includes a sense strand comprising, consisting of, or consisting essentially of the sequence of any of the sequences in Tables 2, 3, or 5. In some embodiments, disclosed herein are methods of inhibiting expression of an APOC3 gene, wherein the methods include administering an APOC3 RNAi agent that includes a sense strand comprising the sequence of any of the sequences in Table 5, and the antisense strand comprising, consisting of, or consisting essentially of the sequence of any of the sequences in Table 4.

In some embodiments, disclosed herein are methods of inhibiting expression of an APOC3 gene in a cell or a subject, wherein the methods include administering to the cell or subject an APOC3 RNAi agent that includes a sense strand that includes the nucleobase sequence of any of the sequences in Table 5, and an antisense strand that includes the nucleobase sequence of any of the sequences in Table 4. In other embodiments, disclosed herein are methods of inhibiting expression of an APOC3 gene, wherein the methods include administering to a subject an APOC3 RNAi agent that includes a sense strand consisting of the modified sequence of any of the modified sequences in Table 5, and the antisense strand consisting of the modified sequence of any of the modified sequences in Table 4.

In some embodiments, compositions for delivering an APOC3 RNAi agent to a liver cell, particularly hepatocytes, in vivo, are described, the compositions comprising: an APOC3 RNAi agent conjugated to a targeting group. In some embodiments, the targeting group is an asialoglycoprotein receptor ligand (i.e., a ligand that includes a compound having affinity for the asialoglycoprotein receptor). In some embodiments, the targeting group comprises N-acetylgalactosamine.

In some embodiments, disclosed herein are methods for inhibiting expression of an APOC3 gene in a cell, the methods include administering one or more APOC3 RNAi agents having the duplex structure of a duplex set forth in Table 6.

In some embodiments, disclosed herein are methods of treatment (including prophylactic or preventative treatment) of diseases, disorders, or symptoms caused by elevated TG levels and/or elevated cholesterol levels, wherein the methods include administering to a subject in need thereof a therapeutically effective amount of an APOC3 RNAi agent that includes an antisense strand that is at least partially complementary to the portion of the APOC3 mRNA having the sequence in Table 1. In some embodiments, disclosed herein are methods of treatment (including prophylactic or preventative treatment) of diseases or symptoms caused by elevated TG levels and/or elevated cholesterol levels, wherein the methods include administering to a subject in need thereof a therapeutically effective amount of an APOC3 RNAi agent that includes an antisense strand comprising the sequence of any of the sequences in Tables 2, 3, or 4, and a sense strand that comprises any of the sequences in Tables 2, 3, or 5 that is at least partially complementary to the antisense strand. In some embodiments, disclosed herein are methods of treatment (including prophylactic or preventative treatment) of diseases or symptoms caused by elevated TG levels and/or elevated cholesterol levels, wherein the methods include administering to a subject in need thereof a therapeutically effective amount of an APOC3 RNAi agent that includes a sense strand that comprises any of the sequences in Tables 2, 3, or 5, and an antisense strand comprising the sequence of any of the sequences in Tables 2, 3, or 4 that is at least partially complementary to the sense strand.

In some embodiments, disclosed herein are methods for inhibiting expression of an APOC3 gene in a cell, wherein the methods include administering to the cell an APOC3 RNAi agent that includes an antisense strand that is at least partially complementary to the portion of the APOC3 mRNA having the sequence in Table 1. In some embodiments, disclosed herein are methods of inhibiting expression of an APOC3 gene in a cell, wherein the methods include administering to a cell an APOC3 RNAi agent that includes an antisense strand comprising the sequence of any of the sequences in Tables 2, 3, or 4, and a sense strand that comprises any of the sequences in Tables 2, 3, or 5 that is at least partially complementary to the antisense strand. In some embodiments, disclosed herein are methods of inhibiting expression of an APOC3 gene in a cell, wherein the methods include administering an APOC3 RNAi agent that includes a sense strand that comprises any of the sequences in Tables 2, 3, or 5, and an antisense strand that includes the sequence of any of the sequences in Tables 2, 3, or 4 that is at least partially complementary to the sense strand.

In some embodiments, disclosed herein are compositions for inhibiting expression of an APOC3 gene in a cell, wherein the methods include administering a composition that comprises an APOC3 RNAi agent having the duplex structure of a duplex set forth in Table 6.

In some embodiments, disclosed herein are compositions for delivering an APOC3 RNAi agent to a liver cell in vivo, the composition including an APOC3 RNAi agent conjugated or linked to a targeting group. In some embodiments, the targeting group is an asialoglycoprotein receptor ligand. In some embodiments, compositions for delivering an APOC3 RNAi agent to a liver cell in vivo are described, the composition including an APOC3 RNAi agent linked to an N-acetyl-galactosamine targeting ligand.

The APOC3 RNAi agents disclosed herein are designed to target specific positions on an APOC3 gene (SEQ ID NO:1). As defined herein, an antisense strand sequence is designed to target an APOC3 gene at a given position on the gene when the 5' terminal nucleobase of the antisense strand would be aligned with the position that is 19 nucleotides downstream (towards the 3' end) from the position on the gene when base pairing to the gene. For example, as illustrated in Tables 1 and 2 herein, an antisense strand sequence designed to target an APOC3 gene at position 438 requires that when base pairing to the gene, the 5' terminal nucleobase of the antisense strand is aligned with position 456 of the APOC3 gene.

As provided herein, an APOC3 RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for an APOC3 RNAi agent disclosed herein that is designed to target position 438 of an APOC3 gene, the 5' terminal nucleobase of the antisense strand of the of the APOC3 RNAi agent must be aligned with position 456 of the gene; however, the 5' terminal nucleobase of the antisense strand may be, but is not required to be, complementary to position 456 of an APOC3 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the APOC3 RNAi agent (e.g., whether the APOC3 RNAi agent is designed to target an APOC3 gene at position 438, at position 506, at position 432, or at some other position) is important to the level of inhibition achieved by the APOC3 RNAi agent.

The use of APOC3 RNAi agents provides methods for therapeutic (including prophylactic) treatment of diseases/disorders associated with elevated TG and/or cholesterol levels and/or enhanced or elevated APOC3 expression. The described APOC3 RNAi agents mediate RNA interference to inhibit the expression of one or more genes necessary for production of APOC3. APOC3 RNAi agents can also be used to treat or prevent various diseases or disorders, including obesity, hyperlipidemia, hypertriglyceridenmia, abnormal lipid and/or cholesterol metabolism, atherosclerosis, cardiovascular disease, coronary artery disease, hypertriglyceridemia mediated pancreatitis, metabolic syndrome, type II diabetes mellitus, familial chylomicronemia syndrome, familial partial lipodystrophy, and other metabolic-related disorders and diseases. Furthermore, compositions for delivery of APOC3 RNAi agents to liver cells in vivo are described.

The pharmaceutical compositions including one or more APOC3 RNAi agents can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

In some embodiments, disclosed herein are compositions for delivering an APOC3 RNAi agent to a liver cell in vivo, wherein the composition includes an APOC3 RNAi agent conjugated or linked to a targeting group. In some embodiments, the targeting group is an asialoglycoprotein receptor ligand. In some embodiments, compositions for delivering an APOC3 RNAi agent to a liver cell in vivo are described, wherein the composition includes an APOC3 RNAi agent linked to a targeting ligand that includes N-acetyl-galactosamine.

In some embodiments, the APOC3 RNAi agents described herein can include one or more targeting groups having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 7.

In some embodiments, the APOC3 RNAi agents described herein include one targeting group at the 5' end of the sense strand having the structure of (NAG25), (NAG25) s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 7.

The described APOC3 RNAi agents and/or compositions that include APOC3 RNAi agents can be used in methods for therapeutic treatment of diseases or conditions caused by elevated TG levels. Such methods include administration of an APOC3 RNAi agent as described herein to a subject, e.g., a human or animal subject. In some embodiments, one or more of the described APOC3 RNAi agents are administered to a subject, such as a mammal, in a pharmaceutically acceptable carrier or diluent. In some embodiments, the mammal is a human.

The APOC3 RNAi agents disclosed herein can be incorporated into a composition comprising one or more disclosed APOC3 RNAi agent and at least one pharmaceutically acceptable excipient. In some embodiments, the compositions disclosed herein comprising one or more of the disclosed APOC3 RNAi agents and at least one pharmaceutically acceptable excipient is a pharmaceutical composition.

In some embodiments, the compositions comprising one or more disclosed APOC3 RNAi agents and at least one pharmaceutically acceptable excipient can further comprise one or more additional therapeutics or treatments.

In some embodiments, the compositions described herein comprising one or more APOC3 RNAi agents are packaged in a kit, container, pack, dispenser, pre-filled syringes, or vials. In some embodiments, the compositions described herein are administered parenterally.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCUC (SEQ ID NO:3). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UCACUGAGAAUACUGUCCCUC (SEQ ID NO:3), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCUC (SEQ ID NO:3), wherein SEQ ID NO:3 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') usCfsasCfuGfagaauAfcUfgUfcCfcUfsc (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1I showing all internucleoside linkages). In some embodiments, an APOC3 RNAi agent disclosed herein includes an antisense strand that consists of, consists essentially of, or comprises the nucleotide sequence (5'→3') usCfsasCfuGfagaauAfcUfgUfcCfcUfsc (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCGU (SEQ ID NO:5). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UCACUGAGAAUACUGUCCCGU (SEQ ID NO:5), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACU-GUCCCGU (SEQ ID NO:5), wherein SEQ ID NO:5 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') usCfsasCfuGfagaauAfcUfgUfcCfcGfsu (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1I showing all internucleoside linkages). In some embodiments, an APOC3 RNAi agent disclosed herein includes an antisense strand that consists of, consists essentially of, or comprises the nucleotide sequence (5'→3') usCfsasCfuGfagaauAfcUfgUfcCfcGfsu (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') usCfsascugagaauAfcUfgUfcCfcUfsc (SEQ ID NO:6), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1I showing all internucleoside linkages). In some embodiments, an APOC3 RNAi agent disclosed herein includes an antisense strand that consists of, consists essentially of, or comprises the nucleotide sequence (5'→3') usCfsascugagaauAfcUfgUfcCfcUfsc (SEQ ID NO:6), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UUCUUGUCCAGCUUUAUUGGC (SEQ ID NO:8). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UUCUUGUCCAGCUUUAUUGGC (SEQ ID NO:8), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UUCUUGUCCAGC-UUUAUUGGC (SEQ ID NO:8), wherein SEQ ID NO:8 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') usUfscsUfuGfuCfcAfgCfuUfuA-fuUfgGfsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an APOC3 RNAi agent disclosed herein includes an antisense strand that consists of, consists essentially of, or comprises the nucleotide sequence (5'→3') usUfscsUfuGfuCfcAfgCfuUfuA-fuUfgGfsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCCUUUUAGGG (SEQ ID NO:10). In some embodiments, an APOC3 RNAi agent disclosed herein includes an antisense strand that consists of, consists essentially of, or comprises a nucleotide sequence differing by no more than 1 nucleotide from the nucleotide sequence (5'→3') AGAAUACUGUCCCUUUUAGGG (SEQ ID NO:10), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCC-UUUUAGGG (SEQ ID NO:10), wherein SEQ ID NO:10 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') asGfsasAfuAfcUfgUfcCfcUfuU-fuAfgGfsg (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an APOC3 RNAi agent disclosed herein includes an antisense strand that consists of, consists essentially of, or comprises the nucleotide sequence (5'→3') asGfsasAfuAfcUfgUfcCfcUfuU-fuAfgGfsg (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCCUUUUAAGC (SEQ ID NO:12). In some embodiments, an APOC3 RNAi agent disclosed herein includes an antisense strand that consists of, consists essentially of, or comprises a nucleotide sequence differing by no more than 1 nucleotide from the nucleotide sequence (5'→3') AGAAUACUGUCCCUUUUAAGC (SEQ ID NO:12), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCCUUUUAAGC (SEQ ID NO:12), wherein SEQ ID NO:12 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') asGfsasAfuAfcUfgUfcCfcUfuUfuAfaGfsc (SEQ ID NO:11), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an APOC3 RNAi agent disclosed herein includes an antisense strand that consists of, consists essentially of, or comprises the nucleotide sequence (5'→3') asGfsasAfuAfcUfgUfcCfcUfuUfuAfaGfsc (SEQ ID NO:11), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UGAGAAUACUGUCCCUUUGCC (SEQ ID NO:14). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UGAGAAUACUGUCCCUUUGCC (SEQ ID NO:14), wherein all or substantially all of the nucleotides are modified nucleotides. In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UGAGAAUACUGUCCCUUUGCC (SEQ ID NO:14), wherein SEQ ID NO:14 is located at positions 1-21 (5'→3') of the antisense strand.

In some embodiments, an APOC3 RNAi agent disclosed herein includes an antisense strand that consists of, consists essentially of, or comprises a modified nucleotide sequence differing by no more than 1 nucleotide from the nucleotide sequence (5'→3') usGfsasGfaAfuAfcUfgUfcCfcUfuUfgcsc (SEQ ID NO:13), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an APOC3 RNAi agent disclosed herein includes an antisense strand that consists of, consists essentially of, or comprises the nucleotide sequence (5'→3') usGfsasGfaAfuAfcUfgUfcCfcUfuUfgcsc (SEQ ID NO:13), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCUC (SEQ ID NO:3) and a sense strand that consists of, consists essentially of, or comprises a nucleobase sequence differing by 0 or 1 nucleobases from the nucleotide sequence (5'→3') GAGGGAC-AGUAUUCUCAGUIA (SEQ ID NO:16). (I represents an inosine nucleotide.) In some embodiments, an APOC3 RNAi agent disclosed herein includes an antisense strand that consists of, consists essentially of, or comprises a nucleotide sequence differing by no more than 1 nucleotide from the nucleotide sequence (5'→3') UCACUGAGAAUA-CUGUCCCUC (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') GAGGGAC-AGUAUUCUCAGUIA (SEQ ID NO:16), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCGU (SEQ ID NO:5) and a sense strand that consists of, consists essentially of, or comprises a nucleobase sequence differing by 0 or 1 nucleobases from the nucleotide sequence (5'→3') ACGGGAC-AGUAUUCUCAGUIA (SEQ ID NO:18). (I represents an inosine nucleotide.) In some embodiments, an APOC3 RNAi agent disclosed herein includes an antisense strand that consists of, consists essentially of, or comprises a nucleotide sequence differing by no more than 1 nucleotide from the nucleotide sequence (5'→3') UCACUGAGAAUA-CUGUCCCGU (SEQ ID NO:5), wherein all or substantially all of the nucleotides are modified nucleotides, and a sense strand that consists of, consists essentially of, or comprises a nucleotide sequence differing by no more than 1 nucleotide from the nucleotide sequence (5'→3') ACGGGAC-AGUAUUCUCAGUIA (SEQ ID NO:18), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UCACUGAGAAUACUGUCCCUC (SEQ ID NO:3) and a sense strand that consists of, consists essentially of, or comprises a nucleobase sequence differing by 0 or 1 nucleobases from the nucleotide sequence (5'→3') GAGGGAC- AGUAUUCUCAGUGA (SEQ ID NO:21). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UCACUGAGAAUACUGUCCCUC (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') GAGGGACAGUAUUCUCAGUGA (SEQ ID NO:21), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UUCUUGUCCAGCUUUAUUGGC (SEQ ID NO:8) and a sense strand that consists of, consists essentially of, or comprises a nucleobase sequence differing by 0 or 1 nucleobases from the nucleotide sequence (5'→3') GCCAAUAAAGCUGGACAAGAA (SEQ ID NO:23). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UUCUUGUCCAGCUUUAUUGGC (SEQ ID NO:8), wherein all or substantially all of the nucleotides are modified nucleotides, and a sense strand that consists of, consists essentially of, or comprises a nucleotide sequence differing by no more than 1 nucleotide from the nucleotide sequence (5'→3') GCCAAUAAAGCUGGACAAGAA (SEQ ID NO:23), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UUCUUGUCCAGCUUUAUUGGC (SEQ ID NO:8) and a sense strand that consists of, consists essentially of, or comprises a nucleobase sequence differing by 0 or 1 nucleobases from the nucleotide sequence (5'→3') GCCAAUAAAICUGGACAAGAA (SEQ ID NO:25). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UUCUUGUCCAGCUUUAUUGGC (SEQ ID NO:8), wherein all or substantially all of the nucleotides are modified nucleotides, and a sense strand that consists of, consists essentially of, or comprises a nucleotide sequence differing by no more than 1 nucleotide from the nucleotide sequence (5'→3') GCCAAUAAAICUGGACAAGAA (SEQ ID NO:25), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCCUUUUAGGG (SEQ ID NO:10) and a sense strand that consists of, consists essentially of, or comprises a nucleobase sequence differing by 0 or 1 nucleobases from the nucleotide sequence (5'→3') CCCUAAAAGGGACAGUAUUCU (SEQ ID NO:27). In some embodiments, an APOC3 RNAi agent disclosed herein includes an antisense strand that consists of, consists essentially of, or comprises a nucleotide sequence differing by no more than 1 nucleotide from the nucleotide sequence (5'→3') AGAAUACUGUCCCUUUUAGGG (SEQ ID NO:10), wherein all or substantially all of the nucleotides are modified nucleotides, and a sense strand that consists of, consists essentially of, or comprises a nucleotide sequence differing by no more than 1 nucleotide from the nucleotide sequence (5'→3') CCCUAAAAGGGACAGUAUUCU (SEQ ID NO:27), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') AGAAUACUGUCCCUUUUAAGC (SEQ ID NO:12) and a sense strand that consists of, consists essentially of, or comprises a nucleobase sequence differing by 0 or 1 nucleobases from the nucleotide sequence (5'→3') GCUUAAAAGGGACAGUAUUCU (SEQ ID NO:29). In some embodiments, an APOC3 RNAi agent disclosed herein includes an antisense strand that consists of, consists essentially of, or comprises a nucleotide sequence differing by no more than 1 nucleotide from the nucleotide sequence (5'→3') AGAAUACUGUCCCUUUUAAGC (SEQ ID NO:12), wherein all or substantially all of the nucleotides are modified nucleotides, and a sense strand that consists of, consists essentially of, or comprises a nucleotide sequence differing by no more than 1 nucleotide from the nucleotide sequence (5'→3') GCUUAAAAGGGACAGUAUUCU (SEQ ID NO:29), wherein all or substantially all of the nucleotides are modified nucleotides.

In some embodiments, an APOC3 RNAi agent disclosed herein includes an antisense strand that consists of, consists essentially of, or comprises a nucleobase sequence differing by 0 or 1 nucleobases from the nucleotide sequence (5'→3') UGAGAAUACUGUCCCUUUGCC (SEQ ID NO:14) and a sense strand that consists of, consists essentially of, or comprises a nucleobase sequence differing by 0 or 1 nucleobases from the nucleotide sequence (5'→3') GGCAAAGGGACAGUAUUCUCA (SEQ ID NO:31). In some embodiments, an APOC3 RNAi agent disclosed herein includes an antisense strand that consists of, consists essentially of, or comprises a nucleotide sequence differing by no more than 1 nucleotide from the nucleotide sequence (5'→3') UGAGAAUACUGUCCCUUUGCC (SEQ ID NO:14), wherein all or substantially all of the nucleotides are modified nucleotides, and a sense strand that consists of, consists essentially of, or comprises a nucleotide sequence differing by no more than 1 nucleotide from the nucleotide sequence (5'→3') GGCAAAGGGACAGUAUUCUCA (SEQ ID NO:31), wherein all or substantially all of the nucleotides are modified nucleotides.

In some embodiments, an APOC3 RNAi agent disclosed herein includes an antisense strand that consists of, consists essentially of, or comprises the modified nucleotide sequence (5'→3') usCfsasCfuGfagaauAfcUfgUfcCfcUfsc (SEQ ID NO:2), and a sense strand that consists of, consists essentially of, or comprises the modified nucleotide sequence (5'→3') gagggacaGfUfAfuucucaguia (SEQ ID NO:15), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usCfsasCfuGfagaauAfcUfgUfcCfcUfsc (SEQ ID NO:2), and a sense strand that consists of, consists essentially of, or comprises the modified nucleotide sequence (5'→3') gagggacaGfUfA-fuucucaguia (SEQ ID NO:15), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') usCfsasCfuGfagaauAfcUfgUfcCfcGfsu (SEQ ID NO:4), and a sense strand that consists of, consists essentially of, or comprises the modified nucleotide sequence (5'→3') acgggacaGfUfAfuucucaguia (SEQ ID NO:17), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usCfsasCfuGf-agaauAfcUfgUfcCfcGfsu (SEQ ID NO:4), and a sense strand that consists of, consists essentially of, or comprises the modified nucleotide sequence (5'→3') acgggacaGfUfA-fuucucaguia (SEQ ID NO:17), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'-3') usCfsascugagaauAfcUfgUfcCfcUfsc (SEQ ID NO:6), and a sense strand that consists of, consists essentially of, or comprises the modified nucleotide sequence (5'→3') gagggacaGfuAfuUfcucaguia (SEQ ID NO:19), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usCfsas-cugagaauAfcUfgUfcCfcUfsc (SEQ ID NO:6), and a sense strand that consists of, consists essentially of, or comprises the modified nucleotide sequence (5'→3') gagggacaGfuA-fuUfcucaguia (SEQ ID NO:19), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') usCfsasCfuGfagaauAfcUfgUfcCfcUfsc (SEQ ID NO:2), and a sense strand that consists of, consists essentially of, or comprises the modified nucleotide sequence (5'→3') gagggacaGfUfAfuucucaguga (SEQ ID NO:20), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usCfsasCfuGf-agaauAfcUfgUfcCfcUfsc (SEQ ID NO:2), and a sense strand that consists of, consists essentially of, or comprises the modified nucleotide sequence (5'→3') gagggacaGfUfA-fuucucaguga (SEQ ID NO:20), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') usUfscsUfuGfuCfcAfgCfuUfuA-fuUfgGfsc (SEQ ID NO:7), and a sense strand that consists of, consists essentially of, or comprises the modified nucleotide sequence (5'→3') gccaauaaAfGfCfuggacaagaa (SEQ ID NO:22), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usUfscsU-fuGfuCfcAfgCfuUfuAfuUfgGfsc (SEQ ID NO:7), and a sense strand that consists of, consists essentially of, or comprises the modified nucleotide sequence (5'→3') gccaauaaAfGfCfuggacaagaa (SEQ ID NO:22), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') usUfscsUfuGfuCfcAfgCfuUfuA-fuUfgGfsc (SEQ ID NO:7), and a sense strand that consists of, consists essentially of, or comprises the modified nucleotide sequence (5'→3') gccaauaaAfIfCfuggacaagaa (SEQ ID NO:24), wherein a, c, g, and u represent 2'-O-methyl adenosine, cytidine, guanosine, or uridine, respectively; Af, Cf, Gf, If, and Uf represent 2'-fluoro adenosine, cytidine, guanosine, inosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usUfscsU-fuGfuCfcAfgCfuUfuAfuUfgGfsc (SEQ ID NO:7), and a sense strand that consists of, consists essentially of, or comprises the modified nucleotide sequence (5'→3') gccaauaaAfIfCfuggacaagaa (SEQ ID NO:24), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') asGfsasAfuAfcUfgUfcCfcUfuUfuAfgGfsg (SEQ ID NO:9), and a sense strand that consists of, consists essentially of, or comprises the modified nucleotide sequence (5'→3') cccuaaaaGfGfGfacaguauucu (SEQ ID NO:26), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') asGfsasAfuAfcUfgUfcCfcUfuUfuAfgGfsg (SEQ ID NO:9), and a sense strand that consists of, consists essentially of, or comprises the modified nucleotide sequence (5'→3') cccuaaaaGfGfGfacaguauucu (SEQ ID NO:26), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') asGfsasAfuAfcUfgUfcCfcUfuUfuAfuAf-aGfsc (SEQ ID NO:11), and a sense strand that consists of, consists essentially of, or comprises the modified nucleotide sequence (5'→3') gcuuaaaaGfGfGfacaguauucu (SEQ ID NO:28), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') asGfsasAfuAfcUfgUfcCfcUfuUfuAfaGfsc (SEQ ID NO:11), and a sense strand that consists of, consists essentially of, or comprises the modified nucleotide sequence (5'→3') gcuuaaaaGfGfGfacaguauucu (SEQ ID NO:28), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises the modified nucleotide sequence (5'→3') usGfsasGfaAfuAfcUfgUfcCfcUfuUfgcsc (SEQ ID NO:13), and a sense strand that consists of, consists essentially of, or comprises the modified nucleotide sequence (5'→3') ggcaaaggGfAfCfaguauucuca (SEQ ID NO:30), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an APOC3 RNAi agent disclosed herein includes an antisense strand that consists of, consists essentially of, or comprises the modified nucleotide sequence (5'→3') usGfsasGfaAfuAfcUfgUfcCfcUfuUfgcsc (SEQ ID NO:13), and a sense strand that consists of, consists essentially of, or comprises the modified nucleotide sequence (5'→3') ggcaaaggGfAfCfaguauucuca (SEQ ID NO:30), and wherein the sense strand further includes inverted abasic residues at the 3' terminal end and at the 5' end of the nucleotide sequence, and the sense strand also includes a targeting ligand that is cova-lently linked to the 5' terminal end, wherein the targeting ligand includes N-acetyl-galactosamine.

In some embodiments, an APOC3 RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 3)
UCACUGAGAAUACUGUCCCUC;

(SEQ ID NO: 5)
UCACUGAGAAUACUGUCCCGU;

(SEQ ID NO: 8)
UUCUUGUCCAGCUUUAUUGGC;

(SEQ ID NO: 10)
AGAAUACUGUCCCUUUUAGGG;

(SEQ ID NO: 12)
AGAAUACUGUCCCUUUUAAGC;
or
                                    (SEQ ID NO: 14)
UGAGAAUACUGUCCCUUUGCC;
``` wherein the APOC3 RNAi agent further includes a sense strand that is at least partially complementary to the antisense strand; and wherein all or substantially all of the nucleotides on both the antisense strand and the sense strand are modified nucleotides.

In some embodiments, an APOC3 RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 3)
UCACUGAGAAUACUGUCCCUC;

(SEQ ID NO: 5)
UCACUGAGAAUACUGUCCCGU;

(SEQ ID NO: 8)
UUCUUGUCCAGCUUUAUUGGC;

(SEQ ID NO: 10)
AGAAUACUGUCCCUUUUAGGG;

(SEQ ID NO: 12)
AGAAUACUGUCCCUUUUAAGC;
or
                                    (SEQ ID NO: 14)
UGAGAAUACUGUCCCUUUGCC;
``` wherein the APOC3 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises a nucleotide sequence that differs by 0 or 1 nucleotides from one of the following nucleotide sequences (5'→3'):

UCACUGAGAAUACUGUCCCUC; (SEQ ID NO: 3)

UCACUGAGAAUACUGUCCCGU; (SEQ ID NO: 5)

UUCUUGUCCAGCUUUAUUGGC; (SEQ ID NO: 8)

AGAAUACUGUCCCUUUUAGGG; (SEQ ID NO: 10)

AGAAUACUGUCCCUUUUAAGC; (SEQ ID NO: 12)
or

UGAGAAUACUGUCCCUUUGCC; (SEQ ID NO: 14)

wherein the APOC3 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine; and wherein the respective antisense strand sequence is located at positions 1-21 of the antisense strand.

In some embodiments, an APOC3 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

UCACUGAGAAUACUGUCCCUC (SEQ ID NO: 3)
and
GAGGGACAGUAUUCUCAGUIA; (SEQ ID NO: 16)

UCACUGAGAAUACUGUCCCGU (SEQ ID NO: 5)
and
ACGGGACAGUAUUCUCAGUIA; (SEQ ID NO: 18)

UCACUGAGAAUACUGUCCCUC (SEQ ID NO: 3)
and
GAGGGACAGUAUUCUCAGUGA; (SEQ ID NO: 21)

UUCUUGUCCAGCUUUAUUGGC (SEQ ID NO: 8)
and
GCCAAUAAAGCUGGACAAGAA; (SEQ ID NO: 23)

UUCUUGUCCAGCUUUAUUGGC (SEQ ID NO: 8)
and
GCCAAUAAAICUGGACAAGAA; (SEQ ID NO: 25)

AGAAUACUGUCCCUUUUAGGG (SEQ ID NO: 10)
and
CCCUAAAAGGGACAGUAUUCU; (SEQ ID NO: 27)

AGAAUACUGUCCCUUUUAAGC (SEQ ID NO: 12)
and
GCUUAAAAGGGACAGUAUUCU; (SEQ ID NO: 29)
or UGAGAAUACUGUCCCUUUGCC (SEQ ID NO: 14)
and
GGCAAAGGGACAGUAUUCUCA; (SEQ ID NO: 31)

wherein all or substantially all of the nucleotides on both the antisense strand and the sense strand are modified nucleotides.

In some embodiments, an APOC3 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

UCACUGAGAAUACUGUCCCUC (SEQ ID NO: 3)
and
GAGGGACAGUAUUCUCAGUIA; (SEQ ID NO: 16)

UCACUGAGAAUACUGUCCCGU (SEQ ID NO: 5)
and
ACGGGACAGUAUUCUCAGUIA; (SEQ ID NO: 18)

UCACUGAGAAUACUGUCCCUC (SEQ ID NO: 3)
and
GAGGGACAGUAUUCUCAGUGA; (SEQ ID NO: 21)

UUCUUGUCCAGCUUUAUUGGC (SEQ ID NO: 8)
and
GCCAAUAAAGCUGGACAAGAA; (SEQ ID NO: 23)

UUCUUGUCCAGCUUUAUUGGC (SEQ ID NO: 8)
and
GCCAAUAAAICUGGACAAGAA; (SEQ ID NO: 25)

AGAAUACUGUCCCUUUUAGGG (SEQ ID NO: 10)
and
CCCUAAAAGGGACAGUAUUCU; (SEQ ID NO: 27)

AGAAUACUGUCCCUUUUAAGC (SEQ ID NO: 12)
and
GCUUAAAAGGGACAGUAUUCU; (SEQ ID NO: 29)
or (SEQ ID NO: 14)
UGAGAAUACUGUCCCUUUGCC
and (SEQ ID NO: 31)
GGCAAAGGGACAGUAUUCUCA;

wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 2)
usCfsasCfuGfagaauAfcUfgUfcCfcUfsc;

(SEQ ID NO: 4)
usCfsasCfuGfagaauAfcUfgUfcCfcGfsu;

(SEQ ID NO: 6)
usCfsascugagaauAfcUfgUfcCfcUfsc;

(SEQ ID NO: 7)
usUfscsUfuGfuCfcAfgCfuUfuAfuUfgGfsc;

(SEQ ID NO: 9)
asGfsasAfuAfcUfgUfcCfcUfuUfuAfgGfsg;

(SEQ ID NO: 11)
asGfsasAfuAfcUfgUfcCfcUfuUfuAfaGfsc;
or (SEQ ID NO: 13)
usGfsasGfaAfuAfcUfgUfcCfcUfuUfgcsc;

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage; and wherein the APOC3 RNAi agent further includes the sense strand that is at least partially complementary to the antisense strand; and wherein all or substantially all of the nucleotides on the sense strand are modified nucleotides.

In some embodiments, an APOC3 RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 2)
usCfsasCfuGfagaauAfcUfgUfcCfcUfsc;

(SEQ ID NO: 4)
usCfsasCfuGfagaauAfcUfgUfcCfcGfsu;

(SEQ ID NO: 6)
usCfsascugagaauAfcUfgUfcCfcUfsc;

(SEQ ID NO: 7)
usUfscsUfuGfuCfcAfgCfuUfuAfuUfgGfsc;

(SEQ ID NO: 9)
asGfsasAfuAfcUfgUfcCfcUfuUfuAfgGfsg;

(SEQ ID NO: 11)
asGfsasAfuAfcUfgUfcCfcUfuUfuAfaGfsc;
or (SEQ ID NO: 13)
usGfsasGfaAfuAfcUfgUfcCfcUfuUfgcsc;

wherein the APOC3 RNAi agent further includes the sense strand that is at least partially complementary to the antisense strand; wherein all or substantially all of the nucleotides on the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

(SEQ ID NO: 2)
usCfsasCfuGfagaauAfcUfgUfcCfcUfsc
and (SEQ ID NO: 15)
gagggacaGfUfAfuucucaguia;

(SEQ ID NO: 4)
usCfsasCfuGfagaauAfcUfgUfcCfcGfsu
and (SEQ ID NO: 17)
acgggacaGfUfAfuucucaguia;

(SEQ ID NO: 6)
usCfsascugagaauAfcUfgUfcCfcUfsc
and (SEQ ID NO: 19)
gagggacaGfuAfuUfcucaguia;

(SEQ ID NO: 2)
usCfsasCfuGfagaauAfcUfgUfcCfcUfsc
and (SEQ ID NO: 20)
gagggacaGfUfAfuucucaguga;

(SEQ ID NO: 7)
usUfscsUfuGfuCfcAfgCfuUfuAfuUfgGfsc
and (SEQ ID NO: 22)
gccaauaaAfGfCfuggacaagaa;

(SEQ ID NO: 7)
usUfscsUfuGfuCfcAfgCfuUfuAfuUfgGfsc
and (SEQ ID NO: 24)
gccaauaaAfIfCfuggacaagaa;

(SEQ ID NO: 9)
asGfsasAfuAfcUfgUfcCfcUfuUfuAfgGfsg
and (SEQ ID NO: 26)
cccuaaaaGfGfGfacaguauucu;

```
                                                    (SEQ ID NO: 11)
asGfsasAfuAfcUfgUfcCfcUfuUfuAfaGfsc
and (SEQ ID NO: 28)
gcuuaaaaGfGfGfacaguauucu;
or (SEQ ID NO: 13)
usGfsasGfaAfuAfcUfgUfcCfcUfuUfgcsc
and (SEQ ID NO: 30)
ggcaaaggGfAfCfaguauucuca;
``` wherein a, c, g, i, and u represent 2'-O-methyl adenosine, cytidine, guanosine, inosine, or uridine, respectively; Af, Cf, Gf, If, and Uf represent 2'-fluoro adenosine, cytidine, guanosine, inosine or uridine, respectively; and s represents a phosphorothioate linkage.

In some embodiments, an APOC3 RNAi agent disclosed herein includes an antisense strand and a sense strand that consists of, consists essentially of, or comprises one of the following nucleotide sequence pairs (5'→3'):

```
                                                    (SEQ ID NO: 2)
usCfsasCfuGfagaauAfcUfgUfcCfcUfsc
and (SEQ ID NO: 15)
gagggacaGfUfAfuucucaguia;

(SEQ ID NO: 4)
usCfsasCfuGfagaauAfcUfgUfcCfcGfsu
and (SEQ ID NO: 17)
acgggacaGfUfAfuucucaguia;

(SEQ ID NO: 6)
usCfsascugagaauAfcUfgUfcCfcUfsc
and (SEQ ID NO: 19)
gagggacaGfuAfuUfcucaguia;

(SEQ ID NO: 2)
usCfsasCfuGfagaauAfcUfgUfcCfcUfsc
and (SEQ ID NO: 20)
gagggacaGfUfAfuucucaguga;

(SEQ ID NO: 7)
usUfscsUfuGfuCfcAfgCfuUfuAfuUfgGfsc
and (SEQ ID NO: 22)
gccaauaaAfGfCfuggacaagaa;

(SEQ ID NO: 7)
usUfscsUfuGfuCfcAfgCfuUfuAfuUfgGfsc
and (SEQ ID NO: 24)
gccaauaaAfIfCfuggacaagaa;

(SEQ ID NO: 9)
asGfsasAfuAfcUfgUfcCfcUfuUfuAfgGfsg
and (SEQ ID NO: 26)
cccuaaaaGfGfGfacaguauucu;

(SEQ ID NO: 11)
asGfsasAfuAfcUfgUfcCfcUfuUfuAfaGfsc
and (SEQ ID NO: 28)
gcuuaaaaGfGfGfacaguauucu;
or (SEQ ID NO: 13)
usGfsasGfaAfuAfcUfgUfcCfcUfuUfgcsc
and (SEQ ID NO: 30)
ggcaaaggGfAfCfaguauucuca;
``` wherein a, c, g, i, and u represent 2'-O-methyl adenosine, cytidine, guanosine, inosine, or uridine, respectively; Af, Cf, Gf, If, and Uf represent 2'-fluoro adenosine, cytidine, guanosine, inosine or uridine, respectively; s represents a phosphorothioate linkage; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an APOC3 RNAi agent disclosed herein includes an antisense strand that includes a nucleobase sequence that differs by 0 or 1 nucleobases from the nucleotide sequences selected from the group consisting of (5'→3'):

```
                                                    (SEQ ID NO: 49)
UCACUGAGAAUACUGUCCC;

(SEQ ID NO: 53)
UUCUUGUCCAGCUUUAUUG;

(SEQ ID NO: 57)
AGAAUACUGUCCCUUUUAA;

(SEQ ID NO: 58)
AGAAUACUGUCCCUUUUAG;
or (SEQ ID NO: 106)
UGAGAAUACUGUCCCUUUG.
```

In some embodiments, an APOC3 RNAi agent disclosed herein includes an antisense strand that includes a nucleobase sequence that differs by 0 or 1 nucleobases from the nucleotide sequences selected from the group consisting of (5'→3'):

```
                                                    (SEQ ID NO: 49)
UCACUGAGAAUACUGUCCC;

(SEQ ID NO: 53)
UUCUUGUCCAGCUUUAUUG;

(SEQ ID NO: 57)
AGAAUACUGUCCCUUUUAA;

(SEQ ID NO: 58)
AGAAUACUGUCCCUUUUAG;
or (SEQ ID NO: 106)
UGAGAAUACUGUCCCUUUG.
```
and
wherein all or substantially all of the nucleotides are modified nucleotides.

In some embodiments, an APOC3 RNAi agent disclosed herein includes an antisense strand that includes a nucleobase sequence that differs by 0 or 1 nucleobases from the nucleotide sequences selected from the group consisting of (5'→3'):

UCACUGAGAAUACUGUCCC;                (SEQ ID NO: 49)

UUCUUGUCCAGCUUUAUUG;                (SEQ ID NO: 53)

AGAAUACUGUCCCUUUUAA;                (SEQ ID NO: 57)

AGAAUACUGUCCCUUUUAG;                (SEQ ID NO: 58)
or

UGAGAAUACUGUCCCUUUG.                (SEQ ID NO: 106)

and wherein all or substantially all of the nucleotides are modified nucleotides, and wherein SEQ ID NO:49, SEQ ID NO:53, SEQ ID NO:57, SEQ ID NO:58, or SEQ ID NO:106, respectively, is located at nucleotide positions 1-19 (5'→3') of the antisense strand.

In some embodiments, an APOC3 RNAi agent disclosed herein includes an antisense strand and a sense strand that each include a nucleobase sequences that differs by 0 or 1 nucleobases from the nucleotide sequence pairs selected from the group consisting of (5'→3'):

UCACUGAGAAUACUGUCCC                 (SEQ ID NO: 49)
and

GGGACAGUAUUCUCAGUIA;                (SEQ ID NO: 113)

UCACUGAGAAUACUGUCCC                 (SEQ ID NO: 49)
and

GGGACAGUAUUCUCAGUGA;                (SEQ ID NO: 112)

UUCUUGUCCAGCUUUAUUG                 (SEQ ID NO: 53)
and

CAAUAAAGCUGGACAAGAA;                (SEQ ID NO: 117)

UUCUUGUCCAGCUUUAUUG                 (SEQ ID NO: 53)
and

CAAUAAAICUGGACAAGAA;                (SEQ ID NO: 118)

AGAAUACUGUCCCUUUUAA                 (SEQ ID NO: 57)
and

UUAAAAGGGACAGUAUUCU;                (SEQ ID NO: 122)

AGAAUACUGUCCCUUUUAG                 (SEQ ID NO: 58)
and

CUAAAAGGGACAGUAUUCU;                (SEQ ID NO: 123)
or

UGAGAAUACUGUCCCUUUG                 (SEQ ID NO: 106)
and

CAAAGGGACAGUAUUCUCA.                (SEQ ID NO: 171)

and wherein all or substantially all of the nucleotides are modified nucleotides.

In some embodiments, an APOC3 RNAi agent disclosed herein includes an antisense strand and a sense strand that each include a nucleobase sequences that differs by 0 or 1 nucleobases from the nucleotide sequence pairs selected from the group consisting of (5'→3'):

UCACUGAGAAUACUGUCCC                 (SEQ ID NO: 49)
and

GGGACAGUAUUCUCAGUIA;                (SEQ ID NO: 113)

UCACUGAGAAUACUGUCCC                 (SEQ ID NO: 49)
and

GGGACAGUAUUCUCAGUGA;                (SEQ ID NO: 112)

UUCUUGUCCAGCUUUAUUG                 (SEQ ID NO: 53)
and

CAAUAAAGCUGGACAAGAA;                (SEQ ID NO: 117)

UUCUUGUCCAGCUUUAUUG                 (SEQ ID NO: 53)
and

CAAUAAAICUGGACAAGAA;                (SEQ ID NO: 118)

AGAAUACUGUCCCUUUUAA                 (SEQ ID NO: 57)
and

UUAAAAGGGACAGUAUUCU;                (SEQ ID NO: 122)

AGAAUACUGUCCCUUUUAG                 (SEQ ID NO: 58)
and

CUAAAAGGGACAGUAUUCU;                (SEQ ID NO: 123)
or

UGAGAAUACUGUCCCUUUG                 (SEQ ID NO: 106)
and

CAAAGGGACAGUAUUCUCA.                (SEQ ID NO: 171)

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e., APOC3 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an APOC3 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the preventative treatment, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol  as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other objects, features, aspects, and advantages of the invention will be apparent from the following detailed description, accompanying figures, and from the claims.

BRIEF DESCRIPTION OF THE DRAWINGS

FIG. 1A. Schematic diagram of the modified sense and antisense strands of APOC3 RNAi agent AD05251 (see Tables 4-6), conjugated to a tridentate N-acetyl-galactosamine-containing targeting ligand having the structure of (NAG37)s (see Table 7). FIG. 1A discloses SEQ ID NOs: 2 and 501.

The following abbreviations are used in FIGS. 1A to 1I:
a, c, g, i, and u are 2'-O-methyl modified nucleotides (for i, the nucleobase is hypoxanthine (i.e., the base for inosine nucleotides)); Af, Cf, Gf, If, and Uf are 2'-fluoro modified nucleotides (for I, the nucleobase is hypoxanthine (i.e., the base for inosine nucleotides); p is a phosphodiester linkage; s is a phosphorothioate linkage; invAb is an inverted abasic (deoxyribose) residue (see Table 7); and (NAG37)s is a tridentate N-acetyl-galactosamine targeting ligand having the structure depicted in Table 7.

FIG. 1B. Schematic diagram of the modified sense and antisense strands of APOC3 RNAi agent AD05876 (see Tables 4-6), conjugated to a tridentate N-acetyl-galactosamine-containing targeting ligand having the structure of (NAG37)s (see Table 7). FIG. 1B discloses SEQ ID NOs: 4 and 572.

FIG. 1C. Schematic diagram of the modified sense and antisense strands of APOC3 RNAi agent AD05769 (see Tables 4-6), conjugated to a tridentate N-acetyl-galactosamine-containing targeting ligand having the structure of (NAG37)s (see Table 7). FIG. 1C discloses SEQ ID NOs: 6 and 557.

FIG. 1D. Schematic diagram of the modified sense and antisense strands of APOC3 RNAi agent AD05169 (see Tables 4-6), conjugated to a tridentate N-acetyl-galactosamine-containing targeting ligand having the structure of (NAG37)s (see Table 7). FIG. 1D discloses SEQ ID NOs: 2 and 482.

FIG. 1E. Schematic diagram of the modified sense and antisense strands of APOC3 RNAi agent AD05220 (see Tables 4-6), conjugated to a tridentate N-acetyl-galactosamine-containing targeting ligand having the structure of (NAG37)s (see Table 7). FIG. 1E discloses SEQ ID NOs: 7 and 494.

FIG. 1F. Schematic diagram of the modified sense and antisense strands of APOC3 RNAi agent AD05547 (see Tables 4-6), conjugated to a tridentate N-acetyl-galactosamine-containing targeting ligand having the structure of (NAG37)s (see Table 7). FIG. 1F discloses SEQ ID NOs: 7 and 545.

FIG. 1G. Schematic diagram of the modified sense and antisense strands of APOC3 RNAi agent AD05299 (see Tables 4-6), conjugated to a tridentate N-acetyl-galactosamine-containing targeting ligand having the structure of (NAG37)s (see Table 7). FIG. 1G discloses SEQ ID NOs: 9 and 521.

FIG. 1H. Schematic diagram of the modified sense and antisense strands of APOC3 RNAi agent AD05223 (see Tables 4-6), conjugated to a tridentate N-acetyl-galactosamine-containing targeting ligand having the structure of (NAG37)s (see Table 7). FIG. 1H discloses SEQ ID NOs: 11 and 497.

FIG. 1I. Schematic diagram of the modified sense and antisense strands of APOC3 RNAi agent AD05171 (see Tables 4-6), conjugated to a tridentate N-acetyl-galactosamine-containing targeting ligand having the structure of (NAG37)s (see Table 7). FIG. 1A discloses SEQ ID NOs: 13 and 483.

Figure 2A:
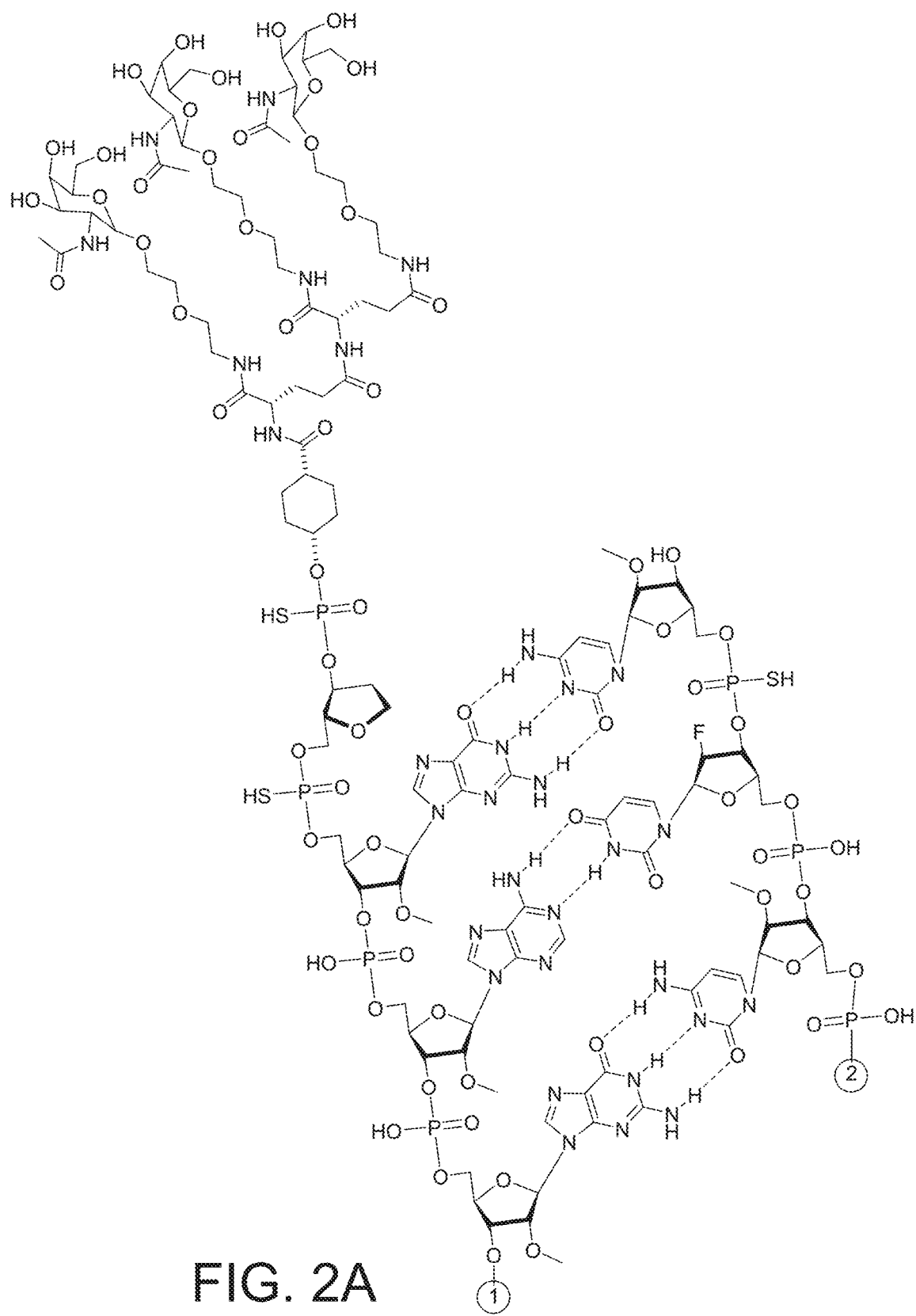
Figure 2B:
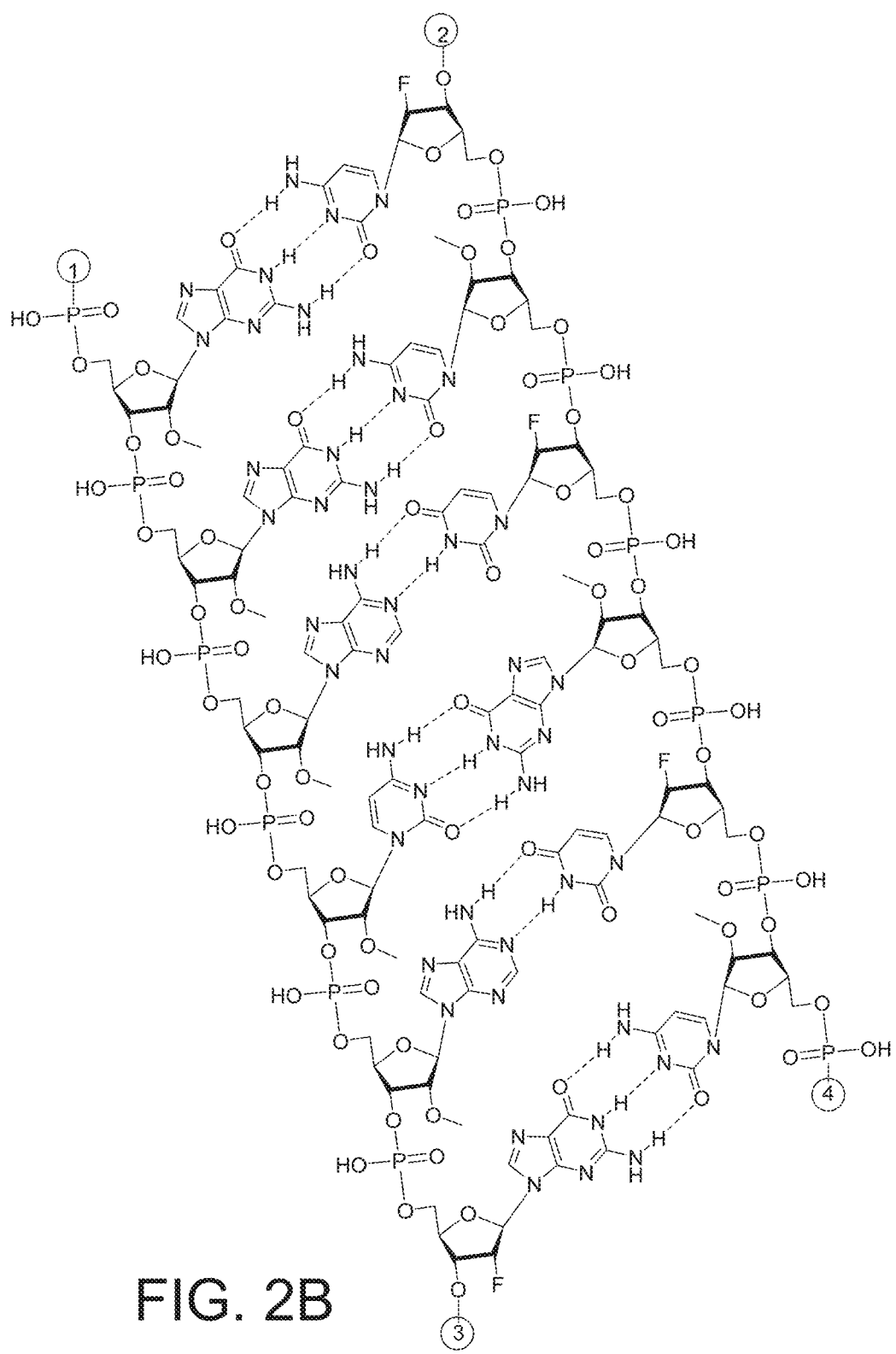
Figure 2C:
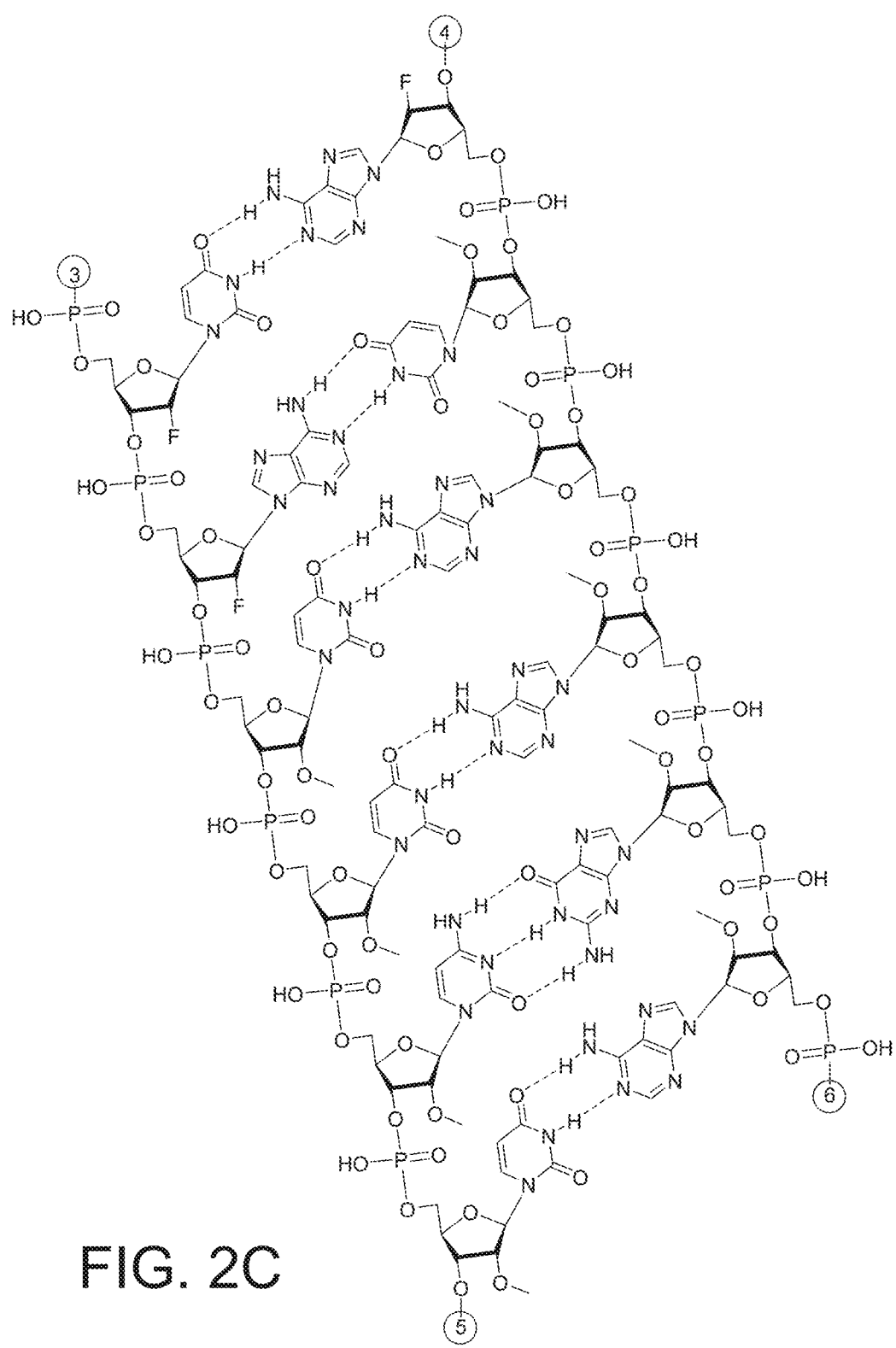
Figure 2D:
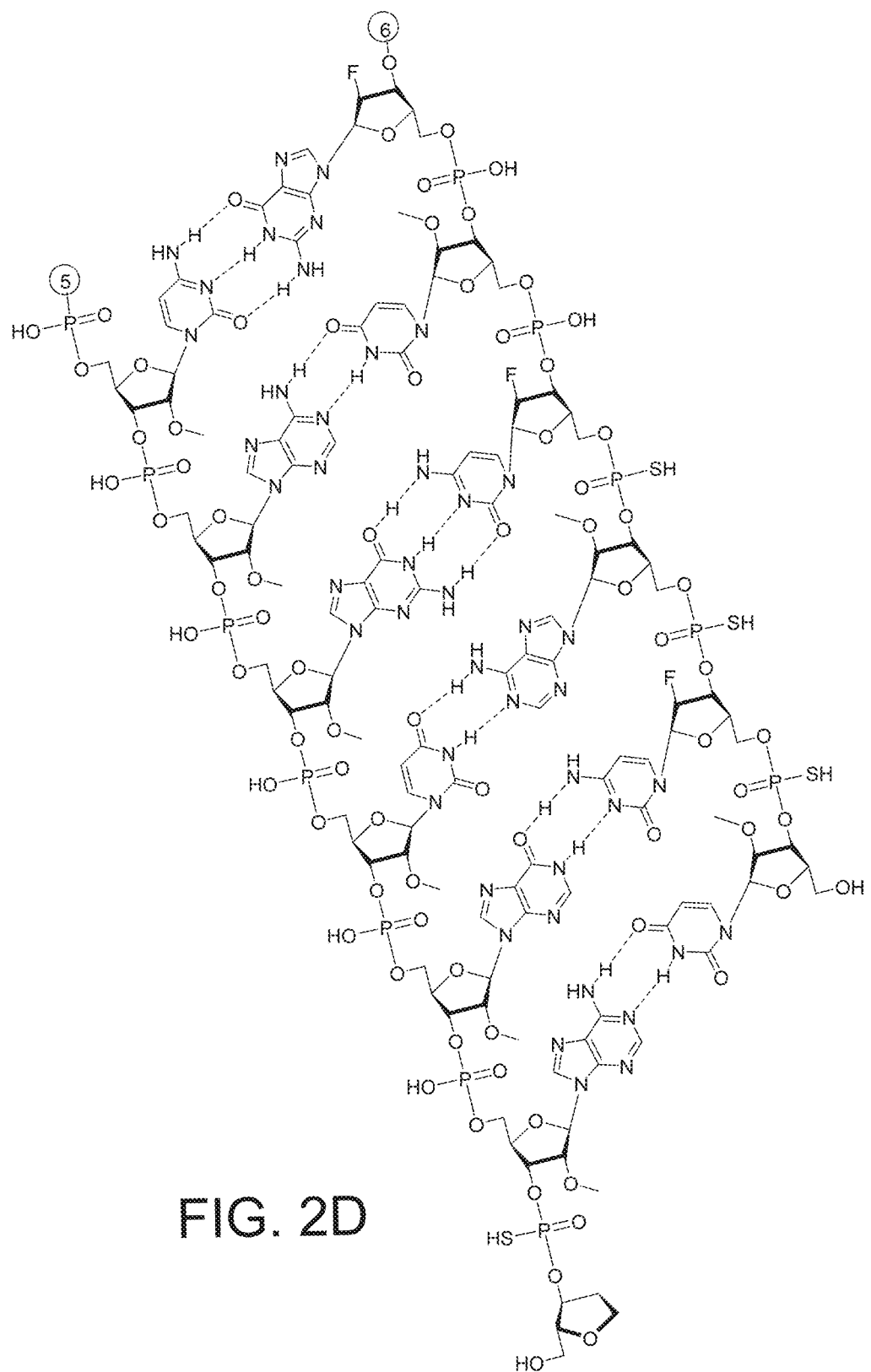

FIG. 2A to 2D. Chemical structure representation of APOC3 RNAi agent AD05251, including a tridentate N-acetyl-galactosamine-containing targeting ligand (having the structure of (NAG37)s) conjugated at the 5' terminal end of the sense strand, shown as a free acid.

Figure 3A:
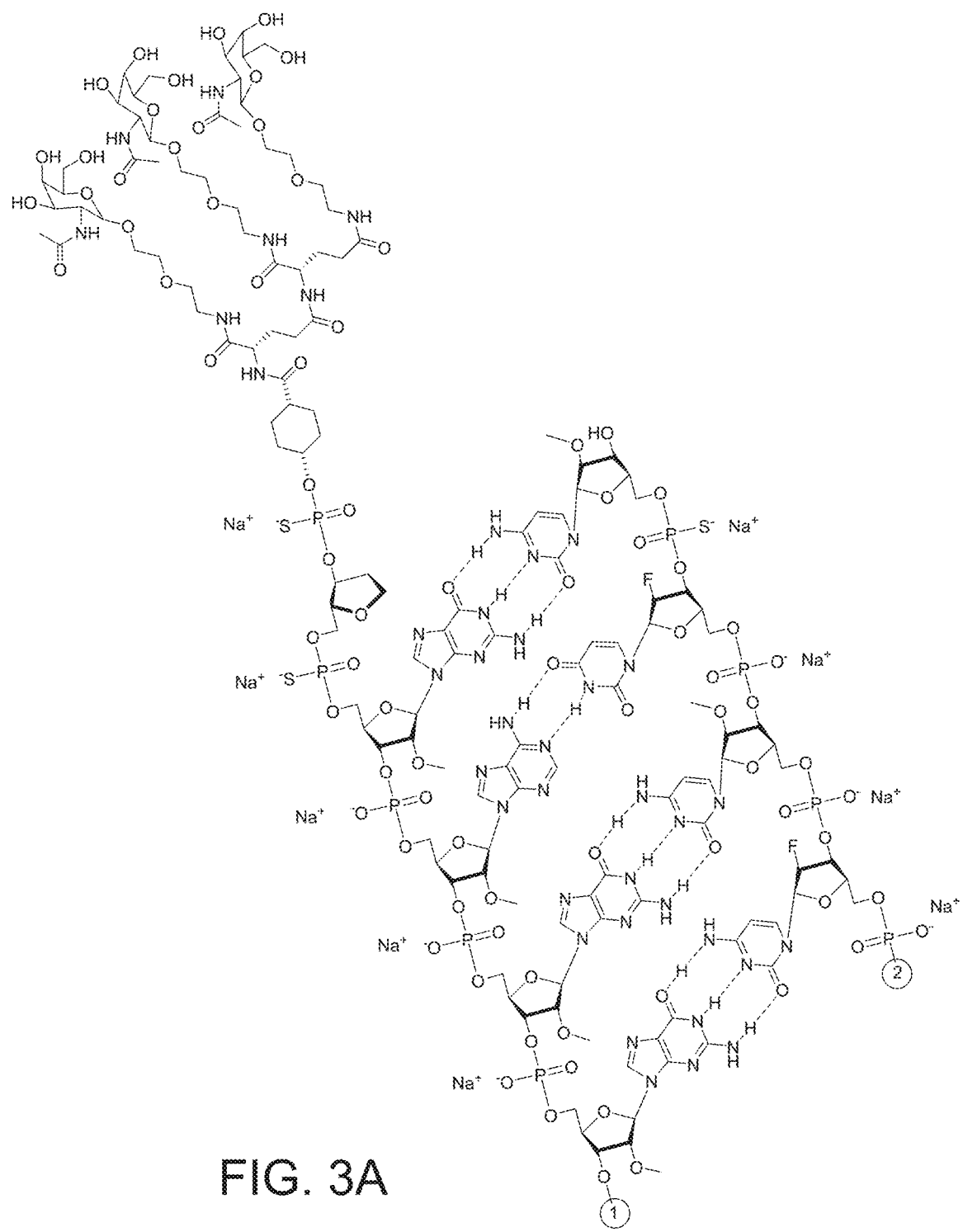
Figure 3B:
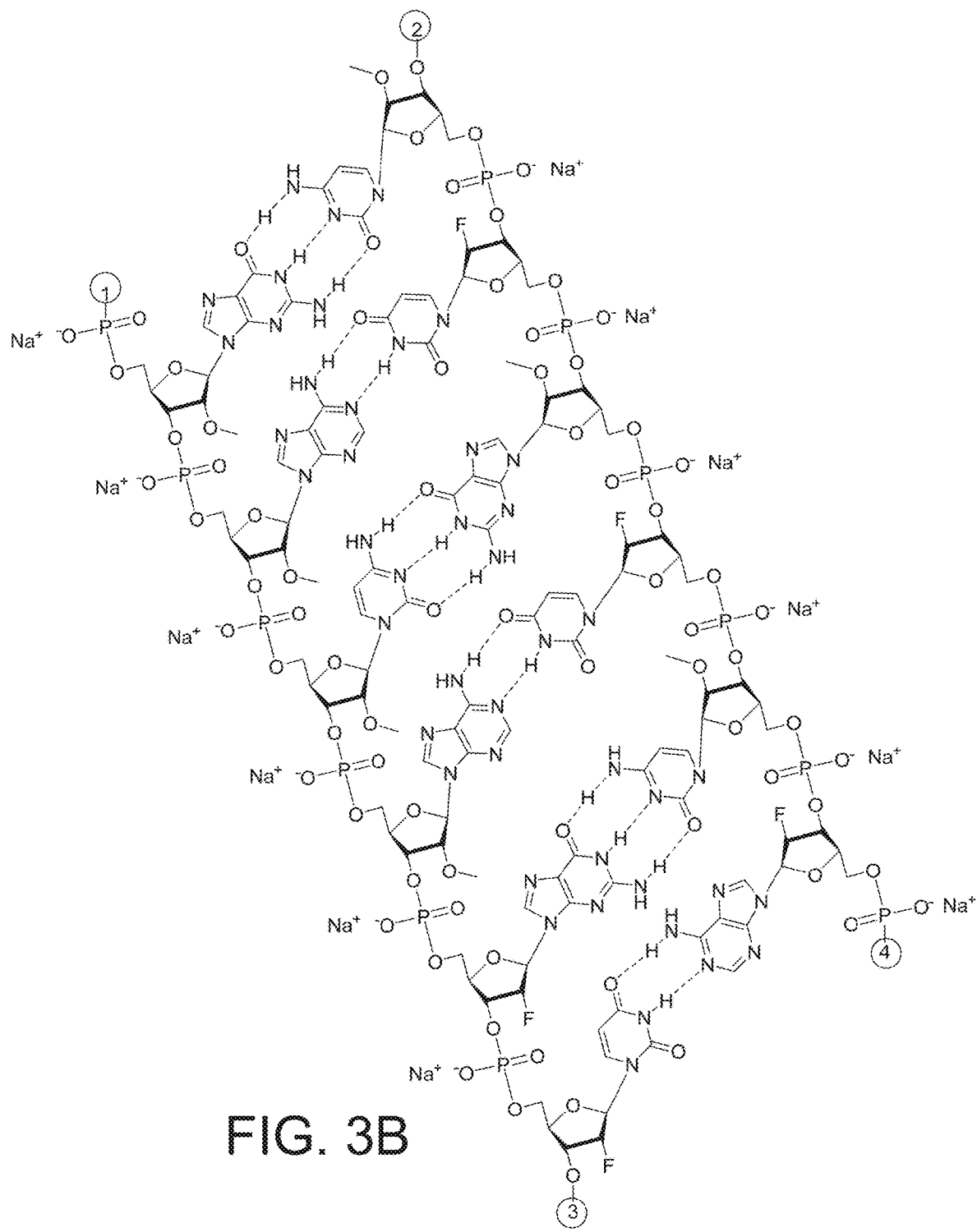
Figure 3C:
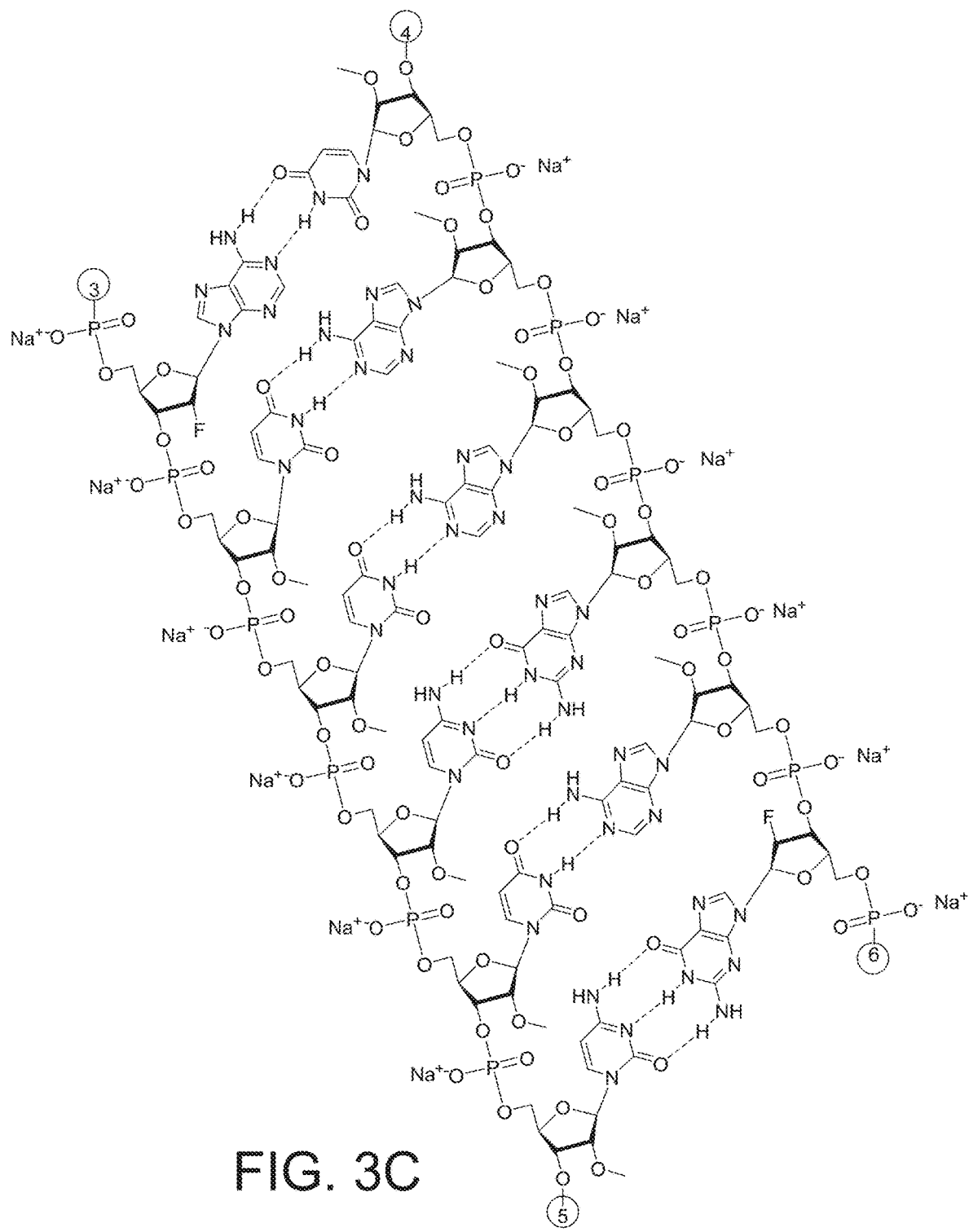
Figure 3D:
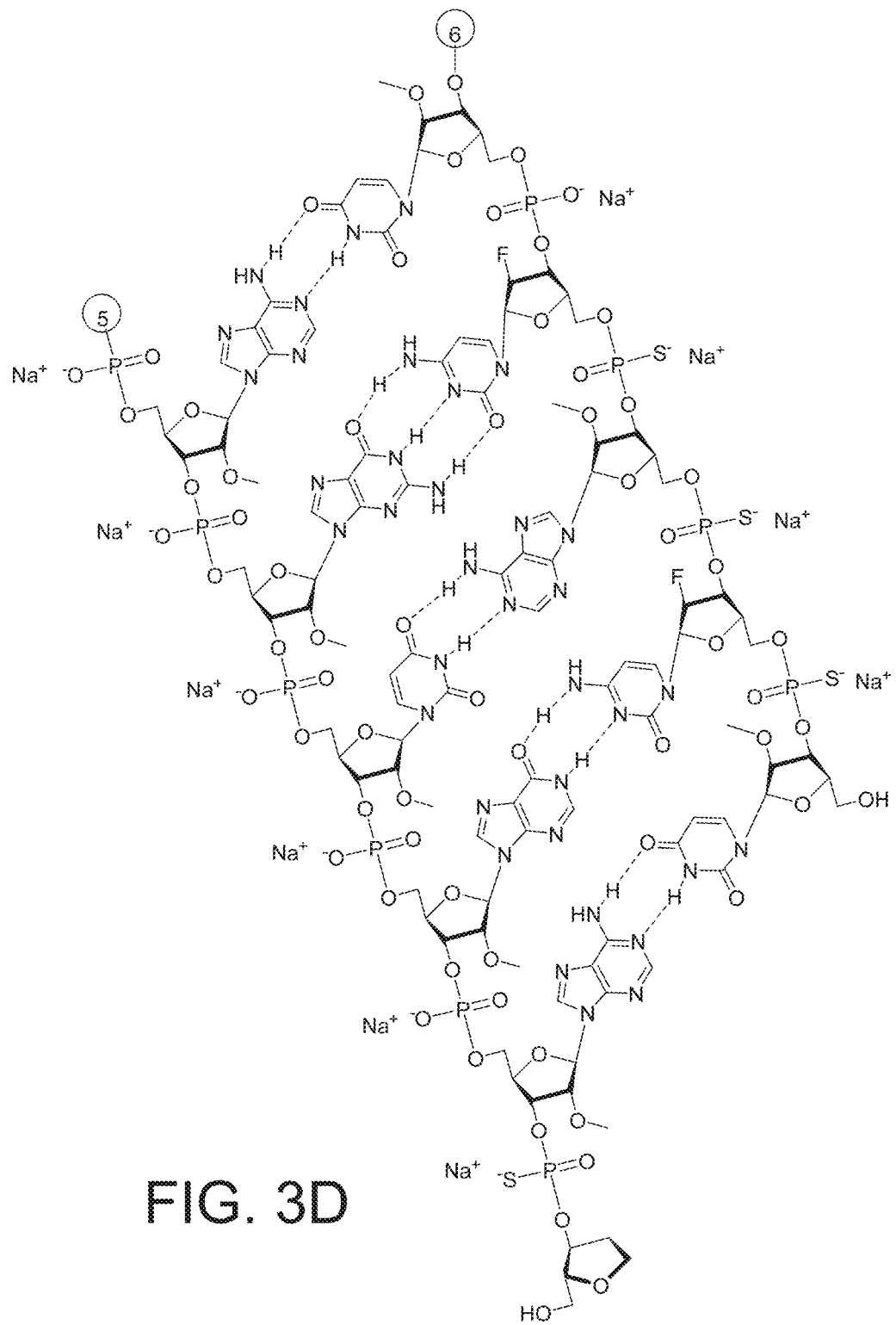

FIG. 3A to 3D. Chemical structure representation of APOC3 RNAi agent AD05251, including a tridentate N-acetyl-galactosamine-containing targeting ligand (having the structure of (NAG37)s) conjugated at the 5' terminal end of the sense strand, shown as a sodium salt.

Figure 4A:
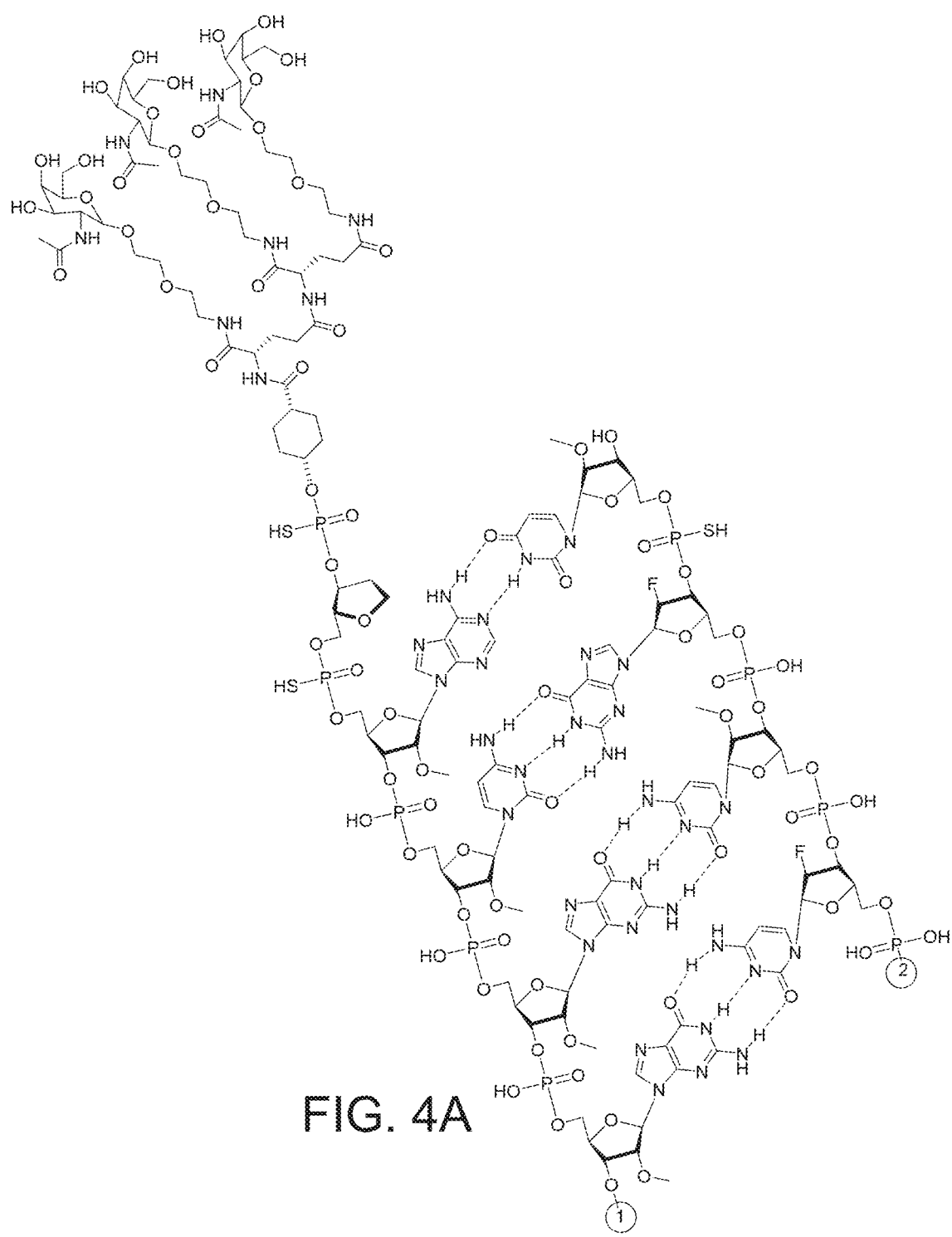
Figure 4B:
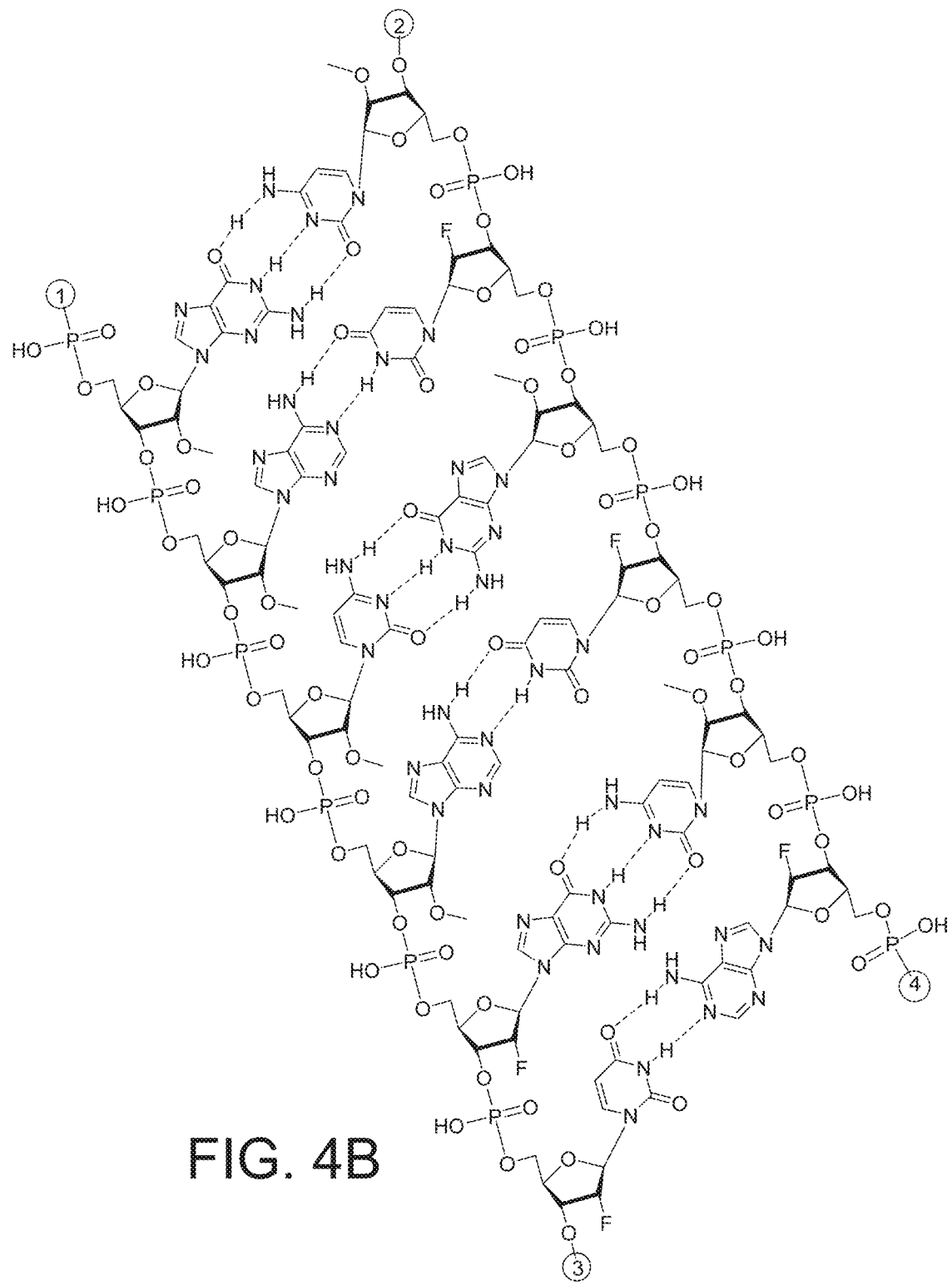
Figure 4C:
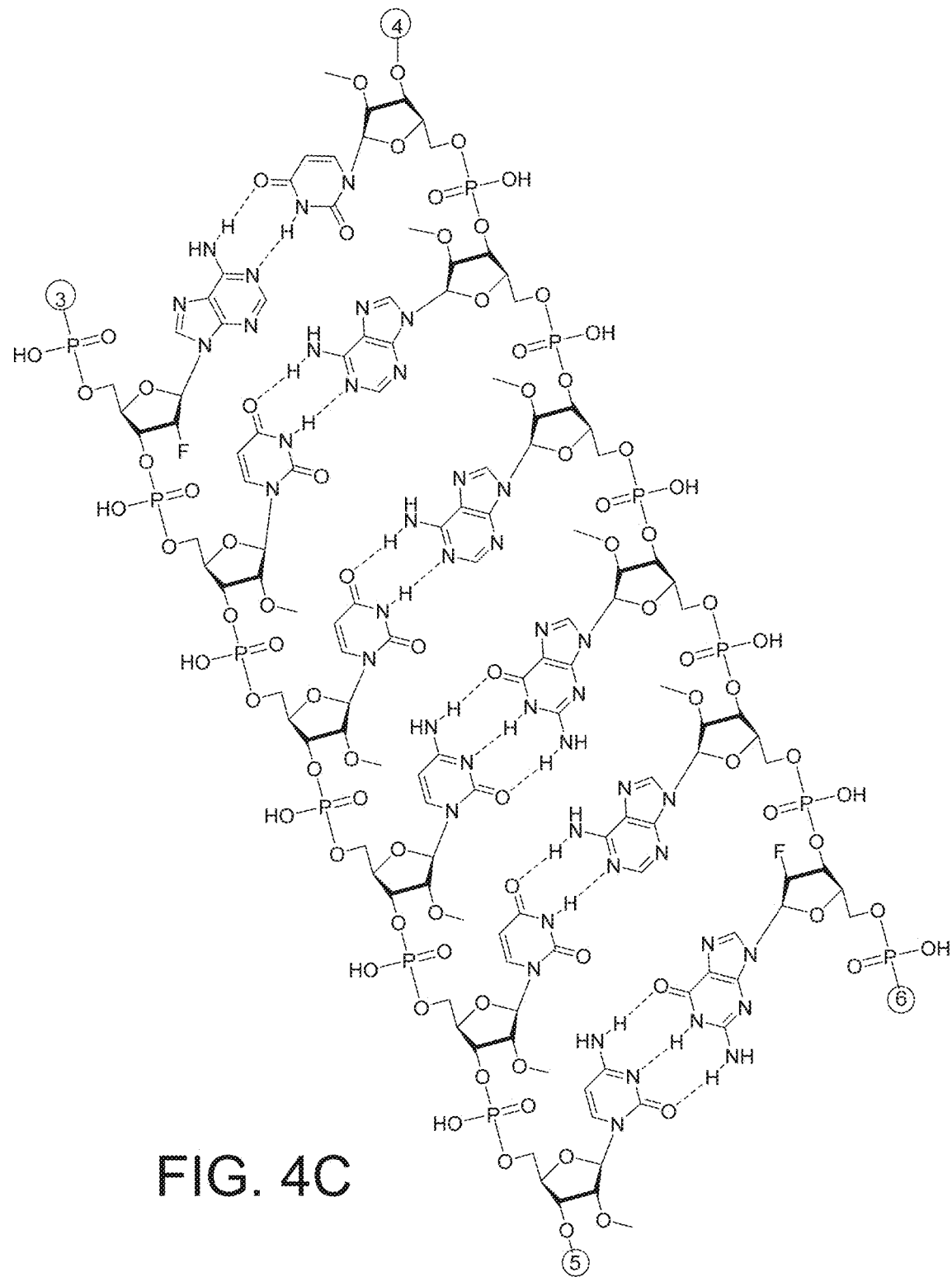
Figure 4D:
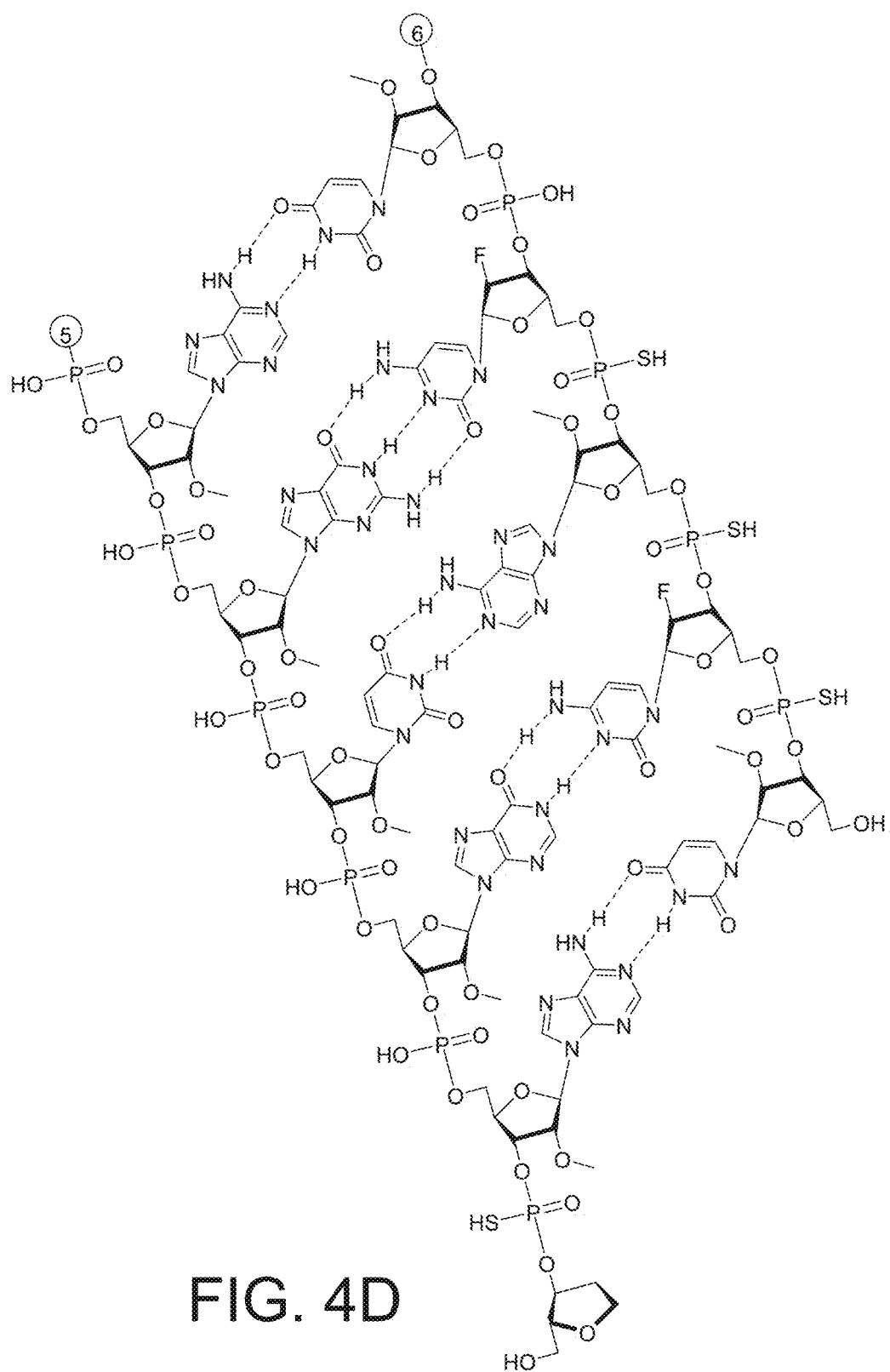

FIG. 4A to 4D. Chemical structure representation of APOC3 RNAi agent AD05876, including a tridentate N-acetyl-galactosamine-containing targeting ligand (having the structure of (NAG37)s) conjugated at the 5' terminal end of the sense strand, shown as a free acid.

Figure 5A:
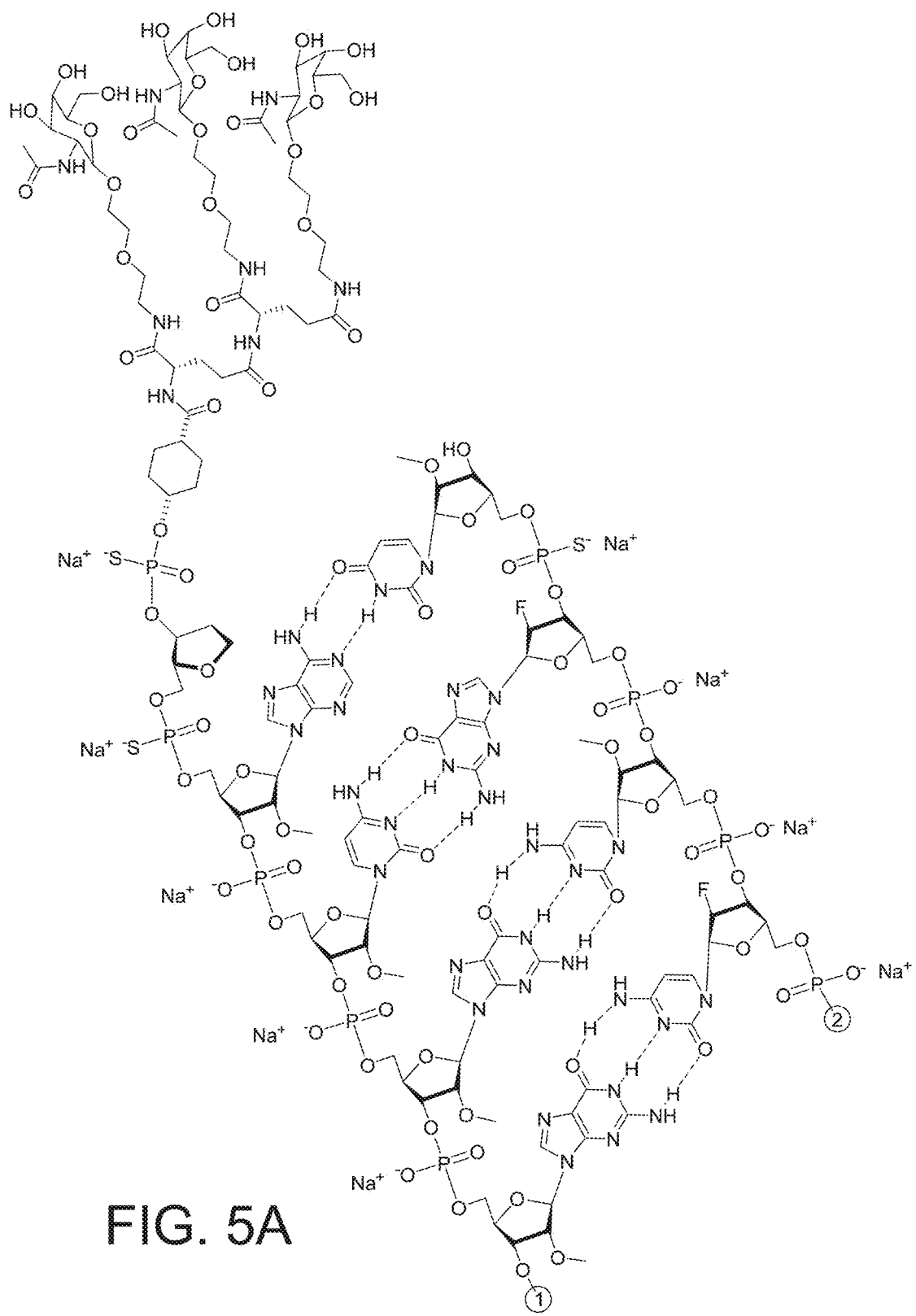
Figure 5B:
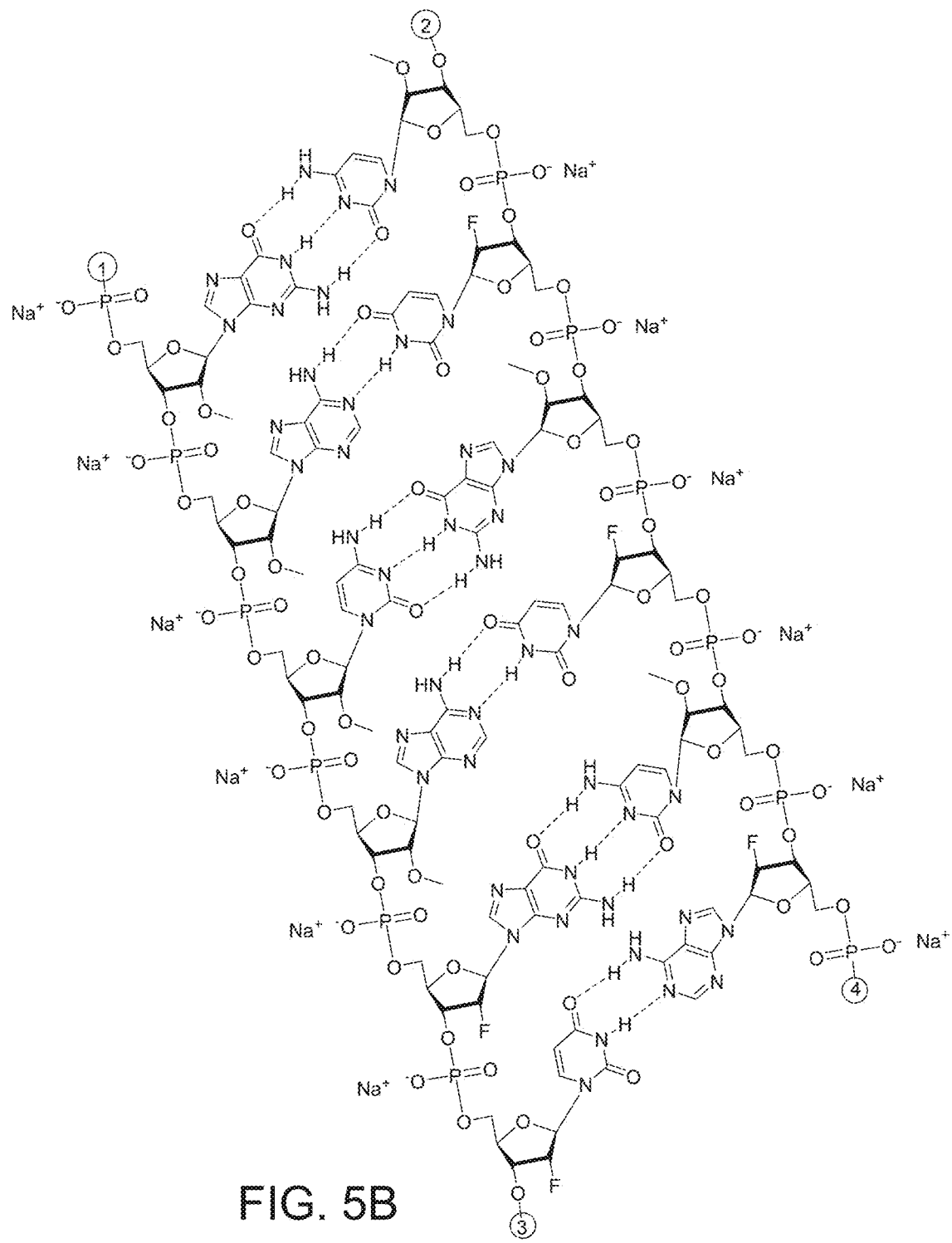
Figure 5C:
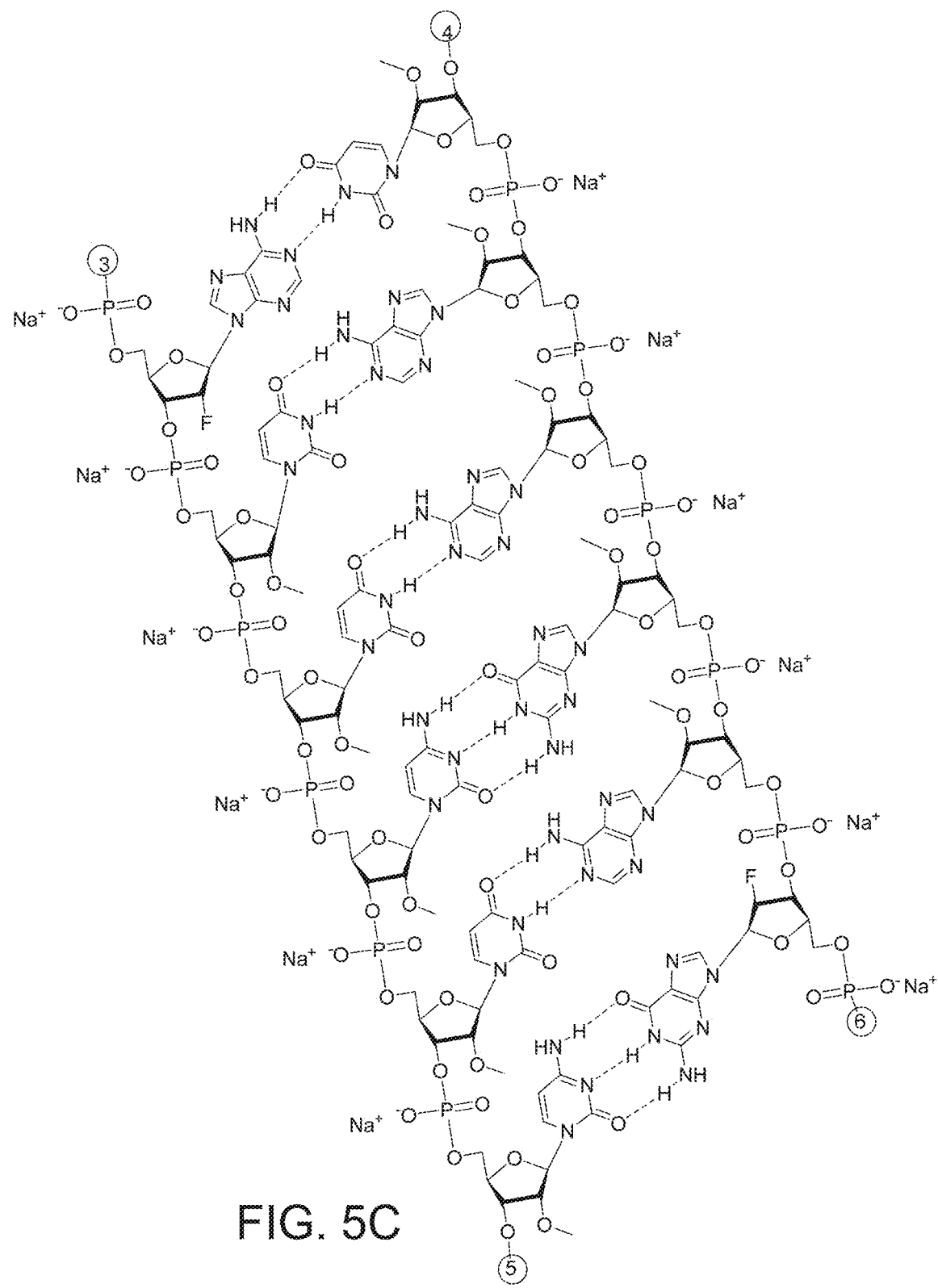
Figure 5D:
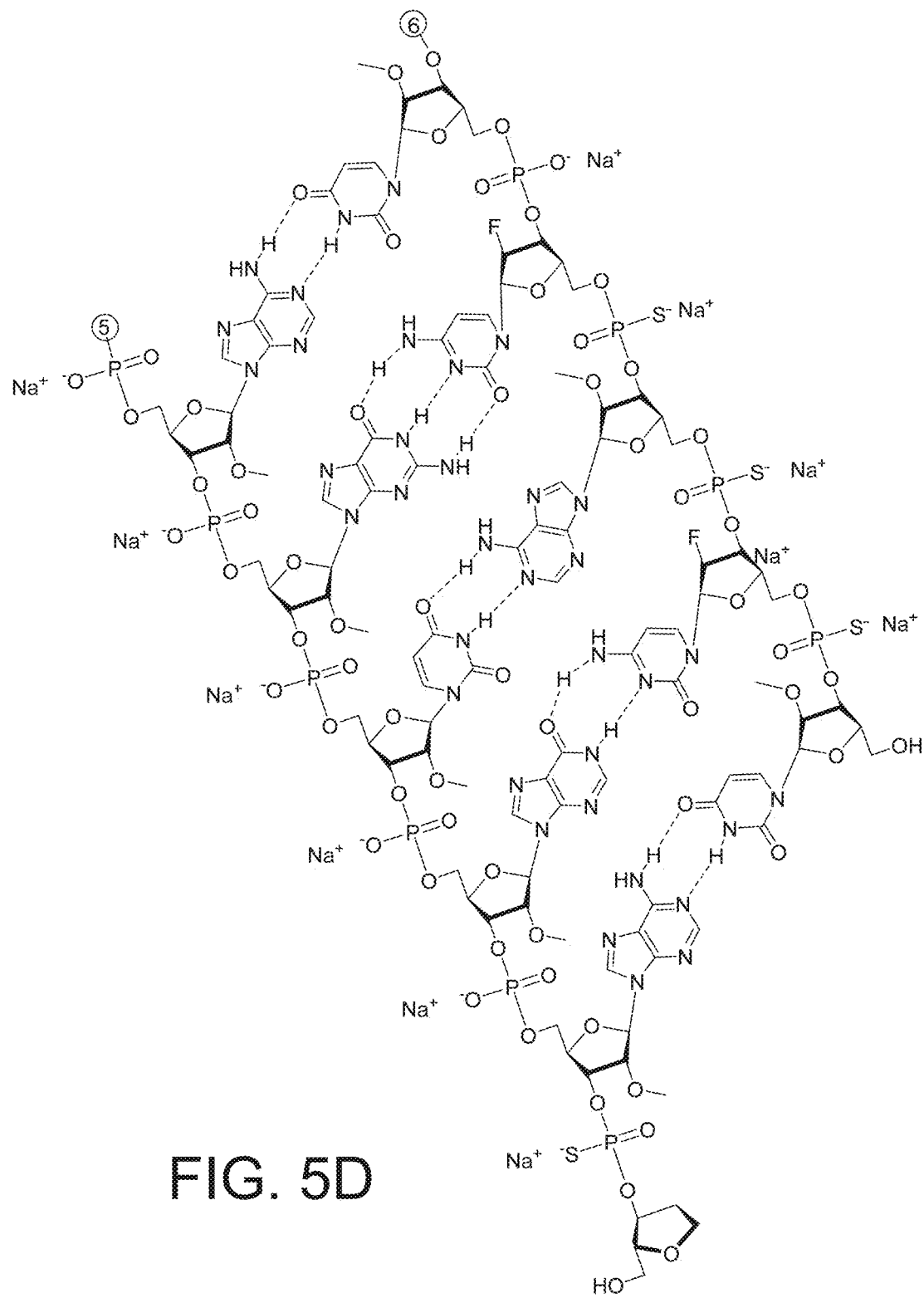

FIG. 5A to 5D. Chemical structure representation of APOC3 RNAi agent AD05876, including a tridentate N-acetyl-galactosamine-containing targeting ligand (having the structure of (NAG37)s) conjugated at the 5' terminal end of the sense strand, shown as a sodium salt.

Figure 6A:
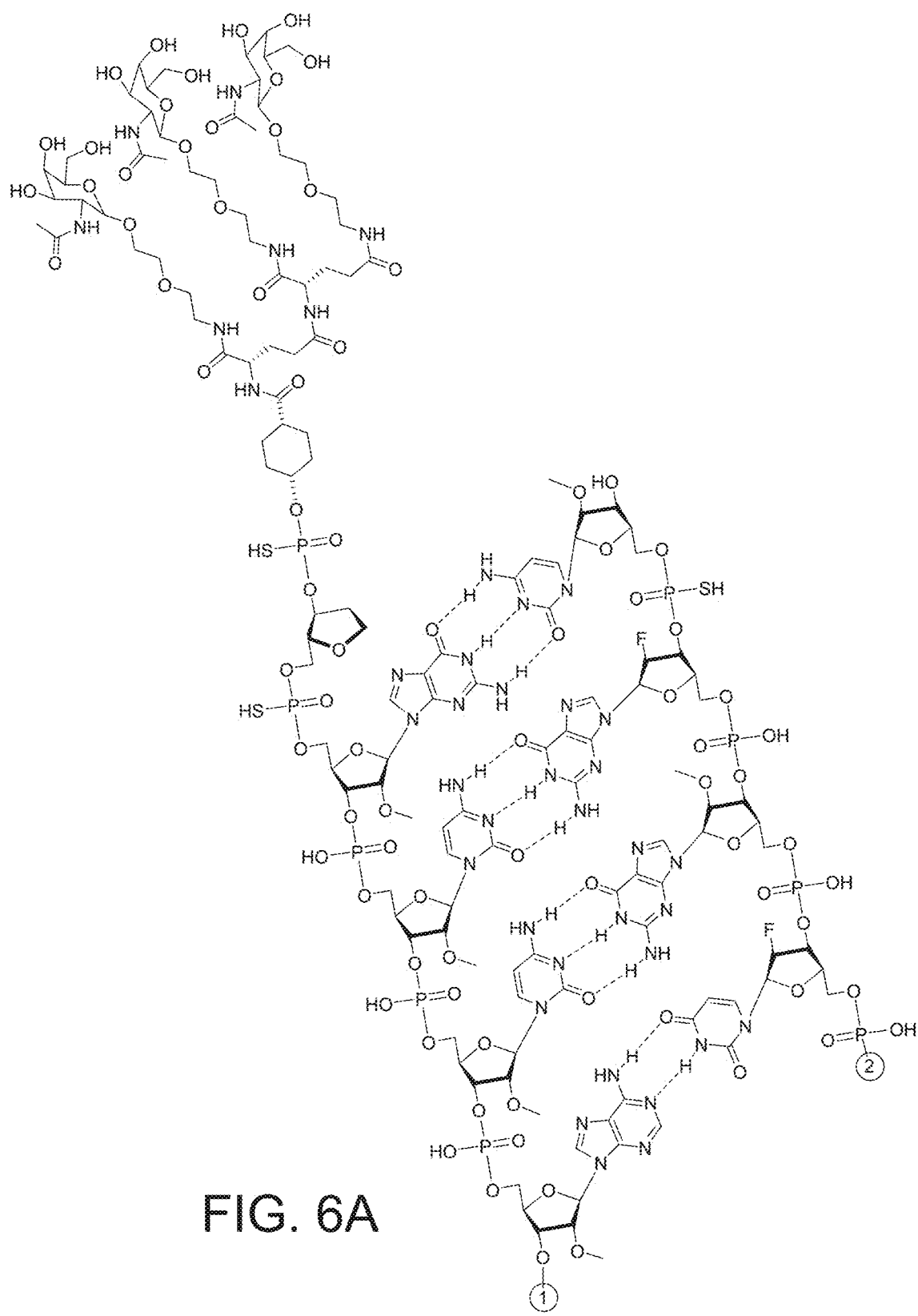
Figure 6B:
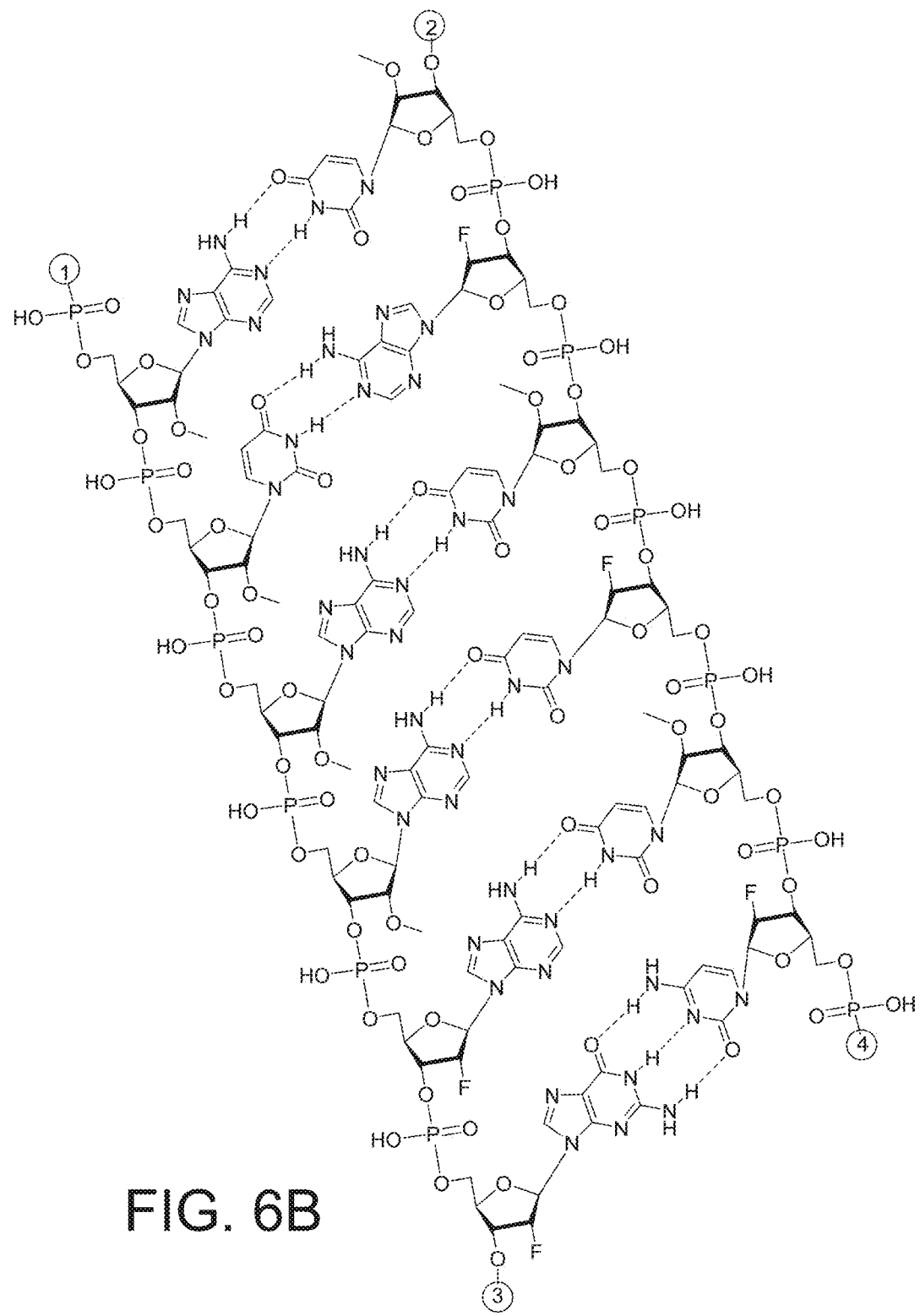
Figure 6C:
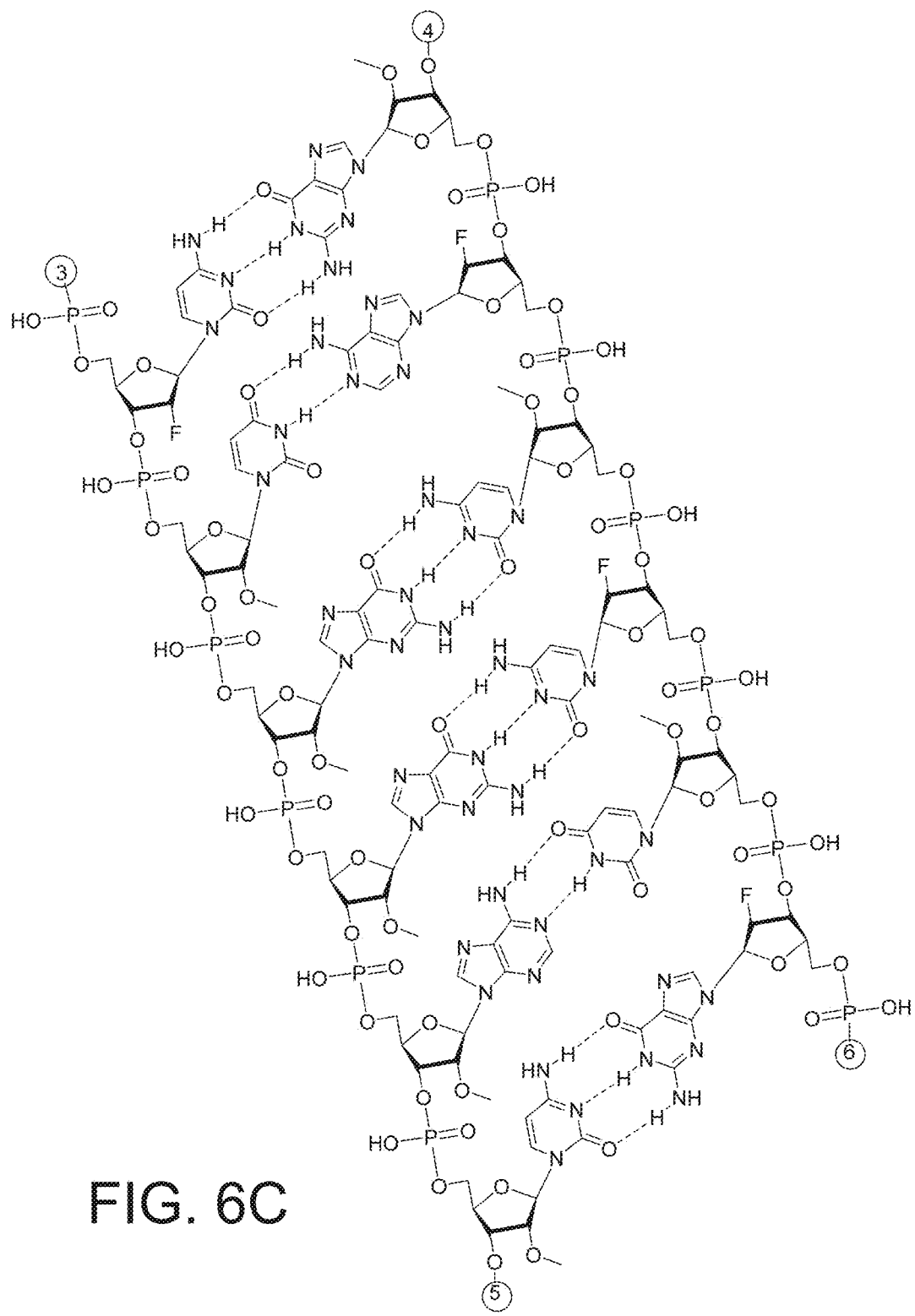
Figure 6D:
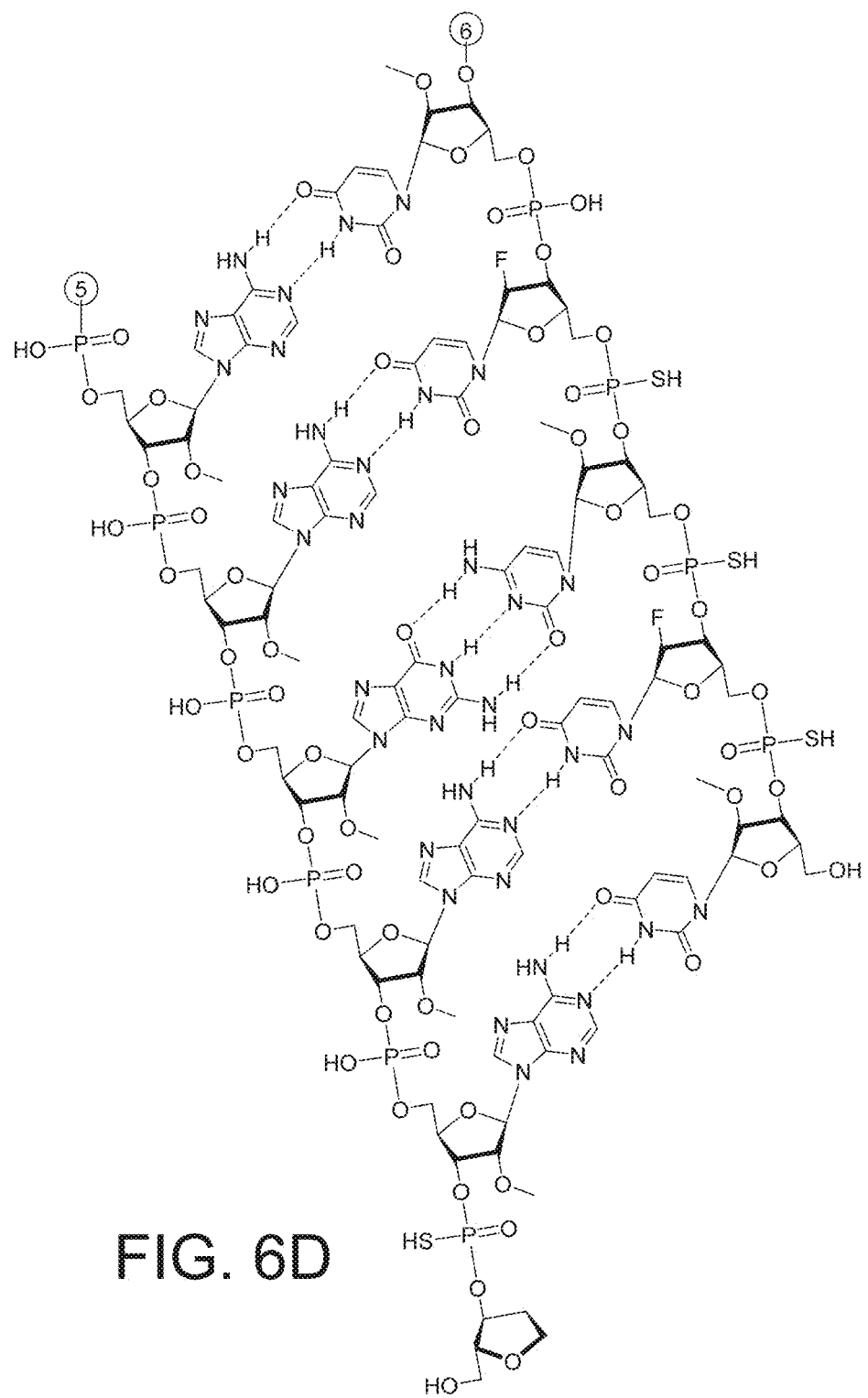

FIG. 6A to 6D. Chemical structure representation of APOC3 RNAi agent AD05220, including a tridentate N-acetyl-galactosamine-containing targeting ligand (having the structure of (NAG37)s) conjugated at the 5' terminal end of the sense strand, shown as a free acid.

Figure 7A:
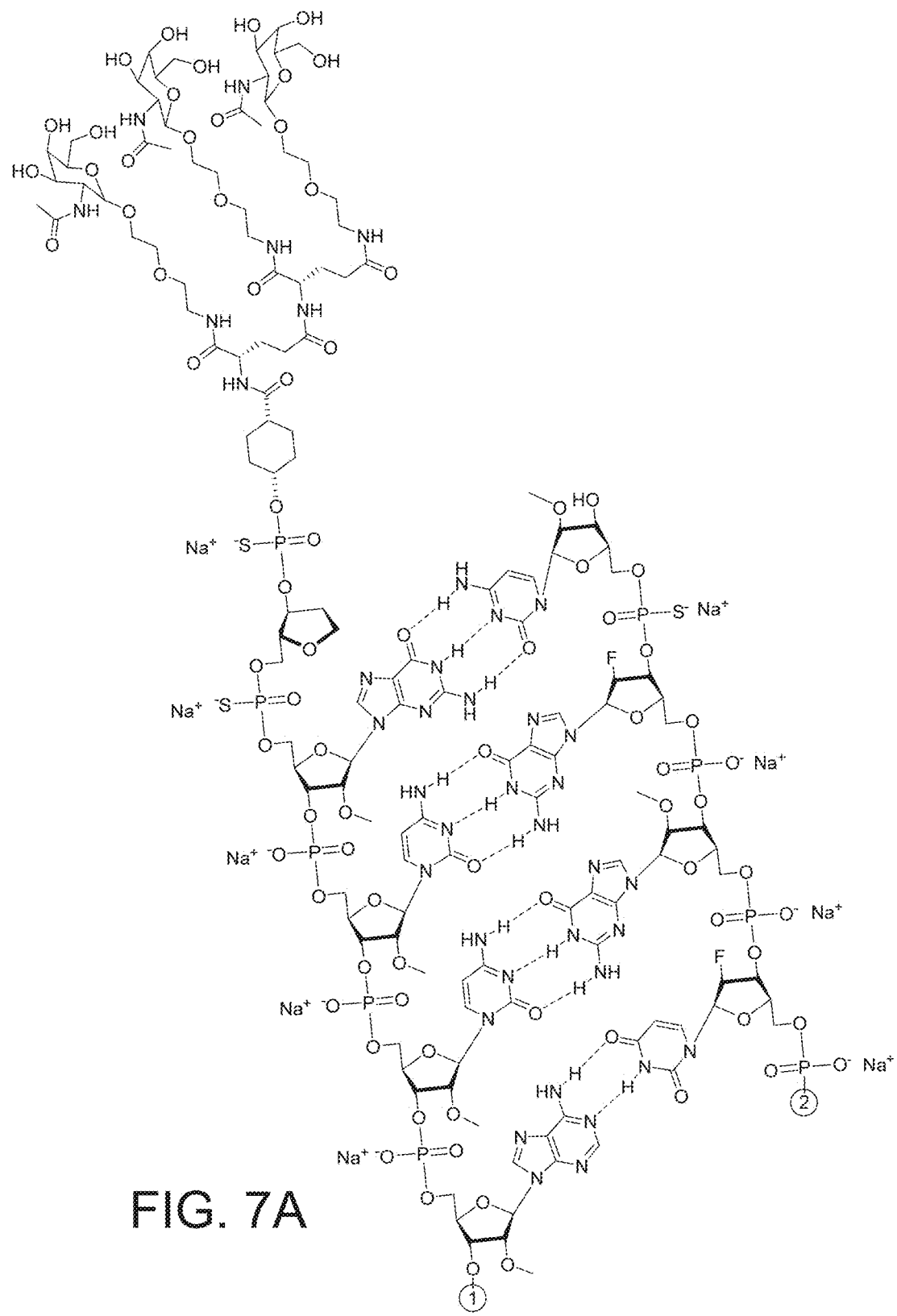
Figure 7B:
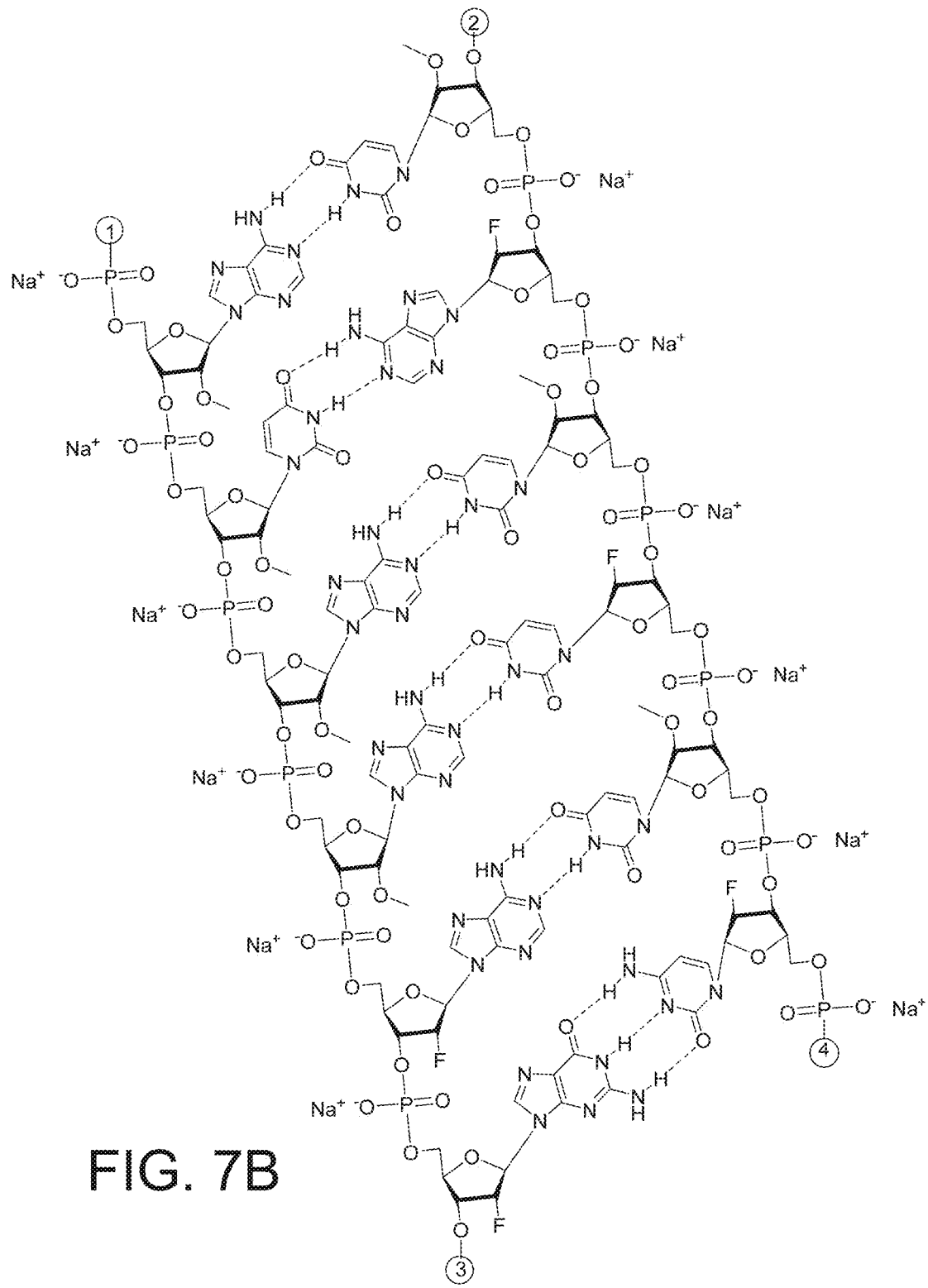
Figure 7C:
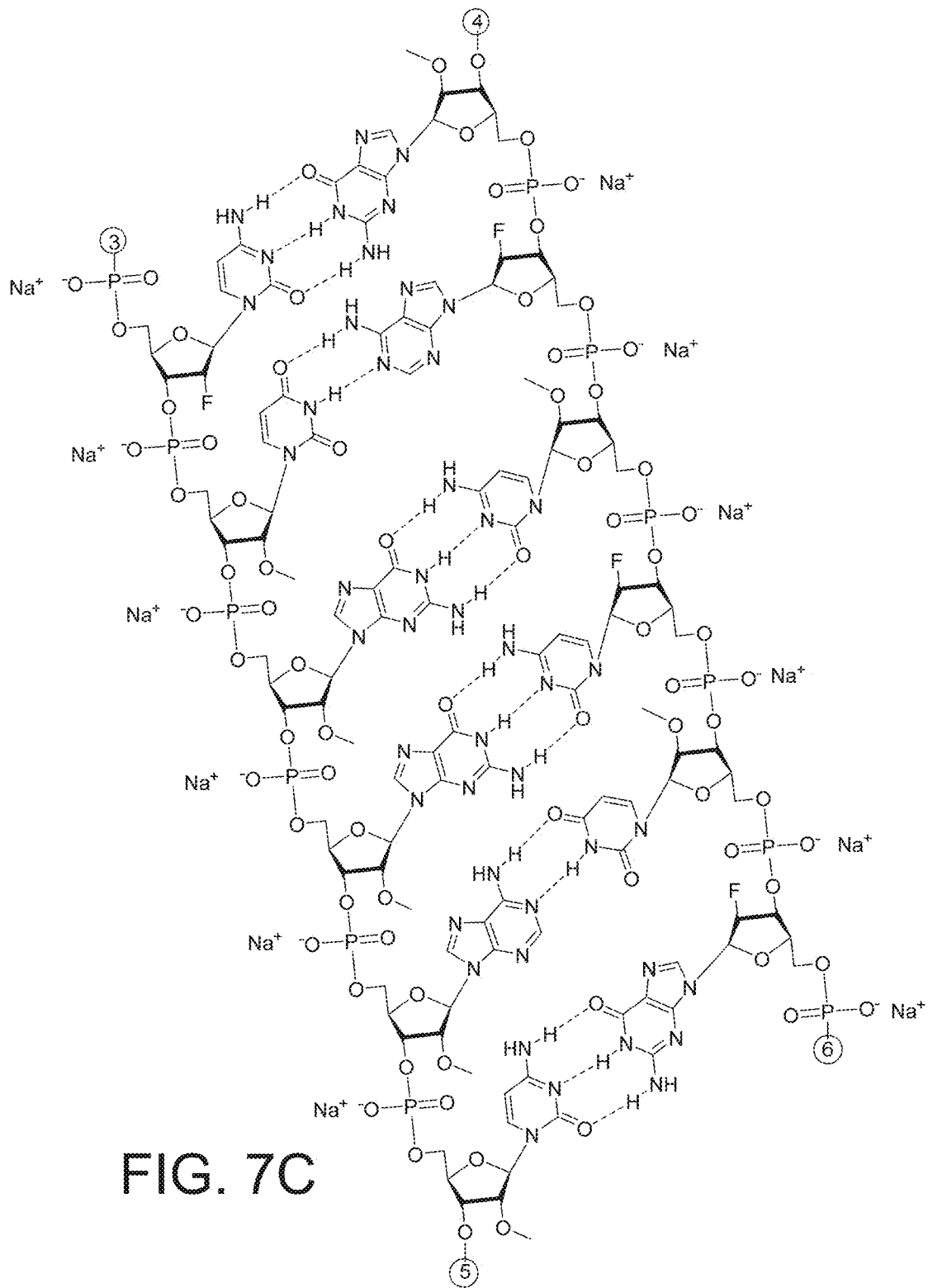
Figure 7D:
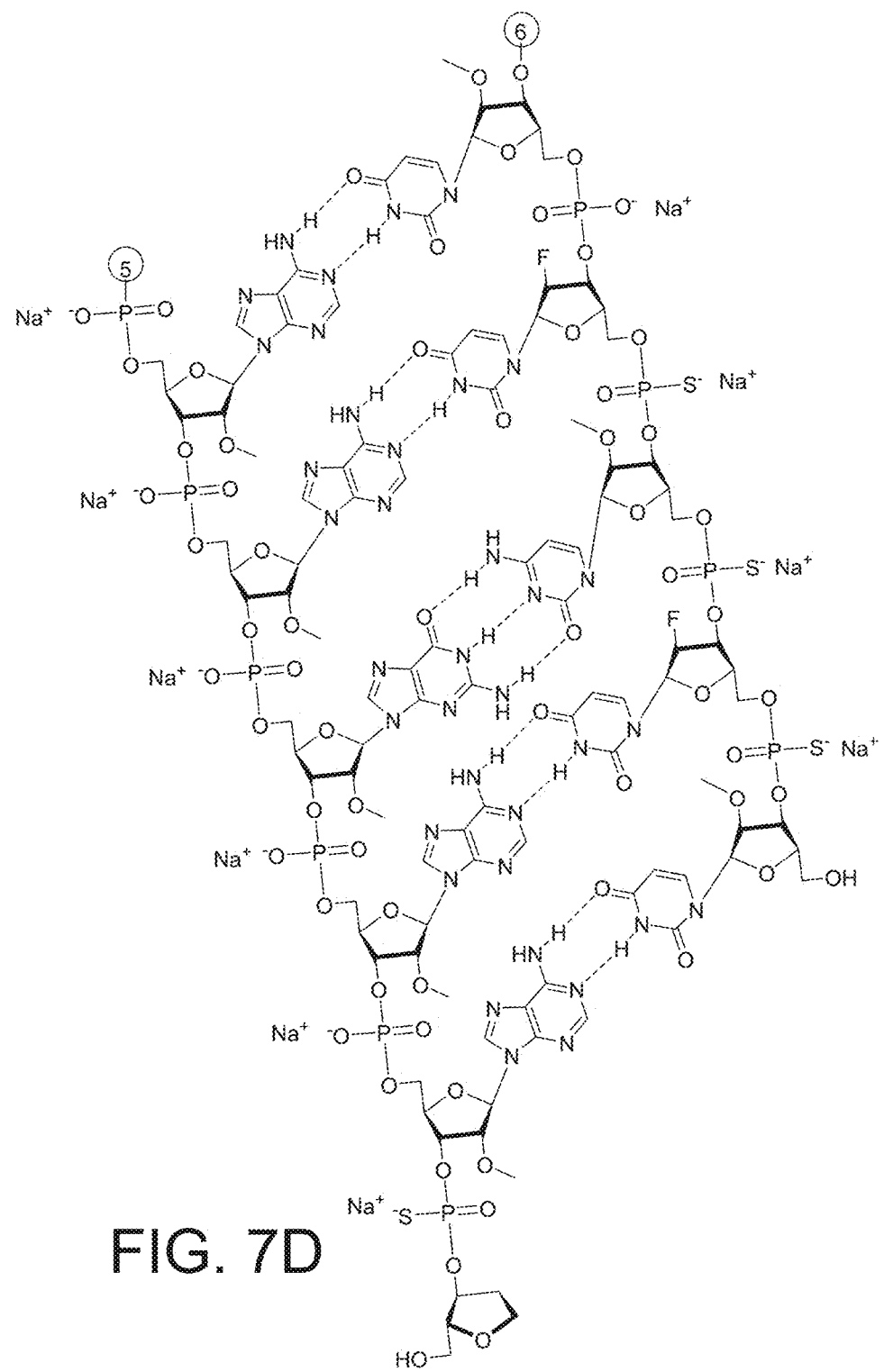

FIG. 7A to 7D. Chemical structure representation of APOC3 RNAi agent AD05220, including a tridentate N-acetyl-galactosamine-containing targeting ligand (having the structure of (NAG37)s) conjugated at the 5' terminal end of the sense strand, shown as a sodium salt.

DETAILED DESCRIPTION

RNAi Agents

RNAi agents for inhibiting expression of an APOC3 gene (referred to herein as APOC3 RNAi agents or APOC3 RNAi triggers) are described herein. Each APOC3 RNAi agent comprises a sense strand and an antisense strand. The sense strand and the antisense strand each can be 16 to 30 nucleotides in length. The sense and antisense strands can be either the same length or they can be different lengths. In some embodiments, the sense and antisense strands are each independently 17 to 27 nucleotides in length. In some embodiments, the sense and antisense strands are each independently 17-21 nucleotides in length. In some embodiments, the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 17, 18, 19, 20, 21, 22, 23, 24, 25, or 26 nucleotides in length. In some embodiments, a double-stranded RNAi agent has a duplex length of about 16, 17, 18, 19, 20, 21, 22, 23 or 24 nucleotides.

In some embodiments, the region of perfect, substantial, or partial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

The sense strand and antisense strand each contain a core stretch (also referred to herein as a "core sequence" or a "core stretch sequence") that is 16 to 23 nucleotides in length. An antisense strand core stretch is 100% (perfectly) complementary or at least about 85% (substantially) complementary to a nucleotide sequence (sometimes referred to, e.g., as a target sequence) present in the APOC3 mRNA target. A sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence (target sequence) present in the APOC3 mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of sense and antisense strand nucleotide sequences used in forming APOC3 RNAi agents are provided in Tables 2, 3, 4, and 5. Examples of RNAi agent duplexes, that include the sense strand and antisense strand sequences in Tables 2, 4, and 5, are shown in Table 6.

The APOC3 RNAi agent sense and antisense strands anneal to form a duplex. A sense strand and an antisense strand of an APOC3 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an APOC3 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an APOC3 RNAi agent disclosed herein differs by 0, 1, 2, or 3 nucleotides from any of the antisense strand sequences in Table 2, Table 3, or Table 4. In some embodiments, the sense strand of an APOC3 RNAi agent disclosed herein differs by 0, 1, 2, or 3 nucleotides from any of the sense strand sequences in Table 2, Table 3, or Table 5.

The sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the APOC3 mRNA. The sense strand additional nucleotides, if present, may or may not be identical to the corresponding sequence in the APOC3 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an APOC3 RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, an APOC3 RNAi agent comprises an antisense strand having a 3' extension of 1, 2, 3, 4, 5, or 6 nucleotides in length. In other embodiments, an APOC3 RNAi agent comprises an antisense strand having a 3' extension of 1, 2, or 3 nucleotides in length. In some embodiments, one or more of the antisense strand extension nucleotides comprise uracil or thymidine nucleotides or nucleotides that are complementary to the corresponding APOC3 mRNA sequence.

In some embodiments, the 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See, e.g., U.S. Pat. No. 5,998,203). In some embodiments, Ab or AbAb can be added to the 3' end of the antisense strand.

In some embodiments, the sense strand or the antisense strand may include a "terminal cap," which as used herein is a non-nucleotide compound or other moiety that can be incorporated at one or more termini of a strand of an RNAi agent disclosed herein, and can provide the RNAi agent, in some instances, with certain beneficial properties, such as, for example, protection against exonuclease degradation. In some embodiments, inverted abasic residues (invAb) are added as terminal caps (see Table 76). (See, e.g., F. Czaudema, Nucleic Acids Res., 2003, 31(11), 2705-16). Terminal caps are generally known in the art, and include, for example, inverted abasic residues as well as carbon chains such as a terminal C3, C6, or C12 groups. In some embodiments, a terminal cap is present at either the 5' terminal end, the 3' terminal end, or both the 5' and 3' terminal ends of the sense strand.

In some embodiments, an APOC3 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to nucleotides in the APOC3 mRNA sequence. In some embodiments, the 3' sense strand extension includes or consists of one of the following sequences, but is not limited to: T, UT, TT, UU, UUT, TTT, or TTTT (each listed 5' to 3').

In some embodiments, the 3' end of the sense strand may include additional abasic residues or inverted abasic terminal caps. In some embodiments, UUAb, UAb, or Ab are added to the 3' end of the sense strand.

In some embodiments, one or more inverted abasic residues (invAb) are added to the 3' end of the sense strand. In some embodiments, one or more inverted abasic residues or inverted abasic sites are inserted between the targeting ligand and the nucleobase sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, an APOC3 RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides that correspond to nucleotides in the APOC3 mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand can have a 3' extension and/or a 5' extension.

In some embodiments, the 5' end of the sense strand can include one or more additional abasic residues (e.g., (Ab) or (AbAb)). In some embodiments, one or more inverted abasic residues (invAb) are added to the 5' end of the sense strand. In some embodiments, one or more inverted abasic residues can be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent. In some embodiments, an abasic (deoxyribose) residue can be replaced with a ribitol (abasic ribose) residue.

In some embodiments, the 3' end of the antisense strand core stretch sequence, or the 3' end of the antisense strand sequence, may include an inverted abasic residue (invAb (see Table 7)).

Examples of sequences used in forming APOC3 RNAi agents are provided in Tables 2, 3, 4, and 5. In some embodiments, an APOC3 RNAi agent antisense strand includes a sequence of any of the sequences in Tables 2, 3, or 4. In certain embodiments, an APOC3 RNAi agent antisense strand comprises or consists of any one of the modified sequences in Table 4. In some embodiments, an APOC3 RNAi agent antisense strand includes the sequence of nucleotides (from 5' end→3' end) 1-17, 2-15, 2-17, 1-18, 2-18, 1-19, 2-19, 1-20, 2-20, 1-21, 2-21, 1-22, 2-22, 1-23, 2-23, 1-24, or 2-24 of any of the sequences in Tables 2 or 4. In some embodiments, an APOC3 RNAi agent sense strand includes the sequence of any of the sequences in Tables 2 or 5. In some embodiments, an APOC3 RNAi agent sense strand includes the sequence of nucleotides (from 5' end→3' end) 1-18, 1-19, 1-20, 1-21, 1-22, 1-23, 1-24, 1-25, 1-26, 2-19, 2-20, 2-21, 2-22, 2-23, 2-24, 3-20, 3-21, 3-22, 3-23, 3-24, 4-21, 4-22, 4-23, 4-24, 5-22, 5-23, or 5-24 of any of the sequences in Tables 2 or 5. In certain embodiments, an APOC3 RNAi agent sense strand comprises or consists of a modified sequence of any one of the modified sequences in Table 5.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

Modified nucleotides, when used in various polynucleotide or oligonucleotide constructs, can preserve activity of the compound in cells while at the same time increasing the serum stability of these compounds, and can also minimize the possibility of activating interferon activity in humans upon administering of the polynucleotide or oligonucleotide construct.

In some embodiments, an APOC3 RNAi agent is prepared or provided as a salt, mixed salt, or a free-acid. In some embodiments, an APOC3 RNAi agent is prepared as a sodium salt. Such forms that are well known in the art are within the scope of the inventions disclosed herein.

Modified Nucleotides

In some embodiments, an APOC3 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn), modified nucleobase-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e., a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (also referred to herein as 2'-fluoro nucleotide, and represented herein as Nf), 2'-deoxy nucleotides (represented herein as dN), 2'-methoxyethyl (2'-O-2-methoxylethyl) nucleotides (also referred to herein as 2'-MOE, and represented herein as NM), 2'-amino nucleotides, and 2'-alkyl nucleotides. It is not necessary for all positions in a given compound to be uniformly modified. Conversely, more than one modification can be incorporated in a single APOC3 RNAi agent or even in a single nucleotide thereof. The APOC3 RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrinidines and N-2, N-6 and O-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

Modified Internucleoside Linkages

In some embodiments, one or more nucleotides of an APOC3 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an APOC3 RNAi agent can contain 1, 2, 3, 4, 5, or 6 phosphorothioate linkages, an antisense strand of an APOC3 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an APOC3 RNAi agent can contain 1, 2, 3, or 4 phosphorothioate linkages, an antisense strand of an APOC3 RNAi agent can contain 1, 2, 3, or 4 phosphorothioate linkages, or both the sense strand and the antisense strand independently can contain 1, 2, 3, or 4 phosphorothioate linkages.

In some embodiments, an APOC3 RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, one phosphorothioate internucleoside linkage is at the 5' end of the sense strand, and another phosphorothioate linkage is at the 3' end of the sense strand. In some embodiments, two phosphorothioate internucleoside linkage are located at the 5' end of the sense strand, and another phosphorothioate linkage is at the 3' end of the sense strand. In some embodiments, the sense strand dose not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, an APOC3 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, an APOC3 RNAi agent contains at least three or four phosphorothioate internucleoside linkages in the antisense strand.

In some embodiments, an APOC3 RNAi agent contains one or more modified nucleotides and one or more modified internucleoside linkages. In some embodiments, a 2'-modified nucleoside is combined with modified internucleoside linkage.

APOC3 RNAi Agents

In some embodiments, the APOC3 RNAi agents disclosed herein target an APOC3 gene at or near the positions of the APOC3 gene show in Table 1. In some embodiments, the antisense strand of an APOC3 RNAi agent disclosed herein includes a core stretch sequence that is fully, substantially, or at least partially complementary to a target APOC3 19-mer sequence disclosed in Table 1.

TABLE 1

APOC3 19-mer mRNA target sequences (taken from homo sapiens apolipoprotein C3 (APOC3) transcript, GenBank NM_000040.1 (SEQ ID NO: 1)).

| SEQ ID No. | APOC3 19-mer Target Sequences (5'→3') | Corresponding Positions on SEQ ID NO: 1 |
|---|---|---|
| 32 | GGGACAGUAUUCUCAGUGC | 438-456 |
| 33 | CAAUAAAGCUGGACAAGAA | 506-524 |
| 34 | UUAAAAGGGACAGUAUUCU | 432-450 |
| 35 | CGGGUACUCCUUGUUGUUG | 56-74 |
| 36 | GGUACUCCUUGUUGUUGCC | 58-76 |
| 37 | GCUGGGUGACCGAUGGCUU | 228-246 |
| 38 | GACCGAUGGCUUCAGUUCC | 235-253 |
| 39 | GCUUCAGUUCCCUGAAAGA | 243-261 |
| 40 | UCAGUUCCCUGAAAGACUA | 246-264 |
| 41 | GACUACUGGAGCACCGUUA | 260-278 |
| 42 | ACUACUGGAGCACCGUUAA | 261-279 |
| 43 | GCACCGUUAAGGACAAGUU | 270-288 |
| 44 | ACCGUUAAGGACAAGUUCU | 272-290 |
| 45 | CCGUUAAGGACAAGUUCUC | 273-291 |
| 46 | CCUCAAUACCCCAAGUCCA | 349-367 |
| 47 | AAAAGGGACAGUAUUCUCA | 434-452 |
| 48 | AGGGACAGUAUUCUCAGUG | 437-455 |

In some embodiments, an APOC3 RNAi agent includes an antisense strand wherein position 19 of the antisense strand (5'→3') is capable of forming a base pair with position 1 of a 19-mer target sequence disclosed in Table 1. In some embodiments, an APOC3 RNAi agent includes an antisense strand wherein position 1 of the antisense strand (5'-3') is capable of forming a base pair with position 19 of the 19-mer target sequence disclosed in Table 1.

In some embodiments, an APOC3 RNAi agent includes an antisense strand wherein position 2 of the antisense strand (5'→3') is capable of forming a base pair with position 18 of the 19-mer target sequence disclosed in Table 1. In some embodiments, an APOC3 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the APOC3 gene, or can be non-complementary to the APOC3 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an APOC3 RNAi agent antisense strand comprises the sequence of nucleotides (from 5' end→3' end) 2-18 or 2-19 of any of the antisense strand sequences in Table 2, Table 3, or Table 4. In some embodiments, an APOC3 RNAi sense strand comprises the sequence of nucleotides (from 5' end→3' end) 1-17, 1-18, or 2-18 of any of the sense strand sequences in Table 2, Table 3, or Table 5.

In some embodiments, an APOC3 RNAi agent is comprised of (i) an antisense strand comprising the sequence of nucleotides (from 5' end→3' end) 2-18 or 2-19 of any of the antisense strand sequences in Table 2, Table 3, or Table 4, and (ii) a sense strand comprising the sequence of nucleotides (from 5' end→3' end) 1-17 or 1-18 of any of the sense strand sequences in Table 2, Table 3, or Table 5.

In some embodiments, the APOC3 RNAi agents include core 19-mer nucleotide sequences shown in the following Table 2.

TABLE 2

APOC3 RNAi Agent Antisense Strand and Sense Strand Core Stretch Base Sequences (N = any nucleobase).

| SEQ ID No. | Antisense Strand Base Sequence (5'→3') (Shown as an Unmodified Nucleotide Sequence) | SEQ ID No. | Sense Strand Base Sequence (5'→3') (Shown as an Unmodified Nucleotide Sequence) | Corresponding Positions on SEQ ID NO: 1 |
|---|---|---|---|---|
| 49 | UCACUGAGAAUACUGUCCC | 114 | GGGACAGUAUUCUCAGUGA | 438-456 |
| 49 | UCACUGAGAAUACUGUCCC | 115 | GGGACAGUAUUCUCAGUIA | 438-456 |
| 50 | GCACUGAGAAUACUGUCCC | 116 | GGGACAGUAUUCUCAGUGC | 438-456 |
| 51 | NCACUGAGAAUACUGUCCC | 117 | GGGACAGUAUUCUCAGUGN | 438-456 |
| 52 | NCACUGAGAAUACUGUCCN | 118 | NGGACAGUAUUCUCAGUGN | 438-456 |
| 53 | UUCUUGUCCAGCUUUAUUG | 119 | CAAUAAAGCUGGACAAGAA | 506-524 |
| 53 | UUCUUGUCCAGCUUUAUUG | 120 | CAAUAAAICUGGACAAGAA | 506-524 |
| 54 | NUCUUGUCCAGCUUUAUUG | 121 | CAAUAAAGCUGGACAAGAN | 506-524 |
| 55 | NUCUUGUCCAGCUUUAUUN | 122 | NAAUAAAGCUGGACAAGAN | 506-524 |
| 56 | UGAAUACUGUCCCUUUUAA | 123 | UUAAAAGGGACAGUAUUCA | 432-450 |
| 57 | AGAAUACUGUCCCUUUUAA | 124 | UUAAAAGGGACAGUAUUCU | 432-450 |
| 58 | AGAAUACUGUCCCUUUUAG | 125 | CUAAAAGGGACAGUAUUCU | 432-450 |
| 59 | NGAAUACUGUCCCUUUUAA | 126 | UUAAAAGGGACAGUAUUCN | 432-450 |
| 60 | NGAAUACUGUCCCUUUUAG | 127 | CUAAAAGGGACAGUAUUCN | 432-450 |
| 61 | NGAAUACUGUCCCUUUUAN | 128 | NUAAAAGGGACAGUAUUCN | 432-450 |
| 62 | UAACAACAAGGAGUACCCG | 129 | CGGGUACUCCUUGUUGUUA | 56-74 |
| 63 | CAACAACAAGGAGUACCCG | 130 | CGGGUACUCCUUGUUGUUG | 56-74 |
| 64 | NAACAACAAGGAGUACCCG | 131 | CGGGUACUCCUUGUUGUUN | 56-74 |
| 65 | NAACAACAAGGAGUACCCN | 132 | NGGGUACUCCUUGUUGUUN | 56-74 |
| 66 | UGCAACAACAAGGAGUACC | 133 | GGUACUCCUUGUUGUUGCA | 58-76 |
| 67 | GGCAACAACAAGGAGUACC | 134 | GGUACUCCUUGUUGUUGCC | 58-76 |
| 68 | NGCAACAACAAGGAGUACC | 135 | GGUACUCCUUGUUGUUGCN | 58-76 |
| 69 | NGCAACAACAAGGAGUACN | 136 | NGUACUCCUUGUUGUUGCN | 58-76 |
| 70 | UAGCCAUCGGUCACCCAGC | 137 | GCUGGGUGACCGAUGGCUA | 228-246 |
| 71 | AAGCCAUCGGUCACCCAGC | 138 | GCUGGGUGACCGAUGGCUU | 228-246 |
| 72 | NAGCCAUCGGUCACCCAGC | 139 | GCUGGGUGACCGAUGGCUN | 228-246 |
| 73 | NAGCCAUCGGUCACCCAGN | 140 | NCUGGGUGACCGAUGGCUN | 228-246 |

TABLE 2-continued

APOC3 RNAi Agent Antisense Strand and Sense Strand Core Stretch Base Sequences
(N = any nucleobase).

| SEQ ID No. | Antisense Strand Base Sequence (5'→3') (Shown as an Unmodified Nucleotide Sequence) | SEQ ID No. | Sense Strand Base Sequence (5'→3') (Shown as an Unmodified Nucleotide Sequence) | Corresponding Positions on SEQ ID NO: 1 |
|---|---|---|---|---|
| 74 | UGAACUGAAGCCAUCGGUC | 141 | GACCGAUGGCUUCAGUUCA | 235-253 |
| 75 | GGAACUGAAGCCAUCGGUC | 142 | GACCGAUGGCUUCAGUUCC | 235-253 |
| 76 | NGAACUGAAGCCAUCGGUC | 143 | GACCGAUGGCUUCAGUUCN | 235-253 |
| 77 | NGAACUGAAGCCAUCGGUN | 144 | NACCGAUGGCUUCAGUUCN | 235-253 |
| 78 | UCUUUCAGGGAACUGAAGC | 145 | GCUUCAGUUCCCUGAAAGA | 243-261 |
| 79 | NCUUUCAGGGAACUGAAGC | 146 | GCUUCAGUUCCCUGAAAGN | 243-261 |
| 80 | NCUUUCAGGGAACUGAAGN | 147 | NCUUCAGUUCCCUGAAAGN | 243-261 |
| 81 | UAGUCUUUCAGGGAACUGA | 148 | UCAGUUCCCUGAAAGACUA | 246-264 |
| 82 | NAGUCUUUCAGGGAACUGA | 149 | UCAGUUCCCUGAAAGACUN | 246-264 |
| 83 | NAGUCUUUCAGGGAACUGN | 150 | NCAGUUCCCUGAAAGACUN | 246-264 |
| 84 | UAACGGUGCUCCAGUAGUC | 151 | GACUACUGGAGCACCGUUA | 260-278 |
| 85 | NAACGGUGCUCCAGUAGUC | 152 | GACUACUGGAGCACCGUUN | 260-278 |
| 86 | NAACGGUGCUCCAGUAGUN | 153 | NACUACUGGAGCACCGUUN | 260-278 |
| 87 | UUAACGGUGCUCCAGUAGU | 154 | ACUACUGGAGCACCGUUAA | 261-279 |
| 88 | NUAACGGUGCUCCAGUAGU | 155 | ACUACUGGAGCACCGUUAN | 261-279 |
| 89 | NUAACGGUGCUCCAGUAGN | 156 | NCUACUGGAGCACCGUUAN | 261-279 |
| 90 | UACUUGUCCUUAACGGUGC | 157 | GCACCGUUAAGGACAAGUA | 270-288 |
| 91 | AACUUGUCCUUAACGGUGC | 158 | GCACCGUUAAGGACAAGUU | 270-288 |
| 92 | NACUUGUCCUUAACGGUGC | 159 | GCACCGUUAAGGACAAGUN | 270-288 |
| 93 | NACUUGUCCUUAACGGUGN | 160 | NCACCGUUAAGGACAAGUN | 270-288 |
| 94 | UGAACUUGUCCUUAACGGU | 161 | ACCGUUAAGGACAAGUUCA | 272-290 |
| 95 | AGAACUUGUCCUUAACGGU | 162 | ACCGUUAAGGACAAGUUCU | 272-290 |
| 96 | NGAACUUGUCCUUAACGGU | 163 | ACCGUUAAGGACAAGUUCN | 272-290 |
| 97 | NGAACUUGUCCUUAACGGN | 164 | NCCGUUAAGGACAAGUUCN | 272-290 |
| 98 | UAGAACUUGUCCUUAACGG | 165 | CCGUUAAGGACAAGUUCUA | 273-291 |
| 99 | GAGAACUUGUCCUUAACGG | 166 | CCGUUAAGGACAAGUUCUC | 273-291 |
| 100 | NAGAACUUGUCCUUAACGG | 167 | CCGUUAAGGACAAGUUCUN | 273-291 |
| 101 | NAGAACUUGUCCUUAACGN | 168 | NCGUUAAGGACAAGUUCUN | 273-291 |
| 102 | UGGACUUGGGGUAUUGAGG | 169 | CCUCAAUACCCCAAGUCCA | 349-367 |
| 103 | NGGACUUGGGGUAUUGAGG | 170 | CCUCAAUACCCCAAGUCCN | 349-367 |
| 104 | NGGACUUGGGGUAUUGAGN | 171 | NCUCAAUACCCCAAGUCCN | 349-367 |
| 105 | UGAGAAUACUGUCCCUUUU | 172 | AAAAGGGACAGUAUUCUCA | 434-452 |
| 106 | UGAGAAUACUGUCCCUUUG | 173 | CAAAGGGACAGUAUUCUCA | 434-452 |
| 107 | NGAGAAUACUGUCCCUUUU | 174 | AAAAGGGACAGUAUUCUCN | 434-452 |
| 108 | NGAGAAUACUGUCCCUUUG | 175 | CAAAGGGACAGUAUUCUCN | 434-452 |
| 109 | NGAGAAUACUGUCCCUUUN | 176 | NAAAGGGACAGUAUUCUCN | 434-452 |

TABLE 2-continued

APOC3 RNAi Agent Antisense Strand and Sense Strand Core Stretch Base Sequences (N = any nucleobase).

| SEQ ID No. | Antisense Strand Base Sequence (5'→3') (Shown as an Unmodified Nucleotide Sequence) | SEQ ID No. | Sense Strand Base Sequence (5'→3') (Shown as an Unmodified Nucleotide Sequence) | Corresponding Positions on SEQ ID NO: 1 |
|---|---|---|---|---|
| 110 | UACUGAGAAUACUGUCCCU | 177 | AGGGACAGUAUUCUCAGUA | 437-455 |
| 111 | CACUGAGAAUACUGUCCCU | 178 | AGGGACAGUAUUCUCAGUG | 437-455 |
| 112 | NACUGAGAAUACUGUCCCU | 179 | AGGGACAGUAUUCUCAGUN | 437-455 |
| 113 | NACUGAGAAUACUGUCCCN | 180 | NGGGACAGUAUUCUCAGUN | 437-455 |

The APOC3 RNAi agent sense strands and antisense strands that comprise or consist of the nucleotide sequences in Table 2 can be modified nucleotides or unmodified nucleotides. In some embodiments, the APOC3 RNAi agents having the sense and antisense strand sequences that comprise or consist of the nucleotide sequences in Table 2 are all or substantially all modified nucleotides.

In some embodiments, the antisense strand of an APOC3 RNAi agent disclosed herein differs by 0, 1, 2, or 3 nucleotides from any of the antisense strand sequences in Table 2. In some embodiments, the sense strand of an APOC3 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified APOC3 RNAi agent antisense strands, as well as their underlying unmodified nucleobase sequences, are provided in Tables 3 and 4. Certain modified APOC3 RNAi agent sense strands, as well as their underlying unmodified nucleobase sequences, are provided in Tables 3 and 5. In forming APOC3 RNAi agents, each of the nucleotides in each of the underlying base sequences listed in Tables 3, 4, and 5, as well as in Table 2, above, can be a modified nucleotide.

The APOC3 RNAi agents described herein are formed by annealing an antisense strand with a sense strand. A sense strand containing a sequence listed in Table 2, Table 3, or Table 5, can be hybridized to any antisense strand containing a sequence listed in Table 2, Table 3, or Table 4, provided the two sequences have a region of at least 85% complementarity over a contiguous 16, 17, 18, 19, 20, or 21 nucleotide sequence.

In some embodiments, an APOC3 RNAi agent antisense strand comprises a nucleotide sequence of any of the sequences in Table 2, Table 3, or Table 4.

In some embodiments, an APOC3 RNAi agent comprises or consists of a duplex having the nucleobase sequences of the sense strand and the antisense strand of any of the sequences in Table 2, Table 3, Table 4, or Table 5.

Examples of antisense strands containing modified nucleotides are provided in Table 4. Examples of sense strands containing modified nucleotides are provided in Table 5. Further examples of antisense strands and sense strands containing modified nucleotides are provided in Table 3.

As used in Tables 3, 4, and 5, the following notations are used to indicate modified nucleotides, targeting groups, and linking groups:

A=adenosine-3'-phosphate;
C=cytidine-3'-phosphate;
G=guanosine-3'-phosphate;
U=uridine-3'-phosphate
I=inosine-3'-phosphate
n=any 2'-OMe modified nucleotide
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
i=2'-O-methylinosine-3'-phosphate
is =2'-O-methylinosine-3'-phosphorothioate
Nf=any 2'-fluoro modified nucleotide
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
If=2'-fluoroinosine-3'-phosphate
Ifs=2'-fluoroinosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dA=2'-deoxyadenosine-3'-phosphate
dAs=2'-deoxyadenosine-3'-phosphorothioate
dC=2'-deoxycytidine-3'-phosphate
dCs=2'-deoxycytidine-3'-phosphorothioate
dG=2'-deoxyguanosine-3'-phosphate dGs=2'-deoxyguanosine-3'-phosphorothioate
dT=2'-deoxythymidine-3'-phosphate
dTs=2'-deoxythymidine-3'-phosphorothioate
dU=2'-deoxyuridine-3'-phosphate
dUs=2'-deoxyuridine-3'-phosphorothioate
$N_{UNA}$=2',3'-seco nucleotide mimics (unlocked nucleobase analogs)-3'-Phosphate
$N_{UNA}$s=2',3'-seco nucleotide mimics (unlocked nucleobase analogs)-3'-phosphorothioate
$A_{UNA}$=2',3'-seco-adenosine-3'-phosphate
$A_{UNA}$s=2',3'-seco-adenosine-3'-phosphorothioate
$C_{UNA}$=2',3'-seco-cytidine-3'-phosphate
$C_{UNA}$s=2',3'-seco-cytidine-3'-phosphorothioate
$G_{UNA}$=2',3'-seco-guanosine-3'-phosphate
$G_{UNA}$s=2',3'-seco-guanosine-3'-phosphorothioate
$U_{UNA}$=2',3'-seco-uridine-3'-phosphate
$U_{UNA}$s=2',3'-seco-uridine-3'-phosphorothioate
a_2N=see Table 7
a_2Ns=see Table 7
pu_2N=see Table 7
pu_2Ns=see Table 7
$N_{LNA}$=locked nucleotide
$Nf_{ANA}$=2'-F-Arabino nucleotide
NM=2'-O-methoxyethyl nucleotide
AM=2'-O-methoxyethyladenosine-3'-phosphate
AMs=2'-O-methoxyethyladenosine-3'-phosphorothioate
GM=2'-O-methoxyethylguanosine-3'-phosphate
GMs=2'-O-methoxyethylguanosine-3'-phosphorothioate
TM=2'-O-methoxyethylthymidine-3'-phosphate
TMs=2'-O-methoxyethylthymidine-3'-phosphorothioate
mCM=see Table 7
mCMs=see Table 7
R=ribitol
(invdN)=any inverted deoxyribonucleotide (3'-3' linked nucleotide)
(invAb)=inverted (3'-3' linked) abasic deoxyribonucleotide, see Table 7
(invAb)s=inverted (3'-3' linked) abasic deoxyribonucleotide-5'-phosphorothioate, see Table 7
(invn)=any inverted 2'-OMe nucleotide (3'-3' linked nucleotide)
s=phosphorothioate linkage
sp=see Table 7
D2u=see Table 7
pD2u=see Table 7
vpdN=vinyl phosphonate deoxyribonucleotide
(5Me-Nf)=5'-Me, 2'-fluoro nucleotide
cPrp=cyclopropyl phosphonate, see Table 7
epTcPr=see Table 7
epTM=see Table 7

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1I showing all internucleoside linkages). Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Moreover, as the person of ordinary skill would readily understand and appreciate, while the phosphorothioate chemical structures depicted herein typically show the anion on the sulfur atom, the inventions disclosed herein encompass all phosphorothioate tautomers and/or diastereomers (e.g., where the sulfur atom has a double-bond and the anion is on an oxygen atom). Unless expressly indicated otherwise herein, such understandings of the person of ordinary skill in the art are used when describing the APOC3 RNAi agents and compositions of APOC3 RNAi agents disclosed herein.

Certain examples of targeting groups and linking groups used with the APOC3 RNAi agents disclosed herein are provided below in Table 7. More specifically, targeting groups and linking groups include the following, for which their chemical structures are provided below in Table 7: (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed herein, as well as other targeting or linking groups, conjugated to the 5' and/or 3' end of the sequence.

TABLE 3

APOC3 RNAi Agent Modified Antisense Strand and Modified Sense Strand Duplexes

| DUPLEX ID NO.: | SEQ ID NO. | Antisense Sequence (5'→3') | SEQ ID NO. | Sense Sequence (5'→3') |
| --- | --- | --- | --- | --- |
| 56_1 | 181 | uAfaCfaAfcAfAfGfgAfgUfaCfcCfguu | 246 | cgGfgUfaCfUfCfcUfuGfuUfgUfuauu |
| 56_2 | 182 | uAfaCfaAfcAfaGfgAfgUfaCfcCfguu | 247 | cgggugaCfUfCfcuuguuguuauu |
| 56_3 | 183 | uAfaCfaAfcAfaGfgAfgUfaCfcCfggu | 248 | ccgggugaCfUfCfcuuguuguua |
| 56_4 | 184 | uAfaCfaAfcAfaGfgAfgUfaCfcCfggg | 249 | cccgggugaCfUfCfcuuguuguua |
| 56_5 | 185 | uAfaCfaAfcaaggAfgUfaCfcCfggg | 250 | cccgggugaCfUfCfcuuguuguua |
| 58_1 | 186 | uGfcAfaCfaAfCfAfaGfgAfgUfaCfcuu | 251 | ggUfaCfuCfCfUfuGfuUfgUfuGfcauu |
| 58_2 | 187 | uGfcAfaCfaAfcAfaGfgAfgUfaCfcuu | 252 | gguacuCfCfUfuguuguugcauu |
| 58_3 | 188 | uGfcAfaCfaAfcAfaGfgAfgUfaCfccu | 253 | ggguacuCfCfUfuguuguugca |
| 58_4 | 189 | uGfcAfaCfaAfcAfaGfgAfgUfaCfccg | 254 | cgggtacuCfCfUfuguuguugca |

TABLE 3-continued

APOC3 RNAi Agent Modified Antisense Strand and Modified Sense Strand Duplexes

| DUPLEX ID NO.: | SEQ ID NO. | Antisense Sequence (5'→3') | SEQ ID NO. | Sense Sequence (5'→3') |
|---|---|---|---|---|
| 58_5 | 190 | uGfcAfaCfaacaaGfgAfgUfaCfccg | 255 | cggguacuCfCfUfuguuguugca |
| 228_1 | 191 | uAfgCfcAfuCfgGfuCfaCfcCfaGfcuu | 256 | gcUfgGfgUfGfAfcCfgAfuGfgCfuauu |
| 228_2 | 192 | uAfgCfcAfuCfgGfuCfaCfcCfaGfcuu | 257 | gcugggUfGfAfccgauggcuauu |
| 228_3 | 193 | uAfgCfcAfuCfgGfuCfaCfcCfaGfccu | 258 | ggcugggUfGfAfccgauggcua |
| 228_4 | 194 | uAfgCfcAfuCfgGfuCfaCfcCfaGfccc | 259 | gggcugggUfGfAfccgauggcua |
| 228_5 | 195 | uAfgCfcAfucgguCfaCfcCfaGfccc | 260 | gggcugggUfGfAfccgauggcua |
| 235_1 | 196 | uGfaAfcUfgAfAfgfcCfaUfcGfgUfcuu | 261 | gaCfcGfaUfGfGfcUfuCfaGfuticauu |
| 235_2 | 197 | uGfaAfcUfgAfaGfcCfaUfcGfgUfcuu | 262 | gaccgaUfGfGfcuucaguucauu |
| 235_3 | 198 | uGfaAfcUfgAfaGfcCfaUfcGfgUfcau | 263 | ugaccgaUfGfGfcuucaguuca |
| 235_4 | 199 | uGfaAfcUfgAfaGfcCfaUfcGfgUfcac | 264 | gugaccgaUfGfGfcuucaguuca |
| 235_5 | 200 | uGfaAfcUfgaagcCfaUfcGfgUfcac | 265 | gugaccgaUfGfGfcuucaguuca |
| 243_1 | 201 | uCfuIffuCfaGfgGfaAfcUfgAfaGfcuu | 266 | gcUfuCfaGfUfUfcCfcUfgAfaAfgauu |
| 243_2 | 202 | uCfuIffuCfaGfgGfaAfcUfgAfaGfcuu | 267 | gcuucaGfUfUfcccugaaagauu |
| 243_3 | 203 | uCfuIffuCfaGfgGfaAfcUfgAfaGfccu | 268 | ggcuucaGfUfUfcccugaaaga |
| 243_4 | 204 | uCfuIffuCfaGfgGfaAfcUfgAfaGfcca | 269 | uggcuucaGfUfUfcccugaaaga |
| 243_5 | 205 | uCfuUfuCfagggaAfcUfgAfaGfcca | 270 | uggcuucaGfUfUfcccugaaaga |
| 260_1 | 206 | uAfaCfgGfuGfCfUfcCfaGfuAfgUfcuu | 271 | gaCfuAfcUfGfGffaGfcAfcCfgUfuauu |
| 260_2 | 207 | uAfaCfgGfuGfcUfcCfaGfuAfgUfcuu | 272 | gacuacUfGfGfagcaccguuauu |
| 260_3 | 208 | uAfaCfgGfuGfcUfcCfaGfuAfgUfcuu | 273 | agacuacUfGfGfagcaccguua |
| 260_4 | 209 | uAfaCfgGfuGfcUfcCfaGfuAfgUfcuu | 274 | aagacuacUfGfGfagcaccguua |
| 260_5 | 210 | uAfaCfgGfugcucCfaGfuAfgUfcuu | 275 | aagacuacUfGfGfagcaccguua |
| 261_1 | 211 | uUfaAfcGfgUfGfCfuCfcAfgUfaGfuuu | 276 | acUfaCfuGfGfAfgCfaCfcGfuUfaauu |
| 261_2 | 212 | uUfaAfcGfgUfgCfuCfcAfgUfaGfuuu | 277 | acuacuGfGfAfgcaccguuaauu |
| 261_3 | 213 | uUfaAfcGfgUfgCfuCfcAfgUfaGfucu | 278 | gacuacuGfGfAfgcaccguuaa |
| 261_4 | 214 | uUfaAfcGfgUfgCfuCfcAfgUfaGfucu | 279 | agacuacuGfGfAfgcaccguuaa |
| 261_5 | 215 | uUfaAfcGfgugcuCfcAfgUfaGfucu | 280 | agacuacuGfGfAfgcaccguuaa |
| 270_1 | 216 | uAfcUfuGfuCfCfUfuAfaCfgGfuGfcuu | 281 | gcAfcCfgUfUfAfaGfgAfcAfaGfuauu |
| 270_2 | 217 | uAfcUfuGfuCfcUfuAfaCfgGfuGfcuu | 282 | gcaccgUfUfAfaggacaaguauu |
| 270_3 | 218 | uAfcUfuGfuCfcUfuAfaCfgGfuGfcuu | 283 | agcaccgUfUfAfaggacaagua |
| 270_4 | 219 | uAfcUfuGfuCfcUfuAfaCfgGfuGfcuc | 284 | gagcaccgUfUfAfaggacaagua |
| 270_5 | 220 | uAfcUfuGfuccuuAfaCfgGfuGfcuc | 285 | gagcaccgUfUfAfaggacaagua |
| 272_1 | 221 | uGfaAfcUfuGfuCffcUfuAfaCfgGfuuu | 286 | acCfgUfuAfAfGfgAfcAfaGfuUfcauu |
| 272_2 | 222 | uGfaAfcUfuGfuCfcUfuAfaCfgGfuuu | 287 | accguuAfAfGfgacaaguucauu |
| 272_3 | 223 | uGfaAfcUfuGfuCfcUfuAfaCfgGfugu | 288 | caccguuAfAfGfgacaaguuca |
| 272_4 | 224 | uGfaAfcUfuGfuCfcUfuAfaCfgGfugc | 289 | gcaccguuAfAfGfgacaaguuca |
| 272_5 | 225 | uGfaAfcUfugccuUfuAfaCfgGfugc | 290 | gcaccguuAfAfGfgacaaguuca |
| 273_1 | 226 | uAfgAfaCfuUfGfUfcCfuUfaAfcGfguu | 291 | ccGfuUfaAfGfGfaCfaAfgUfuCfuauu |
| 273_2 | 227 | uAfgAfaCfuUfgUfcCfuUfaAfcGfguu | 292 | ccguuaAfGfGfacaaguucuauu |

TABLE 3-continued

APOC3 RNAi Agent Modified Antisense Strand and Modified Sense Strand Duplexes

| DUPLEX ID NO.: | SEQ ID NO. | Antisense Sequence (5'→3') | SEQ ID NO. | Sense Sequence (5'→3') |
|---|---|---|---|---|
| 273_3 | 228 | uAfgAfaCfuUfgUfcCfuUfaAfcGfguu | 293 | accguuaAfGfGfacaaguucua |
| 273_4 | 229 | uAfgAfaCfuUfgUfcCfuUfaAfcGfgug | 294 | caccguuaAfGfGfacaaguucua |
| 273_5 | 230 | uAfgAfaCfuugucCfuUfaAfcGfgug | 295 | caccguuaAfGfGfacaaguucua |
| 349_1 | 231 | uGfgAfcUfuGfGfGfgUfaUfuGfaGfguu | 296 | ccUfcAfaUfAfCfcCfcAfaGfuCfcauu |
| 349_2 | 232 | uGfgAfcUfuGfgGfgUfaUfuGfaGfguu | 297 | ccucaaUfAfCfcccaaguccauu |
| 349_3 | 233 | uGfgAfcUfuGfgGfgUfaUfuGfaGfguu | 298 | accucaaUfAfCfcccaagucca |
| 349_4 | 234 | uGfgAfcUfuGfgGfgUfaUfuGfaGfguc | 299 | gaccucaaUfAfCfcccaagucca |
| 349_5 | 235 | uGfgAfcUfugggGfUfaUfuGfaGfguc | 300 | gaccucaaUfAfCfcccaagucca |
| 434_1 | 236 | uGfaGfaAfuAfCfUfgUfcCfcUfuUfuuu | 301 | aaAfaGfgGfAfCfaGfuAfuUfcUfcauu |
| 434_2 | 237 | uGfaGfaAfuAfcUfgUfcCfcUfuUfuuu | 302 | aaaaggGfAfCfaguauucucauu |
| 434_3 | 238 | uGfaGfaAfuAfcUfgUfcCfcUfuUfuau | 303 | uaaaaggGfAfCfaguauucuca |
| 434_4 | 239 | uGfaGfaAfuAfcUfgUfcCfcUfuUfuaa | 304 | uuaaaaggGfAfCfaguauucuca |
| 434_5 | 240 | uGfaGfaAfuacugUfcCfcUfuUfuaa | 305 | uuaaaaggGfAfCfaguauucuca |
| 437_1 | 241 | uAfcUfgAfgAfAfUfaCfuGfuCfcCfuuu | 306 | agGfaAfcAfGfUfaUfuCfuCfuCfaGfuauu |
| 437_2 | 242 | uAfcUfgAfgAfaUfaCfuGfuCfcCfuuu | 307 | agggacAfGfGfUfauucucaguauu |
| 437_3 | 243 | uAfcUfgAfgAfaUfaCfuGfuCfcCfuuu | 308 | aagggacAfGfGfUfauucucagua |
| 437_4 | 244 | uAfcUfgAfgAfaUfaCfuGfuCfcCfuuu | 309 | aaagggacAfGfGfUfauucucagua |
| 437_5 | 245 | uAfcUfgAfgaauaCfuGfuCfcCfuuu | 310 | aaagggacAfGfGfUfauucucagua |

TABLE 4

APOC3 RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06203-AS | usAfscsUfuGfuCfcUfuAfaCfgGfuGfcusu | 311 | UACUUGUCCUUAACGGUGCUU | 603 |
| AM06204-AS | usAfscsUfuGfuCfcUfuAfaCfgGfuGfcusc | 312 | UACUUGUCCUUAACGGUGCUC | 604 |
| AM06205-AS | asAfscsUfuGfuCfcUfuAfaCfgGfuGfcusu | 313 | AACUUGUCCUUAACGGUGCUU | 655 |
| AM06210-AS | usGfsgsAfcUfuGfgGfgUfaUfuGfaGfgusu | 314 | UGGACUUGGGGUAUUGAGGUU | 610 |
| AM06211-AS | usGfsgsAfcUfuGfgGfgUfaUfuGfaGfgusc | 315 | UGGACUUGGGGUAUUGAGGUC | 611 |
| AM06214-AS | usCfsusUfcCfaGfgGfaAfcUfgAfaGfcusu | 316 | UCUUUCAGGGAACUGAAGCUU | 597 |
| AM06215-AS | usCfsusUfcCfaGfgGfaAfcUfgAfaGfccsu | 317 | UCUUUCAGGGAACUGAAGCCU | 598 |
| AM06218-AS | usGfsasAfcUfgAfaGfcCfaUfcGfgUfcusu | 318 | UGAACUGAAGCCAUCGGUCUU | 594 |
| AM06219-AS | usGfsasAfcUfgAfaGfcCfaUfcGfgUfcasc | 319 | UGAACUGAAGCCAUCGGUCAC | 596 |
| AM06262-AS | usGfsasGfaAfuAfcUfgUfcCfcUfuUfugsg | 320 | UGAGAAUACUGUCCCUUUUGG | 656 |
| AM06263-AS | usGfsasGfaAfuAfcUfgUfcCfcUfuUfugcsg | 321 | UGAGAAUACUGUCCCUUUUGCG | 657 |
| AM06266-AS | usAfsasCfgGfuGfcUfcCfaGfuAfgUfcusu | 322 | UAACGGUGCUCCAGUAGUCUU | 500 |
| AM06267-AS | usAfsasCfgGfuGfcUfcCfaGfuAfgUfcgsu | 323 | UAACGGUGCUCCAGUAGUCGU | 658 |
| AM06272-AS | usAfscsUfgAfgAfaUfaCfuGfuCfcCfuusu | 324 | UACUGAGAAUACUGUCCCUUU | 615 |

TABLE 4-continued

APOC3 RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06273-AS | usAfscsUfgAfgAfaUfaCfuGfuCfcCfugsu | 325 | UACUGAGAAUACUGUCCCUGU | 659 |
| AM06276-AS | usUfsasAfcGfgUfgCfuCfcAfgUfaGfucsu | 326 | UUAACGGUGCUCCAGUAGUCU | 602 |
| AM06277-AS | usUfsasAfcGfgUfgCfuCfcAfgUfaGfgcsu | 327 | UUAACGGUGCUCCAGUAGGCU | 660 |
| AM06309-AS | usAfsgsCfcAfuCfgGfuCfaCfcCfaGfcusu | 328 | UAGCCAUCGGUCACCCAGCUU | 591 |
| AM06310-AS | asAfsgsCfcAfuCfgGfuCfaCfcCfaGfcusu | 329 | AAGCCAUCGGUCACCCAGCUU | 661 |
| AM06314-AS | usAfsgsAfaCfuUfgUfcCfuUfaAfcGfgusu | 330 | UAGAACUUGUCCUUAACGGUU | 608 |
| AM06315-AS | usAfsgsAfaCfuUfgUfcCfuUfaAfcGfgusg | 331 | UAGAACUUGUCCUUAACGGUG | 609 |
| AM06318-AS | usGfsasAfcUfuGfuCfcUfuAfaCfgGfuusu | 332 | UGAACUUGUCCUUAACGGUUU | 65 |
| AM06319-AS | asGfsasAfcUfuGfuCfcUfuAfaCfgGfuusu | 333 | AGAACUUGUCCUUAACGGUUU | 662 |
| AM06320-AS | usGfsasAfcUfuGfuCfcUfuAfaCfgGfugsc | 334 | UGAACUUGUCCUUAACGGUGC | 607 |
| AM06324-AS | usGfscsAfaCfaAfcAfaGfgAfgUfaCfcusu | 335 | UGCAACAACAAGGAGUACCUU | 588 |
| AM06325-AS | usGfscsAfaCfaAfcAfaGfgAfgUfaCfccsg | 336 | UGCAACAACAAGGAGUACCCG | 590 |
| AM06328-AS | usAfsasCfaAfcAfaGfgAfgUfaCfcCfgusu | 337 | UAACAACAAGGAGUACCCGUU | 585 |
| AM06330-AS | usGfscsAfcUfgAfgAfaUfaCfuGfuCfccusu | 338 | UGCACUGAGAAUACUGUCCCUU | 663 |
| AM06331-AS | asGfscsAfcUfgAfgAfaUfaCfuGfuCfccusu | 339 | AGCACUGAGAAUACUGUCCCUU | 664 |
| AM06469-AS | cPrpusAfscsUfuGfuCfcUfuAfaCfgGfuGfcusu | 340 | UACUUGUCCUUAACGGUGCUU | 603 |
| AM06471-AS | asAfscsUfuGfuCfcUfuAfaCfgGfuGfcusc | 341 | AACUUGUCCUUAACGGUGCUC | 666 |
| AM06472-AS | usAfscsUfuGfuCfcUfuAfaCfgGfugsc | 342 | UACUUGUCCUUAACGGUGC | 667 |
| AM06475-AS | usAfscsUfuGfuCfcUfuAfaCfgGfuGfcucsc | 343 | UACUUGUCCUUAACGGUGCUCC | 668 |
| AM06476-AS | usAfscsUfuGfuCfcUfuAfaCfgGfuGfcucusu | 344 | UACUUGUCCUUAACGGUGCUCUU | 669 |
| AM06477-AS | usAfscsUfuGfuCfcUfuAfaCfgGfuGfcuccsa | 345 | UACUUGUCCUUAACGGUGCUCCA | 670 |
| AM06478-AS | asAfscsUfuGfuCfcUfuAfaCfgGfugsc | 346 | AACUUGUCCUUAACGGUGC | 671 |
| AM06481-AS | asAfscsUfuGfuCfcUfuAfaCfgGfuGfcucsc | 347 | AACUUGUCCUUAACGGUGCUCC | 672 |
| AM06507-AS | usGfsasGfaAfuAfcUfgUfcCfcUfulffuusu | 348 | UGAGAAUACUGUCCCUUUUUU | 612 |
| AM06509-AS | usGfsasGfaAfuAfcUfgUfcCfcUfulffugsu | 349 | UGAGAAUACUGUCCCUUUUGU | 673 |
| AM06511-AS | usGfsaGfaAfuAfcUfgUfcCfcUfuUfugsg | 350 | UGAGAAUACUGUCCCUUUUGG | 656 |
| AM06513-AS | asGfsasGfaAfuAfcUfgUfcCfcUfuUfugsg | 351 | AGAGAAUACUGUCCCUUUUGG | 674 |
| AM06514-AS | usGfscsAfaCfaAfcAfaGfgAfgUfaCfsc | 352 | UGCAACAACAAGGAGUACC | 675 |
| AM06517-AS | usGfscsAfaCfaacaaGfgAfgUfaCfccsu | 353 | UGCAACAACAAGGAGUACCCU | 589 |
| AM06518-AS | usGfscsAfaCfaacaaGfgAfgUfaCfcusu | 354 | UGCAACAACAAGGAGUACCUU | 588 |
| AM06519-AS | usGfscsaacaAfcAfaGfgAfgUfaCfcusu | 355 | UGCAACAACAAGGAGUACCUU | 588 |
| AM06521-AS | usGfcAfaCfaAfcAfaGfgAfgUfaCfcusu | 356 | UGCAACAACAAGGAGUACCUU | 588 |
| AM06523-AS | asGfscsAfaCfaAfcAfaGfgAfgUfaCfcusu | 357 | AGCAACAACAAGGAGUACCUU | 676 |
| AM06712-AS | usCfsusGfaAfgccauCfgGfuCfaCfcCfsa | 358 | UCUGAAGCCAUCGGUCACCCA | 677 |
| AM06714-AS | asCfsusGfaAfgccauCfgGfuCfaCfcCfsa | 359 | ACUGAAGCCAUCGGUCACCCA | 678 |
| AM06716-AS | usGfsgsAfaCfugaagCfcAfuCfgGfuCfsa | 360 | UGGAACUGAAGCCAUCGGUCA | 679 |
| AM06718-AS | usGfsgsAfaCfugaagCfcAfuCfgGfuCfsc | 361 | UGGAACUGAAGCCAUCGGUCC | 680 |

TABLE 4-continued

APOC3 RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06720-AS | usUfscsUfuUfcagggAfaCfuGfaAfgCfsc | 362 | UUCUUUCAGGGAACUGAAGCC | 681 |
| AM06722-AS | usUfsusAfaCfggugcUfcCfaGfuAfgUfsc | 363 | UUUAACGGUGCUCCAGUAGUC | 682 |
| AM06724-AS | usCfscsUfuAfacgguGfcUfcCfaGfuAfsg | 364 | UCCUUAACGGUGCUCCAGUAG | 683 |
| AM06726-AS | usUfscsCfuUfaacggUfgCfuCfcAfgUfsa | 365 | UUCCUUAACGGUGCUCCAGUA | 684 |
| AM06728-AS | usUfscsCfuUfaacggUfgCfuCfcAfgUfsc | 366 | UUCCUUAACGGUGCUCCAGUC | 685 |
| AM06730-AS | usAfscsUfuGfuCfcUfuAfaCfgGfuGfcUfsc | 367 | UACUUGUCCUUAACGGUGCUC | 604 |
| AM06732-AS | asAfscsUfuGfuCfcUfuAfaCfgGfuGfcsUfsc | 368 | AACUUGUCCUUAACGGUGCUC | 666 |
| AM06734-AS | usUfsgsAfgGfucucaGfgCfaGfcCfaCfsu | 369 | UUGAGGUCUCAGGCAGCCACU | 686 |
| AM06736-AS | usUfsasUfuGfaGfgUfcUfcAfgGfcAfgCfsc | 370 | UUAUUGAGGUCUCAGGCAGCC | 687 |
| AM06738-AS | usGfsusAfuUfgAfgGfuCfuCfaGfgCfaGfsc | 371 | UGUAUUGAGGUCUCAGGCAGC | 688 |
| AM06740-AS | usCfsasCfuGfaGfaAfuAfcUfgUfcCfcUfsu | 372 | UCACUGAGAAUACUGUCCCUU | 689 |
| AM06741-AS | usCfsasCfuGfagaauAfcUfgUfcCfcUfsu | 373 | UCACUGAGAAUACUGUCCCUU | 689 |
| AM06743-AS | usCfsasCfuGfagaauAfcUfgUfcCfcGfsu | 4 | UCACUGAGAAUACUGUCCCGU | 5 |
| AM06745-AS | usCfsusUfuUfaAfgCfaAfcCfuAfcAfgGfsg | 374 | UCUUUUAAGCAACCUACAGGG | 690 |
| AM06780-AS | usGfsasGfaAfuAfcUfgUfcCfcUfuUfucsc | 375 | UGAGAAUACUGUCCCUUUUCC | 691 |
| AM06783-AS | usCfsasCfuGfagaauAfcUfgUfcCfcUfsc | 2 | UCACUGAGAAUACUGUCCCUC | 3 |
| AM06784-AS | usUfsasUfuGfaggucUfcAfgGfcAfgCfsc | 376 | UUAUUGAGGUCUCAGGCAGCC | 687 |
| AM06786-AS | usGfsasGfaAfuAfcUfgUfcCfcUfuUfgcsc | 13 | UGAGAAUACUGUCCCUUUGCC | 14 |
| AM06862-AS | usGfsasGfaAfuAfcUfgUfcCfcUfuUfuCfsc | 377 | UGAGAAUACUGUCCCUUUUCC | 691 |
| AM06865-AS | usGfsasGfaAfuAfcUfgUfcCfcUfuUfucsu | 378 | UGAGAAUACUGUCCCUUUUCU | 692 |
| AM06868-AS | usUfscsUfuGfuCfcAfgCfuUfuAfuUfgGfsg | 379 | UUCUUGUCCAGCUUUAUUGGG | 693 |
| AM06870-AS | usUfscsUfuGfuCfcAfgCfuUfuAfuUfgGfsc | 7 | UUCUUGUCCAGCUUUAUUGGC | 8 |
| AM06872-AS | usAfsgsUfcUfuUfcAfgGfgAfaCfuGfaAfsg | 380 | UAGUCUUUCAGGGAACUGAAG | 694 |
| AM06874-AS | usAfsgsUfcUfuUfcAfgGfgAfaCfuGfaAfsc | 381 | UAGUCUUUCAGGGAACUGAAC | 695 |
| AM06876-AS | asGfsasAfuAfcUfgUfcCfcUfuUfuAfaGfsc | 11 | AGAAUACUGUCCCUUUUAAGC | 12 |
| AM06908-AS | usCfsasCfuGfagaauAfcUfgUfcCfcusu | 382 | UCACUGAGAAUACUGUCCCUU | 689 |
| AM06928-AS | usCfsasCfuGfagaauAfcUfgUfcCfgusu | 383 | UCACUGAGAAUACUGUCCGUU | 696 |
| AM06951-AS | usAfsgsUfcUfuUfcAfgGfgAfaCfuGfaCfsg | 384 | UAGUCUUUCAGGGAACUGACG | 697 |
| AM06953-AS | usAfsgsUfcUfuUfcAfgGfgAfaCfuGfaGfsg | 385 | UAGUCUUUCAGGGAACUGAGG | 698 |
| AM06956-AS | usAfsgsUfcUfuUfcAfgGfgAfaCfuGfaCfsc | 386 | UAGUCUUUCAGGGAACUGACC | 699 |
| AM06958-AS | usAfsgsUfcUfuUfcAfgGfgAfaCfuGfaGfsc | 387 | UAGUCUUUCAGGGAACUGAGC | 700 |
| AM06961-AS | asGfsasAfuAfcUfgUfcCfcUfuUfuAfgGfsc | 388 | AGAAUACUGUCCCUUUUAGGC | 701 |
| AM06963-AS | asGfsasAfuAfcUfgUfcCfcUfuUfuAfaGfsg | 389 | AGAAUACUGUCCCUUUUAAGG | 702 |
| AM06988-AS | asGfsasAfuAfcUfgUfcCfcUfuUfuAfgGfsg | 9 | AGAAUACUGUCCCUUUUAGGG | 10 |
| AM07179-AS | usGfscsAfaCfA$_{UNA}$acaaGfgAfgUfaCfcsu | 390 | UGCAACAACAAGGAGUACCCU | 589 |
| AM07182-AS | usAfsgsUfcUfU$_{UNA}$UfcAfgGfgAfaCfuGfaAfsg | 391 | UAGUCUUUCAGGGAACUGAAG | 694 |
| AM07185-AS | asGfsasAfuAfcC$_{UNA}$UfgUfcCfcUfuUfuAfaGfsc | 392 | AGAAUACUGUCCCUUUUAAGC | 12 |

TABLE 4-continued

APOC3 RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07188-AS | usGfsasGfaAfU$_{UNA}$AfcUfgUfcCfcUfuUfgcsc | 393 | UGAGAAUACUGUCCCUUUGCC | 14 |
| AM07190-AS | usCfsasCfuGfA$_{UNA}$gaauAfcUfgUfcCfcUfsc | 394 | UCACUGAGAAUACUGUCCCUC | 3 |
| AM07193-AS | usUfscsUfuGfU$_{UNA}$CfcAfgCfuUfuAfuUfgGfsc | 395 | UUCUUGUCCAGCUUUAUUGGC | 8 |
| AM07518-AS | asGfsasAfuAfcUfgUfcCfcUfuUfuAfgGfsu | 396 | AGAAUACUGUCCCUUUUAGGU | 707 |
| AM07520-AS | asGfsasAfuAfcUfgUfcCfcUfuUfuAfcGfsc | 397 | AGAAUACUGUCCCUUUUACGC | 708 |
| AM07522-AS | asGfsasAfuAfcUfgUfcCfcUfuUfuAfgAfsc | 398 | AGAAUACUGUCCCUUUUAGAC | 709 |
| AM07524-AS | usCfsascugagaauAfcUfgUfcCfcUfsc | 6 | UCACUGAGAAUACUGUCCCUC | 3 |
| AM07600-AS | asGfsasauacugucCfcUfuUfuAfgGfsc | 399 | AGAAUACUGUCCCUUUUAGGC | 701 |
| AM07645-AS | usUfscsuuguccagCfuUfuAfuUfgGfsc | 400 | UUCUUGUCCAGCUUUAUUGGC | 8 |
| AM07750-AS | usCfsasCfuGfagaauAfcUfgUfcCfcUfsg | 401 | UCACUGAGAAUACUGUCCCUG | 710 |
| AM07753-AS | usCfsasCfuGfagaauAfcUfgUfcCfcCfsu | 402 | UCACUGAGAAUACUGUCCCCU | 711 |
| AM07755-AS | usCfsA$_{UNA}$SCfuGfagaauAfcUfgUfcCfcUfsc | 403 | UCACUGAGAAUACUGUCCCUC | 3 |
| AM07756-AS | usCfsasC$_{UNA}$uGfagaauAfcUfgUfcCfcUfsc | 404 | UCACUGAGAAUACUGUCCCUC | 3 |
| AM07757-AS | usCfsasCfU$_{UNA}$GfagaauAfcUfgUfcCfcUfsc | 405 | UCACUGAGAAUACUGUCCCUC | 3 |
| AM07758-AS | usCfsasCfuG$_{UNA}$agaauAfcUfgUfcCfcUfsc | 406 | UCACUGAGAAUACUGUCCCUC | 3 |
| AM07760-AS | asGfsusGfcAfuccuuGfgCfgGfuCfuusu | 407 | AGUGCAUCCUUGGCGGUCUUU | 712 |
| AM07762-AS | asGfsusGfcAfU$_{UNA}$ccuuGfgCfgGfuCfuusu | 408 | AGUGCAUCCUUGGCGGUCUUU | 712 |
| AM07764-AS | asGfsusAfgUfcuuucAfgGfgAfaCfuGfsa | 409 | AGUAGUCUUUCAGGGAACUGA | 713 |
| AM07765-AS | asGfsusAfgUfC$_{UNA}$uuucAfgGfgAfaCfuGfsa | 410 | AGUAGUCUUUCAGGGAACUGA | 713 |
| AM07767-AS | usGfsusAfgUfcuuucAfgGfgAfaCfuGfsa | 411 | UGUAGUCUUUCAGGGAACUGA | 714 |
| AM07769-AS | usCfsusUfaAfcggugCfuCfcAfgUfaGfsu | 412 | UCUUAACGGUGCUCCAGUAGU | 715 |
| AM07771-AS | usCfscsUfuUfuaagcAfaCfcUfaCfaGfsg | 413 | UCCUUUUAAGCAACCUACAGG | 716 |
| AM07773-AS | usCfscsUfuUfuaagcAfaCfcUfaCfaGfsc | 414 | UCCUUUUAAGCAACCUACAGC | 717 |
| AM07775-AS | usAfsgsUfcUfuucagGfgAfaCfuGfaCfsc | 415 | UAGUCUUUCAGGGAACUGACC | 699 |

TABLE 5

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM06206-SS | (NAG37)s(invAb)sgcaccgUfUfAfaggacaaguauus(invAb) | 416 | GCACCGUUAAGGACAAGUAUU | 718 |
| AM06207-SS | (NAG37)s(invAb)sgagcaccgUfUfAfaggacaagus(invdA) | 417 | GAGCACCGUUAAGGACAAGUA | 719 |
| AM06208-SS | (NAG37)s(invAb)sgcaccgUfUfAfaggacaagus(invdA) | 418 | GCACCGUUAAGGACAAGUA | 720 |
| AM06209-SS | (NAG37)s(invAb)sgcaccgUfUfAfaggacaaguus(invAb) | 419 | GCACCGUUAAGGACAAGUU | 721 |
| AM06212-SS | (NAG37)s(invAb)sccucaaUfAfCfcccaaguccs(invdA) | 420 | CCUCAAUACCCCAAGUCCA | 722 |
| AM06213-SS | (NAG37)s(invAb)sgaccucaaUfAfCfcccaaguccs(invdA) | 421 | GACCUCAAUACCCCAAGUCCA | 723 |
| AM06216-SS | (NAG37)s(invAb)sgcuucaGfUfUfcccugaaags(invdA) | 422 | GCUUCAGUUCCCUGAAAGA | 724 |

TABLE 5-continued

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM06217-SS | (NAG37)s(invAb)sggcuucaGfUfUfcccugaaags(invdA) | 423 | GGCUUCAGUUCCCUGAAAGA | 725 |
| AM06220-SS | (NAG37)s(invAb)sgaccgaUfGfGfcuucaguucs(invdA) | 424 | GACCGAUGGCUUCAGUUCA | 726 |
| AM06221-SS | (NAG37)s(invAb)sgugaccgaUfGfGfcuucaguucs(invdA) | 425 | GUGACCGAUGGCUUCAGUUCA | 727 |
| AM06264-SS | (NAG37)s(invAb)sccaaaaggGfAfCfaguauucucs(invdA) | 426 | CCAAAAGGGACAGUAUUCUCA | 728 |
| AM06265-SS | (NAG37)scsgcaaaaggGfAfCfaguauucucs(invdA) | 427 | CGCAAAAGGGACAGUAUUCUCA | 729 |
| AM06268-SS | (NAG37)s(invAb)sgacuacUfGfGfagcaccguus(invdA) | 428 | GACUACUGGAGCACCGUUA | 730 |
| AM06269-SS | (NAG37)s(invAb)sgacuacUfGfGfagcacuguus(invdA) | 429 | GACUACUGGAGCACUGUUA | 731 |
| AM06270-SS | (NAG37)s(invAb)scgacuacUfGfGfagcaccguus(invdA) | 430 | CGACUACUGGAGCACCGUUA | 732 |
| AM06271-SS | (NAG37)s(invAb)sgacuacUfGfGfagcaucguus(invdA) | 431 | GACUACUGGAGCAUCGUUA | 733 |
| AM06274-SS | (NAG37)s(invAb)sagggacAfGfUfauucucagus(invdA) | 432 | AGGGACAGUAUUCUCAGUA | 734 |
| AM06275-SS | (NAG37)s(invAb)scagggacAfGfUfauucucagus(invdA) | 433 | CAGGGACAGUAUUCUCAGUA | 735 |
| AM06278-SS | (NAG37)s(invAb)sgacuacuGfGfAfgcaccguuas(invdA) | 434 | GACUACUGGAGCACCGUUAA | 736 |
| AM06279-SS | (NAG37)s(invAb)sgccuacuGfGfAfgcaccguuas(invdA) | 435 | GCCUACUGGAGCACCGUUAA | 737 |
| AM06280-SS | (NAG37)s(invAb)sgccuacuGfGfAfgcacuguuas(invdA) | 436 | GCCUACUGGAGCACUGUUAA | 738 |
| AM06311-SS | (NAG37)s(invAb)sgcugggUfGfAfccgauggcus(invdA) | 437 | GCUGGGUGACCGAUGGCUA | 739 |
| AM06312-SS | (NAG37)s(invAb)sgcugggUfGfAfccgauggcuus(invAb) | 438 | GCUGGGUGACCGAUGGCUU | 740 |
| AM06313-SS | (NAG37)s(invAb)sgcugggUfGfAfccgaugacus(invdA) | 439 | GCUGGGUGACCGAUGACUA | 741 |
| AM06316-SS | (NAG37)s(invAb)sccguuaAfGfGfacaaguucus(invdA) | 440 | CCGUUAAGGACAAGUUCUA | 742 |
| AM06317-SS | (NAG37)s(invAb)scaccguuaAfGfGfacaaguucus(invdA) | 441 | CACCGUUAAGGACAAGUUCUA | 743 |
| AM06321-SS | (NAG37)saccguuAfAfGfgacaaguucs(invdA) | 442 | ACCGUUAAGGACAAGUUCA | 744 |
| AM06322-SS | (NAG37)s(invAb)saccguuAfAfGfgacaaguucus(invAb) | 443 | ACCGUUAAGGACAAGUUCU | 745 |
| AM06323-SS | (NAG37)s(invAb)sgcaccguuAfAfGfgacaaguucs(invdA) | 444 | GCACCGUUAAGGACAAGUUCA | 746 |
| AM06326-SS | (NAG37)s(invAb)sgguacuCfCfUfuguuguugcs(invdA) | 445 | GGUACUCCUUGUUGUUGCA | 747 |
| AM06327-SS | (NAG37)s(invAb)scggguacuCfCfUfuguuguugcs(invdA) | 446 | CGGGUACUCCUUGUUGUUGCA | 748 |
| AM06329-SS | (NAG37)s(invAb)scggguaCfUfCfcuuguuguus(invdA) | 447 | CGGGUACUCCUUGUUGUUA | 749 |
| AM06332-SS | (NAG37)s(invAb)sgggacagUfAfUfucucagugcs(invdA) | 448 | GGGACAGUAUUCUCAGUGCA | 750 |
| AM06333-SS | (NAG37)s(invAb)sgggacagUfAfUfucucagugcus(invAb) | 449 | GGGACAGUAUUCUCAGUGCU | 751 |
| AM06470-SS | (NAG37)sgscaccgUfUfAfaggacaaguuuus(invAb) | 450 | GCACCGUUAAGGACAAGUUUU | 752 |
| AM06473-SS | (NAG37)sgsagcaccgUfUfAfaggacaagus(invdA) | 451 | GAGCACCGUUAAGGACAAGUA | 719 |
| AM06474-SS | (NAG37)sgsgagcaccgUfUfAfaggacaagus(invdA) | 452 | GGAGCACCGUUAAGGACAAGUA | 753 |
| AM06479-SS | (NAG37)sgsagcaccgUfUfAfaggacaaguus(invAb) | 453 | GAGCACCGUUAAGGACAAGUU | 754 |
| AM06480-SS | (NAG37)sgsgagcaccgUfUfAfaggacaaguus(invAb) | 454 | GGAGCACCGUUAAGGACAAGUU | 755 |
| AM06506-SS | (NAG37)s(invAb)saaaaggGfAfCfaguauucucauus(invAb) | 455 | AAAAGGGACAGUAUUCUCAUU | 756 |
| AM06508-SS | (NAG37)s(invAb)scaaaaggGfAfCfaguauucucs(invdA) | 456 | CAAAAGGGACAGUAUUCUCA | 757 |
| AM06510-SS | (NAG37)(invAb)ccaaaaggGfAfCfaguauucuc(invdA) | 457 | CCAAAAGGGACAGUAUUCUCA | 728 |
| AM06512-SS | (NAG37)s(invAb)sccaaaaggGfAfCfaguauucucus(invAb) | 458 | CCAAAAGGGACAGUAUUCUCU | 758 |
| AM06515-SS | (NAG37)s(invAb)sgguacuCfCfUfuguuguugcauus(invAb) | 459 | GGUACUCCUUGUUGUUGCAUU | 759 |

TABLE 5-continued

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM06516-SS | (NAG37)s(invAb)sgguacuCfCfUfuguuguugcs(invdA) | 460 | GGGUACUCCUUGUUGUUGCA | 760 |
| AM06520-SS | (NAG37)(invAb)gguacuCfCfUfuguuguugc(invdA) | 461 | GGUACUCCUUGUUGUUGCA | 747 |
| AM06522-SS | (NAG37)s(invAb)sgguacuCfCfUfuguuguugcus(invAb) | 462 | GGUACUCCUUGUUGUUGCU | 761 |
| AM06711-SS | (NAG37)s(invAb)sugggugacCfGfAfuggcuucagas(invAb) | 463 | UGGGUGACCGAUGGCUUCAGA | 762 |
| AM06713-SS | (NAG37)s(invAb)sugggugacCfGfAfuggcuucagus(invAb) | 464 | UGGGUGACCGAUGGCUUCAGU | 763 |
| AM06715-SS | (NAG37)s(invAb)sugaccgauGfGfCfuucaguuccas(invAb) | 465 | UGACCGAUGGCUUCAGUUCCA | 764 |
| AM06717-SS | (NAG37)s(invAb)sggaccgauGfGfCfuucaguuccas(invAb) | 466 | GGACCGAUGGCUUCAGUUCCA | 765 |
| AM06719-SS | (NAG37)s(invAb)sggcuucagUfUfCfccugaaagaas(invAb) | 467 | GGCUUCAGUUCCCUGAAAGAA | 766 |
| AM06721-SS | (NAG37)s(invAb)sgacuacugGfAfGfcaccguuaaas(invAb) | 468 | GACUACUGGAGCACCGUUAAA | 767 |
| AM06723-SS | (NAG37)s(invAb)scuacuggaGfCfAfccguuaaggas(invAb) | 469 | CUACUGGAGCACCGUUAAGGA | 768 |
| AM06725-SS | (NAG37)s(invAb)suacuggagCfAfCfcguuaaggaas(invAb) | 470 | UACUGGAGCACCGUUAAGGAA | 769 |
| AM06727-SS | (NAG37)s(invAb)sgacuggagCfAfCfcguuaaggaas(invAb) | 471 | GACUGGAGCACCGUUAAGGAA | 770 |
| AM06729-SS | (NAG37)s(invAb)sgagcaccgUfUfAfaggacaaguas(invAb) | 472 | GAGCACCGUUAAGGACAAGUA | 719 |
| AM06731-SS | (NAG37)s(invAb)sgagcaccgUfUfAfaggacaaguus(invAb) | 473 | GAGCACCGUUAAGGACAAGUU | 754 |
| AM06733-SS | (NAG37)s(invAb)saguggcugCfCfUfgagaccucaas(invAb) | 474 | AGUGGCUGCCUGAGACCUCAA | 771 |
| AM06735-SS | (NAG37)s(invAb)sggcugccuGfAfGfaccucaauaas(invAb) | 475 | GGCUGCCUGAGACCUCAAUAA | 772 |
| AM06737-SS | (NAG37)s(invAb)sgcugccugAfGfAfccucaauacas(invAb) | 476 | GCUGCCUGAGACCUCAAUACA | 773 |
| AM06739-SS | (NAG37)s(invAb)saagggacaGfUfAfuucucagugas(invAb) | 477 | AAGGGACAGUAUUCUCAGUGA | 774 |
| AM06742-SS | (NAG37)s(invAb)sacgggacaGfUfAfuucucagugas(invAb) | 478 | ACGGGACAGUAUUCUCAGUGA | 775 |
| AM06744-SS | (NAG37)s(invAb)scccuguagGfUfUfgcuuaaaagas(invAb) | 479 | CCCUGUAGGUUGCUUAAAAGA | 776 |
| AM06779-SS | (NAG37)s(invAb)sggaaaaggGfAfCfaguauucucas(invAb) | 480 | GGAAAAGGGACAGUAUUCUCA | 777 |
| AM06781-SS | (NAG37)gsgaaaaggGfAfCfaguauucucas(invAb) | 481 | GGAAAAGGGACAGUAUUCUCA | 777 |
| AM06782-SS | (NAG37)s(invAb)sgagggacaGfUfAfuucucagugas(invAb) | 482 | GAGGGACAGUAUUCUCAGUGA | 21 |
| AM06785-SS | (NAG37)s(invAb)sggcaaaggGfAfCfaguauucucas(invAb) | 483 | GGCAAAGGGACAGUAUUCUCA | 31 |
| AM06787-SS | (NAG37)gsgcaaaggGfAfCfaguauucucas(invAb) | 484 | GGCAAAGGGACAGUAUUCUCA | 31 |
| AM06788-SS | (NAG37)s(invAb)susgaccgauGfGfCfuucaiuuccas(invAb) | 485 | UGACCGAUGGCUUCAIUUCCA | 780 |
| AM06789-SS | (NAG37)usgaccgauGfGfCfuucaguuccas(invAb) | 486 | UGACCGAUGGCUUCAGUUCCA | 764 |
| AM06790-SS | (NAG37)usgaccgauGfGfCfuucaiuuccas(invAb) | 487 | UGACCGAUGGCUUCAIUUCCA | 780 |
| AM06791-SS | (NAG37)gsagggacaGfUfAfuucucagugas(invAb) | 488 | GAGGGACAGUAUUCUCAGUGA | 21 |
| AM06792-SS | (NAG37)gsgcugccuGfAfGfaccucaauaas(invAb) | 489 | GGCUGCCUGAGACCUCAAUAA | 772 |
| AM06863-SS | (NAG37)s(invAb)sgga_2NaaaaggGfAfCfaguauucucas(invAb) | 490 | GG(A$^{2N}$)AAAGGGACAGUAUUCUCA | 781 |
| AM06864-SS | (NAG37)s(invAb)sa_2NgaaaaggGfAfCfaguauucucas(invAb) | 491 | (A$^{2N}$)GAAAAGGGACAGUAUUCUCA | 782 |
| AM06866-SS | (NAG37)s(invAb)sa_2Na_2NaaaaggGfAfCfaguauucucas(invAb) | 492 | (A$^{2N}$)(A$^{2N}$)AAAAGGGACAGUAUUCUCA | 783 |
| AM06867-SS | (NAG37)s(invAb)scccaauaaAfGfCfuggacaagaas(invAb) | 493 | CCCAAUAAAGCUGGACAAGAA | 784 |
| AM06869-SS | (NAG37)s(invAb)sgccaauaaAfGfCfuggacaagaas(invAb) | 494 | GCCAAUAAAGCUGGACAAGAA | 23 |
| AM06871-SS | (NAG37)s(invAb)scuucaguuCfCfCfugaaagacuas(invAb) | 495 | CUUCAGUUCCCUGAAAGACUA | 786 |

TABLE 5-continued

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM06873-SS | (NAG37)s(invAb)sguucaguuCfCfCfugaaagacuas(invAb) | 496 | GUUCAGUUCCCUGAAAGACUA | 787 |
| AM06875-SS | (NAG37)s(invAb)sgcuuaaaaGfGfGfacaguauucus(invAb) | 497 | GCUUAAAAGGGACAGUAUUCU | 29 |
| AM06907-SS | (NAG37)s(invAb)sgggacaGfUfAfuucucagugauus(invAb) | 498 | GGGACAGUAUUCUCAGUGAUU | 789 |
| AM06922-SS | (NAG37)s(invAb)sa_2NagggacaGfUfAfuucucagugas(invAb) | 499 | (A$^{2N}$)AGGGACAGUAUUCUCAGUGA | 790 |
| AM06923-SS | (NAG37)s(invAb)sgagggacaGfUfAfuucucaiugas(invAb) | 500 | GAGGGACAGUAUUCUCAIUGA | 791 |
| AM06924-SS | (NAG37)s(invAb)sgagggacaGfUfAfuucucaguias(invAb) | 501 | GAGGGACAGUAUUCUCAGUIA | 16 |
| AM06925-SS | (NAG37)ascgggacaGfUfAfuucucagugas(invAb) | 502 | ACGGGACAGUAUUCUCAGUGA | 775 |
| AM06926-SS | (NAG37)gsggacaGfUfAfuucucagugauus(invAb) | 503 | GGGACAGUAUUCUCAGUGAUU | 789 |
| AM06927-SS | (NAG37)s(invAb)scggacaGfUfAfuucucagugauus(invAb) | 504 | CGGACAGUAUUCUCAGUGAUU | 793 |
| AM06929-SS | (NAG37)gsgcaaaggGfAfCfaGuauucucas(invAb) | 505 | GGCAAAGGGACAGUAUUCUCA | 31 |
| AM06932-SS | (NAG37)s(invAb)sggcaaagiGfAfCfaguauucucas(invAb) | 506 | GGCAAAGIGACAGUAUUCUCA | 794 |
| AM06933-SS | (NAG37)s(invAb)sggcaaaiGfAfCfaguauucucas(invAb) | 507 | GGCAAAIGGACAGUAUUCUCA | 778 |
| AM06934-SS | (NAG37)s(invAb)sagggacuCfCfUfuguuguugcas(invAb) | 508 | AGGGUACUCCUUGUUGUUGCA | 795 |
| AM06948-SS | (NAG37)s(invAb)scuucaguuCfUfCfugaaagacuas(invAb) | 509 | CUUCAGUUCUCUGAAAGACUA | 796 |
| AM06949-SS | (NAG37)s(invAb)scuucaguuUfCfCfugaaagacuas(invAb) | 510 | CUUCAGUUUCCUGAAAGACUA | 797 |
| AM06950-SS | (NAG37)s(invAb)scgucaguuCfCfCfugaaagacuas(invAb) | 511 | CGUCAGUUCCCUGAAAGACUA | 798 |
| AM06952-SS | (NAG37)s(invAb)sccucaguuCfCfCfugaaagacuas(invAb) | 512 | CCUCAGUUCCCUGAAAGACUA | 799 |
| AM06954-SS | (NAG37)s(invAb)scgucaguuCfUfCfugaaagacuas(invAb) | 513 | CGUCAGUUCUCUGAAAGACUA | 800 |
| AM06955-SS | (NAG37)s(invAb)sggucaguuCfCfCfugaaagacuas(invAb) | 514 | GGUCAGUUCCCUGAAAGACUA | 801 |
| AM06957-SS | (NAG37)s(invAb)sgcucaguuCfCfCfugaaagacuas(invAb) | 515 | GCUCAGUUCCCUGAAAGACUA | 802 |
| AM06960-SS | (NAG37)s(invAb)sgccuaaaaGfGfGfacaguauucus(invAb) | 516 | GCCUAAAAGGGACAGUAUUCU | 803 |
| AM06962-SS | (NAG37)s(invAb)sccuuaaaaGfGfGfacaguauucus(invAb) | 517 | CCUUAAAAGGGACAGUAUUCU | 804 |
| AM06964-SS | (NAG37)s(invAb)sgcuuaaaaGfGfiacaguauucus(invAb) | 518 | GCUUAAAAGGIACAGUAUUCU | 805 |
| AM06965-SS | (NAG37)s(invAb)sgcuuaaaaGfiGfacaguauucus(invAb) | 519 | GCUUAAAAGIGACAGUAUUCU | 779 |
| AM06966-SS | (NAG37)s(invAb)sgcuuaaaaiGfGfacaguauucus(invAb) | 520 | GCUUAAAAIGGACAGUAUUCU | 785 |
| AM06987-SS | (NAG37)s(invAb)scccuaaaaGfGfGfacaguauucus(invAb) | 521 | CCCUAAAAGGGACAGUAUUCU | 27 |
| AM07178-SS | (NAG37)s(invAb)sagggacucCfCfUfuguuguuicas(invAb) | 522 | AGGGUACUCCUUGUUGUUICA | 807 |
| AM07180-SS | (NAG37)s(invAb)sagggacucCfCfUfuGuuguugcas(invAb) | 523 | AGGGUACUCCUUGUUGUUGCA | 795 |
| AM07181-SS | (NAG37)s(invAb)scuucaguuCfCfCfugaaagaiuas(invAb) | 524 | CUUCAGUUCCCUGAAAGAIUA | 808 |
| AM07183-SS | (NAG37)s(invAb)scuucaguuCfCfCfuGaaagacuas(invAb) | 525 | CUUCAGUUCCCUGAAAGACUA | 786 |
| AM07184-SS | (NAG37)s(invAb)sgcuuaaaaGfGfGfacaguauuius(invAb) | 526 | GCUUAAAAGGGACAGUAUUIU | 809 |
| AM07186-SS | (NAG37)s(invAb)sgcuuaaaaGfGfGfaCaguauucus(invAb) | 527 | GCUUAAAAGGGACAGUAUUCU | 29 |
| AM07187-SS | (NAG37)s(invAb)sggcaaaggGfAfCfaguauucuias(invAb) | 528 | GGCAAAGGGACAGUAUUCUIA | 810 |
| AM07189-SS | (NAG37)s(invAb)sggcaaaggGfAfCfaGuauucucas(invAb) | 529 | GGCAAAGGGACAGUAUUCUCA | 31 |
| AM07191-SS | (NAG37)s(invAb)sgagggacaGfUfAfuUcucaguias(invAb) | 530 | GAGGGACAGUAUUCUCAGUIA | 16 |
| AM07192-SS | (NAG37)s(invAb)sgccaauaaAfGfCfuggacaaiaas(invAb) | 531 | GCCAAUAAAGCUGGACAAIAA | 811 |
| AM07194-SS | (NAG37)s(invAb)sgccaauaaAfGfCfuGgacaagaas(invAb) | 532 | GCCAAUAAAGCUGGACAAGAA | 23 |

TABLE 5-continued

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM07309-SS | (NAG37)s(invAb)saggguacuCfIfUfuguuguugcas(invAb) | 533 | AGGGUACUCIUUGUUGUUGCA | 812 |
| AM07310-SS | (NAG37)s(invAb)saggguacuIfCfUfuguuguugcas(invAb) | 534 | AGGGUACUICUUGUUGUUGCA | 788 |
| AM07311-SS | (NAG37)s(invAb)scuucaguuCfCfIfugaaagacuas(invAb) | 535 | CUUCAGUUCCIUGAAAGACUA | 813 |
| AM07312-SS | (NAG37)s(invAb)scuucaguuCfIfCfugaaagacuas(invAb) | 536 | CUUCAGUUCICUGAAAGACUA | 792 |
| AM07313-SS | (NAG37)s(invAb)scuucaguuIfCfCfugaaagacuas(invAb) | 537 | CUUCAGUUICCUGAAAGACUA | 806 |
| AM07314-SS | (NAG37)s(invAb)sgcuuaaaaGfGfIfacaguauucus(invAb) | 538 | GCUUAAAAGGIACAGUAUUCU | 805 |
| AM07315-SS | (NAG37)s(invAb)sgcuuaaaaGfIfGfacaguauucus(invAb) | 539 | GCUUAAAAGIGACAGUAUUCU | 817 |
| AM07316-SS | (NAG37)s(invAb)sgcuuaaaaIfGfGfacaguauucus(invAb) | 540 | GCUUAAAAIGGACAGUAUUCU | 824 |
| AM07317-SS | (NAG37)s(invAb)sggcaaaggGfAfIfaguauucucas(invAb) | 541 | GGCAAAGGGAIAGUAUUCUCA | 814 |
| AM07318-SS | (NAG37)s(invAb)sggcaaaggIfAfCfaguauucucas(invAb) | 542 | GGCAAAGGIACAGUAUUCUCA | 794 |
| AM07319-SS | (NAG37)s(invAb)sgagggacaIfUfAfuucucaguias(invAb) | 543 | GAGGGACAIUAUUCUCAGUIA | 815 |
| AM07320-SS | (NAG37)s(invAb)sgccaauaaAfGfIfuggacaagaas(invAb) | 544 | GCCAAUAAAGIUGGACAAGAA | 816 |
| AM07321-SS | (NAG37)s(invAb)sgccaauaaAfIfCfuggacaagaas(invAb) | 545 | GCCAAUAAAICUGGACAAGAA | 25 |
| AM07515-SS | (NAG37)s(invAb)sgccuaaaaGfGfiacaguauucus(invAb) | 546 | GCCUAAAAGGIACAGUAUUCU | 818 |
| AM07516-SS | (NAG37)s(invAb)sgccuaaaaGfGfIfacaguauucus(invAb) | 547 | GCCUAAAAGGIACAGUAUUCU | 818 |
| AM07517-SS | (NAG37)s(invAb)saccuaaaaGfGfGfacaguauucus(invAb) | 548 | ACCUAAAAGGGACAGUAUUCU | 819 |
| AM07519-SS | (NAG37)s(invAb)sgcguaaaaGfGfGfacaguauucus(invAb) | 549 | GCGUAAAAGGGACAGUAUUCU | 820 |
| AM07521-SS | (NAG37)s(invAb)sgucuaaaaGfGfGfacaguauucus(invAb) | 550 | GUCUAAAAGGGACAGUAUUCU | 821 |
| AM07523-SS | (NAG37)s(invAb)sgagggacaGfUfAfuUcucagugas(invAb) | 551 | GAGGGACAGUAUUCUCAGUGA | 21 |
| AM07525-SS | (NAG37)s(invAb)sgggacaGfUfAfuucucaguiauus(invAb) | 552 | GGGACAGUAUUCUCAGUIAUU | 822 |
| AM07526-SS | (NAG37)s(invAb)sgccaauaaAfGfCfudGgacaagaas(invAb) | 553 | GCCAAUAAAGCUGGACAAGAA | 23 |
| AM07598-SS | (NAG37)s(invAb)sgccuaaaaGfgGfaCfaguauucus(invAb) | 554 | GCCUAAAAGGGACAGUAUUCU | 803 |
| AM07599-SS | (NAG37)s(invAb)sgccuaaaaGfgIfaCfaguauucus(invAb) | 555 | GCCUAAAAGGIACAGUAUUCU | 818 |
| AM07601-SS | (NAG37)s(invAb)sgagggacaGfuAfuUfcucagugas(invAb) | 556 | GAGGGACAGUAUUCUCAGUGA | 21 |
| AM07602-SS | (NAG37)s(invAb)sgagggacaGfuAfuUfcucaguias(invAb) | 557 | GAGGGACAGUAUUCUCAGUIA | 16 |
| AM07644-SS | (NAG37)s(invAb)sgcCfaAfuUAfaAfGfCfuggacaagaas(invAb) | 558 | GCCAAUAAAGCUGGACAAGAA | 23 |
| AM07646-SS | (NAG37)s(invAb)sgcCfaAfuUAfaAfgCfuggacaagaas(invAb) | 559 | GCCAAUAAAGCUGGACAAGAA | 23 |
| AM07647-SS | (NAG37)s(invAb)sgCfaAfUfAfaAfGfCfuggacaagaas(invAb) | 560 | GCCAAUAAAGCUGGACAAGAA | 23 |
| AM07648-SS | (NAG37)s(invAb)sgccaauaAMAfGfCfuggacaagaas(invAb) | 561 | GCCAAUAAAGCUGGACAAGAA | 23 |
| AM07649-SS | (NAG37)s(invAb)sgccAMauaaAfGfCfuggacaagaas(invAb) | 562 | GCCAAUAAAGCUGGACAAGAA | 23 |
| AM07650-SS | (NAG37)s(invAb)sgCfaAfuAfaAfIfCfuggacaagaas(invAb) | 563 | GCCAAUAAAICUGGACAAGAA | 25 |
| AM07651-SS | (NAG37)s(invAb)sgcCfaAfUfAfaAfIfCfuggacaagaas(invAb) | 564 | GCCAAUAAAICUGGACAAGAA | 25 |
| AM07652-SS | (NAG37)s(invAb)sgccaauaaAfiCfuggacaagaas(invAb) | 565 | GCCAAUAAAICUGGACAAGAA | 25 |
| AM07653-SS | (NAG37)s(invAb)sgcCfaAfuAfaAfGfCfuigacaagaas(invAb) | 566 | GCCAAUAAAGCUIGACAAGAA | 823 |
| AM07654-SS | (NAG37)s(invAb)sgcCfaAfuAfaAfGfCfugiacaagaas(invAb) | 567 | GCCAAUAAAGCUGIACAAGAA | 836 |
| AM07655-SS | (NAG37)s(invAb)sgcCfuAfaAfaGfGfGfacaguauucus(invAb) | 568 | GCCUAAAAGGGACAGUAUUCU | 803 |

TABLE 5-continued

APOC3 RNAi Agent Sense Strand Sequences

| Sense Strand ID: | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM07656-SS | (NAG37)s(invAb)sgcCfuAfaAfaGfgGfacaguauucus(invAb) | 569 | GCCUAAAAGGGACAGUAUUCU | 803 |
| AM07657-SS | (NAG37)s(invAb)sgcCfuAfaAfaGfGfifacaguauuucus(invAb) | 570 | GCCUAAAAGGIACAGUAUUCU | 818 |
| AM07658-SS | (NAG37)s(invAb)sgcCfuAfaAfaGfgIfacaguauucus(invAb) | 571 | GCCUAAAAGGIACAGUAUUCU | 818 |
| AM07748-SS | (NAG37)s(invAb)sacgggacaGfUfAfuucucaguias(invAb) | 572 | ACGGGACAGUAUUCUCAGUIA | 18 |
| AM07749-SS | (NAG37)s(invAb)scagggacaGfUfAfuucucagugas(invAb) | 573 | CAGGGACAGUAUUCUCAGUGA | 825 |
| AM07751-SS | (NAG37)s(invAb)scagggacaGfUfAfuucucaguias(invAb) | 574 | CAGGGACAGUAUUCUCAGUIA | 837 |
| AM07752-SS | (NAG37)s(invAb)sagggacaGfUfAfuucucagugas(invAb) | 575 | AGGGGACAGUAUUCUCAGUGA | 826 |
| AM07754-SS | (NAG37)s(invAb)sagggacaGfUfAfuucucaguias(invAb) | 576 | AGGGGACAGUAUUCUCAGUIA | 827 |
| AM07759-SS | (NAG37)s(invAb)sagaccgCfCfAfaggaugcacuuus(invAb) | 577 | AGACCGCCAAGGAUGCACUUU | 828 |
| AM07761-SS | (NAG37)s(invAb)sagaccgCfCfAfaggauicacuuus(invAb) | 578 | AGACCGCCAAGGAUICACUUU | 829 |
| AM07763-SS | (NAG37)s(invAb)sucaguuccCfUfGfaaagacuacus(invAb) | 579 | UCAGUUCCCUGAAAGACUACU | 830 |
| AM07766-SS | (NAG37)s(invAb)sucaguuccCfUfGfaaagacuacas(invAb) | 580 | UCAGUUCCCUGAAAGACUACA | 831 |
| AM07768-SS | (NAG37)s(invAb)sacuacuggAfGfCfacciuuaagas(invAb) | 581 | ACUACUGGAGCACCIUUAAGA | 832 |
| AM07770-SS | (NAG37)s(invAb)sccuguaggUfUfGfcuuaaaaggas(invAb) | 582 | CCUGUAGGUUGCUUAAAAGGA | 833 |
| AM07772-SS | (NAG37)s(invAb)sgcuguaggUfUfGfcuuaaaaggas(invAb) | 583 | GCUGUAGGUUGCUUAAAAGGA | 834 |
| AM07774-SS | (NAG37)s(invAb)sggucaguuCfUfCfugaaagacuas(invAb) | 584 | GGUCAGUUCUCUGAAAGACUA | 835 |

$(A^{2N})$ = 2-aminoadenine nucleotide

The APOC3 RNAi agents described herein are formed by annealing an antisense strand with a sense strand. A sense strand containing a sequence listed in Table 2, Table 3, or Table 5 can be hybridized to any antisense strand containing a sequence listed in Table 2, Table 3, or Table 4, provided the two sequences have a region of at least 85% complementarity over a contiguous 16, 17, 18, 19, 20, or 21 nucleotide sequence.

In some embodiments, the antisense strand of an APOC3 RNAi agent disclosed herein differs by 0, 1, 2, or 3 nucleotides from any of the antisense strand sequences in Table 4. In some embodiments, the sense strand of an APOC3 RNAi agent disclosed herein differs by 0, 1, 2, or 3 nucleotides from any of the sense strand sequences in Table 5.

In some embodiments, an APOC3 RNAi agent antisense strand comprises a nucleotide sequence of any of the sequences in Table 2, Table 3, or Table 4. In some embodiments, an APOC3 RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24, 1-25, 2-25, 1-16, or 2-16 of any of the sequences in Table 2, Table 3, or Table 4. In certain embodiments, an APOC3 RNAi agent antisense strand comprises or consists of a modified sequence of any one of the modified sequences in Table 4. In certain embodiments, an APOC3 RNAi agent antisense strand comprises or consists of a modified sequence of any one of the modified sequences in Table 3.

In some embodiments, an APOC3 RNAi agent sense strand comprises the nucleotide sequence of any of the sequences in Table 2, Table 3, or Table 5. In some embodiments, an APOC3 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, 4-24, 1-25, 2-25, 3-25, 4-25, 1-26, 2-26, 3-26, or 4-26, of any of the sequences in Table 2, Table 3, or Table 5. In certain embodiments, an APOC3 RNAi agent sense strand comprises or consists of a modified sequence of any one of the modified sequences in Table 5. In certain embodiments, an APOC3 RNAi agent sense strand comprises or consists of a modified sequence of any one of the modified sequences in Table 3.

For the APOC3 RNAi agents disclosed herein, the nucleotide at position 1 of the antisense strand (from 5' end→3' end) can be perfectly complementary to an APOC3 gene, or can be non-complementary to an APOC3 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

In some embodiments, an APOC3 RNAi agent antisense strand comprises the sequence of nucleotides (from 5' end→3' end) 2-18 or 2-19 of any of the antisense strand sequences in Table 2 or Table 4. In some embodiments, an APOC3 RNAi sense strand comprises the sequence of nucleotides (from 5' end→3' end) 1-17 or 1-18 of any of the sense strand sequences in Table 2 or Table 5.

In some embodiments, an APOC3 RNAi agent includes (i) an antisense strand comprising the sequence of nucleotides (from 5' end→3' end) 2-18 or 2-19 of any of the antisense strand sequences in Table 2, Table 3, or Table 4, and (ii) a sense strand comprising the sequence of nucleotides (from 5' end→3' end) 1-17 or 1-18 of any of the sense strand sequences in Table 2, Table 3, or Table 5.

A sense strand containing a sequence listed in Table 2, Table 3, or Table 5 can be hybridized to any antisense strand containing a sequence listed in Table 2, Table 3, or Table 4, provided the two sequences have a region of at least 85% complementarity over a contiguous 16, 17, 18, 19, 20, or 21 nucleotide sequence. In some embodiments, the APOC3 RNAi agent has a sense strand consisting of the modified sequence of any of the modified sequences in Table 5, and an antisense strand consisting of the modified sequence of any of the modified sequences in Table 4. Representative sequence pairings are exemplified by the Duplex ID Nos. shown in Table 3 and Table 6.

In some embodiments, an APOC3 RNAi agent comprises any of the duplexes represented by any of the Duplex ID Nos. presented herein. In some embodiments, an APOC3 RNAi agent consists of any of the duplexes represented by any of the Duplex ID Nos. presented herein. In some embodiments, an APOC3 RNAi agent comprises the sense strand and antisense strand nucleotide sequences of any of the duplexes represented by any of the Duplex ID Nos. presented herein. In some embodiments, an APOC3 RNAi agent includes the sense strand and antisense strand nucleotide sequences of any of the duplexes represented by any of the Duplex ID Nos. presented herein and a targeting group and/or linking group, wherein the targeting group and/or linking group is covalently linked (i.e., conjugated) to the sense strand or the antisense strand. In some embodiments, an APOC3 RNAi agent includes the sense strand and antisense strand modified nucleotide sequences of any of the duplexes represented by any of the Duplex ID Nos. presented herein. In some embodiments, an APOC3 RNAi agent comprises the sense strand and antisense strand modified nucleotide sequences of any of the duplexes represented by any of the Duplex ID Nos. presented herein and a targeting group and/or linking group, wherein the targeting group and/or linking group is covalently linked to the sense strand or the antisense strand.

In some embodiments, an APOC3 RNAi agent comprises an antisense strand and a sense strand having the nucleotide sequences of any of the antisense strand/sense strand duplexes of Table 2, Table 3, or Table 6, and comprises an asialoglycoprotein receptor ligand targeting group.

In some embodiments, an APOC3 RNAi agent comprises an antisense strand and a sense strand having the nucleotide sequences of any of the antisense strand/sense strand duplexes of Table 2, Table 3, or Table 6, and further comprises a targeting group selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. In some embodiments, the targeting group is (NAG25) or (NAG25)s as defined in Table 7. In other embodiments, the targeting group is (NAG37) or (NAG37)s as defined in Table 7.

In some embodiments, an APOC3 RNAi agent comprises an antisense strand and a sense strand having the modified nucleotide sequence of any of the antisense strand and/or sense strand nucleotide sequences of any of the duplexes of Table 2, Table 3, or Table 6.

In some embodiments, an APOC3 RNAi agent comprises an antisense strand and a sense strand having a modified nucleotide sequence of any of the antisense strand and/or sense strand nucleotide sequences of any of the duplexes of Table 2, Table 3, or Table 6, and comprises an asialoglycoprotein receptor ligand targeting group.

In some embodiments, an APOC3 RNAi agent comprises any of the duplexes of Table 2, Table 3, or Table 6.

In some embodiments, an APOC3 RNAi agent consists of any of the duplexes of Table 2, Table 3, or Table 6.

TABLE 6

APOC3 RNAi Agents Identified by Duplex ID NO. with Corresponding Sense and Antisense Strands.

| Duplex ID | Antisense Strand ID | Sense Strand ID |
|---|---|---|
| AD04812 | AM06203-AS | AM06206-SS |
| AD04813 | AM06204-AS | AM06207-SS |
| AD04814 | AM06203-AS | AM06208-SS |
| AD04815 | AM06205-AS | AM06209-SS |
| AD04816 | AM06210-AS | AM06212-SS |
| AD04817 | AM06211-AS | AM06213-SS |
| AD04818 | AM06214-AS | AM06216-SS |
| AD04819 | AM06215-AS | AM06217-SS |
| AD04820 | AM06218-AS | AM06220-SS |
| AD04821 | AM06219-AS | AM06221-SS |
| AD04860 | AM06262-AS | AM06264-SS |
| AD04861 | AM06263-AS | AM06265-SS |
| AD04862 | AM06266-AS | AM06268-SS |
| AD04863 | AM06266-AS | AM06269-SS |
| AD04864 | AM06267-AS | AM06270-SS |
| AD04865 | AM06266-AS | AM06271-SS |
| AD04866 | AM06272-AS | AM06274-SS |
| AD04867 | AM06273-AS | AM06275-SS |
| AD04868 | AM06276-AS | AM06278-SS |
| AD04869 | AM06277-AS | AM06279-SS |
| AD04870 | AM06277-AS | AM06280-SS |
| AD04886 | AM06309-AS | AM06311-SS |
| AD04887 | AM06310-AS | AM06312-SS |
| AD04888 | AM06309-AS | AM06313-SS |
| AD04889 | AM06314-AS | AM06316-SS |
| AD04890 | AM06315-AS | AM06317-SS |
| AD04891 | AM06318-AS | AM06321-SS |
| AD04892 | AM06319-AS | AM06322-SS |
| AD04893 | AM06320-AS | AM06323-SS |
| AD04894 | AM06324-AS | AM06326-SS |
| AD04895 | AM06325-AS | AM06327-SS |
| AD04896 | AM06328-AS | AM06329-SS |
| AD04897 | AM06330-AS | AM06332-SS |
| AD04898 | AM06331-AS | AM06333-SS |
| AD04987 | AM06469-AS | AM06206-SS |
| AD04988 | AM06469-AS | AM06208-SS |
| AD04989 | AM06471-AS | AM06470-SS |
| AD04990 | AM06205-AS | AM06470-SS |
| AD04991 | AM06472-AS | AM06208-SS |
| AD04992 | AM06204-AS | AM06473-SS |
| AD04993 | AM06475-AS | AM06474-SS |
| AD04994 | AM06476-AS | AM06207-SS |
| AD04995 | AM06477-AS | AM06207-SS |
| AD04996 | AM06478-AS | AM06209-SS |
| AD04997 | AM06471-AS | AM06479-SS |
| AD04998 | AM06481-AS | AM06480-SS |
| AD05007 | AM06507-AS | AM06506-SS |
| AD05008 | AM06509-AS | AM06508-SS |
| AD05009 | AM06511-AS | AM06510-SS |
| AD05010 | AM06513-AS | AM06512-SS |
| AD05011 | AM06514-AS | AM06326-SS |
| AD05012 | AM06324-AS | AM06515-SS |
| AD05013 | AM06517-AS | AM06516-SS |
| AD05014 | AM06518-AS | AM06326-SS |
| AD05015 | AM06519-AS | AM06326-SS |
| AD05016 | AM06521-AS | AM06520-SS |

TABLE 6-continued

APOC3 RNAi Agents Identified by Duplex ID NO. with Corresponding Sense and Antisense Strands.

| Duplex ID | Antisense Strand ID | Sense Strand ID |
|---|---|---|
| AD05017 | AM06523-AS | AM06522-SS |
| AD05127 | AM06712-AS | AM06711-SS |
| AD05128 | AM06714-AS | AM06713-SS |
| AD05129 | AM06716-AS | AM06715-SS |
| AD05130 | AM06718-AS | AM06717-SS |
| AD05131 | AM06720-AS | AM06719-SS |
| AD05132 | AM06722-AS | AM06721-SS |
| AD05133 | AM06724-AS | AM06723-SS |
| AD05134 | AM06726-AS | AM06725-SS |
| AD05135 | AM06728-AS | AM06727-SS |
| AD05136 | AM06730-AS | AM06729-SS |
| AD05137 | AM06732-AS | AM06731-SS |
| AD05138 | AM06734-AS | AM06733-SS |
| AD05139 | AM06736-AS | AM06735-SS |
| AD05140 | AM06738-AS | AM06737-SS |
| AD05141 | AM06740-AS | AM06739-SS |
| AD05142 | AM06741-AS | AM06739-SS |
| AD05143 | AM06743-AS | AM06742-SS |
| AD05144 | AM06745-AS | AM06744-SS |
| AD05167 | AM06780-AS | AM06779-SS |
| AD05168 | AM06780-AS | AM06781-SS |
| AD05169 | AM06783-AS | AM06782-SS |
| AD05170 | AM06784-AS | AM06735-SS |
| AD05171 | AM06786-AS | AM06785-SS |
| AD05172 | AM06786-AS | AM06787-SS |
| AD05173 | AM06716-AS | AM06788-SS |
| AD05174 | AM06716-AS | AM06789-SS |
| AD05175 | AM06716-AS | AM06790-SS |
| AD05176 | AM06783-AS | AM06791-SS |
| AD05177 | AM06784-AS | AM06792-SS |
| AD05215 | AM06862-AS | AM06779-SS |
| AD05216 | AM06780-AS | AM06863-SS |
| AD05217 | AM06865-AS | AM06864-SS |
| AD05218 | AM06507-AS | AM06866-SS |
| AD05219 | AM06868-AS | AM06867-SS |
| AD05220 | AM06870-AS | AM06869-SS |
| AD05221 | AM06872-AS | AM06871-SS |
| AD05222 | AM06874-AS | AM06873-SS |
| AD05223 | AM06876-AS | AM06875-SS |
| AD05239 | AM06908-AS | AM06907-SS |
| AD05249 | AM06741-AS | AM06922-SS |
| AD05250 | AM06783-AS | AM06923-SS |
| AD05251 | AM06783-AS | AM06924-SS |
| AD05252 | AM06743-AS | AM06925-SS |
| AD05253 | AM06908-AS | AM06926-SS |
| AD05254 | AM06928-AS | AM06927-SS |
| AD05255 | AM06786-AS | AM06929-SS |
| AD05258 | AM06786-AS | AM06932-SS |
| AD05259 | AM06786-AS | AM06933-SS |
| AD05260 | AM06517-AS | AM06934-SS |
| AD05275 | AM06872-AS | AM06948-SS |
| AD05276 | AM06872-AS | AM06949-SS |
| AD05277 | AM06951-AS | AM06950-SS |
| AD05278 | AM06953-AS | AM06952-SS |
| AD05279 | AM06951-AS | AM06954-SS |
| AD05280 | AM06956-AS | AM06955-SS |
| AD05281 | AM06958-AS | AM06957-SS |
| AD05282 | AM06959-AS | AM06875-SS |
| AD05283 | AM06961-AS | AM06960-SS |
| AD05284 | AM06963-AS | AM06962-SS |
| AD05285 | AM06876-AS | AM06964-SS |
| AD05286 | AM06876-AS | AM06965-SS |
| AD05287 | AM06876-AS | AM06966-SS |
| AD05299 | AM06988-AS | AM06987-SS |
| AD05431 | AM06517-AS | AM07178-SS |
| AD05432 | AM07179-AS | AM06934-SS |
| AD05433 | AM06517-AS | AM07180-SS |
| AD05434 | AM06872-AS | AM07181-SS |
| AD05435 | AM07182-AS | AM06871-SS |
| AD05436 | AM06872-AS | AM07183-SS |
| AD05437 | AM06876-AS | AM07184-SS |
| AD05438 | AM07185-AS | AM06875-SS |
| AD05439 | AM06876-AS | AM07186-SS |
| AD05440 | AM06786-AS | AM07187-SS |
| AD05441 | AM07188-AS | AM06785-SS |
| AD05442 | AM06786-AS | AM07189-SS |
| AD05443 | AM07190-AS | AM06924-SS |
| AD05444 | AM06783-AS | AM07191-SS |
| AD05445 | AM06870-AS | AM07192-SS |
| AD05446 | AM07193-AS | AM06869-SS |
| AD05447 | AM06870-AS | AM07194-SS |
| AD05535 | AM06517-AS | AM07309-SS |
| AD05536 | AM06517-AS | AM07310-SS |
| AD05537 | AM06872-AS | AM07311-SS |
| AD05538 | AM06872-AS | AM07312-SS |
| AD05539 | AM06872-AS | AM07313-SS |
| AD05540 | AM06876-AS | AM07314-SS |
| AD05541 | AM06876-AS | AM07315-SS |
| AD05542 | AM06876-AS | AM07316-SS |
| AD05543 | AM06786-AS | AM07317-SS |
| AD05544 | AM06786-AS | AM07318-SS |
| AD05545 | AM06783-AS | AM07319-SS |
| AD05546 | AM06870-AS | AM07320-SS |
| AD05547 | AM06870-AS | AM07321-SS |
| AD05705 | AM06961-AS | AM07515-SS |
| AD05706 | AM06961-AS | AM07516-SS |
| AD05707 | AM07518-AS | AM07517-SS |
| AD05708 | AM07520-AS | AM07519-SS |
| AD05709 | AM07522-AS | AM07521-SS |
| AD05710 | AM07190-AS | AM06782-SS |
| AD05711 | AM06783-AS | AM07523-SS |
| AD05712 | AM07524-AS | AM06924-SS |
| AD05713 | AM06908-AS | AM07525-SS |
| AD05714 | AM06870-AS | AM07526-SS |
| AD05761 | AM06961-AS | AM07598-SS |
| AD05762 | AM06961-AS | AM07599-SS |
| AD05763 | AM07600-AS | AM06960-SS |
| AD05764 | AM07600-AS | AM07516-SS |
| AD05765 | AM07600-AS | AM07598-SS |
| AD05766 | AM07600-AS | AM07599-SS |
| AD05767 | AM07524-AS | AM06782-SS |
| AD05768 | AM07524-AS | AM07601-SS |
| AD05769 | AM07524-AS | AM07602-SS |
| AD05811 | AM06870-AS | AM07644-SS |
| AD05812 | AM07645-AS | AM07644-SS |
| AD05813 | AM07645-AS | AM07646-SS |
| AD05814 | AM07645-AS | AM07647-SS |
| AD05815 | AM06870-AS | AM07648-SS |
| AD05816 | AM06870-AS | AM07649-SS |
| AD05817 | AM07645-AS | AM07650-SS |
| AD05818 | AM07645-AS | AM07651-SS |
| AD05819 | AM06870-AS | AM07652-SS |
| AD05820 | AM07645-AS | AM07653-SS |
| AD05821 | AM07645-AS | AM07654-SS |
| AD05822 | AM07600-AS | AM07655-SS |
| AD05823 | AM07600-AS | AM07656-SS |
| AD05824 | AM07600-AS | AM07657-SS |
| AD05825 | AM07600-AS | AM07658-SS |
| AD05876 | AM06743-AS | AM07748-SS |
| AD05877 | AM07750-AS | AM07749-SS |
| AD05878 | AM07750-AS | AM07751-SS |
| AD05879 | AM07753-AS | AM07752-SS |
| AD05880 | AM07753-AS | AM07754-SS |
| AD05881 | AM07755-AS | AM06782-SS |
| AD05882 | AM07756-AS | AM06782-SS |
| AD05883 | AM07757-AS | AM06782-SS |
| AD05884 | AM07758-AS | AM06782-SS |
| AD05885 | AM07755-AS | AM06924-SS |
| AD05886 | AM07756-AS | AM06924-SS |
| AD05887 | AM07757-AS | AM06924-SS |
| AD05888 | AM07758-AS | AM06924-SS |
| AD05889 | AM07760-AS | AM07759-SS |
| AD05890 | AM07762-AS | AM07761-SS |
| AD05891 | AM07764-AS | AM07763-SS |
| AD05892 | AM07765-AS | AM07763-SS |
| AD05893 | AM07767-AS | AM07766-SS |
| AD05894 | AM07769-AS | AM07768-SS |
| AD05895 | AM07771-AS | AM07770-SS |

TABLE 6-continued

APOC3 RNAi Agents Identified by Duplex ID NO.
with Corresponding Sense and Antisense Strands.

| Duplex ID | Antisense Strand ID | Sense Strand ID |
|---|---|---|
| AD05896 | AM07773-AS | AM07772-SS |
| AD05897 | AM07775-AS | AM07774-SS |

In some embodiments, an APOC3 RNAi agent is prepared or provided as a salt, mixed salt, or a free-acid. The RNAi agents described herein, upon delivery to a cell expressing an APOC3 gene, inhibit or knockdown expression of one or more APOC3 genes in vivo.

Targeting Groups, Linking Groups, and Delivery Vehicles

In some embodiments, an APOC3 RNAi agent is conjugated to one or more non-nucleotide groups including, but not limited to a targeting group, linking group, delivery polymer, or a delivery vehicle. The non-nucleotide group can enhance targeting, delivery or attachment of the RNAi agent. Examples of targeting groups and linking groups are provided in Table 7. The non-nucleotide group can be covalently linked to the 3' and/or 5' end of either the sense strand and/or the antisense strand. In some embodiments, an APOC3 RNAi agent contains a non-nucleotide group linked to the 3' and/or 5' end of the sense strand. In some embodiments, a non-nucleotide group is linked to the 5' end of an APOC3 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties can enhance the pharmacokinetic or biodistribution properties of a conjugate or RNAi agent to which they are attached to improve cell-specific distribution and cell-specific uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers. In some embodiments, a targeting group comprises a galactose-derivative cluster.

The APOC3 RNAi agents described herein can be synthesized having a reactive group, such as an amine group, at the 5'-terminus. The reactive group can be used to subsequently attach a targeting group using methods typical in the art.

In some embodiments, a targeting group comprises an asialoglycoprotein receptor ligand. As used herein, an asialoglycoprotein receptor ligand is a ligand that contains a compound having affinity for the asialoglycoprotein receptor, which is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoyl-galactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative) or multimeric (e.g., having multiple galactose derivatives). The galactose derivative or galactose derivative cluster can be attached to the 3' or 5' end of the sense or antisense strand of the RNAi agent using methods known in the art. The preparation of targeting groups, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem. 1995 Vol. 39 p. 1538-1546). In some embodiments, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering an APOC3 RNAi agent to a liver cell in vivo. Such pharmaceutical compositions can include, for example, an APOC3 RNAi agent conjugated to a galactose derivative cluster.

In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

Targeting groups include, but are not limited to, (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s as defined in Table 7. Other targeting groups, including galactose cluster targeting ligands, are known in the art.

In some embodiments, a linking group is conjugated to the RNAi agent. The linking group facilitates covalent linkage of the agent to a targeting group or delivery polymer or delivery vehicle. The linking group can be linked to the 3' or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage may optionally include a spacer that increases the distance between the two joined atoms. A spacer can further add flexibility and/or length to the linkage. Spacers can include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

Any of the APOC3 RNAi agent nucleotide sequences listed in Tables 2, 3, 4, or 5, whether modified or unmodified, may contain 3' or 5' targeting group or linking group. Any of the APOC3 RNAi agent sequences listed in Table 4 or 5 which contain a 3' or 5' targeting group or linking group, may alternatively contain no 3' or 5' targeting group or linking group, or may contain a different 3' or 5' targeting group or linking group including, but not limited to, those depicted in Table 7. Any of the APOC3 RNAi agent duplexes listed in Table 2, Table 3, or Table 6, whether modified or unmodified, may further comprise a targeting group or linking group, including, but not limited to, those depicted in Table 7, and the targeting group or linking group may be attached to the 3' or 5' terminus of either the sense strand or the antisense strand of the APOC3 RNAi agent duplex.

Examples of targeting groups and linking groups are provided in Table 7. Table 5 provides several embodiments of APOC3 RNAi agent sense strands having a targeting group or linking group linked to the 5' or 3' end.

TABLE 7

Structure Representing Various Modified Nucleotides, Targeting Groups, and Linking Groups.

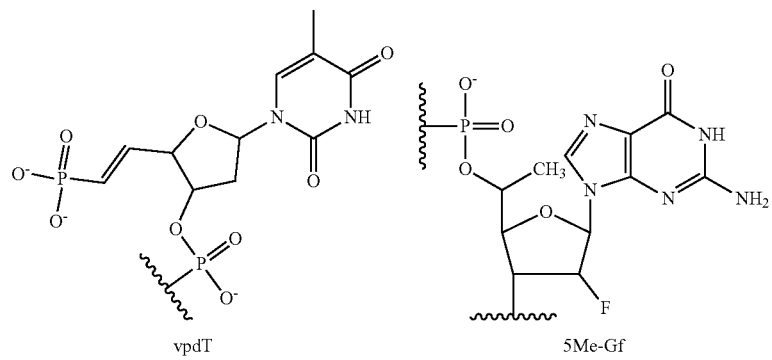 [SMILES: *P(=O)([O-])OC1CC(n2cc(C)c(=O)[nH]c2=O)OC1/C=C/P(=O)([O-])[O-] ; *C1C(F)C(n2cnc3c(=O)[nH]c(N)nc32)OC1C(C)OP(*)(=O)[O-]]

vpdT                    5Me-Gf

TABLE 7-continued
Structure Representing Various Modified Nucleotides, Targeting Groups, and Linking Groups.
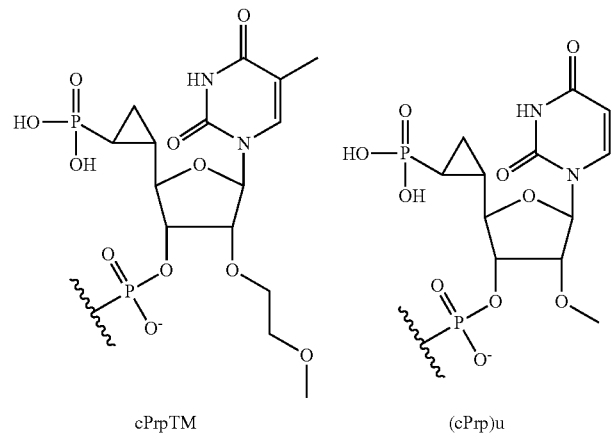 [SMILES: *P(=O)([O-])OC1C(C2CC2P(=O)(O)O)OC(n2cc(C)c(=O)[nH]c2=O)C1OCCOC ; *P(=O)([O-])OC1C(C2CC2P(=O)(O)O)OC(n2ccc(=O)[nH]c2=O)C1OC]
cPrpTM                (cPrp)u
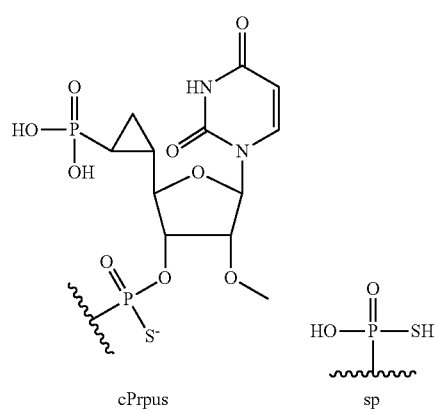 [SMILES: *P(=O)([S-])OC1C(C2CC2P(=O)(O)O)OC(n2ccc(=O)[nH]c2=O)C1OC ; *P(=O)(O)S]
cPrpus                sp
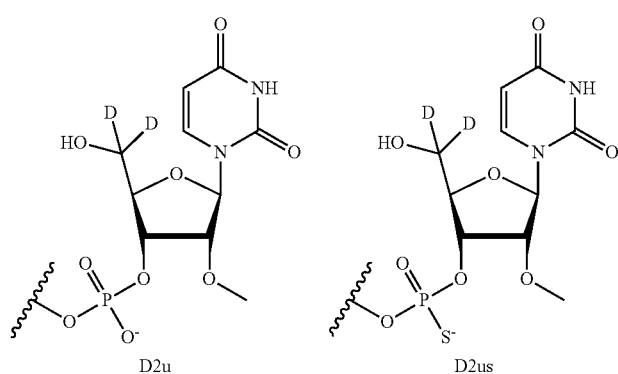
D2u                D2us
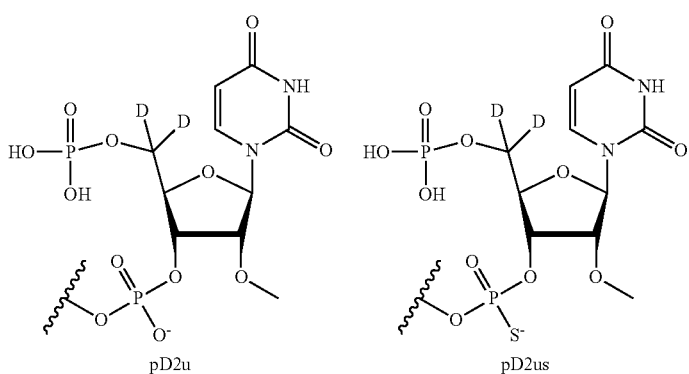
pD2u                pD2us TABLE 7-continued
Structure Representing Various Modified Nucleotides, Targeting Groups, and Linking Groups.
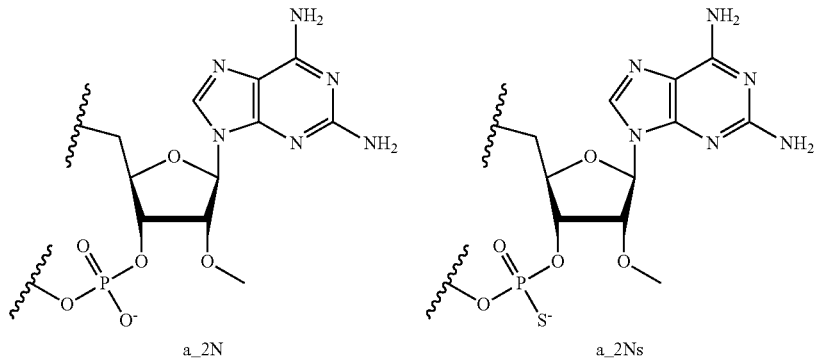
a_2N  a_2Ns
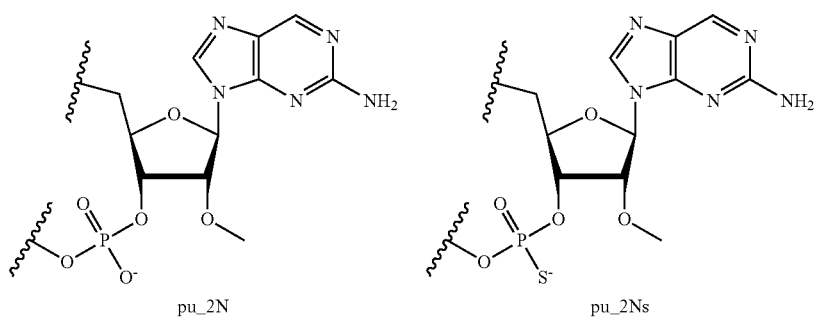
pu_2N  pu_2Ns
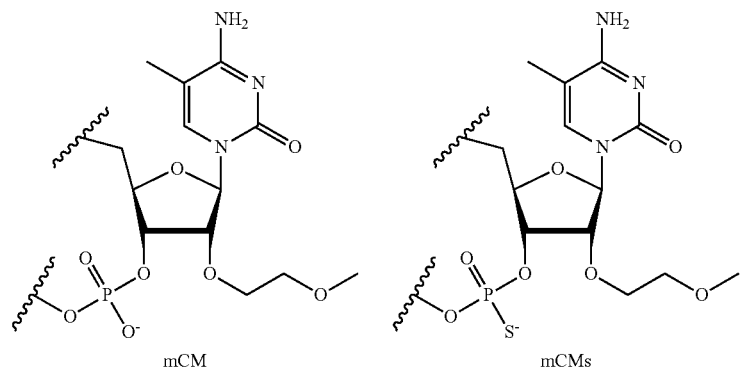
mCM  mCMs
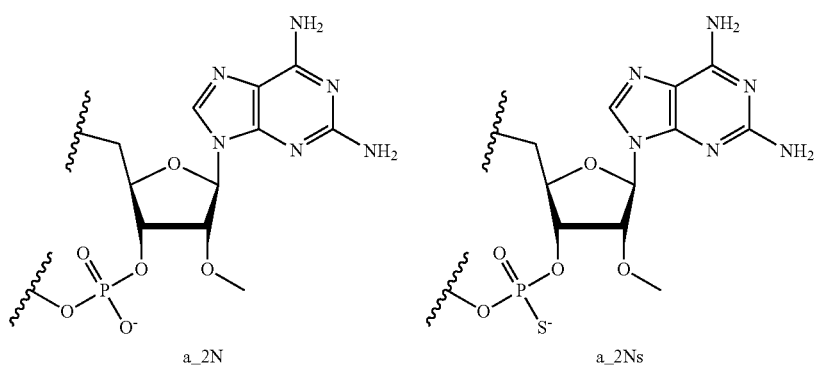
a_2N  a_2Ns TABLE 7-continued
Structure Representing Various Modified Nucleotides, Targeting Groups, and Linking Groups.
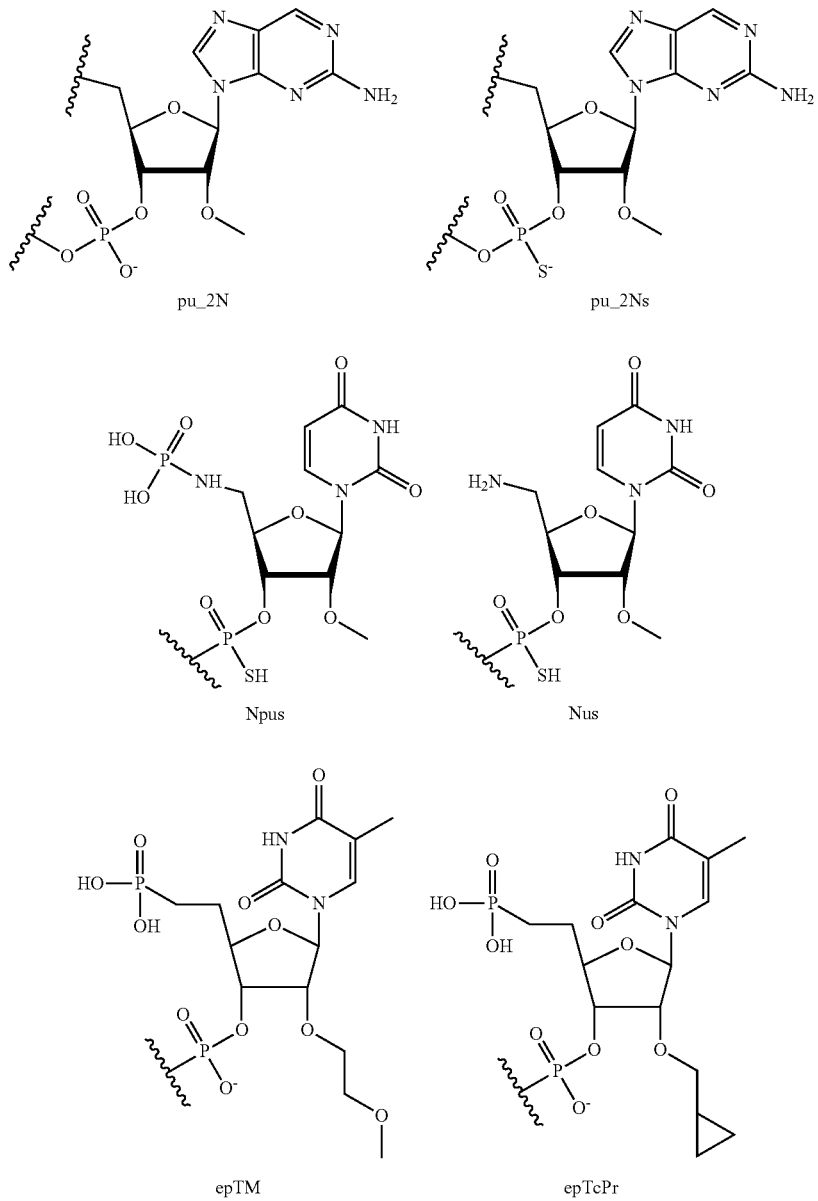
When positioned internally in oligonucleotide:
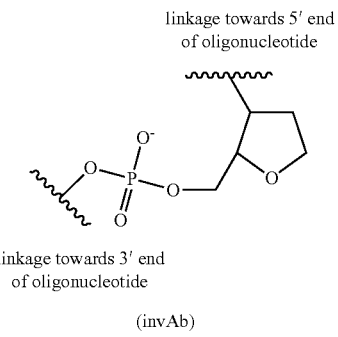
(invAb)

TABLE 7-continued

Structure Representing Various Modified Nucleotides, Targeting Groups, and Linking Groups.

When positioned internally in oligonucleotide:

linkage towards 5' end
of oligonucleotide

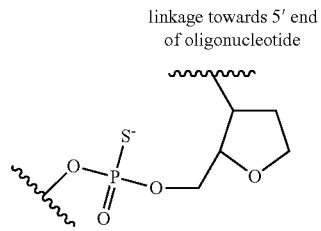

linkage towards 3' end
of oligonucleotide (invAb)s

When positioned at the 3' terminal end of oligonucleotide:

linkage towards 5' end
of oligonucleotide

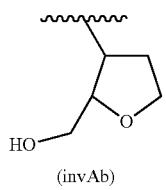

(invAb)

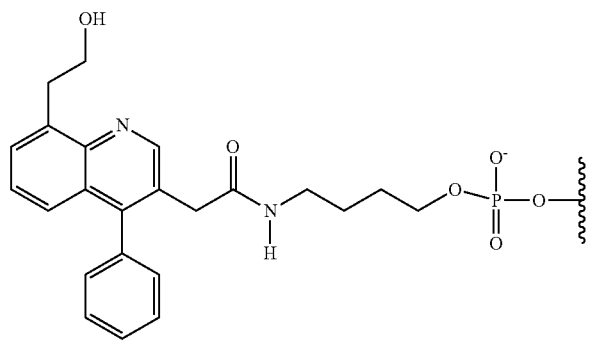

(PAZ)

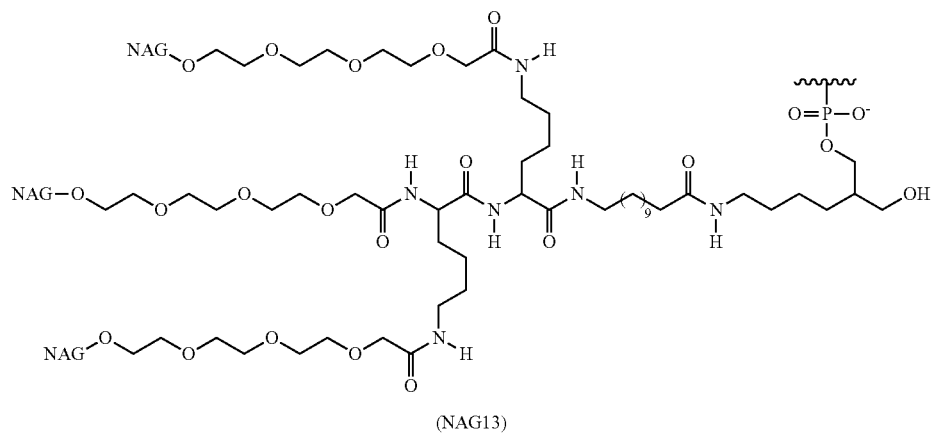

(NAG13)

TABLE 7-continued
Structure Representing Various Modified Nucleotides, Targeting Groups, and Linking Groups.
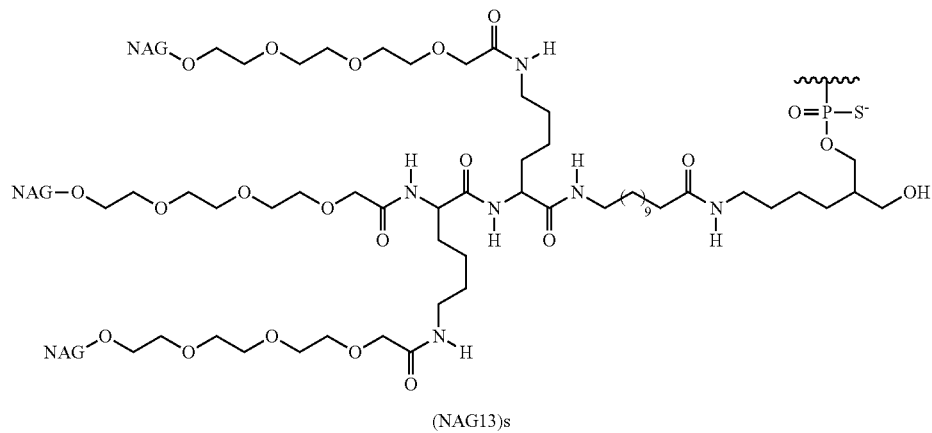
(NAG13)s
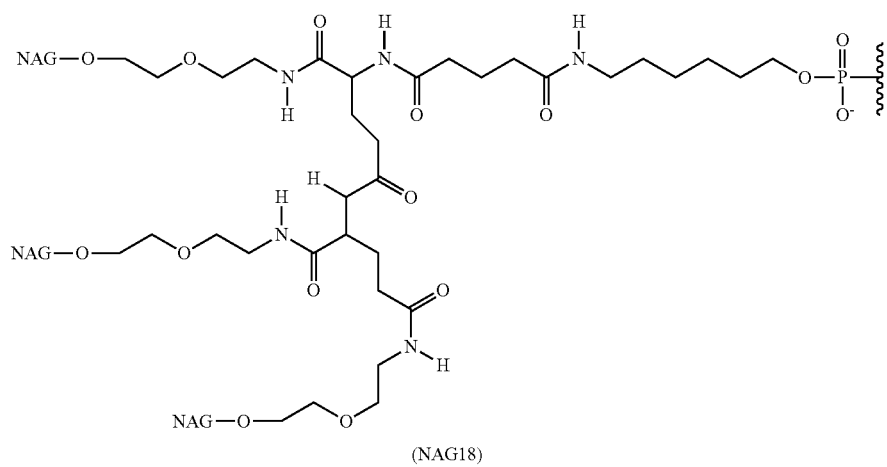
(NAG18)
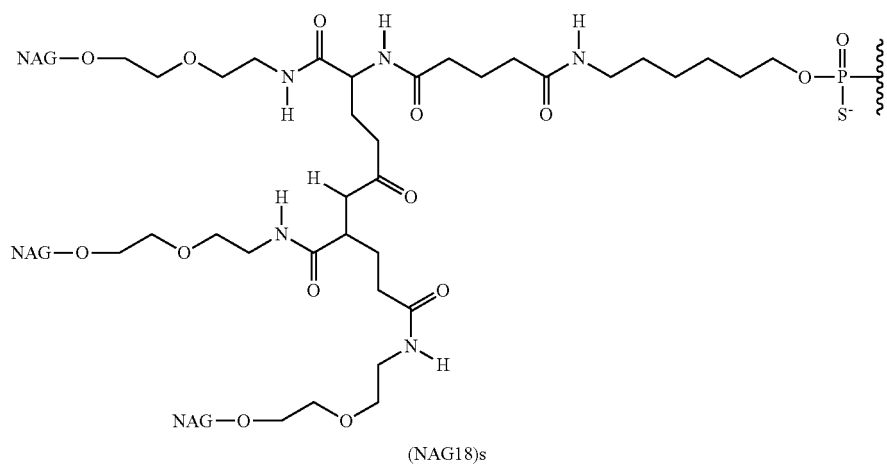
(NAG18)s TABLE 7-continued
Structure Representing Various Modified Nucleotides, Targeting Groups, and Linking Groups.
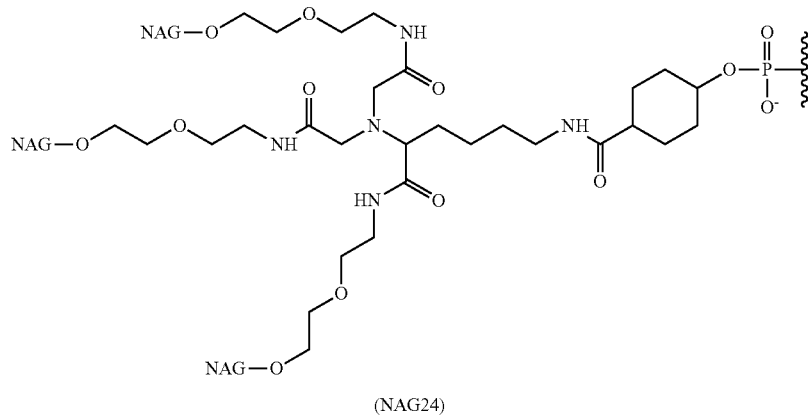
(NAG24)
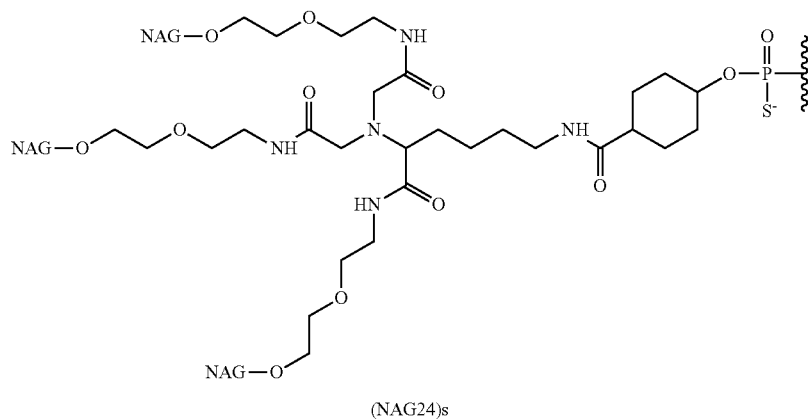
(NAG24)s
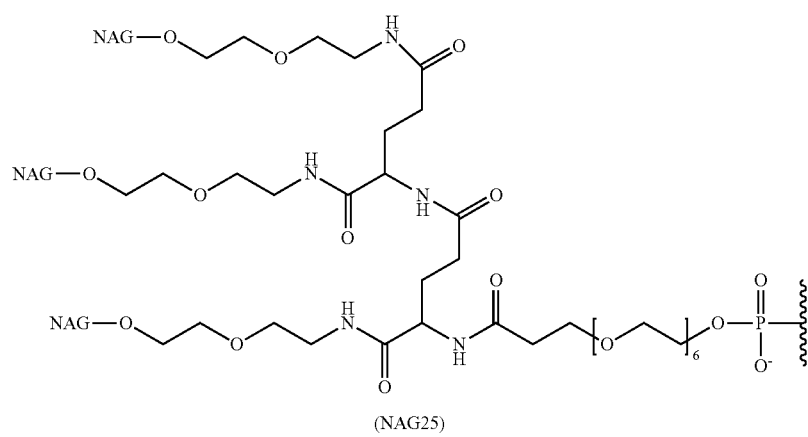
(NAG25)

TABLE 7-continued
Structure Representing Various Modified Nucleotides, Targeting Groups, and Linking Groups.
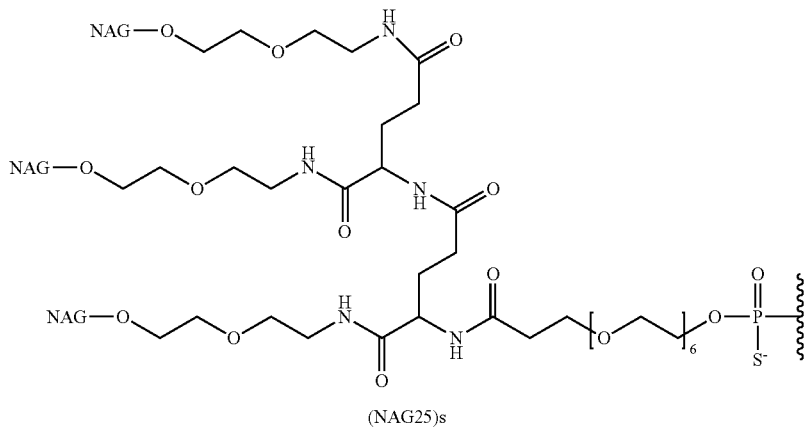
(NAG25)s
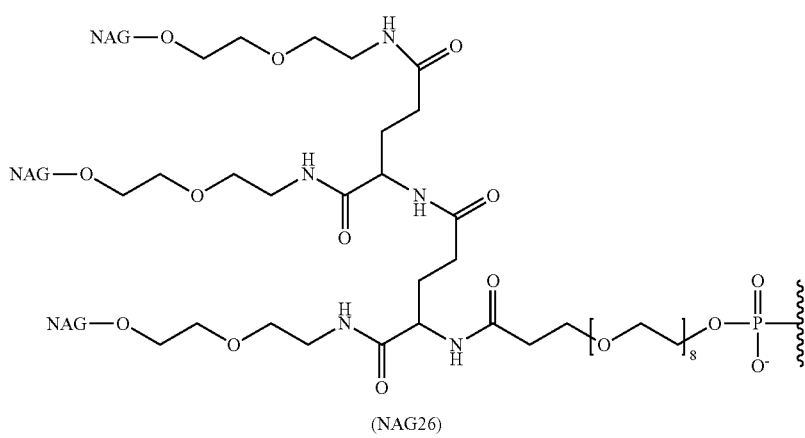
(NAG26)
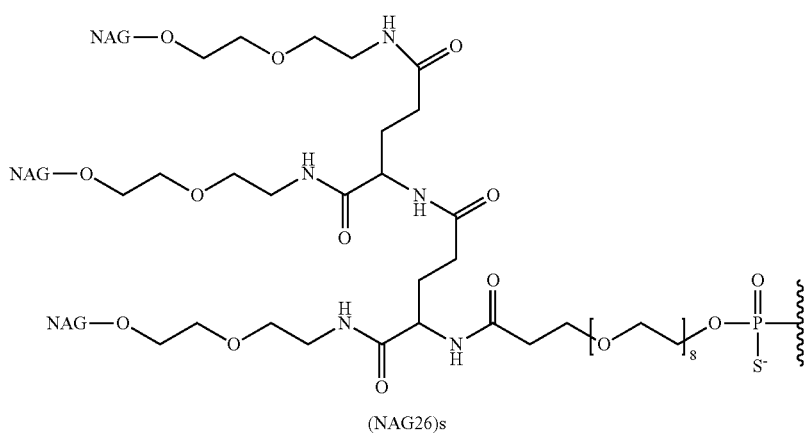
(NAG26)s
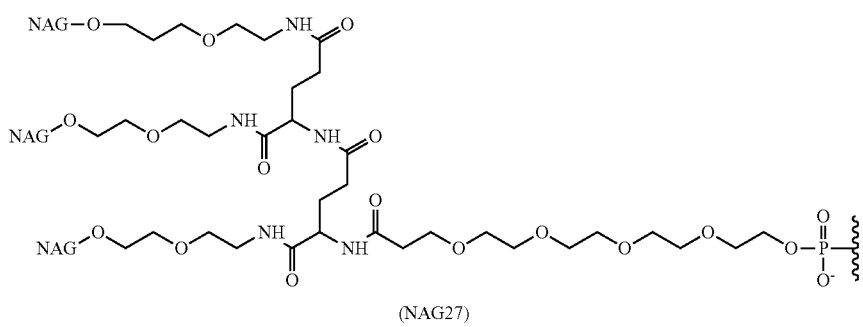
(NAG27)

TABLE 7-continued
Structure Representing Various Modified Nucleotides, Targeting Groups, and Linking Groups.
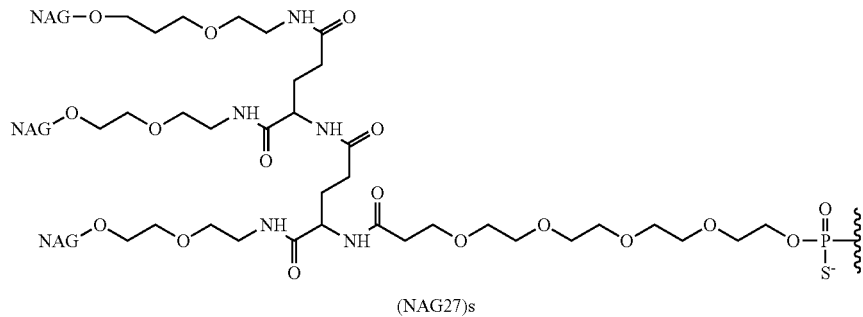
(NAG27)s
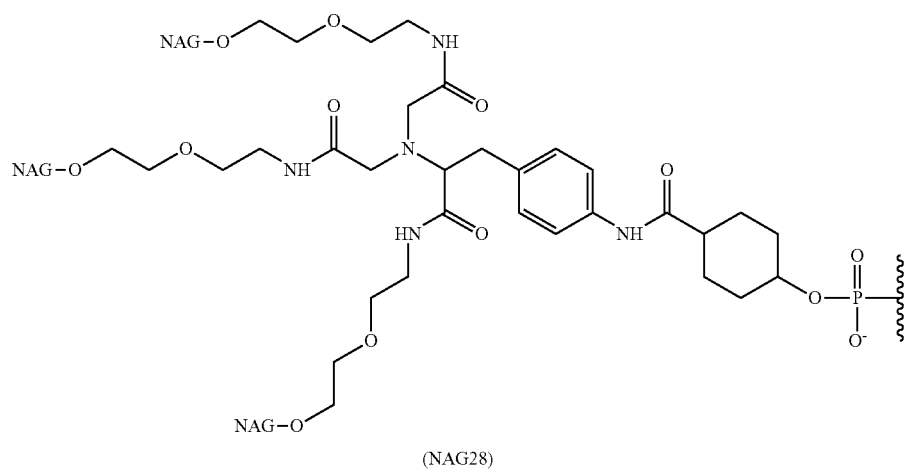
(NAG28)
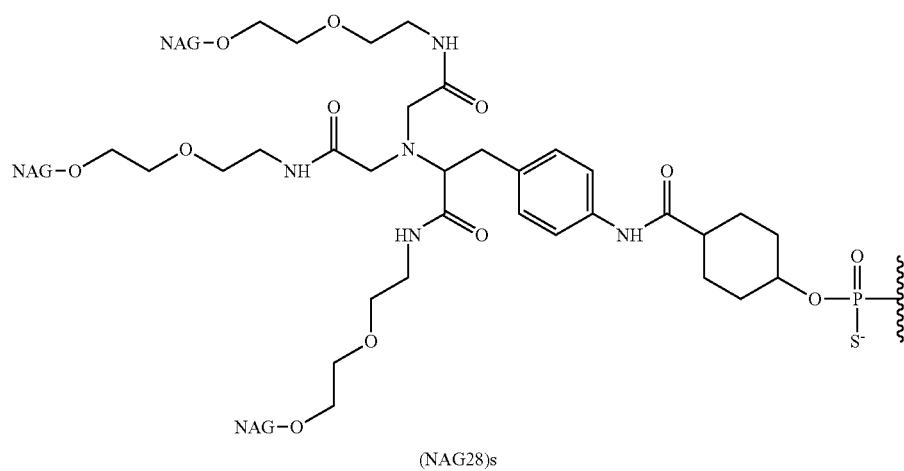
(NAG28)s TABLE 7-continued
Structure Representing Various Modified Nucleotides, Targeting Groups, and Linking Groups.
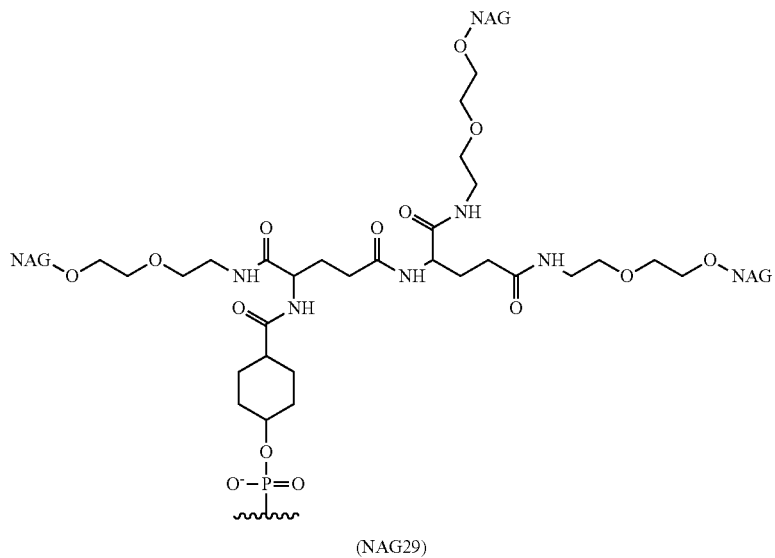
(NAG29)
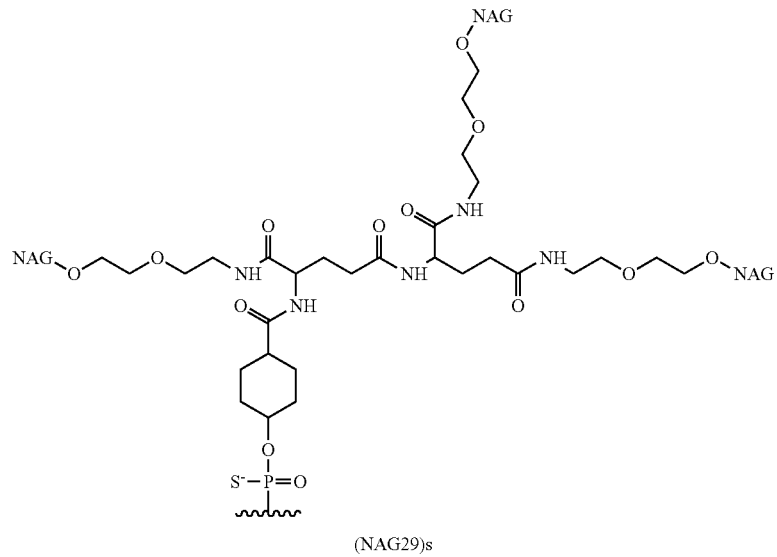
(NAG29)s
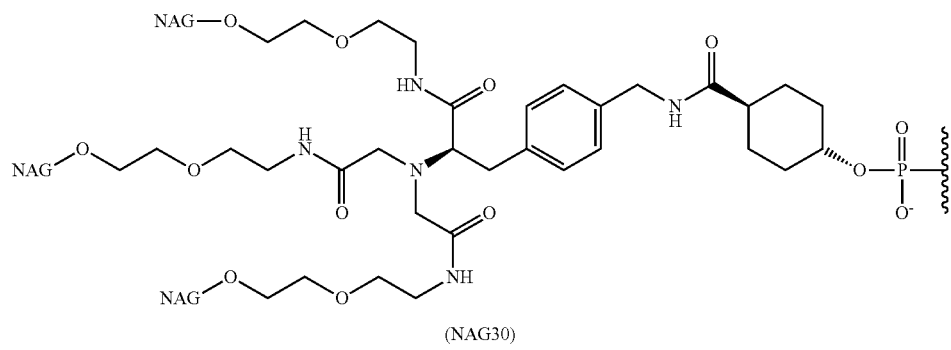
(NAG30)

TABLE 7-continued
Structure Representing Various Modified Nucleotides, Targeting Groups, and Linking Groups.
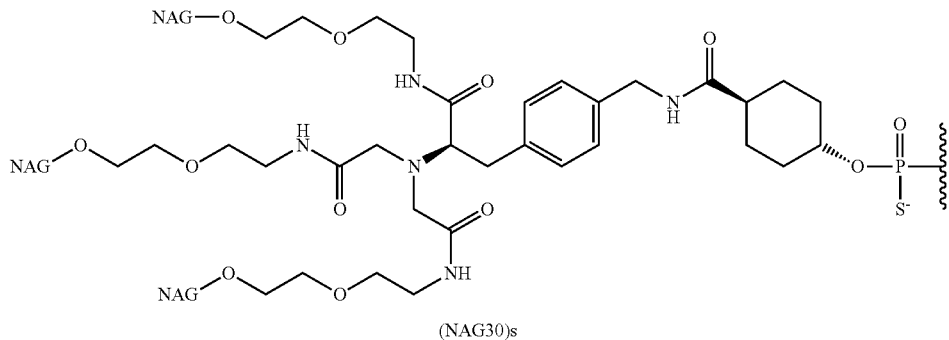
(NAG30)s
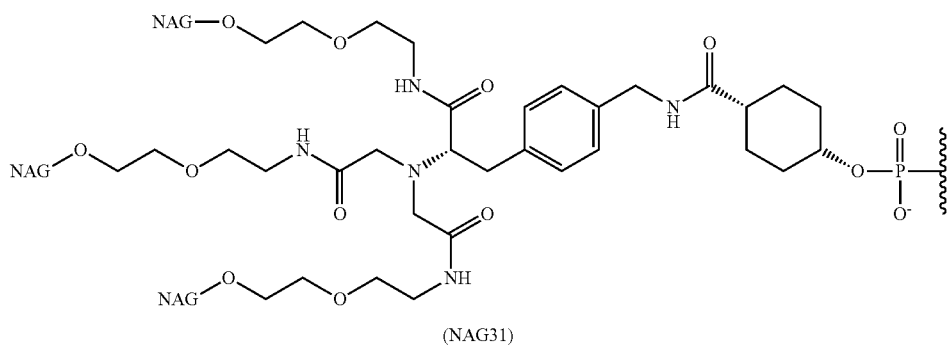
(NAG31)
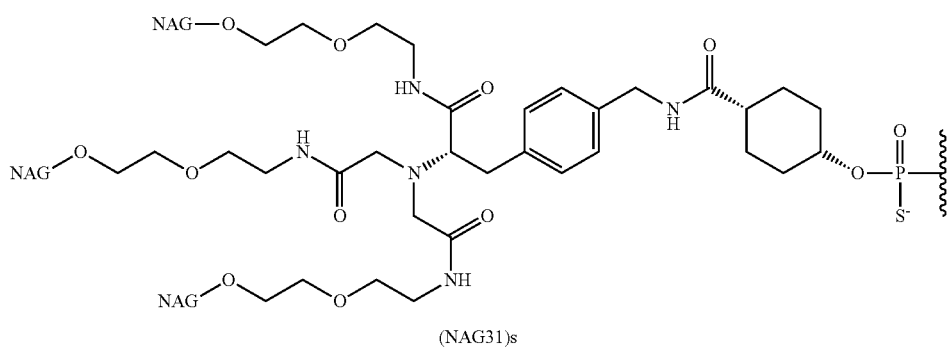
(NAG31)s
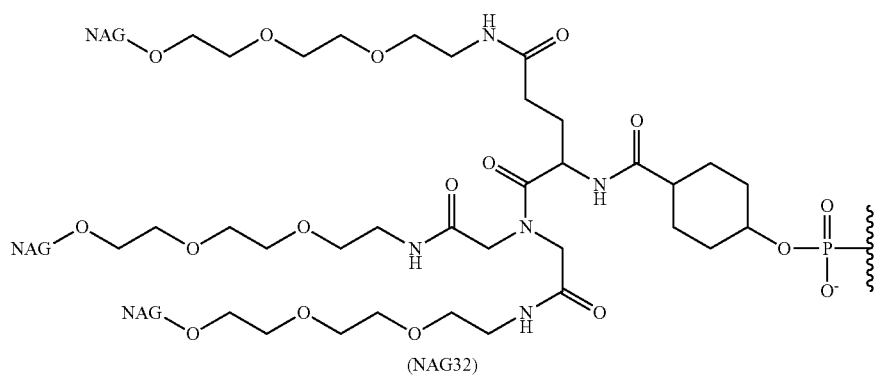
(NAG32)

TABLE 7-continued
Structure Representing Various Modified Nucleotides, Targeting Groups, and Linking Groups.
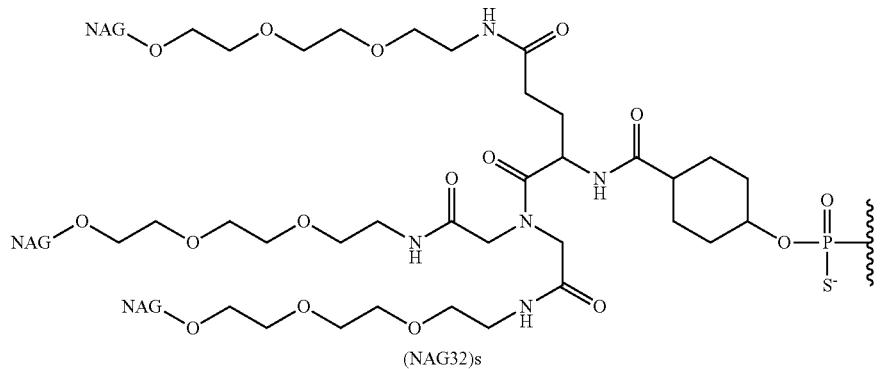
(NAG32)s
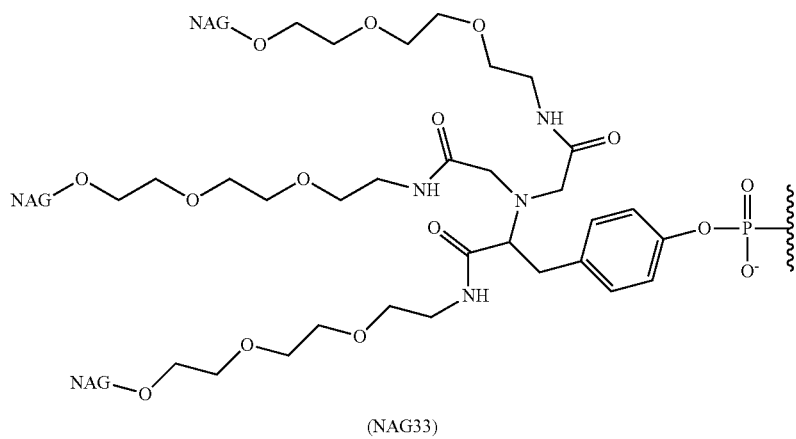
(NAG33)
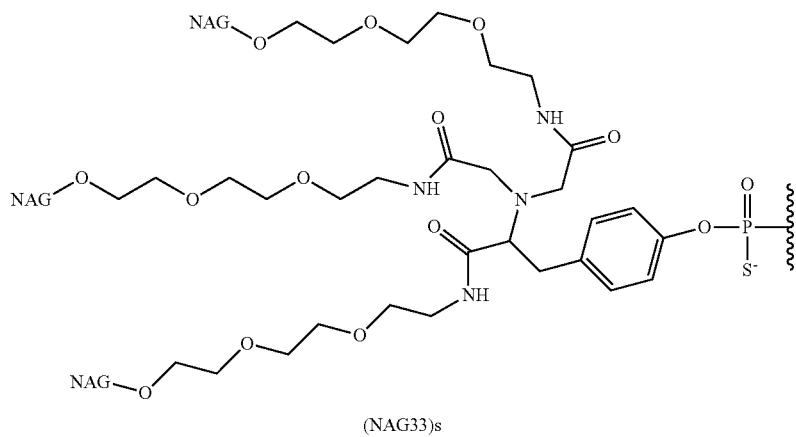
(NAG33)s TABLE 7-continued
Structure Representing Various Modified Nucleotides, Targeting Groups, and Linking Groups.
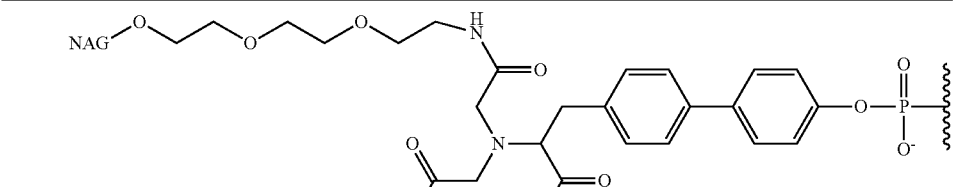
(NAG34)
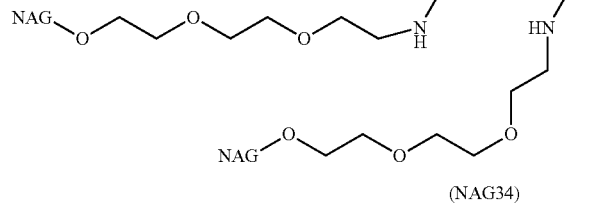
(NAG34)s
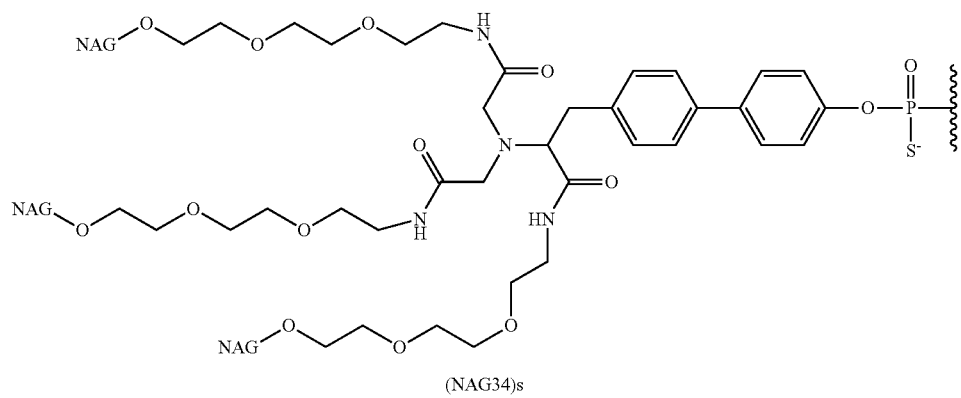
(NAG35)
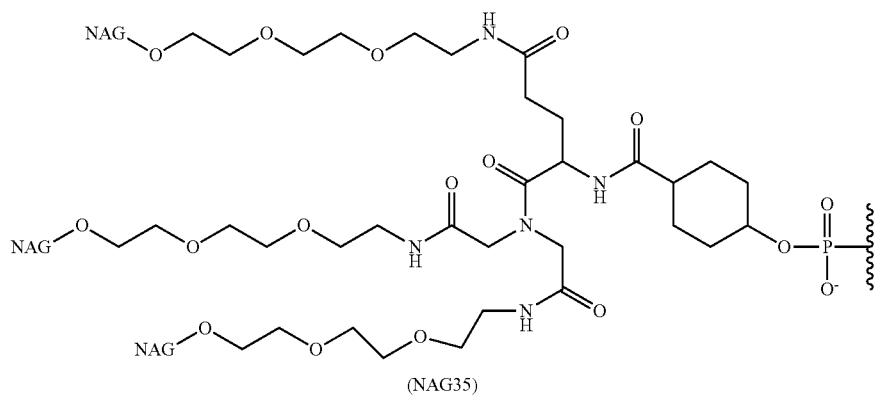
(NAG35)s TABLE 7-continued
Structure Representing Various Modified Nucleotides, Targeting Groups, and Linking Groups.
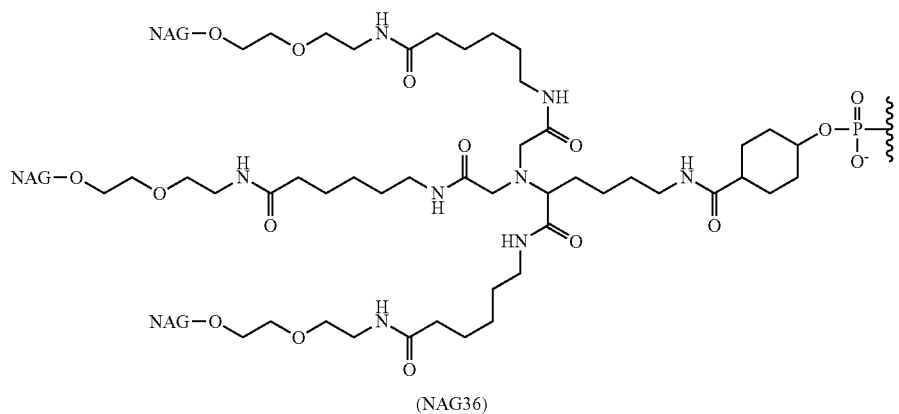
(NAG36)
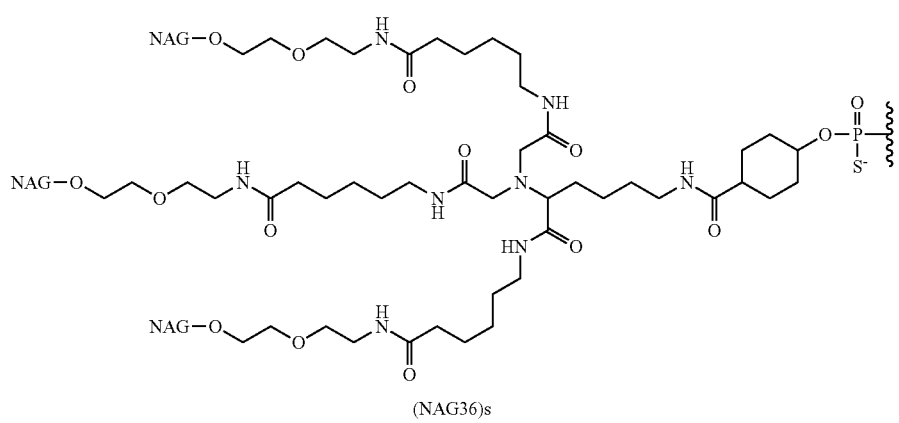
(NAG36)s
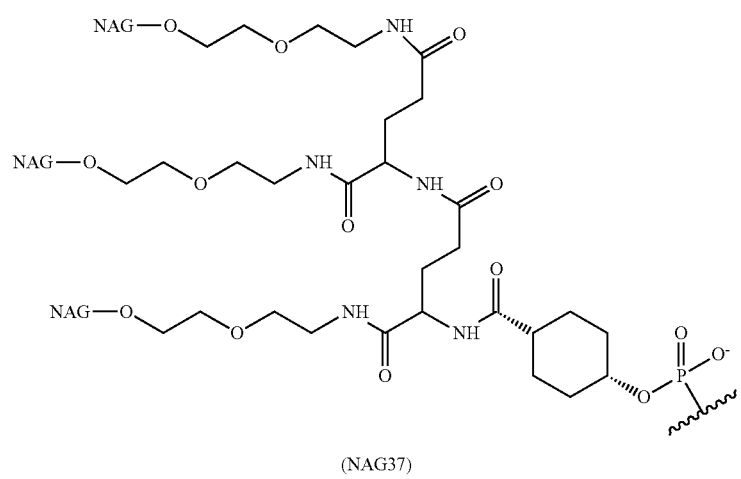
(NAG37)

TABLE 7-continued
Structure Representing Various Modified Nucleotides, Targeting Groups, and Linking Groups.
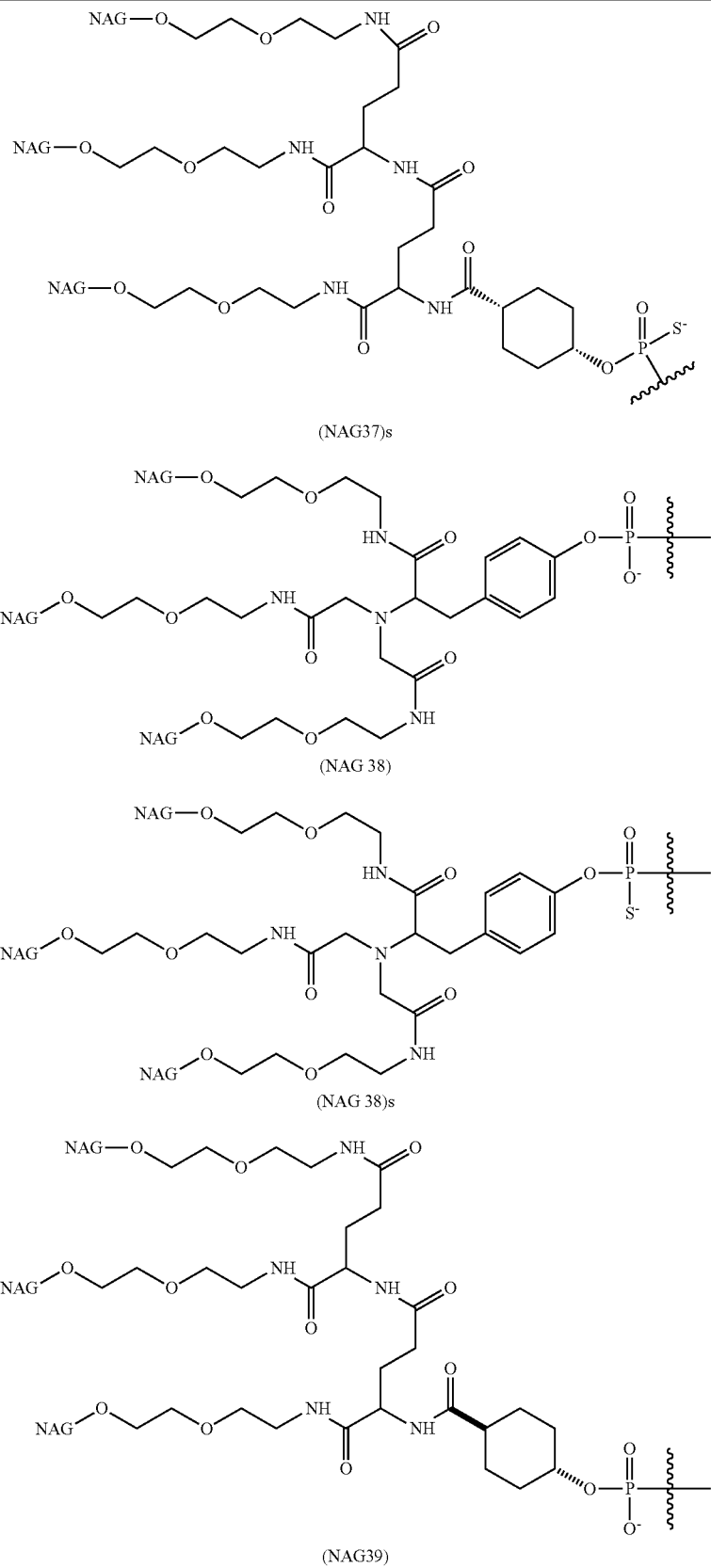
(NAG37)s
(NAG 38)
(NAG 38)s
(NAG39)

TABLE 7-continued

Structure Representing Various Modified Nucleotides, Targeting Groups, and Linking Groups.

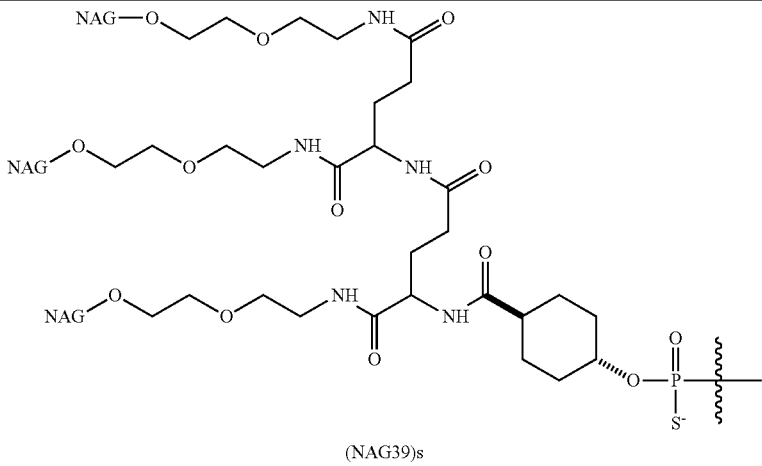

(NAG39)s

In each of the above structures in Table 7, NAG comprises an N-acetyl-galactosamine or another galactose derivative, as would be understood by a person of ordinary skill in the art to be attached in view of the structures above and description provided herein. For example, in some embodiments, NAG in the structures provided in Table 7 is represented by the following structure:

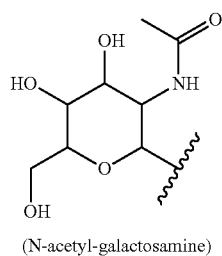 [SMILES: *C1OC(CO)C(O)C(O)C1NC(C)=O]

(N-acetyl-galactosamine)

Each (NAGx) may be attached to an APOC3 RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

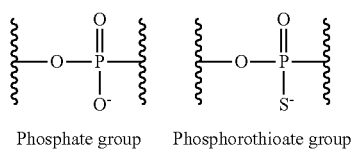 [SMILES: *OP(*)(=O)[O-] ; *OP(*)(=O)[S-]]

Phosphate group    Phosphorothioate group

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

Pharmaceutical Compositions and Formulations

The APOC3 RNAi agents disclosed herein can be prepared as pharmaceutical compositions or formulations. In some embodiments, pharmaceutical compositions include at least one APOC3 RNAi agent. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease, disorder, or condition that would benefit from reduction of the level of the target mRNA or an inhibition in expression the target gene. In one embodiment, the method includes administering an APOC3 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions including an APOC3 RNAi agent, thereby forming a pharmaceutical formulation suitable for in vivo delivery to a subject, including a human.

The pharmaceutical compositions that include an APOC3 RNAi agent and methods disclosed herein may decrease the level of the target mRNA in a cell, group of cells, group of cells, tissue, or subject, including: administering to the subject a therapeutically effective amount of a herein described APOC3 RNAi agent, thereby inhibiting the expression of APOC3 mRNA in the subject. In some embodiments, the subject has been previously identified as having a pathogenic upregulation of the target gene in the targeted cell or tissue.

In some embodiments, the described pharmaceutical compositions including an APOC3 RNAi agent are used for treating or managing clinical presentations associated with elevated TG levels and/or over-expression of APOC3 mRNA in a subject. In some embodiments, a therapeutically (including prophylactically) effective amount of one or more of pharmaceutical compositions is administered to a subject in need of such treatment (including the prevention or management of symptoms, diseases, or disorders). In some embodiments, administration of any of the disclosed APOC3 RNAi agents can be used to decrease the number, severity, and/or frequency of symptoms of a disease in a subject.

The described pharmaceutical compositions including an APOC3 RNAi agent can be used to treat at least one symptom in a subject having a disease or disorder that would benefit from reduction or inhibition in expression of APOC3 mRNA. In some embodiments, the subject is administered a therapeutically effective amount of one or more pharmaceutical compositions including an APOC3 RNAi agent thereby treating the symptom. In other embodiments, the subject is administered a prophylactically effective amount of one or more APOC3 RNAi agents, thereby preventing the at least one symptom.

The route of administration is the path by which an APOC3 RNAi agent is brought into contact with the body. In general, methods of administering drugs and oligonucleotides and nucleic acids for treatment of a mammal are well known in the art and can be applied to administration of the compositions described herein. The APOC3 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including an APOC3 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., APOC3 RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, N.J.) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The APOC3 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

In some embodiments, the methods disclosed herein further comprise the step of administering a second therapeutic or treatment in addition to administering an RNAi agent disclosed herein. In some embodiments, the second therapeutic is another APOC3 RNAi agent (e.g., an APOC3 RNAi agent which targets a different sequence within the APOC3 target). In other embodiments, the second therapeutic can be a small molecule drug, an antibody, an antibody fragment, or an aptamer.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can, in some instances, be increased beyond the above upper level in order to rapidly achieve the desired blood-level or tissue level, or the initial dosage can, in some instances, be smaller than the optimum.

For treatment of disease or for formation of a medicament or composition for treatment of a disease, the pharmaceutical compositions described herein including an APOC3 RNAi agent can be combined with an excipient or with a second therapeutic agent or treatment including, but not limited to: a second or other RNAi agent, a small molecule drug, an antibody, an antibody fragment, peptide and/or a aptamer.

The described APOC3 RNAi agents, when added to pharmaceutically acceptable excipients or adjuvants, can be packaged into kits, containers, packs, or dispensers. The pharmaceutical compositions described herein may be packaged in pre-filled syringes or vials.

Methods of Treatment and Inhibition of Expression

The APOC3 RNAi agents disclosed herein can be used to treat a subject (e.g., a human or other mammal) having a disease or disorder that would benefit from administration of the compound. In some embodiments, the RNAi agents disclosed herein can be used to treat a subject (e.g., a human) having a disease or disorder that would benefit from a reduction and/or an inhibition in expression of APOC3 mRNA, for example, a subject that has been diagnosed with or is at risk of developing symptoms related to obesity, hyperlipidemia, hypertriglyceridemia, abnormal lipid and/or cholesterol metabolism, atherosclerosis, cardiovascular disease, coronary artery disease, hypertriglyceridemia mediated pancreatitis, metabolic syndrome, type II diabetes mellitus, familial chylomicronemia syndrome, familial partial lipodystrophy, and/or other metabolic-related disorders and diseases.

The subject is administered a therapeutically effective amount of any one or more RNAi agents. The subject can be a human, patient, or human patient. The subject may be an adult, adolescent, child, or infant. Administration of a pharmaceutical composition described herein can be to a human being or animal.

In some embodiments, the APOC3 RNAi agents described herein are used to treat a subject with an APOC3-related disease or disorder. In some embodiments, the APOC3 RNAi agents described herein are used to treat a subject that would benefit from a reduction and/or inhibition of APOC3 gene expression. In some embodiments, the described APOC3 RNAi agents are used to treat (including prophylactically) at least one symptom or pathological stated mediated at least in part by APOC3 gene expression. The subject is administered a therapeutically effective amount of any one or more of the described RNAi agents. In some embodiments, the subject is administered a prophylactically effective amount of any one or more of the described RNAi agents, thereby preventing the at least one symptom.

In certain embodiments, the present invention provides methods for treatment of diseases, disorders, conditions, or pathological states mediated at least in part by APOC3 expression, in a patient in need thereof, wherein the methods include administering to the patient any of the APOC3 RNAi agents described herein.

In some embodiments, the APOC3 RNAi agents are used to treat or manage a clinical presentation of a subject with an APOC3-related disease or disorder. The subject is administered a therapeutically effective amount of one or more of the APOC3 RNAi agents or APOC3 RNAi agent-containing compositions described herein. In some embodiments, the method comprises administering a composition comprising an APOC3 RNAi agent described herein to a subject to be treated.

In some embodiments, the gene expression level and/or mRNA level of an APOC3 gene in a subject to whom a described APOC3 RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the APOC3 RNAi agent or to a subject not receiving the APOC3 RNAi agent. The gene expression level and/or mRNA level in the subject is reduced in a cell, group of cells, and/or tissue of the subject.

In some embodiments, the protein level of APOC3 in a subject to whom a described APOC3 RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the APOC3 RNAi agent or to a subject not receiving the APOC3 RNAi agent. The protein level in the subject is reduced in a cell, group of cells, tissue, blood, and/or other fluid of the subject.

In some embodiments, the triglyceride (TG) levels in a subject to whom a described APOC3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the APOC3 RNAi agent or to a subject not receiving the APOC3 RNAi agent. The TG level in the subject may be reduced in a cell, group of cells, tissue, blood, and/or other fluid of the subject.

In some embodiments, the total cholesterol levels in a subject to whom a described APOC3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the APOC3 RNAi agent or to a subject not receiving the APOC3 RNAi agent. In some embodiments, the low-density lipoprotein (LDL) cholesterol levels in a subject to whom a described APOC3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the APOC3 RNAi agent or to a subject not receiving the APOC3 RNAi agent. The total cholesterol levels and/or LDL cholesterol levels in the subject may be reduced in a cell, group of cells, tissue, blood, and/or other fluid of the subject.

A reduction in gene expression, mRNA, APOC3 protein levels, TG levels, cholesterol levels, and LDL cholesterol levels can be assessed by any methods known in the art. As used herein, a reduction or decrease in APOC3 mRNA level and/or protein level are collectively referred to herein as a reduction or decrease in APOC3 or inhibiting or reducing or knocking down the expression of APOC3. The Examples set forth herein illustrate known methods for assessing inhibition of APOC3 gene expression.

Cells, Tissues, Organs, and Non-Human Organisms

Cells, tissues, organs, and non-human organisms that include at least one of the APOC3 RNAi agents described herein are contemplated. The cell, tissue, organ, or non-human organism is made by delivering the RNAi agent to the cell, tissue, organ, or non-human organism.

The above provided embodiments and items are now illustrated with the following, non-limiting examples.

EXAMPLES

Example 1. Synthesis of APOC3 RNAi Agents

APOC3 RNAi agent duplexes shown in Table 3 and Table 6, above, were synthesized in accordance with the following general procedures:

A. Synthesis.

The sense and antisense strands of the APOC3 RNAi agents were synthesized according to phosphoramidite technology on solid phase used in oligonucleotide synthesis. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). Specifically, the following 2'-O-methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-dimethoxytrityl-2'-O-methyl-inosine-3'-O-(2-cyanoethyl-N,N-diisopropylamino) phosphoramidites were purchased from Glen Research (Virginia) or Hongene Biotech. The inverted abasic (3'-O-dimethoxytrityl-2'-deoxyribose-5'-O-(2-cyanoethyl-N,N-diisopropylamino) phosphoramidites were purchased from ChemGenes (Wilmington, Mass., USA). 5'-(4, 4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. The 5'-O-dimethoxytrityl-$N^2$,$N^6$-(phenoxyacetate)-2'-O-methyl-diaminopurine-3'-O-(2-cyanoethyl-N,N-diisopropylamino) phosphoramidite was obtained from ChemGenes or Hongene Biotech.

Targeting ligand containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed. Unless specifically identified as a "naked" RNAi agent having no targeting ligand present, each of the APOC3 RNAi agent duplexes synthesized and tested in the following Examples utilized N-acetyl-galactosamine as "NAG" in the targeting ligand chemical structures represented in Table 7.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 µm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1×Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1×Phosphate-Buffered Saline. The solution absorbance at 260 nm was then multiplied by a conversion factor and the dilution factor to determine the duplex concentration. Unless otherwise stated, all conversion factor was 0.037 mg/ (mL·cm). For some experiments, a conversion factor was calculated from an experimentally determined extinction coefficient.

Example 2. In Vitro Testing of APOC3 RNAi Agents

Candidate sequence duplexes shown in Table 3, above, were tested in vitro. The APOC3 RNAi agents were prepared in accordance with the procedures set forth in Example 1.

Evaluation of APOC3 RNAi agents in vitro was performed by transfection of HuH7 cells, a human hepatocellular carcinoma line. Cells were plated at ~7,500 cells per well in 96-well format, and each of the 65 APOC3 RNAi agent duplexes shown in Table 3 was transfected at three concentrations (10 nM, 1 nM, and 0.1 nM), using Lipofectamine RNAiMax (Thermo Fisher) transfection reagent. Relative expression of each of the APOC3 RNAi agents was determined by qRT-PCR by comparing the expression levels of APOC3 mRNA to an endogenous control, and normalized to untreated HuH7 cells ($\Delta\Delta C_T$ analysis), as shown in Table 8. Thus, for Duplex ID No. 56_1, average relative expression at 1 nM of 0.126 shows APOC3 gene knockdown of 87.4%.

TABLE 8

In Vitro Testing of APOC3 RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| 56_1 | 0.081 | 0.013 | 0.016 | 0.126 | 0.033 | 0.045 | 0.249 | 0.083 | 0.125 |
| 56_2 | 0.076 | 0.014 | 0.017 | 0.116 | 0.027 | 0.035 | 0.190 | 0.060 | 0.088 |
| 56_3 | 0.084 | 0.016 | 0.020 | 0.124 | 0.028 | 0.036 | 0.313 | 0.114 | 0.179 |
| 56_4 | 0.098 | 0.023 | 0.031 | 0.155 | 0.045 | 0.063 | 0.534 | 0.122 | 0.157 |
| 56_5 | 0.100 | 0.026 | 0.034 | 0.138 | 0.029 | 0.036 | 0.511 | 0.161 | 0.236 |
| 58_1 | 0.130 | 0.028 | 0.035 | 0.237 | 0.021 | 0.023 | 0.713 | 0.177 | 0.235 |
| 58_2 | 0.118 | 0.018 | 0.021 | 0.319 | 0.039 | 0.045 | 0.602 | 0.058 | 0.064 |
| 58_3 | 0.070 | 0.011 | 0.013 | 0.152 | 0.018 | 0.020 | 0.383 | 0.025 | 0.026 |
| 58_4 | 0.069 | 0.012 | 0.015 | 0.168 | 0.022 | 0.025 | 0.453 | 0.031 | 0.034 |
| 58_5 | 0.062 | 0.009 | 0.011 | 0.189 | 0.047 | 0.062 | 0.557 | 0.045 | 0.049 |
| 228_1 | 0.055 | 0.011 | 0.014 | 0.377 | 0.039 | 0.043 | 0.684 | 0.043 | 0.046 |
| 228_2 | 0.096 | 0.011 | 0.013 | 0.472 | 0.040 | 0.043 | 0.720 | 0.074 | 0.083 |
| 228_3 | 0.143 | 0.023 | 0.027 | 0.525 | 0.021 | 0.022 | 0.804 | 0.035 | 0.036 |
| 228_4 | 0.115 | 0.018 | 0.022 | 0.518 | 0.036 | 0.038 | 0.740 | 0.029 | 0.030 |
| 228_5 | 0.165 | 0.029 | 0.035 | 0.547 | 0.040 | 0.043 | 0.721 | 0.036 | 0.038 |
| 235_1 | 0.142 | 0.025 | 0.030 | 0.566 | 0.045 | 0.049 | 0.737 | 0.035 | 0.036 |
| 235_2 | 0.064 | 0.013 | 0.016 | 0.370 | 0.030 | 0.033 | 0.713 | 0.042 | 0.045 |
| 235_3 | 0.029 | 0.008 | 0.011 | 0.085 | 0.015 | 0.018 | 0.535 | 0.048 | 0.053 |
| 235_4 | 0.050 | 0.010 | 0.012 | 0.197 | 0.018 | 0.019 | 0.652 | 0.045 | 0.048 |
| 235_5 | 0.079 | 0.019 | 0.025 | 0.328 | 0.043 | 0.050 | 0.719 | 0.113 | 0.134 |
| 243_1 | 0.044 | 0.012 | 0.017 | 0.222 | 0.046 | 0.058 | 0.671 | 0.114 | 0.137 |
| 243_2 | 0.035 | 0.008 | 0.011 | 0.358 | 0.041 | 0.047 | 0.701 | 0.068 | 0.076 |
| 243_3 | 0.022 | 0.007 | 0.009 | 0.142 | 0.033 | 0.042 | 0.567 | 0.070 | 0.080 |
| 243_4 | 0.016 | 0.007 | 0.013 | 0.115 | 0.018 | 0.021 | 0.502 | 0.073 | 0.086 |
| 243_5 | 0.039 | 0.011 | 0.016 | 0.123 | 0.019 | 0.022 | 0.597 | 0.050 | 0.055 |
| 260_1 | 0.021 | 0.007 | 0.011 | 0.390 | 0.062 | 0.074 | 0.719 | 0.034 | 0.035 |
| 260_2 | 0.042 | 0.008 | 0.010 | 0.728 | 0.062 | 0.068 | 0.719 | 0.042 | 0.045 |
| 260_3 | 0.026 | 0.008 | 0.012 | 0.747 | 0.067 | 0.073 | 0.685 | 0.044 | 0.047 |
| 260_4 | 0.021 | 0.009 | 0.015 | 0.507 | 0.064 | 0.073 | 0.749 | 0.064 | 0.070 |
| 260_5 | 0.057 | 0.014 | 0.019 | 0.572 | 0.040 | 0.043 | 0.745 | 0.051 | 0.054 |
| 261_1 | 0.046 | 0.007 | 0.008 | 0.295 | 0.039 | 0.045 | 0.766 | 0.044 | 0.046 |
| 261_2 | 0.052 | 0.017 | 0.024 | 0.611 | 0.037 | 0.039 | 0.823 | 0.050 | 0.053 |
| 261_3 | 0.032 | 0.007 | 0.009 | 0.303 | 0.025 | 0.028 | 0.727 | 0.024 | 0.025 |
| 261_4 | 0.027 | 0.005 | 0.007 | 0.756 | 0.031 | 0.032 | 0.690 | 0.032 | 0.033 |
| 261_5 | 0.041 | 0.005 | 0.006 | 0.868 | 0.099 | 0.112 | 0.737 | 0.031 | 0.032 |
| 270_1 | 0.031 | 0.006 | 0.008 | 0.294 | 0.052 | 0.063 | 0.719 | 0.046 | 0.049 |
| 270_2 | 0.055 | 0.015 | 0.020 | 0.344 | 0.066 | 0.082 | 0.738 | 0.036 | 0.038 |
| 270_3 | 0.047 | 0.014 | 0.019 | 0.359 | 0.019 | 0.020 | 0.811 | 0.028 | 0.029 |
| 270_4 | 0.023 | 0.005 | 0.006 | 0.212 | 0.019 | 0.021 | 0.706 | 0.034 | 0.035 |
| 270_5 | 0.027 | 0.007 | 0.010 | 0.615 | 0.030 | 0.032 | 0.685 | 0.036 | 0.038 |
| 272_1 | 0.046 | 0.011 | 0.015 | 0.398 | 0.024 | 0.025 | 0.696 | 0.015 | 0.015 |
| 272_2 | 0.057 | 0.012 | 0.015 | 0.343 | 0.030 | 0.033 | 0.719 | 0.059 | 0.064 |
| 272_3 | 0.071 | 0.010 | 0.012 | 0.269 | 0.034 | 0.039 | 0.736 | 0.034 | 0.036 |
| 272_4 | 0.061 | 0.018 | 0.026 | 0.135 | 0.016 | 0.018 | 0.747 | 0.041 | 0.044 |
| 272_5 | 0.089 | 0.023 | 0.031 | 0.322 | 0.025 | 0.027 | 0.793 | 0.029 | 0.030 |
| 273_1 | 0.014 | 0.004 | 0.006 | 0.066 | 0.019 | 0.026 | 0.665 | 0.043 | 0.046 |
| 273_2 | 0.016 | 0.004 | 0.005 | 0.064 | 0.012 | 0.015 | 0.676 | 0.040 | 0.042 |
| 273_3 | 0.012 | 0.003 | 0.005 | 0.041 | 0.007 | 0.008 | 0.606 | 0.041 | 0.044 |
| 273_4 | 0.016 | 0.003 | 0.004 | 0.060 | 0.009 | 0.011 | 0.687 | 0.036 | 0.038 |
| 273_5 | 0.024 | 0.004 | 0.004 | 0.101 | 0.008 | 0.009 | 0.736 | 0.055 | 0.059 |
| 349_1 | 0.044 | 0.007 | 0.009 | 0.196 | 0.017 | 0.018 | 0.711 | 0.091 | 0.104 |

TABLE 8-continued

In Vitro Testing of APOC3 RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| 349_2 | 0.054 | 0.017 | 0.025 | 0.226 | 0.015 | 0.016 | 0.820 | 0.058 | 0.063 |
| 349_3 | 0.031 | 0.012 | 0.020 | 0.157 | 0.019 | 0.021 | 0.761 | 0.073 | 0.081 |
| 349_4 | 0.033 | 0.013 | 0.022 | 0.148 | 0.015 | 0.017 | 0.810 | 0.096 | 0.108 |
| 349_5 | 0.043 | 0.016 | 0.024 | 0.214 | 0.013 | 0.014 | 0.853 | 0.077 | 0.084 |
| 434_1 | 0.074 | 0.008 | 0.009 | 0.147 | 0.019 | 0.021 | 0.860 | 0.044 | 0.047 |
| 434_2 | 0.031 | 0.004 | 0.005 | 0.055 | 0.012 | 0.016 | 0.390 | 0.080 | 0.101 |
| 434_3 | 0.026 | 0.003 | 0.004 | 0.053 | 0.011 | 0.015 | 0.418 | 0.015 | 0.016 |
| 434_4 | 0.020 | 0.004 | 0.005 | 0.085 | 0.023 | 0.032 | 0.488 | 0.018 | 0.019 |
| 434_5 | 0.024 | 0.002 | 0.002 | 0.096 | 0.024 | 0.032 | 0.661 | 0.039 | 0.042 |
| 437_1 | 0.028 | 0.005 | 0.006 | 0.073 | 0.022 | 0.031 | 0.689 | 0.033 | 0.034 |
| 437_2 | 0.046 | 0.006 | 0.006 | 0.150 | 0.037 | 0.049 | 0.798 | 0.030 | 0.031 |
| 437_3 | 0.044 | 0.005 | 0.005 | 0.043 | 0.006 | 0.007 | 0.591 | 0.023 | 0.024 |
| 437_4 | 0.023 | 0.004 | 0.006 | 0.030 | 0.005 | 0.006 | 0.759 | 0.033 | 0.035 |
| 437_5 | 0.024 | 0.002 | 0.003 | 0.061 | 0.006 | 0.006 | 0.750 | 0.048 | 0.051 |

Example 3. APOC3-SEAP Mouse Model

Six to eight week old female C57BL/6 albino mice were transiently transfected in vivo with plasmid by hydrodynamic tail vein injection, administered at least 15 days prior to administration of an APOC3 RNAi agent or control. The plasmid contains the APOC3 cDNA sequence (GenBank NM_000040.1 (SEQ ID NO:1)) inserted into the 3' UTR of the SEAP (secreted human placental alkaline phosphatase) reporter gene. 50 μg of the plasmid containing the APOC3 cDNA sequence in Ringer's Solution in a total volume of 10% of the animal's body weight was injected into mice via the tail vein to create APOC3-SEAP model mice. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737). Inhibition of expression of APOC3 by an APOC3 RNAi agent results in concomitant inhibition of SEAP expression, which is measured. At day −1, SEAP expression levels in serum were measured by the Phospha-Light™ SEAP Reporter Gene Assay System (Invitrogen), and the mice were grouped according to average SEAP levels.

Analyses:

SEAP levels may be measured at various times, both before and after administration of APOC3 RNAi agents.

i) Serum Collection:

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

ii) Serum SEAP Levels:

Serum was collected and measured by the Phospha-Light™ SEAP Reporter Gene Assay System (Invitrogen) according to the manufacturer's instructions. Serum SEAP levels for each animal was normalized to the control group of mice injected with saline in order to account for the non-treatment related decline in APOC3 expression with this model. First, the SEAP level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal saline control group. Alternatively, in some Examples set forth herein, the serum SEAP levels for each animal were assessed by normalizing to pre-treatment levels only.

Example 4. In Vivo Testing of APOC3 RNAi Agents in APOC3-SEAP Mice

The APOC3-SEAP mouse model described in Example 3, above, was used. At day 1, each mouse was given a single subcutaneous administration of 200 μl containing either 5 mg/kg (mpk) of an APOC3 RNAi agent, 3 mg/kg of an APOC3 RNAi agent, or 200 μl of phosphate buffered saline without an APOC3 RNAi agent to be used as a control, according to the following Table 9.

TABLE 9

Dosing groups of APOC3-SEAP mice of Example 4.

| Group | RNAi Agent and Dose | Dosing Regimen |
|---|---|---|
| A | Saline (no RNAi agent) | Single injection on day 1 |
| B | 5.0 mg/kg AD04812 | Single injection on day 1 |
| C | 5.0 mg/kg AD04813 | Single injection on day 1 |
| D | 5.0 mg/kg AD04814 | Single injection on day 1 |
| E | 3.0 mg/kg AD04814 | Single injection on day 1 |
| F | 5.0 mg/kg AD04815 | Single injection on day 1 |
| G | 5.0 mg/kg AD04816 | Single injection on day 1 |
| H | 3.0 mg/kg AD04816 | Single injection on day 1 |
| I | 5.0 mg/kg AD04817 | Single injection on day 1 |
| J | 5.0 mg/kg AD04818 | Single injection on day 1 |
| K | 5.0 mg/kg AD04819 | Single injection on day 1 |
| L | 5.0 mg/kg AD04820 | Single injection on day 1 |
| M | 5.0 mg/kg AD04821 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 4, 5, 6, and 7 for specific modifications and structure information related to the APOC3 RNAi agents).

The injections were performed between the skin and muscle (i.e. subcutaneous injections) into the loose skin over the neck and shoulder area. Three (3) mice in each group were tested (n=3). Serum was collected on day 8, day 15, day 22, and day 29, and SEAP expression levels were determined pursuant to the procedure set forth in Example 3, above. Data from the experiment is shown in the following Table 10, with Average SEAP reflecting the normalized average value of SEAP:

TABLE 10

Average SEAP Normalized to Pre-Treatment and Saline Control in APOC3-SEAP Mice from Example 4.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group A (Saline) | 1.000 | 0.157 | 1.000 | 0.603 | 1.000 | 0.864 | 1.000 | 0.701 |
| Group B (5.0 mg/kg AD04812) | 0.112 | 0.009 | 0.112 | 0.009 | 0.047 | 0.014 | 0.089 | 0.032 |
| Group C (5.0 mg/kg AD04813) | 0.091 | 0.009 | 0.046 | 0.015 | 0.052 | 0.019 | 0.102 | 0.045 |
| Group D (5.0 mg/kg AD04814) | 0.065 | 0.023 | 0.045 | 0.016 | 0.039 | 0.017 | 0.073 | 0.027 |
| Group E (3.0 mg/kg AD04814) | 0.075 | 0.021 | 0.041 | 0.037 | 0.047 | 0.046 | 0.059 | 0.053 |
| Group F (5.0 mg/kg AD04815) | 0.090 | 0.005 | 0.032 | 0.015 | 0.026 | 0.012 | 0.046 | 0.018 |
| Group G (5.0 mg/kg AD04816) | 0.401 | 0.122 | 0.399 | 0.136 | 0.274 | 0.053 | 0.331 | 0.094 |
| Group H (3.0 mg/kg AD04816) | 0.389 | 0.129 | 0.292 | 0.090 | 0.218 | 0.070 | 0.185 | 0.039 |
| Group I (5.0 mg/kg AD04817) | 0.371 | 0.210 | 0.266 | 0.091 | 0.098 | 0.014 | 0.144 | 0.033 |
| Group J (5.0 mg/kg AD04818) | 0.373 | 0.028 | 0.467 | 0.190 | 0.218 | 0.153 | 0.323 | 0.232 |
| Group K (5.0 mg/kg AD04819) | 0.216 | 0.123 | 0.334 | 0.034 | 0.407 | 0.053 | 0.408 | 0.042 |
| Group L (5.0 mg/kg AD04820) | 0.164 | 0.085 | 0.226 | 0.206 | 0.219 | 0.165 | 0.252 | 0.157 |
| Group M (5.0 mg/kg AD04821) | 0.169 | 0.097 | 0.128 | 0.061 | 0.150 | 0.105 | 0.191 | 0.143 |

Each of the APOC3 RNAi agents in each of the dosing groups (i.e., Groups B through M) showed substantial reduction in SEAP as compared to the saline control (Group A) across all measured time points. For example, APOC3 RNAi agent AD04815 exhibited approximately a 97.4% reduction in SEAP at day 22 after a single 5.0 mg/kg injection (0.026).

Example 5. APOC3 Transgenic Mouse Model

To assess and evaluate the effect of certain other APOC3 RNAi agents in vivo, APOC3 transgenic mice were acquired commercially and used (The Jackson Laboratory, 006907-B6; CBA-Tg(APOC3)3707Bres/J). For APOC3 transgenic mice, human APOC3 protein levels in serum were measured on a Cobas® Integra 400 (Roche Diagnostics), according to the manufacturer's recommendations.

For normalization, the APOC3 level for each animal at a time point was divided by the pre-treatment level of expression in that animal to determine the ratio of expression "normalized to pre-dose". In some Examples reported herein, the expression at a specific time point was also then normalized to the vehicle control group by dividing the "normalized to pre-dose" ratio for an individual animal by the mean "normalized to pre-dose" ratio of all mice in the vehicle control group. This resulted in expression for each time point normalized to that in the control group.

APOC3 levels may be measured at various times, both before and after administration of APOC3 RNAi agents. Unless noted otherwise herein, mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

Example 6. In Vivo Testing of APOC3 RNAi Agents in APOC3 Transgenic Mice

The APOC3 Transgenic Mouse Model described in Example 5, above, was used. At day 1, each mouse was given a single subcutaneous administration of 200 µl of the respective RNAi agent dissolved in D5W (dextrose in 5% water) or control (D5W), which included the dosing groups shown in the following Table 11.

TABLE 11

Dosing Groups of APOC3 Transgenic Mice of Example 6.

| Group | RNAi Agent and Dose | Dosing Regimen |
|---|---|---|
| A | D5W (no RNAi agent) | Single injection on day 1 |
| B | 4.0 mg/kg AD05172 | Single injection on day 1 |
| C | 2.0 mg/kg AD05172 | Single injection on day 1 |
| D | 1.0 mg/kg AD05172 | Single injection on day 1 |
| E | 0.5 mg/kg AD05172 | Single injection on day 1 |
| F | 1.0 mg/kg AD05215 | Single injection on day 1 |
| G | 1.0 mg/kg AD05216 | Single injection on day 1 |
| H | 1.0 mg/kg AD05217 | Single injection on day 1 |
| I | 1.0 mg/kg AD05218 | Single injection on day 1 |
| J | 1.0 mg/kg AD05171 | Single injection on day 1 |
| K | 2.0 mg/kg AD05219 | Single injection on day 1 |
| L | 2.0 mg/kg AD05222 | Single injection on day 1 |
| M | 2.0 mg/kg AD05221 | Single injection on day 1 |
| N | 2.0 mg/kg AD05223 | Single injection on day 1 |

Each of the APOC3 RNAi agents was conjugated to a targeting ligand that included three N-acetyl-galactosamines (i.e., a tridentate NAG ligand), having the modified sequences and NAG structures as set forth herein. (See Tables 4, 5, 6, and 7 for specific modifications and structure information for the APOC3 RNAi agents used in Example 6).

The injections were performed between the skin and muscle (i.e. subcutaneous injections) into the loose skin over the neck and shoulder area. Three (3) mice in each group were tested (n=3). Serum was collected from the mice, including on day −1 (pre-dose bleed with a four hour fast), and days 8, 15, 22, and 29. Mice were fasted for four hours prior to each collection. APOC3 expression levels were determined pursuant to the procedure set forth in Example 5, above. Data are shown in the following Table 12, with Average APOC3 reflecting the normalized average value of APOC3 protein expressed in serum:

TABLE 12

Average APOC3 Protein Normalized to Pre-Treatment and Vehicle Control (D5W) in APOC3 Transgenic Mice from Example 6.

| | Day 8 | | Day 15 | | Day 22 | | Day 29 | |
|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) |
| Group A (D5W) | 1.000 | 0.038 | 1.000 | 0.177 | 1.000 | 0.154 | 1.000 | 0.152 |
| Group B (4.0 mg/kg AD05172) | 0.074 | 0.018 | 0.067 | 0.018 | 0.083 | 0.008 | 0.105 | 0.019 |
| Group C (2.0 mg/kg AD05172) | 0.094 | 0.022 | 0.084 | 0.017 | 0.101 | 0.013 | 0.126 | 0.029 |
| Group D (1.0 mg/kg AD05172) | 0.113 | 0.039 | 0.115 | 0.038 | 0.150 | 0.050 | 0.212 | 0.095 |
| Group E (0.5 mg/kg AD05172) | 0.153 | 0.050 | 0.191 | 0.087 | 0.245 | 0.102 | 0.461 | 0.169 |
| Group F (1.0 mg/kg AD05215) | 0.114 | 0.003 | 0.124 | 0.016 | 0.173 | 0.037 | 0.550 | 0.119 |
| Group G (1.0 mg/kg AD05216) | 0.148 | 0.042 | 0.136 | 0.016 | 0.185 | 0.031 | 0.342 | 0.034 |
| Group H (1.0 mg/kg AD05217) | 0.161 | 0.020 | 0.179 | 0.025 | 0.241 | 0.048 | 0.464 | 0.306 |
| Group I (1.0 mg/kg AD05218) | 0.168 | 0.064 | 0.210 | 0.127 | 0.517 | 0.248 | 0.779 | 0.418 |
| Group J (1.0 mg/kg AD05171) | 0.125 | 0.039 | 0.126 | 0.043 | 0.165 | 0.050 | 0.302 | 0.117 |
| Group K (2.0 mg/kg AD05219) | 0.091 | 0.044 | 0.070 | 0.018 | 0.084 | 0.025 | 0.095 | 0.034 |
| Group L (2.0 mg/kg AD05222) | 0.130 | 0.054 | 0.230 | 0.114 | 0.265 | 0.147 | 0.484 | 0.047 |
| Group M (2.0 mg/kg AD05221) | 0.131 | 0.026 | 0.148 | 0.041 | 0.289 | 0.126 | 0.410 | 0.098 |
| Group N (2.0 mg/kg AD05223) | 0.082 | 0.047 | 0.062 | 0.019 | 0.073 | 0.021 | 0.080 | 0.022 |

Each of the APOC3 RNAi agents in each of the dosing groups (i.e., Groups B through M) showed a reduction in APOC3 as compared to the control (Group A) across the measured time points. For example, after a single 2.0 mg/kg dose on day 1, APOC3 RNAi agent AD05223 showed an approximately 94% reduction (0.062) at day 15.

Example 7. In Vivo Testing of APOC3 RNAi Agents in APOC3 Transgenic Mice

The APOC3 Transgenic Mouse Model described in Example 5, above, was used. At day 1, each mouse was given a single subcutaneous administration of 200 µl of the respective RNAi agent dissolved in D5W (dextrose in 5% water) or control (D5W) according to the dosing groups shown in the following Table 13.

TABLE 13

Dosing Groups of APOC3 Transgenic Mice of Example 7.

| Group | RNAi Agent and Dose | Dosing Regimen |
|---|---|---|
| 1 | D5W (no RNAi agent) | Single injection on day 1 |
| 2 | 1.0 mg/kg AD05172 | Single injection on day 1 |
| 3 | 1.0 mg/kg AD05255 | Single injection on day 1 |
| 4 | 1.0 mg/kg AD05169 | Single injection on day 1 |
| 5 | 1.0 mg/kg AD05249 | Single injection on day 1 |
| 6 | 1.0 mg/kg AD05250 | Single injection on day 1 |
| 7 | 1.0 mg/kg AD05251 | Single injection on day 1 |

TABLE 13-continued

Dosing Groups of APOC3 Transgenic Mice of Example 7.

| Group | RNAi Agent and Dose | Dosing Regimen |
|---|---|---|
| 8 | 1.0 mg/kg AD05252 | Single injection on day 1 |
| 9 | 1.0 mg/kg AD05253 | Single injection on day 1 |
| 10 | 1.0 mg/kg AD05254 | Single injection on day 1 |
| 11 | 1.0 mg/kg AD05220 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 4, 5, 6, and 7 for specific modifications and structure information related to the APOC3 RNAi agents).

The injections were performed between the skin and muscle (i.e. subcutaneous injections) into the loose skin over the neck and shoulder area. Three (3) mice in each group were tested (n=3). Serum was collected from the mice, including on day −1 (pre-dose bleed with a four hour fast), and days 8, 15, 22, and 29. Mice were fasted for four hours prior to each collection. APOC3 expression levels were determined pursuant to the procedure set forth in Example 5, above. Data from day 8 of the experiment are shown in the following Table 14, with Average APOC3 reflecting the normalized average value of APOC3 protein expressed in serum:

TABLE 14

Average APOC3 Protein Normalized to Pre-Treatment and Vehicle Control (D5W) in APOC3 Transgenic Mice from Example 7.

| | Day 8 | | Day 15 | | Day 22 | | Day 29 | |
|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) |
| Group 1 (D5W) | 1.000 | 0.092 | 1.000 | 0.096 | 1.000 | 0.089 | 1.000 | 0.103 |
| Group 2 (1.0 mg/kg AD05172) | 0.125 | 0.033 | 0.133 | 0.040 | 0.175 | 0.050 | 0.198 | 0.061 |
| Group 3 (1.0 mg/kg AD05255) | N/A* | N/A* | 0.279 | 0.394 | 0.969 | 0.050 | 1.103 | 0.216 |
| Group 4 (1.0 mg/kg AD05169) | 0.179 | 0.056 | 0.185 | 0.067 | 0.206 | 0.058 | 0.245 | 0.084 |
| Group 5 (1.0 mg/kg AD05249) | 0.212 | 0.045 | 0.263 | 0.055 | 0.460 | 0.083 | 0.863 | 0.586 |
| Group 6 (1.0 mg/kg AD05250) | 0.167 | 0.070 | 0.146 | 0.048 | 0.169 | 0.062 | 0.203 | 0.051 |
| Group 7 (1.0 mg/kg AD05251) | 0.140 | 0.071 | 0.121 | 0.077 | 0.170 | 0.094 | 0.181 | 0.103 |
| Group 8 (1.0 mg/kg AD05252) | 0.143 | 0.045 | 0.167 | 0.050 | 0.184 | 0.048 | 0.296 | 0.088 |

TABLE 14-continued

Average APOC3 Protein Normalized to Pre-Treatment and Vehicle Control (D5W) in APOC3 Transgenic Mice from Example 7.

| Group ID | Day 8 | | Day 15 | | Day 22 | | Day 29 | |
|---|---|---|---|---|---|---|---|---|
| | Avg APOC3 | Std Dev (+/−) | Avg APOC3 | Std Dev (+/−) | Avg APOC3 | Std Dev (+/−) | Avg APOC3 | Std Dev (+/−) |
| Group 9 (1.0 mg/kg AD05253) | 0.192 | 0.068 | 0.202 | 0.063 | 0.238 | 0.096 | 0.473 | 0.220 |
| Group 10 (1.0 mg/kg AD05254) | 0.184 | 0.075 | 0.225 | 0.075 | 0.296 | 0.124 | 0.294 | 0.137 |
| Group 11 (1.0 mg/kg AD05220) | 0.089 | 0.012 | 0.109 | 0.014 | 0.107 | 0.018 | 0.118 | 0.027 |

*samples for Group 3, Day 8 were lost due to equipment failure

Each of the APOC3 RNAi agents in each of the dosing groups (i.e., Groups 2 through 11) showed a reduction in APOC3 protein levels as compared to the control (Group 1) at days 8 and 15. In particular, APOC3 RNAi agents AD05251 and AD05169 (each having an antisense strand sequence designed to target position 438 of an APOC3 gene (i.e., SEQ ID NO:1), as well as APOC3 RNA agent AD05220 (having an antisense strand sequence designed to target position 506 of an APOC3 gene), showed particularly potent inhibitory effect. (See, e.g., Groups 4, 7, and 11 in Table 14, above).

Example 8. In Vivo Testing of APOC3 RNAi Agents in APOC3 Transgenic Mice

The APOC3 Transgenic Mouse Model described in Example 5, above, was used. At day 1, each mouse was given a single subcutaneous administration of 200 µl of the respective RNAi agent dissolved in D5W (dextrose in 5% water) or control (D5W) according to the dosing groups shown in the following Table 13.

TABLE 15

Dosing groups of Example 8.

| Group | RNAi Agent and Dose | Dosing Regimen |
|---|---|---|
| 1 | D5W (no RNAi agent) | Single injection on day 1 |
| 2 | 0.5 mg/kg AD05540 | Single injection on day 1 |
| 3 | 0.5 mg/kg AD05283 | Single injection on day 1 |
| 4 | 0.5 mg/kg AD05705 | Single injection on day 1 |
| 5 | 0.5 mg/kg AD05706 | Single injection on day 1 |
| 6 | 0.5 mg/kg AD05707 | Single injection on day 1 |
| 7 | 0.5 mg/kg AD05708 | Single injection on day 1 |
| 8 | 0.5 mg/kg AD05709 | Single injection on day 1 |
| 9 | 0.5 mg/kg AD05251 | Single injection on day 1 |
| 10 | 0.5 mg/kg AD05169 | Single injection on day 1 |
| 11 | 0.5 mg/kg AD05710 | Single injection on day 1 |
| 12 | 0.5 mg/kg AD05711 | Single injection on day 1 |
| 13 | 0.5 mg/kg AD05712 | Single injection on day 1 |
| 14 | 0.5 mg/kg AD05713 | Single injection on day 1 |
| 15 | 0.5 mg/kg AD05220 | Single injection on day 1 |
| 16 | 0.5 mg/kg AD05714 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 4, 5, 6, and 7 for specific modifications and structure information related to the APOC3 RNAi agents).

The injections were performed between the skin and muscle (i.e. subcutaneous injections) into the loose skin over the neck and shoulder area. Three (3) mice in each Group were tested (n=3), except for Group 1 (D5W vehicle) where four (4) mice were tested (n=4). Serum was collected on day −1 (pre-dose bleed with a 4 hour fast), and days 8, and 15, 22, and 29. Mice were fasted for four hours prior to each collection. APOC3 expression levels were determined pursuant to the procedure set forth in Example 5, above. Triglycerides, high-density lipoprotein (HDL), low-density lipoprotein (LDL), and total cholesterol in serum were also measured on a Cobas® Integra 400 (Roche Diagnostics), according to the manufacturer's recommendations.

The APOC3 protein levels, triglyceride levels, HDL levels, and total cholesterol levels for each animal were normalized. For normalization, the level of APOC3 protein, triglyceride, HDL, LDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the vehicle control group by dividing the "normalized to pre-treatment" ratio for an individual animal by the mean "normalized to pretreatment" ratio of all mice in the vehicle control group. This resulted in expression for each time point normalized to that in the control group. Data from the experiment are shown in the following Tables 16 through 20:

TABLE 16

Average APOC3 Protein Normalized to Pre-Treatment and Vehicle Control (D5W) from Example 8.

| Group ID | Day 8 | | Day 15 | | Day 22 | | Day 29 | |
|---|---|---|---|---|---|---|---|---|
| | Avg APOC3 | Std Dev (+/−) | Avg APOC3 | Std Dev (+/−) | Avg APOC3 | Std Dev (+/−) | Avg APOC3 | Std Dev (+/−) |
| Group 1 (D5W) | 1.000 | 0.104 | 1.000 | 0.297 | 1.000 | 0.343 | 1.000 | 0.354 |
| Group 2 (0.5 mg/kg AD05540) | 0.196 | 0.020 | 0.203 | 0.044 | 0.254 | 0.079 | 0.370 | 0.128 |
| Group 3 (0.5 mg/kg AD05283) | 0.178 | 0.077 | 0.195 | 0.080 | 0.282 | 0.070 | 0.331 | 0.038 |

TABLE 16-continued

Average APOC3 Protein Normalized to Pre-Treatment and Vehicle Control (D5W) from Example 8.

| | Day 8 | | Day 15 | | Day 22 | | Day 29 | |
|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) |
| Group 4 (0.5 mg/kg AD05705) | 0.146 | 0.053 | 0.150 | 0.050 | 0.239 | 0.080 | 0.330 | 0.111 |
| Group 5 (0.5 mg/kg AD05706) | 0.153 | 0.067 | 0.156 | 0.076 | 0.206 | 0.068 | 0.309 | 0.065 |
| Group 6 (0.5 mg/kg AD05707) | 0.102 | 0.030 | 0.158 | 0.023 | 0.227 | 0.035 | 0.441 | 0.160 |
| Group 7 (0.5 mg/kg AD05708) | 0.203 | 0.091 | 0.211 | 0.079 | 0.264 | 0.098 | 0.504 | 0.237 |
| Group 8 (0.5 mg/kg AD05709) | 0.213 | 0.086 | 0.190 | 0.078 | 0.299 | 0.143 | 0.467 | 0.250 |
| Group 9 (0.5 mg/kg AD05251) | 0.170 | 0.062 | 0.142 | 0.062 | 0.138 | 0.073 | 0.184 | 0.061 |
| Group 10 (0.5 mg/kg AD05169) | 0.290 | 0.131 | 0.320 | 0.054 | 0.309 | 0.039 | 0.433 | 0.060 |
| Group 11 (0.5 mg/kg AD05710) | 0.379 | 0.024 | 0.481 | 0.146 | 0.696 | 0.116 | 0.790 | 0.171 |
| Group 12 (0.5 mg/kg AD05711) | 0.331 | 0.028 | 0.325 | 0.036 | 0.334 | 0.037 | 0.545 | 0.238 |
| Group 13 (0.5 mg/kg AD05712) | 0.208 | 0.058 | 0.223 | 0.130 | 0.247 | 0.132 | 0.419 | 0.227 |
| Group 14 (0.5 mg/kg AD05713) | 0.216 | 0.092 | 0.305 | 0.131 | 0.453 | 0.070 | 0.646 | 0.053 |
| Group 15 (0.5 mg/kg AD05220) | 0.232 | 0.104 | 0.125 | 0.071 | 0.205 | 0.129 | 0.333 | 0.192 |
| Group 16 (0.5 mg/kg AD05714) | 0.338 | 0.025 | 0.259 | 0.069 | 0.422 | 0.012 | 0.550 | 0.092 |

TABLE 17

Average Triglycerides Normalized to Pre-Treatment and Vehicle Control (D5W) from Example 8.

| | Day 8 | | Day 15 | | Day 22 | | Day 29 | |
|---|---|---|---|---|---|---|---|---|
| Group ID | Avg TG | Std Dev (+/−) | Avg TG | Std Dev (+/−) | Avg TG | Std Dev (+/−) | Avg TG | Std Dev (+/−) |
| Group 1 (D5W) | 1.000 | 0.279 | 1.000 | 0.454 | 1.000 | 0.423 | 1.000 | 0.440 |
| Group 2 (0.5 mg/kg AD05540) | 0.232 | 0.041 | 0.218 | 0.072 | 0.264 | 0.111 | 0.370 | 0.192 |
| Group 3 (0.5 mg/kg AD05283) | 0.222 | 0.154 | 0.225 | 0.153 | 0.319 | 0.188 | 0.358 | 0.117 |
| Group 4 (0.5 mg/kg AD05705) | 0.141 | 0.036 | 0.123 | 0.033 | 0.237 | 0.088 | 0.338 | 0.098 |
| Group 5 (0.5 mg/kg AD05706) | 0.154 | 0.073 | 0.145 | 0.093 | 0.218 | 0.124 | 0.316 | 0.121 |
| Group 6 (0.5 mg/kg AD05707) | 0.109 | 0.049 | 0.156 | 0.069 | 0.184 | 0.030 | 0.433 | 0.267 |
| Group 7 (0.5 mg/kg AD05708) | 0.279 | 0.154 | 0.259 | 0.139 | 0.229 | 0.118 | 0.674 | 0.426 |
| Group 8 (0.5 mg/kg AD05709) | 0.283 | 0.155 | 0.221 | 0.134 | 0.274 | 0.154 | 0.606 | 0.393 |
| Group 9 (0.5 mg/kg AD05251) | 0.340 | 0.248 | 0.322 | 0.232 | 0.294 | 0.203 | 0.372 | 0.262 |
| Group 10 (0.5 mg/kg AD05169) | 0.274 | 0.202 | 0.306 | 0.078 | 0.276 | 0.062 | 0.341 | 0.118 |
| Group 11 (0.5 mg/kg AD05710) | 0.360 | 0.087 | 0.409 | 0.197 | 0.700 | 0.155 | 0.707 | 0.276 |
| Group 12 (0.5 mg/kg AD05711) | 0.268 | 0.096 | 0.288 | 0.061 | 0.293 | 0.054 | 0.488 | 0.248 |
| Group 13 (0.5 mg/kg AD05712) | 0.170 | 0.068 | 0.171 | 0.100 | 0.213 | 0.127 | 0.448 | 0.264 |
| Group 14 (0.5 mg/kg AD05713) | 0.183 | 0.088 | 0.262 | 0.148 | 0.399 | 0.083 | 0.581 | 0.135 |
| Group 15 (0.5 mg/kg AD05220) | 0.208 | 0.121 | 0.081 | 0.048 | 0.280 | 0.135 | 0.351 | 0.263 |
| Group 16 (0.5 mg/kg AD05714) | 0.319 | 0.082 | 0.242 | 0.101 | 0.461 | 0.059 | 0.596 | 0.150 |

TABLE 18

Average Total Cholesterol Normalized to Pre-Treatment and Vehicle Control (D5W) from Example 8.

| | Day 8 | | Day 15 | | Day 22 | | Day 29 | |
|---|---|---|---|---|---|---|---|---|
| Group ID | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.063 | 1.000 | 0.370 | 1.000 | 0.386 | 1.000 | 0.335 |
| Group 2 (0.5 mg/kg AD05540) | 0.414 | 0.103 | 0.464 | 0.144 | 0.483 | 0.179 | 0.583 | 0.214 |
| Group 3 (0.5 mg/kg AD05283) | 0.488 | 0.215 | 0.498 | 0.203 | 0.573 | 0.197 | 0.597 | 0.155 |
| Group 4 (0.5 mg/kg AD05705) | 0.377 | 0.230 | 0.359 | 0.205 | 0.401 | 0.198 | 0.429 | 0.199 |
| Group 5 (0.5 mg/kg AD05706) | 0.342 | 0.108 | 0.357 | 0.099 | 0.360 | 0.098 | 0.437 | 0.091 |
| Group 6 (0.5 mg/kg AD05707) | 0.271 | 0.196 | 0.294 | 0.176 | 0.322 | 0.176 | 0.441 | 0.235 |
| Group 7 (0.5 mg/kg AD05708) | 0.435 | 0.203 | 0.457 | 0.203 | 0.523 | 0.230 | 0.629 | 0.290 |
| Group 8 (0.5 mg/kg AD05709) | 0.455 | 0.233 | 0.436 | 0.197 | 0.454 | 0.216 | 0.590 | 0.321 |
| Group 9 (0.5 mg/kg AD05251) | 0.504 | 0.313 | 0.554 | 0.345 | 0.533 | 0.327 | 0.636 | 0.398 |
| Group 10 (0.5 mg/kg AD05169) | 0.544 | 0.240 | 0.595 | 0.285 | 0.538 | 0.235 | 0.578 | 0.155 |
| Group 11 (0.5 mg/kg AD05710) | 0.686 | 0.138 | 0.810 | 0.240 | 0.916 | 0.185 | 0.987 | 0.242 |
| Group 12 (0.5 mg/kg AD05711) | 0.493 | 0.105 | 0.457 | 0.094 | 0.483 | 0.076 | 0.658 | 0.222 |
| Group 13 (0.5 mg/kg AD05712) | 0.414 | 0.214 | 0.440 | 0.258 | 0.416 | 0.227 | 0.556 | 0.322 |
| Group 14 (0.5 mg/kg AD05713) | 0.354 | 0.148 | 0.441 | 0.187 | 0.557 | 0.108 | 0.658 | 0.014 |
| Group 15 (0.5 mg/kg AD05220) | 0.393 | 0.227 | 0.418 | 0.273 | 0.427 | 0.288 | 0.526 | 0.271 |
| Group 16 (0.5 mg/kg AD05714) | 0.632 | 0.014 | 0.706 | 0.011 | 0.797 | 0.030 | 0.932 | 0.070 |

TABLE 19

Average HDL Normalized to Pre-Treatment and Vehicle Control (D5W) from Example 8.

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 1 (D5W) | 1.000 | 0.365 | 1.000 | 0.141 | 1.000 | 0.100 | 1.000 | 0.338 |
| Group 2 (0.5 mg/kg AD05540) | 1.489 | 0.197 | 1.676 | 0.305 | 2.040 | 0.388 | 1.629 | 0.375 |
| Group 3 (0.5 mg/kg AD05283) | 2.192 | 1.116 | 2.227 | 1.009 | 2.859 | 1.499 | 1.982 | 0.785 |
| Group 4 (0.5 mg/kg AD05705) | 1.558 | 0.433 | 1.531 | 0.260 | 1.772 | 0.334 | 0.953 | 0.316 |
| Group 5 (0.5 mg/kg AD05706) | 2.248 | 0.626 | 2.556 | 0.938 | 2.736 | 0.875 | 1.878 | 0.629 |
| Group 6 (0.5 mg/kg AD05707) | 1.179 | 0.038 | 1.221 | 0.162 | 1.352 | 0.204 | 1.100 | 0.266 |
| Group 7 (0.5 mg/kg AD05708) | 1.086 | 0.158 | 1.187 | 0.252 | 1.670 | 0.203 | 0.972 | 0.400 |
| Group 8 (0.5 mg/kg AD05709) | 1.251 | 0.187 | 1.308 | 0.280 | 1.519 | 0.299 | 1.000 | 0.346 |
| Group 9 (0.5 mg/kg AD05251) | 1.337 | 0.326 | 1.369 | 0.372 | 1.961 | 0.901 | 1.426 | 0.438 |
| Group 10 (0.5 mg/kg AD05169) | 1.239 | 0.023 | 1.050 | 0.436 | 1.180 | 0.633 | 1.242 | 0.416 |
| Group 11 (0.5 mg/kg AD05710) | 1.169 | 0.089 | 1.417 | 0.356 | 1.359 | 0.149 | 1.244 | 0.290 |
| Group 12 (0.5 mg/kg AD05711) | 1.666 | 0.481 | 1.360 | 0.314 | 1.607 | 0.627 | 1.486 | 0.824 |
| Group 13 (0.5 mg/kg AD05712) | 1.255 | 0.577 | 1.214 | 0.560 | 1.344 | 0.587 | 0.939 | 0.427 |
| Group 14 (0.5 mg/kg AD05713) | 1.324 | 0.264 | 1.347 | 0.402 | 1.519 | 0.673 | 1.047 | 0.507 |
| Group 15 (0.5 mg/kg AD05220) | 0.763 | 0.345 | 0.954 | 0.539 | 1.042 | 0.533 | 0.963 | 0.093 |
| Group 16 (0.5 mg/kg AD05714) | 0.960 | 0.145 | 1.099 | 0.151 | 1.382 | 0.108 | 1.124 | 0.022 |

TABLE 20

Average LDL Normalized to Pre-Treatment and Vehicle Control (D5W) from Example 8.

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) |
|---|---|---|---|---|---|---|---|---|
| Group 1 (D5W) | 1.000 | 0.314 | 1.000 | 0.350 | 1.000 | 0.448 | 1.000 | 0.268 |
| Group 2 (0.5 mg/kg AD05540) | 0.265 | 0.076 | 0.318 | 0.100 | 0.340 | 0.104 | 0.517 | 0.199 |
| Group 3 (0.5 mg/kg AD05283) | 0.404 | 0.201 | 0.426 | 0.209 | 0.560 | 0.292 | 0.596 | 0.166 |
| Group 4 (0.5 mg/kg AD05705) | 0.303 | 0.245 | 0.271 | 0.209 | 0.315 | 0.191 | 0.378 | 0.224 |
| Group 5 (0.5 mg/kg AD05706) | 0.226 | 0.101 | 0.272 | 0.056 | 0.266 | 0.052 | 0.367 | 0.067 |
| Group 6 (0.5 mg/kg AD05707) | 0.160 | 0.128 | 0.204 | 0.146 | 0.259 | 0.159 | 0.337 | 0.164 |
| Group 7 (0.5 mg/kg AD05708) | 0.251 | 0.130 | 0.281 | 0.100 | 0.459 | 0.214 | 0.445 | 0.137 |
| Group 8 (0.5 mg/kg AD05709) | 0.242 | 0.135 | 0.230 | 0.077 | 0.389 | 0.209 | 0.371 | 0.166 |
| Group 9 (0.5 mg/kg AD05251) | 0.467 | 0.338 | 0.542 | 0.351 | 0.688 | 0.478 | 0.836 | 0.547 |
| Group 10 (0.5 mg/kg AD05169) | 0.341 | 0.064 | 0.495 | 0.395 | 0.396 | 0.197 | 0.459 | 0.106 |
| Group 11 (0.5 mg/kg AD05710) | 0.742 | 0.257 | 0.997 | 0.398 | 0.944 | 0.357 | 1.228 | 0.474 |
| Group 12 (0.5 mg/kg AD05711) | 0.526 | 0.135 | 0.401 | 0.116 | 0.737 | 0.388 | 0.919 | 0.367 |
| Group 13 (0.5 mg/kg AD05712) | 0.373 | 0.156 | 0.423 | 0.182 | 0.440 | 0.193 | 0.477 | 0.294 |
| Group 14 (0.5 mg/kg AD05713) | 0.312 | 0.159 | 0.370 | 0.144 | 0.736 | 0.194 | 1.007 | 0.242 |
| Group 15 (0.5 mg/kg AD05220) | 0.369 | 0.164 | 0.337 | 0.204 | 0.401 | 0.278 | 0.465 | 0.191 |
| Group 16 (0.5 mg/kg AD05714) | 0.440 | 0.062 | 0.500 | 0.055 | 0.710 | 0.114 | 0.842 | 0.229 |

Each of the APOC3 RNAi agents in each of the dosing groups (i.e., Groups 2 through 16) showed a reduction in APOC3 protein levels, triglyceride levels, total cholesterol levels, and LDL levels as compared to the control (Group 1). For example, a single 0.5 mg/kg dose of APOC3 RNAi agent AD05251 (Group 7) showed at day 22 a reduction of approximately 86% of APOC3 protein levels (0.138), a reduction of approximately 70% in triglyceride levels (0.294), a reduction of approximately 47% of total cholesterol levels (0.533), and a reduction of approximately 31% in LDL levels (0.688). Further, as anticipated, on day 22 the administration of AD05251 showed an increase in HDL levels (see, e.g., Table 19 above).

Example 9. In Vivo Dose Response Testing of APOC3 RNAi Agents in APOC3 Transgenic Mice The APOC3 Transgenic Mouse Model described in Example 5, above, was used. At day 1, each mouse was given a single subcutaneous administration of 200 µl of the respective RNAi agent dissolved in D5W (dextrose in 5% water) or control (D5W) according to the dosing groups shown in the following Table 21:

TABLE 21

Dosing groups of Example 9.

| Group | RNAi Agent and Dose | Dosing Regimen |
|---|---|---|
| 1 | D5W (no RNAi agent) | Single injection on day 1 |
| 2 | 0.01 mg/kg AD05876 | Single injection on day 1 |
| 3 | 0.05 mg/kg AD05876 | Single injection on day 1 |
| 4 | 0.1 mg/kg AD05876 | Single injection on day 1 |
| 5 | 0.25 mg/kg AD05876 | Single injection on day 1 |
| 6 | 0.5 mg/kg AD05876 | Single injection on day 1 |
| 7 | 1.0 mg/kg AD05876 | Single injection on day 1 |
| 8 | 3.0 mg/kg AD05876 | Single injection on day 1 |
| 9 | 0.01 mg/kg AD05251 | Single injection on day 1 |
| 10 | 0.05 mg/kg AD05251 | Single injection on day 1 |
| 11 | 0.1 mg/kg AD05251 | Single injection on day 1 |
| 12 | 0.25 mg/kg AD05251 | Single injection on day 1 |
| 13 | 0.5 mg/kg AD05251 | Single injection on day 1 |
| 14 | 1.0 mg/kg AD05251 | Single injection on day 1 |
| 15 | 3.0 mg/kg AD05251 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the structure of (NAG37)s. (See Tables 4, 5, 6, and 7 for specific modifications and structure information related to the APOC3 RNAi agents).

The injections were performed between the skin and muscle (i.e. subcutaneous injections) into the loose skin over the neck and shoulder area. Four (4) mice in each Group were tested. Serum was collected on day −1 (pre-dose bleed with a 4 hour fast), and days 8, 15, 22, 29, and 36. Mice were fasted for four hours prior to each collection. APOC3 expression levels, triglycerides, high-density lipoprotein (HDL), low-density lipoprotein (LDL), and total cholesterol in serum were measured on a Cobas® Integra 400 (Roche Diagnostics), according to the manufacturer's recommendations.

The APOC3 protein levels, triglyceride levels, HDL levels, and total cholesterol levels for each animal were normalized. For normalization, the level of APOC3 protein, triglyceride, HDL, LDL, and total cholesterol, respectively, for each animal at a time point, was divided by the pre-treatment level of expression in that animal (in this case at day −1) to determine the ratio of expression "normalized to pre-dose." Data from the experiment are shown in the following Tables 22 through 26:

TABLE 22

Average APOC3 Protein Normalized to Pre-Dose from Example 9.

| | Day 8 | | Day 15 | | Day 22 | | Day 29 | | Day 36 | |
|---|---|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) | Avg APOC3 | Std Dev (+/−) |
| Group 1 (D5W) | 1.205 | 0.162 | 1.224 | 0.145 | 1.102 | 0.257 | 1.011 | 0.148 | 1.103 | 0.133 |
| Group 2 (0.01 mg/kg AD05876) | 0.859 | 0.255 | 0.970 | 0.231 | 1.050 | 0.101 | 1.001 | 0.091 | 0.990 | 0.121 |
| Group 3 (0.05 mg/kg AD05876) | 0.835 | 0.048 | 0.933 | 0.154 | 0.919 | 0.166 | 1.094 | 0.259 | 1.111 | 0.244 |
| Group 4 (0.1 mg/kg AD05876) | 0.472 | 0.053 | 0.630 | 0.047 | 0.742 | 0.100 | 0.798 | 0.117 | 0.937 | 0.064 |
| Group 5 (0.25 mg/kg AD05876) | 0.342 | 0.049 | 0.423 | 0.045 | 0.495 | 0.056 | 0.734 | 0.066 | 0.812 | 0.097 |
| Group 6 (0.5 mg/kg AD05876) | 0.188 | 0.030 | 0.211 | 0.045 | 0.289 | 0.029 | 0.386 | 0.047 | 0.504 | 0.050 |
| Group 7 (1.0 mg/kg AD05876) | 0.164 | 0.033 | 0.207 | 0.036 | 0.250 | 0.045 | 0.332 | 0.097 | 0.446 | 0.152 |
| Group 8 (3.0 mg/kg AD05876) | 0.086 | 0.015 | 0.110 | 0.024 | 0.128 | 0.037 | 0.141 | 0.023 | 0.157 | 0.031 |
| Group 9 (0.01 mg/kg AD05251) | 1.165 | 0.101 | 1.051 | 0.040 | 0.955 | 0.105 | 1.038 | 0.033 | 0.968 | 0.079 |
| Group 10 (0.05 mg/kg AD05251) | 0.675 | 0.051 | 0.694 | 0.056 | 0.692 | 0.046 | 0.836 | 0.139 | 0.921 | 0.087 |
| Group 11 (0.1 mg/kg AD05251) | 0.590 | 0.098 | 0.478 | 0.073 | 0.562 | 0.067 | 0.625 | 0.054 | 0.686 | 0.084 |
| Group 12 (0.25 mg/kg AD05251) | 0.273 | 0.067 | 0.295 | 0.039 | 0.354 | 0.055 | 0.479 | 0.137 | 0.580 | 0.071 |
| Group 13 (0.5 mg/kg AD05251) | 0.219 | 0.066 | 0.211 | 0.045 | 0.283 | 0.070 | 0.291 | 0.090 | 0.338 | 0.085 |
| Group 14 (1.0 mg/kg AD05251) | 0.157 | 0.026 | 0.143 | 0.034 | 0.230 | 0.067 | 0.280 | 0.093 | 0.310 | 0.072 |
| Group 15 (3.0 mg/kg AD05251) | 0.135 | 0.033 | 0.131 | 0.022 | 0.164 | 0.036 | 0.157 | 0.048 | 0.191 | 0.056 |

TABLE 23

Average Triglycerides Normalized to Pre-Dose from Example 9.

| | Day 8 | | Day 15 | | Day 22 | | Day 29 | | Day 36 | |
|---|---|---|---|---|---|---|---|---|---|---|
| Group ID | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 1(D5W) | 1.441 | 0.335 | 1.723 | 0.177 | 1.253 | 0.377 | 1.151 | 0.301 | 1.304 | 0.221 |
| Group 2 (0.01 mg/kg AD05876) | 0.988 | 0.436 | 1.139 | 0.421 | 1.177 | 0.271 | 1.209 | 0.242 | 1.259 | 0.325 |
| Group 3 (0.05 mg/kg AD05876) | 1.146 | 0.303 | 1.321 | 0.459 | 0.964 | 0.355 | 1.428 | 0.613 | 1.275 | 0.456 |
| Group 4 (0.1 mg/kg AD05876) | 0.671 | 0.176 | 0.700 | 0.131 | 0.912 | 0.204 | 0.918 | 0.265 | 1.073 | 0.175 |
| Group 5 (0.25 mg/kg AD05876) | 0.391 | 0.081 | 0.581 | 0.174 | 0.608 | 0.141 | 0.960 | 0.205 | 0.989 | 0.196 |
| Group 6 (0.5 mg/kg AD05876) | 0.216 | 0.060 | 0.202 | 0.054 | 0.306 | 0.092 | 0.465 | 0.147 | 0.493 | 0.066 |
| Group 7 (1.0 mg/kg AD05876) | 0.227 | 0.099 | 0.326 | 0.147 | 0.366 | 0.096 | 0.427 | 0.150 | 0.600 | 0.261 |
| Group 8 (3.0 mg/kg AD05876) | 0.090 | 0.024 | 0.166 | 0.037 | 0.165 | 0.044 | 0.184 | 0.048 | 0.222 | 0.037 |
| Group 9 (0.01 mg/kg AD05251) | 1.357 | 0.266 | 1.197 | 0.099 | 1.024 | 0.129 | 1.197 | 0.101 | 1.118 | 0.215 |
| Group 10 (0.05 mg/kg AD05251) | 0.784 | 0.137 | 0.950 | 0.278 | 0.725 | 0.137 | 1.013 | 0.270 | 1.108 | 0.257 |
| Group 11 (0.1 mg/kg AD05251) | 0.634 | 0.182 | 0.583 | 0.110 | 0.587 | 0.160 | 0.641 | 0.123 | 0.702 | 0.172 |
| Group 12 (0.25 mg/kg AD05251) | 0.330 | 0.119 | 0.397 | 0.076 | 0.393 | 0.042 | 0.583 | 0.236 | 0.614 | 0.057 |
| Group 13 (0.5 mg/kg AD05251) | 0.250 | 0.084 | 0.197 | 0.040 | 0.283 | 0.034 | 0.309 | 0.102 | 0.355 | 0.118 |
| Group 14 (1.0 mg/kg AD05251) | 0.213 | 0.054 | 0.171 | 0.073 | 0.273 | 0.059 | 0.384 | 0.135 | 0.347 | 0.079 |
| Group 15 (3.0 mg/kg AD05251) | 0.210 | 0.067 | 0.172 | 0.024 | 0.235 | 0.089 | 0.213 | 0.032 | 0.263 | 0.106 |

TABLE 24

Average Total Cholesterol Normalized to Pre-Dose from Example 9.

| | Day 8 | | Day 15 | | Day 22 | | Day 29 | | Day 36 | |
|---|---|---|---|---|---|---|---|---|---|---|
| Group ID | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.177 | 0.079 | 1.261 | 0.169 | 1.161 | 0.297 | 1.049 | 0.188 | 1.151 | 0.167 |
| Group 2 (0.01 mg/kg AD05876) | 1.020 | 0.231 | 1.099 | 0.186 | 1.193 | 0.147 | 1.132 | 0.087 | 1.141 | 0.157 |
| Group 3 (0.05 mg/kg AD05876) | 0.975 | 0.105 | 1.003 | 0.193 | 1.010 | 0.192 | 1.169 | 0.296 | 1.160 | 0.265 |
| Group 4 (0.1 mg/kg AD05876) | 0.694 | 0.115 | 0.749 | 0.101 | 0.851 | 0.122 | 0.876 | 0.155 | 1.005 | 0.063 |
| Group 5 (0.25 mg/kg AD05876) | 0.670 | 0.188 | 0.744 | 0.229 | 0.792 | 0.190 | 0.953 | 0.116 | 0.928 | 0.157 |
| Group 6 (0.5 mg/kg AD05876) | 0.556 | 0.146 | 0.600 | 0.178 | 0.628 | 0.127 | 0.672 | 0.126 | 0.768 | 0.107 |
| Group 7 (1.0 mg/kg AD05876) | 0.596 | 0.081 | 0.634 | 0.145 | 0.664 | 0.134 | 0.710 | 0.101 | 0.760 | 0.083 |
| Group 8 (3.0 mg/kg AD05876) | 0.547 | 0.057 | 0.556 | 0.104 | 0.589 | 0.130 | 0.564 | 0.098 | 0.572 | 0.101 |
| Group 9 (0.01 mg/kg AD05251) | 1.236 | 0.107 | 1.142 | 0.063 | 1.023 | 0.139 | 1.099 | 0.107 | 1.106 | 0.115 |
| Group 10 (0.05 mg/kg AD05251) | 0.785 | 0.083 | 0.813 | 0.107 | 0.784 | 0.106 | 0.944 | 0.147 | 0.995 | 0.135 |
| Group 11 (0.1 mg/kg AD05251) | 0.721 | 0.080 | 0.691 | 0.068 | 0.706 | 0.065 | 0.737 | 0.028 | 0.814 | 0.060 |
| Group 12 (0.25 mg/kg AD05251) | 0.562 | 0.115 | 0.617 | 0.104 | 0.632 | 0.081 | 0.705 | 0.076 | 0.777 | 0.044 |
| Group 13 (0.5 mg/kg AD05251) | 0.479 | 0.055 | 0.492 | 0.037 | 0.540 | 0.073 | 0.543 | 0.098 | 0.564 | 0.095 |
| Group 14 (1.0 mg/kg AD05251) | 0.634 | 0.137 | 0.687 | 0.163 | 0.634 | 0.172 | 0.669 | 0.163 | 0.700 | 0.174 |
| Group 15 (3.0 mg/kg AD05251) | 0.602 | 0.106 | 0.611 | 0.101 | 0.632 | 0.121 | 0.627 | 0.167 | 0.594 | 0.121 |

TABLE 25

Average HDL Normalized to Pre-Dose from Example 9.

| | Day 8 | | Day 15 | | Day 22 | | Day 29 | | Day 36 | |
|---|---|---|---|---|---|---|---|---|---|---|
| Group ID | Avg HDL | Std Dev (+/−) | Avg HDL | Std Dev (+/−) | Avg HDL | Std Dev (+/−) | Avg HDL | Std Dev (+/−) | Avg HDL | Std Dev (+/−) |
| Group 1 (D5W) | 0.883 | 0.115 | 0.855 | 0.013 | 0.919 | 0.081 | 1.070 | 0.128 | 0.905 | 0.109 |
| Group 2 (0.01 mg/kg AD05876) | 1.029 | 0.087 | 1.086 | 0.209 | 0.987 | 0.191 | 1.096 | 0.088 | 0.969 | 0.100 |
| Group 3 (0.05 mg/kg AD05876) | 0.786 | 0.184 | 0.968 | 0.121 | 1.052 | 0.130 | 0.951 | 0.252 | 0.886 | 0.221 |
| Group 4 (0.1 mg/kg AD05876) | 1.129 | 0.133 | 1.147 | 0.098 | 1.022 | 0.213 | 1.109 | 0.106 | 0.911 | 0.177 |
| Group 5 (0.25 mg/kg AD05876) | 1.280 | 0.238 | 1.336 | 0.253 | 1.244 | 0.172 | 1.083 | 0.083 | 0.992 | 0.082 |
| Group 6 (0.5 mg/kg AD05876) | 1.516 | 0.241 | 1.574 | 0.182 | 1.368 | 0.185 | 1.327 | 0.172 | 1.350 | 0.237 |
| Group 7 (1.0 mg/kg AD05876) | 1.361 | 0.243 | 1.327 | 0.318 | 1.298 | 0.173 | 1.330 | 0.208 | 1.206 | 0.262 |
| Group 8 (3.0 mg/kg AD05876) | 1.620 | 0.459 | 1.452 | 0.347 | 1.542 | 0.371 | 1.477 | 0.227 | 1.417 | 0.322 |
| Group 9 (0.01 mg/kg AD05251) | 0.833 | 0.143 | 0.808 | 0.133 | 0.856 | 0.154 | 0.936 | 0.127 | 1.041 | 0.193 |
| Group 10 (0.05 mg/kg AD05251) | 1.036 | 0.111 | 0.913 | 0.017 | 1.027 | 0.030 | 0.974 | 0.168 | 0.976 | 0.142 |
| Group 11 (0.1 mg/kg AD05251) | 1.075 | 0.087 | 1.087 | 0.065 | 1.033 | 0.116 | 1.021 | 0.114 | 1.074 | 0.074 |
| Group 12 (0.25 mg/kg AD05251) | 1.118 | 0.094 | 1.175 | 0.062 | 1.100 | 0.051 | 1.142 | 0.146 | 1.152 | 0.113 |
| Group 13 (0.5 mg/kg AD05251) | 1.344 | 0.178 | 1.455 | 0.124 | 1.329 | 0.190 | 1.347 | 0.156 | 1.279 | 0.188 |
| Group 14 (1.0 mg/kg AD05251) | 1.338 | 0.143 | 1.501 | 0.175 | 1.179 | 0.221 | 1.218 | 0.247 | 1.282 | 0.179 |
| Group 15 (3.0 mg/kg AD05251) | 1.332 | 0.150 | 1.426 | 0.264 | 1.348 | 0.133 | 1.431 | 0.339 | 1.265 | 0.184 |

TABLE 26

Average LDL Normalized to Pre-Dose from Example 9.

| | Day 8 | | Day 15 | | Day 22 | | Day 29 | | Day 36 | |
|---|---|---|---|---|---|---|---|---|---|---|
| Group ID | Avg LDL | Std Dev (+/−) | Avg LDL | Std Dev (+/−) | Avg LDL | Std Dev (+/−) | Avg LDL | Std Dev (+/−) | Avg LDL | Std Dev (+/−) |
| Group 1 (D5W) | 1.060 | 0.159 | 0.990 | 0.210 | 1.078 | 0.325 | 0.989 | 0.365 | 0.881 | 0.135 |
| Group 2 (0.01 mg/kg AD05876) | 1.031 | 0.068 | 1.071 | 0.181 | 1.077 | 0.082 | 0.992 | 0.154 | 0.958 | 0.081 |
| Group 3 (0.05 mg/kg AD05876) | 0.799 | 0.179 | 0.682 | 0.223 | 0.859 | 0.177 | 0.959 | 0.289 | 0.954 | 0.176 |
| Group 4 (0.1 mg/kg AD05876) | 0.535 | 0.019 | 0.593 | 0.071 | 0.636 | 0.145 | 0.692 | 0.100 | 0.840 | 0.089 |
| Group 5 (0.25 mg/kg AD05876) | 0.645 | 0.153 | 0.570 | 0.152 | 0.660 | 0.158 | 0.783 | 0.083 | 0.676 | 0.096 |
| Group 6 (0.5 mg/kg AD05876) | 0.624 | 0.238 | 0.645 | 0.192 | 0.620 | 0.067 | 0.581 | 0.086 | 0.893 | 0.088 |
| Group 7 (1.0 mg/kg AD05876) | 0.481 | 0.124 | 0.464 | 0.201 | 0.396 | 0.127 | 0.524 | 0.181 | 0.588 | 0.174 |
| Group 8 (3.0 mg/kg AD05876) | 0.455 | 0.161 | 0.465 | 0.154 | 0.428 | 0.159 | 0.359 | 0.099 | 0.382 | 0.140 |
| Group 9 (0.01 mg/kg AD05251) | 1.260 | 0.097 | 1.237 | 0.202 | 1.091 | 0.244 | 1.162 | 0.209 | 1.356 | 0.249 |
| Group 10 (0.05 mg/kg AD05251) | 0.682 | 0.048 | 0.641 | 0.127 | 0.715 | 0.032 | 0.792 | 0.123 | 0.847 | 0.223 |
| Group 11 (0.1 mg/kg AD05251) | 0.717 | 0.293 | 0.635 | 0.146 | 0.693 | 0.260 | 0.679 | 0.234 | 0.845 | 0.128 |
| Group 12 (0.25 mg/kg AD05251) | 0.439 | 0.151 | 0.502 | 0.147 | 0.614 | 0.190 | 0.552 | 0.037 | 0.716 | 0.205 |
| Group 13 (0.5 mg/kg AD05251) | 0.413 | 0.086 | 0.474 | 0.048 | 0.508 | 0.149 | 0.542 | 0.209 | 0.514 | 0.162 |
| Group 14 (1.0 mg/kg AD05251) | 0.614 | 0.268 | 0.747 | 0.292 | 0.601 | 0.266 | 0.633 | 0.282 | 0.669 | 0.271 |
| Group 15 (3.0 mg/kg AD05251) | 0.488 | 0.162 | 0.469 | 0.099 | 0.498 | 0.176 | 0.445 | 0.230 | 0.405 | 0.142 |

Each of the APOC3 RNAi agents tested exhibited a dose response in the reduction of APOC3 protein levels, triglyceride levels, total cholesterol levels, and LDL levels.

Example 10. In Vivo Dose Response Testing of APOC3 RNAi Agents in APOC3 Transgenic Mice The APOC3 Transgenic Mouse Model described in Example 5, above, was used. At day 1, each mouse was given a single subcutaneous administration of 200 µl of the respective RNAi agent dissolved in D5W (dextrose in 5% water) or control vehicle (D5W) according to the dosing groups shown in the following Table 27:

TABLE 27

Dosing groups of Example 10.

| Group | RNAi Agent and Dose | Dosing Regimen |
|---|---|---|
| 1 | D5W (no RNAi agent) | Single injection on day 1 |
| 2 | 0.25 mg/kg AD05891 | Single injection on day 1 |
| 3 | 0.25 mg/kg AD05892 | Single injection on day 1 |
| 4 | 0.25 mg/kg AD05893 | Single injection on day 1 |
| 5 | 0.25 mg/kg AD05894 | Single injection on day 1 |
| 6 | 0.25 mg/kg AD05895 | Single injection on day 1 |
| 7 | 0.25 mg/kg AD05896 | Single injection on day 1 |
| 8 | 0.25 mg/kg AD05897 | Single injection on day 1 |
| 9 | 0.25 mg/kg AD05889 | Single injection on day 1 |
| 10 | 0.25 mg/kg AD05890 | Single injection on day 1 |
| 11 | 0.25 mg/kg AD05876 | Single injection on day 1 |
| 12 | 0.25 mg/kg AD05877 | Single injection on day 1 |
| 13 | 0.25 mg/kg AD05878 | Single injection on day 1 |
| 14 | 0.25 mg/kg AD05879 | Single injection on day 1 |
| 15 | 0.25 mg/kg AD05880 | Single injection on day 1 |
| 16 | 0.25 mg/kg AD05882 | Single injection on day 1 |
| 17 | 0.25 mg/kg AD05884 | Single injection on day 1 |
| 18 | 0.25 mg/kg AD05885 | Single injection on day 1 |
| 19 | 0.25 mg/kg AD05886 | Single injection on day 1 |
| 20 | 0.25 mg/kg AD05887 | Single injection on day 1 |
| 21 | 0.25 mg/kg AD05888 | Single injection on day 1 |
| 22 | 0.25 mg/kg AD05769 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 4, 5, 6, and 7 for specific modifications and structure information related to the APOC3 RNAi agents).

The APOC3 RNAi agents tested in Example 10 included nucleotide sequences that were designed to target different positions on the APOC3 gene (i.e., SEQ ID NO:1). More specifically, Groups 2-4 (i.e., APOC3 RNAi agents AD05891, AD05892, and AD05893) included antisense strand sequences designed to target position 248 of an APOC3 gene; Group 5 (i.e., APOC3 RNAi agent AD05894) included an antisense strand sequence designed to target position 263 of an APOC3 gene; Groups 6-7 (i.e., APOC3 RNAi agents AD05895 and AD05896) included antisense strand sequences designed to target position 422 of an APOC3 gene; Group 8 (i.e., APOC3 RNAi agent AD05897) included an antisense strand sequence designed to target position 246 of an APOC3 gene; Groups 9-10 (i.e., APOC3 RNAi agents AD05889 and AD05890) included antisense strand sequences designed to target position 168 of an APOC3 gene; and Groups 11-22 (i.e., APOC3 RNAi agents AD05876, AD05877, AD05878, AD05878, AD05880, AD05882, AD05884, AD05885, AD05886, AD05887, AD05888, and AD05769) included antisense strand sequences designed to target position 438 of an APOC3 gene.

The injections were performed between the skin and muscle (i.e. subcutaneous injections) into the loose skin over the neck and shoulder area. Three (3) mice in each Group were tested (n=3). Serum was collected on day −1 (pre-dose bleed with a 4 hour fast), and days 8, 15. For mice dosed with the certain RNAi agents that exhibited relatively high inhibitory activity and for the mice dosed with the vehicle control, additional serum samples were collected on days 22 and 29. Mice were fasted for four hours prior to each collection. APOC3 expression levels, triglycerides, high-density lipoprotein (HDL), low-density lipoprotein (LDL), and total cholesterol in serum were measured on a Cobas® Integra 400 (Roche Diagnostics), according to the manufacturer's recommendations.

The APOC3 protein levels, triglyceride levels, HDL levels, and total cholesterol levels for each animal were normalized. For normalization, the level of APOC3 protein, triglyceride, HDL, LDL, and total cholesterol, respectively, for each animal at a time point, was divided by the pre-treatment level of expression in that animal (in this case at day −1) to determine the ratio of expression "normalized to pre-dose." Data from the experiment are shown in the following Tables 28 through 32:

TABLE 28

Average APOC3 Protein Normalized to Pre-Dose from Example 10.

| | Day 8 | | Day 15 | | Day 22 | | Day 29 | |
|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) |
| Group 1 (D5W) | 1.130 | 0.131 | 0.892 | 0.155 | 1.182 | 0.272 | 1.126 | 0.174 |
| Group 2 (0.25 mg/kg AD05891) | 0.944 | 0.060 | 0.874 | 0.037 | N/A | N/A | N/A | N/A |
| Group 3 (0.25 mg/kg AD05892) | 0.831 | 0.101 | 0.840 | 0.116 | N/A | N/A | N/A | N/A |
| Group 4 (0.25 mg/kg AD05893) | 1.030 | 0.030 | 1.020 | 0.137 | N/A | N/A | N/A | N/A |
| Group 5 (0.25 mg/kg AD05894) | 0.835 | 0.136 | 0.774 | 0.134 | N/A | N/A | N/A | N/A |
| Group 6 (0.25 mg/kg AD05895) | 0.771 | 0.186 | 0.632 | 0.157 | N/A | N/A | N/A | N/A |
| Group 7 (0.25 mg/kg AD05896) | 0.912 | 0.109 | 0.836 | 0.218 | N/A | N/A | N/A | N/A |
| Group 8 (0.25 mg/kg AD05897) | 0.726 | 0.102 | 0.777 | 0.134 | N/A | N/A | N/A | N/A |
| Group 9 (0.25 mg/kg AD05889) | 1.059 | 0.187 | 0.987 | 0.123 | N/A | N/A | N/A | N/A |
| Group 10 (0.25 mg/kg AD05890) | 0.984 | 0.091 | 1.119 | 0.145 | N/A | N/A | N/A | N/A |
| Group 11 (0.25 mg/kg AD05876) | 0.222 | 0.021 | 0.258 | 0.034 | 0.361 | 0.027 | 0.523 | 0.126 |
| Group 12 (0.25 mg/kg AD05877) | 0.457 | 0.034 | 0.392 | 0.065 | 0.492 | 0.134 | N/A | N/A |
| Group 13 (0.25 mg/kg AD05878) | 0.366 | 0.115 | 0.406 | 0.134 | 0.567 | 0.232 | N/A | N/A |
| Group 14 (0.25 mg/kg AD05879) | 0.560 | 0.082 | 0.493 | 0.121 | 0.679 | 0.085 | N/A | N/A |
| Group 15 (0.25 mg/kg AD05880) | 0.572 | 0.205 | 0.652 | 0.274 | N/A | N/A | N/A | N/A |
| Group 16 (0.25 mg/kg AD05882) | 1.117 | 0.230 | 1.160 | 0.188 | N/A | N/A | N/A | N/A |

TABLE 28-continued

Average APOC3 Protein Normalized to Pre-Dose from Example 10.

| Group ID | Day 8 | | Day 15 | | Day 22 | | Day 29 | |
|---|---|---|---|---|---|---|---|---|
| | Avg APOC3 | Std Dev (+/−) | Avg APOC3 | Std Dev (+/−) | Avg APOC3 | Std Dev (+/−) | Avg APOC3 | Std Dev (+/−) |
| Group 17 (0.25 mg/kg AD05884) | 0.425 | 0.103 | 0.444 | 0.158 | 0.580 | 0.180 | N/A | N/A |
| Group 18 (0.25 mg/kg AD05885) | 0.629 | 0.024 | 0.782 | 0.109 | N/A | N/A | N/A | N/A |
| Group 19 (0.25 mg/kg AD05886) | 1.041 | 0.474 | 1.256 | 0.634 | N/A | N/A | N/A | N/A |
| Group 20 (0.25 mg/kg AD05887) | 0.390 | 0.106 | 0.608 | 0.159 | N/A | N/A | N/A | N/A |
| Group 21 (0.25 mg/kg AD05888) | 0.429 | 0.107 | 0.591 | 0.105 | N/A | N/A | N/A | N/A |
| Group 22 (0.25 mg/kg AD05769) | 0.229 | 0.039 | 0.346 | 0.078 | 0.325 | 0.061 | 0.407 | 0.017 |

TABLE 29

Average Triglycerides Normalized to Pre-Dose from Example 10.

| Group ID | Day 8 | | Day 15 | | Day 22 | | Day 29 | |
|---|---|---|---|---|---|---|---|---|
| | Avg TG | Std Dev (+/−) | Avg TG | Std Dev (+/−) | Avg TG | Std Dev (+/−) | Avg TG | Std Dev (+/−) |
| Group 1 (D5W) | 1.357 | 0.213 | 0.942 | 0.220 | 1.389 | 0.468 | 1.225 | 0.268 |
| Group 2 (0.25 mg/kg AD05891) | 1.123 | 0.127 | 0.908 | 0.057 | N/A | N/A | N/A | N/A |
| Group 3 (0.25 mg/kg AD05892) | 0.924 | 0.039 | 0.859 | 0.202 | N/A | N/A | N/A | N/A |
| Group 4 (0.25 mg/kg AD05893) | 1.262 | 0.056 | 1.168 | 0.189 | N/A | N/A | N/A | N/A |
| Group 5 (0.25 mg/kg AD05894) | 0.903 | 0.297 | 0.834 | 0.239 | N/A | N/A | N/A | N/A |
| Group 6 (0.25 mg/kg AD05895) | 0.728 | 0.300 | 0.632 | 0.207 | N/A | N/A | N/A | N/A |
| Group 7 (0.25 mg/kg AD05896) | 0.929 | 0.107 | 0.907 | 0.268 | N/A | N/A | N/A | N/A |
| Group 8 (0.25 mg/kg AD05897) | 0.836 | 0.178 | 0.936 | 0.212 | N/A | N/A | N/A | N/A |
| Group 9 (0.25 mg/kg AD05889) | 1.162 | 0.270 | 1.096 | 0.270 | N/A | N/A | N/A | N/A |
| Group 10 (0.25 mg/kg AD05890) | 0.992 | 0.341 | 1.486 | 0.505 | N/A | N/A | N/A | N/A |
| Group 11 (0.25 mg/kg AD05876) | 0.234 | 0.054 | 0.316 | 0.091 | 0.333 | 0.026 | 0.581 | 0.203 |
| Group 12 (0.25 mg/kg AD05877) | 0.496 | 0.096 | 0.530 | 0.175 | 0.653 | 0.215 | N/A | N/A |
| Group 13 (0.25 mg/kg AD05878) | 0.450 | 0.214 | 0.619 | 0.314 | 0.781 | 0.434 | N/A | N/A |
| Group 14 (0.25 mg/kg AD05879) | 0.664 | 0.033 | 0.664 | 0.072 | 0.905 | 0.030 | N/A | N/A |
| Group 15 (0.25 mg/kg AD05880) | 0.726 | 0.384 | 0.790 | 0.399 | N/A | N/A | N/A | N/A |
| Group 16 (0.25 mg/kg AD05882) | 1.289 | 0.436 | 1.695 | 0.408 | N/A | N/A | N/A | N/A |
| Group 17 (0.25 mg/kg AD05884) | 0.376 | 0.132 | 0.554 | 0.283 | 0.605 | 0.296 | N/A | N/A |
| Group 18 (0.25 mg/kg AD05885) | 0.620 | 0.064 | 0.998 | 0.219 | N/A | N/A | N/A | N/A |
| Group 19 (0.25 mg/kg AD05886) | 1.315 | 0.665 | 1.941 | 1.267 | N/A | N/A | N/A | N/A |
| Group 20 (0.25 mg/kg AD05887) | 0.445 | 0.193 | 0.867 | 0.335 | N/A | N/A | N/A | N/A |
| Group 21 (0.25 mg/kg AD05888) | 0.467 | 0.227 | 0.700 | 0.190 | N/A | N/A | N/A | N/A |
| Group 22 (0.25 mg/kg AD05769) | 0.204 | 0.033 | 0.377 | 0.068 | 0.373 | 0.097 | 0.370 | 0.071 |

TABLE 30

Average Total Cholesterol Normalized to Pre-Dose from Example 10.

| Group ID | Day 8 | | Day 15 | | Day 22 | | Day 29 | |
|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.186 | 0.199 | 0.761 | 0.107 | 1.131 | 0.325 | 1.203 | 0.267 |
| Group 2 (0.25 mg/kg AD05891) | 1.056 | 0.104 | 0.947 | 0.161 | N/A | N/A | N/A | N/A |
| Group 3 (0.25 mg/kg AD05892) | 0.860 | 0.111 | 0.856 | 0.142 | N/A | N/A | N/A | N/A |
| Group 4 (0.25 mg/kg AD05893) | 1.132 | 0.037 | 1.137 | 0.163 | N/A | N/A | N/A | N/A |
| Group 5 (0.25 mg/kg AD05894) | 0.776 | 0.145 | 0.795 | 0.144 | N/A | N/A | N/A | N/A |
| Group 6 (0.25 mg/kg AD05895) | 0.852 | 0.275 | 0.808 | 0.220 | N/A | N/A | N/A | N/A |
| Group 7 (0.25 mg/kg AD05896) | 0.995 | 0.080 | 0.943 | 0.114 | N/A | N/A | N/A | N/A |
| Group 8 (0.25 mg/kg AD05897) | 0.978 | 0.160 | 1.015 | 0.136 | N/A | N/A | N/A | N/A |
| Group 9 (0.25 mg/kg AD05889) | 1.094 | 0.205 | 1.018 | 0.166 | N/A | N/A | N/A | N/A |
| Group 10 (0.25 mg/kg AD05890) | 1.032 | 0.055 | 1.015 | 0.196 | N/A | N/A | N/A | N/A |
| Group 11 (0.25 mg/kg AD05876) | 0.573 | 0.180 | 0.565 | 0.117 | 0.657 | 0.107 | 0.782 | 0.052 |
| Group 12 (0.25 mg/kg AD05877) | 0.673 | 0.141 | 0.595 | 0.156 | 0.688 | 0.235 | N/A | N/A |
| Group 13 (0.25 mg/kg AD05878) | 0.598 | 0.231 | 0.609 | 0.227 | 0.689 | 0.293 | N/A | N/A |
| Group 14 (0.25 mg/kg AD05879) | 0.705 | 0.052 | 0.655 | 0.041 | 0.848 | 0.111 | N/A | N/A |
| Group 15 (0.25 mg/kg AD05880) | 0.596 | 0.230 | 0.635 | 0.235 | N/A | N/A | N/A | N/A |
| Group 16 (0.25 mg/kg AD05882) | 1.169 | 0.241 | 1.268 | 0.327 | N/A | N/A | N/A | N/A |
| Group 17 (0.25 mg/kg AD05884) | 0.597 | 0.290 | 0.574 | 0.254 | 0.668 | 0.284 | N/A | N/A |
| Group 18 (0.25 mg/kg AD05885) | 0.765 | 0.192 | 0.837 | 0.089 | N/A | N/A | N/A | N/A |
| Group 19 (0.25 mg/kg AD05886) | 1.043 | 0.285 | 1.336 | 0.497 | N/A | N/A | N/A | N/A |

TABLE 30-continued

Average Total Cholesterol Normalized to Pre-Dose from Example 10.

| Group ID | Day 8 Avg Total Chol | Day 8 Std Dev (+/−) | Day 15 Avg Total Chol | Day 15 Std Dev (+/−) | Day 22 Avg Total Chol | Day 22 Std Dev (+/−) | Day 29 Avg Total Chol | Day 29 Std Dev (+/−) |
|---|---|---|---|---|---|---|---|---|
| Group 20 (0.25 mg/kg AD05887) | 0.679 | 0.087 | 0.843 | 0.174 | N/A | N/A | N/A | N/A |
| Group 21 (0.25 mg/kg AD05888) | 0.674 | 0.292 | 0.807 | 0.302 | N/A | N/A | N/A | N/A |
| Group 22 (0.25 mg/kg AD05769) | 0.479 | 0.094 | 0.551 | 0.122 | 0.537 | 0.075 | 0.583 | 0.125 |

TABLE 31

Average HDL Normalized to Pre-Dose from Example 10.

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 1 (D5W) | 0.837 | 0.062 | 0.761 | 0.079 | 0.697 | 0.019 | 0.910 | 0.079 |
| Group 2 (0.25 mg/kg AD05891) | 0.668 | 0.206 | 0.809 | 0.267 | N/A | N/A | N/A | N/A |
| Group 3 (0.25 mg/kg AD05892) | 0.612 | 0.231 | 0.833 | 0.182 | N/A | N/A | N/A | N/A |
| Group 4 (0.25 mg/kg AD05893) | 0.779 | 0.343 | 0.820 | 0.331 | N/A | N/A | N/A | N/A |
| Group 5 (0.25 mg/kg AD05894) | 0.856 | 0.148 | 0.942 | 0.212 | N/A | N/A | N/A | N/A |
| Group 6 (0.25 mg/kg AD05895) | 1.235 | 0.117 | 1.241 | 0.079 | N/A | N/A | N/A | N/A |
| Group 7 (0.25 mg/kg AD05896) | 1.279 | 0.792 | 1.248 | 0.740 | N/A | N/A | N/A | N/A |
| Group 8 (0.25 mg/kg AD05897) | 1.122 | 0.285 | 0.992 | 0.298 | N/A | N/A | N/A | N/A |
| Group 9 (0.25 mg/kg AD05889) | 0.783 | 0.278 | 0.718 | 0.203 | N/A | N/A | N/A | N/A |
| Group 10 (0.25 mg/kg AD05890) | 0.885 | 0.294 | 0.661 | 0.131 | N/A | N/A | N/A | N/A |
| Group 11 (0.25 mg/kg AD05876) | 2.059 | 0.818 | 1.747 | 0.597 | 1.981 | 0.319 | 1.748 | 0.825 |
| Group 12 (0.25 mg/kg AD05877) | 1.317 | 0.148 | 1.295 | 0.273 | 1.176 | 0.130 | N/A | N/A |
| Group 13 (0.25 mg/kg AD05878) | 1.421 | 0.294 | 1.273 | 0.262 | 0.999 | 0.328 | N/A | N/A |
| Group 14 (0.25 mg/kg AD05879) | 1.037 | 0.074 | 0.945 | 0.125 | 0.924 | 0.141 | N/A | N/A |
| Group 15 (0.25 mg/kg AD05880) | 0.905 | 0.266 | 0.855 | 0.051 | N/A | N/A | N/A | N/A |
| Group 16 (0.25 mg/kg AD05882) | 0.784 | 0.098 | 0.621 | 0.103 | N/A | N/A | N/A | N/A |
| Group 17 (0.25 mg/kg AD05884) | 1.529 | 0.486 | 1.228 | 0.309 | 1.149 | 0.257 | N/A | N/A |
| Group 18 (0.25 mg/kg AD05885) | 1.123 | 0.323 | 0.651 | 0.143 | N/A | N/A | N/A | N/A |
| Group 19 (0.25 mg/kg AD05886) | 1.047 | 0.343 | 0.675 | 0.181 | N/A | N/A | N/A | N/A |
| Group 20 (0.25 mg/kg AD05887) | 2.093 | 1.089 | 1.487 | 0.748 | N/A | N/A | N/A | N/A |
| Group 21 (0.25 mg/kg AD05888) | 1.452 | 0.065 | 1.245 | 0.177 | N/A | N/A | N/A | N/A |
| Group 22 (0.25 mg/kg AD05769) | 1.289 | 0.219 | 1.186 | 0.202 | 1.125 | 0.231 | 1.325 | 0.044 |

TABLE 32

Average LDL Normalized to Pre-Dose from Example 10.

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) |
|---|---|---|---|---|---|---|---|---|
| Group 1 (D5W) | 1.456 | 0.391 | 1.107 | 0.243 | 1.506 | 0.751 | 1.568 | 0.650 |
| Group 2 (0.25 mg/kg AD05891) | 1.417 | 0.351 | 1.593 | 0.488 | N/A | N/A | N/A | N/A |
| Group 3 (0.25 mg/kg AD05892) | 0.875 | 0.398 | 0.951 | 0.170 | N/A | N/A | N/A | N/A |
| Group 4 (0.25 mg/kg AD05893) | 1.243 | 0.217 | 1.400 | 0.311 | N/A | N/A | N/A | N/A |
| Group 5 (0.25 mg/kg AD05894) | 0.776 | 0.175 | 0.934 | 0.244 | N/A | N/A | N/A | N/A |
| Group 6 (0.25 mg/kg AD05895) | 1.223 | 0.413 | 1.208 | 0.361 | N/A | N/A | N/A | N/A |
| Group 7 (0.25 mg/kg AD05896) | 1.347 | 0.475 | 1.224 | 0.331 | N/A | N/A | N/A | N/A |
| Group 8 (0.25 mg/kg AD05897) | 1.206 | 0.398 | 1.255 | 0.137 | N/A | N/A | N/A | N/A |
| Group 9 (0.25 mg/kg AD05889) | 1.291 | 0.294 | 1.329 | 0.267 | N/A | N/A | N/A | N/A |
| Group 10 (0.25 mg/kg AD05890) | 1.171 | 0.363 | 1.091 | 0.284 | N/A | N/A | N/A | N/A |
| Group 11 (0.25 mg/kg AD05876) | 0.679 | 0.457 | 0.703 | 0.329 | 0.881 | 0.237 | 0.896 | 0.252 |
| Group 12 (0.25 mg/kg AD05877) | 0.575 | 0.162 | 0.531 | 0.187 | 0.624 | 0.304 | N/A | N/A |
| Group 13 (0.25 mg/kg AD05878) | 0.534 | 0.191 | 0.532 | 0.163 | 0.666 | 0.321 | N/A | N/A |
| Group 14 (0.25 mg/kg AD05879) | 0.602 | 0.043 | 0.671 | 0.060 | 0.939 | 0.171 | N/A | N/A |
| Group 15 (0.25 mg/kg AD05880) | 0.527 | 0.098 | 0.525 | 0.122 | N/A | N/A | N/A | N/A |
| Group 16 (0.25 mg/kg AD05882) | 1.252 | 0.279 | 1.568 | 0.525 | N/A | N/A | N/A | N/A |
| Group 17 (0.25 mg/kg AD05884) | 0.814 | 0.591 | 0.590 | 0.363 | 0.850 | 0.453 | N/A | N/A |
| Group 18 (0.25 mg/kg AD05885) | 0.827 | 0.171 | 0.798 | 0.043 | N/A | N/A | N/A | N/A |
| Group 19 (0.25 mg/kg AD05886) | 1.045 | 0.206 | 1.180 | 0.134 | N/A | N/A | N/A | N/A |
| Group 20 (0.25 mg/kg AD05887) | 0.756 | 0.118 | 0.794 | 0.156 | N/A | N/A | N/A | N/A |
| Group 21 (0.25 mg/kg AD05888) | 0.745 | 0.460 | 0.945 | 0.499 | N/A | N/A | N/A | N/A |
| Group 22 (0.25 mg/kg AD05769) | 0.634 | 0.293 | 0.568 | 0.243 | 0.625 | 0.189 | 0.644 | 0.136 |

As shown in Tables 28-32 above, the RNAi agents in Groups 2 through 10 (i.e., RNAi agents with antisense strands designed to target an APOC3 gene at positions 248, 263, 422, 246, and 168) showed relatively limited inhibitory effect, particularly when compared to the RNAi agents in Groups 11 through 22, which all included antisense strand nucleotide sequences designed to target position 438 of an APOC3 gene. Further, of those RNAi agents that included sequences targeting position 438 of the APOC3 gene, Group 11 (AD05876) and Group 22 (AD05769) showed the greatest level of inhibitory effect with respect to APOC3 protein levels, triglycerides, and total cholesterol levels.

Example 11. In Vivo Testing of APOC3 RNAi Agents in APOC3 Transgenic Mice

The APOC3 Transgenic Mouse Model described in Example 5, above, was used. At day 1, each mouse was given a single subcutaneous administration of 200 μl of the respective RNAi agent dissolved in D5W (dextrose in 5% water) or control vehicle (D5W) according to the dosing groups shown in the following Table 33:

TABLE 33

Dosing groups of Example 11.

| Group | RNAi Agent and Dose | Dosing Regimen |
|---|---|---|
| 1 | D5W (no RNAi agent) | Single injection on day 1 |
| 2 | 0.5 mg/kg AD05260 | Single injection on day 1 |
| 3 | 0.5 mg/kg AD05221 | Single injection on day 1 |
| 4 | 0.5 mg/kg AD05223 | Single injection on day 1 |
| 5 | 0.5 mg/kg AD05299 | Single injection on day 1 |
| 6 | 0.5 mg/kg AD05283 | Single injection on day 1 |
| 7 | 0.5 mg/kg AD05284 | Single injection on day 1 |
| 8 | 0.5 mg/kg AD05167 | Single injection on day 1 |
| 9 | 0.5 mg/kg AD05168 | Single injection on day 1 |
| 10 | 0.5 mg/kg AD05171 | Single injection on day 1 |
| 11 | 0.5 mg/kg AD05258 | Single injection on day 1 |
| 12 | 0.5 mg/kg AD05259 | Single injection on day 1 |
| 13 | 0.5 mg/kg AD05169 | Single injection on day 1 |
| 14 | 0.5 mg/kg AD05239 | Single injection on day 1 |
| 15 | 0.5 mg/kg AD05251 | Single injection on day 1 |
| 16 | 0.5 mg/kg AD05220 | Single injection on day 1 |

Each of the APOC3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 4, 5, 6, and 7 for specific modifications and structure information related to the APOC3 RNAi agents).

The APOC3 RNAi agents tested in Example 11 included nucleotide sequences that were designed to target different positions on the APOC3 gene (i.e., SEQ ID NO:1). More specifically, Group 2 (i.e., APOC3 RNAi agent AD05260) included an antisense strand sequence designed to target position 58 of an APOC3 gene; Group 3 (i.e., APOC3 RNAi agent AD05221) included an antisense strand sequence designed to target position 246 of an APOC3 gene; Groups 4-7 (i.e., APOC3 RNAi agents AD05223, AD05299, AD05283, and AD05284) included antisense strand sequences designed to target position 432 of an APOC3 gene; Groups 8-12 (i.e., APOC3 RNAi agents AD05167, AD05168, AD05171, AD05258, and AD05259) included antisense strand sequences designed to target position 434 of an APOC3 gene; Groups 13-15 (i.e., APOC3 RNAi agents AD05169, AD05239, and AD05251) included antisense strand sequences designed to target position 438 of an APOC3 gene; and Group 16 (i.e., APOC3 RNAi agent AD05220) included an antisense strand sequence designed to target position 506 of an APOC3 gene.

The injections were performed between the skin and muscle (i.e. subcutaneous injections) into the loose skin over the neck and shoulder area. Three (3) mice in each Group were tested (n=3). Serum was collected on day −1 (pre-dose bleed with a 4 hour fast), and days 8, 15. For mice dosed with the certain RNAi agents that exhibited relatively high inhibitory activity and for the mice dosed with the vehicle control, additional serum samples were collected on days 22 and 29. Mice were fasted for four hours prior to each collection. APOC3 expression levels, triglycerides, high-density lipoprotein (HDL), low-density lipoprotein (LDL), and total cholesterol in serum were measured on a Cobas® Integra 400 (Roche Diagnostics), according to the manufacturer's recommendations.

The APOC3 protein levels, triglyceride levels, HDL levels, and total cholesterol levels for each animal were normalized. For normalization, the level of APOC3 protein, triglyceride, HDL, LDL, and total cholesterol, respectively, for each animal at a time point, was divided by the pre-treatment level of expression in that animal (in this case at day −1) to determine the ratio of expression "normalized to pre-dose." Data from the experiment are shown in the following Tables 34 through 38:

TABLE 34

Average APOC3 Protein Normalized to Pre-Dose from Example 11.

| | Day 8 | | Day 15 | | Day 22 | | Day 29 | |
|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) |
| Group 1 (D5W) | 0.854 | 0.102 | 0.866 | 0.140 | 0.881 | 0.079 | 0.857 | 0.140 |
| Group 2 (0.5 mg/kg AD05260) | 0.297 | 0.031 | 0.352 | 0.042 | N/A | N/A | N/A | N/A |
| Group 3 (0.5 mg/kg AD05221) | 0.483 | 0.060 | 0.619 | 0.046 | N/A | N/A | N/A | N/A |
| Group 4 (0.5 mg/kg AD05223) | 0.123 | 0.048 | 0.242 | 0.101 | 0.311 | 0.099 | 0.424 | 0.152 |
| Group 5 (0.5 mg/kg AD05299) | 0.272 | 0.047 | 0.589 | 0.016 | N/A | N/A | N/A | N/A |
| Group 6 (0.5 mg/kg AD05283) | 0.108 | 0.014 | 0.121 | 0.011 | 0.163 | 0.009 | 0.201 | 0.032 |
| Group 7 (0.5 mg/kg AD05284) | 0.174 | 0.111 | 0.208 | 0.123 | 0.313 | 0.124 | 0.405 | 0.144 |
| Group 8 (0.5 mg/kg AD05167) | 0.466 | 0.093 | 0.656 | 0.286 | N/A | N/A | N/A | N/A |
| Group 9 (0.5 mg/kg AD05168) | 0.146 | 0.046 | 0.452 | 0.098 | N/A | N/A | N/A | N/A |
| Group 10 (0.5 mg/kg AD05171) | 0.191 | 0.088 | 0.199 | 0.095 | 0.419 | 0.070 | 0.548 | 0.087 |
| Group 11 (0.5 mg/kg AD05258) | 0.545 | 0.147 | 0.624 | 0.142 | N/A | N/A | N/A | N/A |
| Group 12 (0.5 mg/kg AD05259) | 0.236 | 0.047 | 0.300 | 0.115 | N/A | N/A | N/A | N/A |
| Group 13 (0.5 mg/kg AD05169) | 0.643 | 0.172 | 0.613 | 0.161 | N/A | N/A | N/A | N/A |
| Group 14 (0.5 mg/kg AD05239) | 0.438 | 0.065 | 0.542 | 0.014 | N/A | N/A | N/A | N/A |

TABLE 34-continued

Average APOC3 Protein Normalized to Pre-Dose from Example 11.

| Group ID | Day 8 | | Day 15 | | Day 22 | | Day 29 | |
|---|---|---|---|---|---|---|---|---|
| | Avg APOC3 | Std Dev (+/−) | Avg APOC3 | Std Dev (+/−) | Avg APOC3 | Std Dev (+/−) | Avg APOC3 | Std Dev (+/−) |
| Group 15 (0.5 mg/kg AD05251) | 0.125 | 0.013 | 0.132 | 0.037 | 0.157 | 0.033 | 0.188 | 0.049 |
| Group 16 (0.5 mg/kg AD05220) | 0.211 | 0.012 | 0.201 | 0.087 | 0.230 | 0.045 | 0.342 | 0.166 |

TABLE 35

Average Triglycerides Normalized to Pre-Dose from Example 11.

| Group ID | Day 8 | | Day 15 | | Day 22 | | Day 29 | |
|---|---|---|---|---|---|---|---|---|
| | Avg TG | Std Dev (+/−) | Avg TG | Std Dev (+/−) | Avg TG | Std Dev (+/−) | Avg TG | Std Dev (+/−) |
| Group 1 (D5W) | 0.939 | 0.217 | 0.835 | 0.235 | 0.965 | 0.215 | 1.051 | 0.136 |
| Group 2 (0.5 mg/kg AD05260) | 0.259 | 0.085 | 0.324 | 0.124 | N/A | N/A | N/A | N/A |
| Group 3 (0.5 mg/kg AD05221) | 0.352 | 0.134 | 0.481 | 0.077 | N/A | N/A | N/A | N/A |
| Group 4 (0.5 mg/kg AD05223) | 0.133 | 0.034 | 0.228 | 0.057 | 0.327 | 0.060 | 0.451 | 0.105 |
| Group 5 (0.5 mg/kg AD05299) | 0.352 | 0.134 | 0.481 | 0.086 | N/A | N/A | N/A | N/A |
| Group 6 (0.5 mg/kg AD05283) | 0.130 | 0.022 | 0.150 | 0.026 | 0.245 | 0.056 | 0.286 | 0.023 |
| Group 7 (0.5 mg/kg AD05284) | 0.203 | 0.162 | 0.275 | 0.231 | 0.350 | 0.199 | 0.477 | 0.260 |
| Group 8 (0.5 mg/kg AD05167) | 0.318 | 0.126 | 0.483 | 0.330 | N/A | N/A | N/A | N/A |
| Group 9 (0.5 mg/kg AD05168) | 0.188 | 0.014 | 0.330 | 0.010 | N/A | N/A | N/A | N/A |
| Group 10 (0.5 mg/kg AD05171) | 0.183 | 0.092 | 0.282 | 0.150 | 0.423 | 0.124 | 0.549 | 0.138 |
| Group 11 (0.5 mg/kg AD05258) | 0.479 | 0.167 | 0.622 | 0.187 | N/A | N/A | N/A | N/A |
| Group 12 (0.5 mg/kg AD05259) | 0.294 | 0.015 | 0.360 | 0.190 | N/A | N/A | N/A | N/A |
| Group 13 (0.5 mg/kg AD05169) | 0.728 | 0.253 | 0.561 | 0.163 | N/A | N/A | N/A | N/A |
| Group 14 (0.5 mg/kg AD05239) | 0.381 | 0.038 | 0.422 | 0.057 | N/A | N/A | N/A | N/A |
| Group 15 (0.5 mg/kg AD05251) | 0.110 | 0.032 | 0.092 | 0.019 | 0.134 | 0.051 | 0.186 | 0.072 |
| Group 16 (0.5 mg/kg AD05220) | 0.161 | 0.045 | 0.216 | 0.029 | 0.184 | 0.075 | 0.358 | 0.141 |

TABLE 36

Average Total Cholesterol Normalized to Pre-Dose from Example 11.

| Group ID | Day 8 | | Day 15 | | Day 22 | | Day 29 | |
|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 0.769 | 0.127 | 0.684 | 0.182 | 0.835 | 0.167 | 0.796 | 0.180 |
| Group 2 (0.5 mg/kg AD05260) | 0.320 | 0.081 | 0.367 | 0.072 | N/A | N/A | N/A | N/A |
| Group 3 (0.5 mg/kg AD05221) | 0.397 | 0.078 | 0.456 | 0.050 | N/A | N/A | N/A | N/A |
| Group 4 (0.5 mg/kg AD05223) | 0.393 | 0.176 | 0.450 | 0.189 | 0.476 | 0.186 | 0.606 | 0.193 |
| Group 5 (0.5 mg/kg AD05299) | 0.522 | 0.092 | 0.611 | 0.031 | N/A | N/A | N/A | N/A |
| Group 6 (0.5 mg/kg AD05283) | 0.413 | 0.058 | 0.372 | 0.053 | 0.450 | 0.100 | 0.501 | 0.040 |
| Group 7 (0.5 mg/kg AD05284) | 0.430 | 0.270 | 0.444 | 0.241 | 0.519 | 0.252 | 0.604 | 0.315 |
| Group 8 (0.5 mg/kg AD05167) | 0.464 | 0.231 | 0.557 | 0.382 | N/A | N/A | N/A | N/A |
| Group 9 (0.5 mg/kg AD05168) | 0.298 | 0.034 | 0.388 | 0.012 | N/A | N/A | N/A | N/A |
| Group 10 (0.5 mg/kg AD05171) | 0.360 | 0.179 | 0.391 | 0.180 | 0.473 | 0.147 | 0.538 | 0.141 |
| Group 11 (0.5 mg/kg AD05258) | 0.619 | 0.094 | 0.668 | 0.135 | N/A | N/A | N/A | N/A |
| Group 12 (0.5 mg/kg AD05259) | 0.643 | 0.053 | 0.511 | 0.187 | N/A | N/A | N/A | N/A |
| Group 13 (0.5 mg/kg AD05169) | 0.731 | 0.089 | 0.636 | 0.013 | N/A | N/A | N/A | N/A |
| Group 14 (0.5 mg/kg AD05239) | 0.571 | 0.106 | 0.561 | 0.085 | N/A | N/A | N/A | N/A |
| Group 15 (0.5 mg/kg AD05251) | 0.248 | 0.065 | 0.287 | 0.147 | 0.260 | 0.074 | 0.305 | 0.114 |
| Group 16 (0.5 mg/kg AD05220) | 0.400 | 0.081 | 0.438 | 0.048 | 0.422 | 0.065 | 0.524 | 0.080 |

TABLE 37

Average HDL Normalized to Pre-Dose from Example 11.

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 1 (D5W) | 0.825 | 0.119 | 0.893 | 0.217 | 0.912 | 0.179 | 0.886 | 0.262 |
| Group 2 (0.5 mg/kg AD05260) | 1.356 | 0.337 | 1.331 | 0.435 | N/A | N/A | N/A | N/A |
| Group 3 (0.5 mg/kg AD05221) | 1.483 | 0.266 | 0.953 | 0.166 | N/A | N/A | N/A | N/A |
| Group 4 (0.5 mg/kg AD05223) | 1.058 | 0.198 | 1.032 | 0.300 | 0.856 | 0.209 | 0.868 | 0.349 |
| Group 5 (0.5 mg/kg AD05299) | 1.456 | 0.345 | 1.137 | 0.460 | N/A | N/A | N/A | N/A |
| Group 6 (0.5 mg/kg AD05283) | 2.494 | 0.174 | 2.150 | 0.465 | 1.731 | 0.397 | 1.738 | 0.156 |
| Group 7 (0.5 mg/kg AD05284) | 1.559 | 0.237 | 1.791 | 0.849 | 1.598 | 0.448 | 1.605 | 0.131 |
| Group 8 (0.5 mg/kg AD05167) | 1.239 | 0.287 | 1.310 | 0.108 | N/A | N/A | N/A | N/A |
| Group 9 (0.5 mg/kg AD05168) | 1.666 | 0.551 | 1.425 | 0.251 | N/A | N/A | N/A | N/A |
| Group 10 (0.5 mg/kg AD05171) | 1.514 | 0.286 | 1.435 | 0.248 | 0.941 | 0.005 | 0.827 | 0.111 |
| Group 11 (0.5 mg/kg AD05258) | 1.170 | 0.082 | 1.081 | 0.212 | N/A | N/A | N/A | N/A |
| Group 12 (0.5 mg/kg AD05259) | 1.964 | 0.955 | 1.221 | 0.228 | N/A | N/A | N/A | N/A |
| Group 13 (0.5 mg/kg AD05169) | 1.059 | 0.236 | 1.101 | 0.230 | N/A | N/A | N/A | N/A |
| Group 14 (0.5 mg/kg AD05239) | 1.323 | 0.088 | 1.120 | 0.224 | N/A | N/A | N/A | N/A |
| Group 15 (0.5 mg/kg AD05251) | 1.728 | 0.173 | 2.143 | 0.688 | 1.632 | 0.312 | 1.737 | 0.452 |
| Group 16 (0.5 mg/kg AD05220) | 1.660 | 0.391 | 1.797 | 0.384 | 1.803 | 0.637 | 1.479 | 0.333 |

TABLE 38

Average LDL Normalized to Pre-Dose from Example 11.

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) |
|---|---|---|---|---|---|---|---|---|
| Group 1 (D5W) | 0.699 | 0.129 | 0.621 | 0.201 | 0.778 | 0.259 | 0.646 | 0.216 |
| Group 2 (0.5 mg/kg AD05260) | 0.398 | 0.108 | 0.317 | 0.046 | N/A | N/A | N/A | N/A |
| Group 3 (0.5 mg/kg AD05221) | 0.441 | 0.024 | 0.422 | 0.013 | N/A | N/A | N/A | N/A |
| Group 4 (0.5 mg/kg AD05223) | 0.441 | 0.280 | 0.437 | 0.219 | 0.514 | 0.264 | 0.589 | 0.219 |
| Group 5 (0.5 mg/kg AD05299) | 0.504 | 0.160 | 0.577 | 0.100 | N/A | N/A | N/A | N/A |
| Group 6 (0.5 mg/kg AD05283) | 0.464 | 0.122 | 0.428 | 0.173 | 0.551 | 0.277 | 0.595 | 0.195 |
| Group 7 (0.5 mg/kg AD05284) | 0.394 | 0.258 | 0.404 | 0.179 | 0.398 | 0.214 | 0.471 | 0.290 |
| Group 8 (0.5 mg/kg AD05167) | 0.572 | 0.306 | 0.678 | 0.536 | N/A | N/A | N/A | N/A |
| Group 9 (0.5 mg/kg AD05168) | 0.329 | 0.067 | 0.374 | 0.017 | N/A | N/A | N/A | N/A |
| Group 10 (0.5 mg/kg AD05171) | 0.303 | 0.186 | 0.280 | 0.134 | 0.401 | 0.113 | 0.429 | 0.180 |
| Group 11 (0.5 mg/kg AD05258) | 0.669 | 0.105 | 0.702 | 0.140 | N/A | N/A | N/A | N/A |
| Group 12 (0.5 mg/kg AD05259) | 0.588 | 0.208 | 0.407 | 0.211 | N/A | N/A | N/A | N/A |
| Group 13 (0.5 mg/kg AD05169) | 0.626 | 0.116 | 0.672 | 0.057 | N/A | N/A | N/A | N/A |
| Group 14 (0.5 mg/kg AD05239) | 0.473 | 0.138 | 0.488 | 0.124 | N/A | N/A | N/A | N/A |
| Group 15 (0.5 mg/kg AD05251) | 0.254 | 0.147 | 0.344 | 0.257 | 0.234 | 0.063 | 0.306 | 0.166 |
| Group 16 (0.5 mg/kg AD05220) | 0.364 | 0.043 | 0.439 | 0.045 | 0.461 | 0.157 | 0.455 | 0.101 |

Example 12. In Vivo Testing of APOC3 RNAi Agents in Cynomolgus Monkeys

APOC3 RNAi agents were evaluated in cynomolgus monkeys. On day 1, cynomolgus macaque (*Macaca fascicularis*) primates (also referred to herein as "cynos") were administered a single subcutaneous injection of 0.3 mL/kg (approximately 2-3 mL volume, depending on animal mass) containing 3.0 mg/kg of APOC3 RNAi agent AD05876, formulated in saline. APOC3 RNAi agent AD05876 included modified nucleotides and a tridentate N-acetylgalactosamine targeting ligand ((NAG37)s) conjugated to the 5'-terminal end of the sense strand, as shown in Tables 4, 5, 6, and 7.

Two (2) cynos were tested (n=2). On days −8 (pre-dose), 29, and 50, liver biopsies were taken. For one of the monkeys, additional liver biopsy samples were taken on day 15. On the date of each biopsy collection, cynos were anesthetized and ultrasound-guided liver biopsies were performed to extract two or three liver tissue samples approximately 1 mm×4 mm in size. The biopsy samples were then homogenized, and levels of APOC3 mRNA in the cyno livers were measured by RT-qPCR. Resulting values were then normalized to the pre-dose (in this case, at day −8) APOC3 mRNA measurements. The resulting mRNA data is reflected in the following Tables 39 and 40:

TABLE 39

APOC3 mRNA Levels Normalized to Pre-Dose from Example 12 of Cyno #1 (cy0713).

| Relative APOC3 mRNA Expression | Low Error | High Error |
|---|---|---|
| Day 29 | | |
| 0.125 | 0.003 | 0.003 |
| Day 50 | | |
| 0.167 | 0.002 | 0.002 |

TABLE 40

APOC3 mRNA Levels Normalized to Pre-Dose from Example 12 of Cyno #2 (cy0716).

| Relative APOC3 mRNA Expression | Low Error | High Error |
|---|---|---|
| Day 15 | | |
| 0.250 | 0.007 | 0.007 |
| Day 29 | | |
| 0.112 | 0.005 | 0.00 |
| Day 50 | | |
| 0.239 | 0.003 | 0.003 |

Both of the cynos dosed with AD05876 showed a significant reduction in liver-specific APOC3 mRNA compared to pre-treatment measurements at all measured time points. On day 29, for example, the first cyno had a reduction of APOC3 mRNA of approximately 87.5% (0.125), while the second cyno had a reduction of approximately 88.8% (0.112), compared to pre-dose levels.

Example 13. In Vivo Testing of APOC3 RNAi Agents in High Fructose Corn Syrup (HFCS) Diet-Fed Rhesus Monkeys APOC3 RNAi agent AD05876 was further evaluated in high-fructose corn syrup (HFCS) diet-fed Rhesus monkeys. Rhesus monkeys were placed on an HFCS diet 37 days prior to dosing. These animals were known to develop increased plasma triglycerides greater than 180 mg/dL on the HFCS diet. On day 1 and again on day 29, four (4) Rhesus monkeys were administered a subcutaneous injection containing 4.0 mg/kg of APOC3 RNAi agent AD05876 formulated in saline (n=4). Two additional Rhesus monkeys were administered normal saline control. APOC3 RNAi agent AD05876 contained modified nucleotides and included N-acetyl-galactosamine targeting ligands conjugated to the 5'-terminal end of the sense strand, as shown in Tables 4, 5, 6, and 7.

Both fed and fasting blood samples were drawn for analysis, and fasting serum samples were analyzed on days −8 (predose), 8, and 15. Monkeys were fasted overnight prior to each collection. APOC3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The APOC3 protein levels, triglyceride levels, total cholesterol levels, HDL levels, and LDL levels for each animal were normalized. For normalization, the level of APCO3 protein, triglyceride, HDL, and total cholesterol, respectively, for each animal at a time point, was divided by the pre-treatment level of expression in that animal (in this case at day −8) to determine the ratio of expression "normalized to pre-treatment."

Data from the study set forth in this Example are shown in the following Tables 41-45:

TABLE 41

Average APOC3 Protein Normalized to Pre-Treatment from Example 13 (Fasted)

| | Day 8 | | Day 15 | | Day 21 | | Day 29 | | Day 36 | |
|---|---|---|---|---|---|---|---|---|---|---|
| Group ID | Avg APOC3 | Std Dev (+/−) | Avg APOC3 | Std Dev (+/−) | Avg APOC3 | Std Dev (+/−) | Avg APOC3 | Std Dev (+/−) | Avg APOC3 | Std Dev (+/−) |
| Group 1 (saline control) | 0.921 | 0.007 | 0.902 | 0.009 | 0.922 | 0.026 | 0.905 | 0.025 | 0.922 | 0.006 |
| Group 2 (4.0 mg/kg AD05876) | 0.509 | 0.150 | 0.388 | 0.159 | 0.347 | 0.114 | 0.358 | 0.086 | 0.335 | 0.100 |

TABLE 42

Average TG Normalized to Pre-Treatment from Example 13 (Fasted)

| | Day 8 | | Day 15 | | Day 21 | | Day 29 | | Day 36 | |
|---|---|---|---|---|---|---|---|---|---|---|
| Group ID | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 1 (saline control) | 0.743 | 0.055 | 0.717 | 0.054 | 1.017 | 0.155 | 0.758 | 0.263 | 0.659 | 0.111 |
| Group 2 (4.0 mg/kg AD05876) | 0.599 | 0.338 | 0.433 | 0.286 | 0.395 | 0.247 | 0.435 | 0.212 | 0.408 | 0.269 |

TABLE 43

Average Total Cholesterol Normalized to Pre-Treatment from Example 13 (Fasted)

| | Day 8 | | Day 15 | | Day 21 | | Day 29 | | Day 36 | |
|---|---|---|---|---|---|---|---|---|---|---|
| Group ID | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (saline control) | 0.972 | 0.050 | 0.944 | 0.079 | 0.957 | 0.0.18 | 0.882 | 0.021 | 0.894 | 0.038 |

TABLE 43-continued

Average Total Cholesterol Normalized to Pre-Treatment from Example 13 (Fasted)

| Group ID | Day 8 | | Day 15 | | Day 21 | | Day 29 | | Day 36 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 2 (4.0 mg/kg AD05876) | 0.860 | 0.177 | 0.826 | 0.1119 | 0.825 | 0.084 | 0.780 | 0.162 | 0.751 | 0.203 |

TABLE 44

Average HDL Normalized to Pre-Treatment from Example 13 (Fasted)

| Group ID | Day 8 | | Day 15 | | Day 21 | | Day 29 | | Day 36 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (saline control) | 1.082 | 0.098 | 1.071 | 0.111 | 1.003 | 0.158 | 1.025 | 0.131 | 1.027 | 0.071 |
| Group 2 (4.0 mg/kg AD05876) | 1.370 | 0.267 | 1.445 | 0.479 | 1.465 | 0.537 | 1.316 | 0.294 | 1.370 | 0.425 |

TABLE 45

Average LDL Normalized to Pre-Treatment from Example 13 (Fasted)

| Group ID | Day 8 | | Day 15 | | Day 21 | | Day 29 | | Day 36 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (saline control) | 0.892 | 0.060 | 0.928 | 0.046 | 0.823 | 0.034 | 0.804 | 0.076 | 0.804 | 0.172 |
| Group 2 (4.0 mg/kg AD05876) | 0.777 | 0.129 | 0.856 | 0.136 | 0.842 | 0.186 | 0.755 | 0.144 | 0.716 | 0.228 |

The Rhesus monkeys dosed with AD05876 at 4.0 mg/kg dosage levels showed a reduction in APOC3 protein compared to pre-treatment measurements across each of the measured time points. Further, substantial reductions in both triglyceride levels and total cholesterol levels are also shown. For example, in one animal, triglycerides were reduced by approximately 89% on day 22, and as shown in Table 42 above, mean triglyceride levels were reduced by approximately 60% (0.395) on day 22. Additionally, mean HDL levels increased by approximately 47% on day 22 (see Table 44 (1.465)), with one animal having a 2.2-fold increase in HDL levels.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of an APOC3 gene, comprising:
   an antisense strand, wherein nucleotides 1-21 (5'→3') of the antisense strand comprise the nucleotides of (i)   UCACUGAGAAUACUGUCCCUC;     (SEQ ID NO: 3)
   (ii)  UCACUGAGAAUACUGUCCCGU;     (SEQ ID NO: 5)
   (iii) UCACUGAGAAUACUGUCCCUG;     (SEQ ID NO: 710)
         or
   (iv)  UCACUGAGAAUACUGUCCCCU;     (SEQ ID NO: 711)

and
   a sense strand comprising a nucleotide sequence that is partially complementary, substantially complementary, or fully complementary to the antisense strand.

2. The RNAi agent of claim 1, wherein at least one nucleotide of the RNAi agent is a modified nucleotide or includes a modified internucleoside linkage.

3. The RNAi agent of claim 2, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate deoxyribonucleotide, cyclopropyl phosphonate deoxyribonucleotide, and 3'-O-methyl nucleotide.

4. The RNAi agent of claim 1, wherein all or substantially all of the nucleotides of the sense and/or antisense strand of the RNAi agent are modified nucleotides.

5. The RNAi agent of claim 4, wherein all or substantially all of the modified nucleotides are either 2'-O-methyl nucleotides or 2'-fluoro nucleotides.

6. The RNAi agent of claim 1, wherein the antisense strand comprises the nucleotide sequence of any one of the modified sequences of SEQ ID NOs: 2, 6, 394, 401, 402, 403, 404, 405, and 406 and the sense strand comprises the nucleotide sequence of any one of the modified sequences of SEQ ID NOs: 482, 488, 500, 501, 502, 530, 543, 551, 556, 557, 572, 573, 574, 575, and 576.

7. The RNAi agent of claim 1, wherein the RNAi agent is linked to a targeting ligand.

8. The RNAi agent of claim 7, wherein the targeting ligand comprises N-acetyl-galactosamine.

9. The RNAi agent of claim 7, wherein the targeting ligand comprises a structure selected from the group consisting of: (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s.

10. The RNAi agent of claim 9, wherein the targeting ligand comprises the structure of (NAG37) or (NAG37)s.

11. The RNAi agent of claim 7, wherein the targeting ligand is conjugated to the sense strand.

12. The RNAi agent of claim 11, wherein the targeting ligand is conjugated to the 5' terminal end of the sense strand.

13. A composition comprising the RNAi agent of claim 1, wherein the composition comprises a pharmaceutically acceptable excipient.

14. The composition of claim 13, wherein the RNAi agent is conjugated to a targeting ligand.

15. The composition of claim 14, wherein the targeting ligand comprises N-acetyl-galactosamine.

16. The composition of claim 13, wherein the composition further comprises a second RNAi agent for inhibiting the expression of APOC3.

17. The composition of claim 13, wherein the composition further comprises one or more additional therapeutics.

18. A method for inhibiting expression of an APOC3 gene in a cell, the method comprising introducing into a cell an effective amount of the composition of claim 13.

19. The method of claim 18, wherein the cell is within a subject.

20. The method of claim 19, wherein the subject is a human subject.

21. The method of claim 18, wherein the APOC3 gene expression is inhibited by at least about 30%.

22. A method of treating an APOC3-related disease or disorder, the method comprising administering to a human subject in need thereof a therapeutically effective amount of the composition of claim 13.

23. The method of claim 22, wherein the disease is a cardiometabolic disease.

24. The method of claim 23, wherein the disease is hypertriglyceridemia, obesity, hyperlipidemia, abnormal lipid and/or cholesterol metabolism, atherosclerosis, cardiovascular disease, coronary artery disease, hypertriglyceridemia induced pancreatitis, metabolic syndrome, type II diabetes mellitus, familial chylomicronemia syndrome, or familial partial lipodystrophy.

25. The method of claim 22, wherein the RNAi agent is administered at a dose of about 0.05 mg/kg to about 5.0 mg/kg of body weight of the human subject.

26. The method of claim 25, wherein the dose is administered by subcutaneous injection.

27. The method of claim 22, wherein the RNAi agent is administered in two or more doses.

28. A method of lowering triglyceride levels in a subject, the method comprising administering to the subject an effective amount of a composition of claim 13.

29. A method of lowering cholesterol levels in a subject, the method comprising administering to the subject an effective amount of a composition of claim 13.

30. A method of lowering low density lipoprotein (LDL) levels in a subject, the method comprising administering to the subject an effective amount of a composition of claim 13.

* * * * *